US012746302B2

(12) United States Patent
Vlad et al.

(10) Patent No.: US 12,746,302 B2
(45) Date of Patent: *Sep. 29, 2026

(54) FRESHENING COMPOSITIONS COMPRISING CONTROLLED RELEASE MODULATORS

(71) Applicant: Arylessence, Inc., Marietta, GA (US)

(72) Inventors: Florin-Iosif Vlad, Annandale, NJ (US); Austin Howard, Dallas, GA (US)

(73) Assignee: Arylessence, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/389,469

(22) Filed: Nov. 14, 2025

(65) Prior Publication Data

US 2026/0069734 A1 Mar. 12, 2026

Related U.S. Application Data

(63) Continuation-in-part of application No. 18/471,555, filed on Sep. 21, 2023, now Pat. No. 12,496,370,
(Continued)

(51) Int. Cl.
*A61L 9/01* (2006.01)
*A61L 9/013* (2006.01)
(Continued)

(52) U.S. Cl.
CPC ................ *A61L 9/01* (2013.01); *A61L 9/013* (2013.01); *A61L 9/03* (2013.01); *A61L 9/032* (2013.01);
(Continued)

(58) Field of Classification Search
CPC ... A61L 9/01; A61L 9/013; A61L 9/03; A61L 9/032; A61L 9/037; A61L 9/12;
(Continued)

(56) References Cited

U.S. PATENT DOCUMENTS 5,081,104 A 1/1992 Orson, Sr.
5,409,694 A 4/1995 Meyer et al.
(Continued)

FOREIGN PATENT DOCUMENTS

EP 0 520 547 A2 12/1992
EP 0 520 547 A3 12/1992
(Continued)

OTHER PUBLICATIONS

Vlad, Florin-Iosif; PCT Search Report and Written Opinion for PCT Application No. PCT/US2019/044102; filed Jul. 30, 2019, mailed Oct. 15, 2019; 10 pages; Jul. 30, 2019.
(Continued)

*Primary Examiner* — Brendan A Hensel
(74) *Attorney, Agent, or Firm* — RUPPERT U.S. IP GmbH; Siegfried J.W. Ruppert

(57) ABSTRACT

The present invention relates to freshening compositions, devices comprising same and methods of using and manufacturing same. A freshening composition of the present invention comprises (i) from about 0.1 wt % to about 95 wt % perfume raw material and (ii) from about 0.01 wt % to about 90 wt % fragrance release modulator. Some freshening compositions further comprise a solvent and/or an ingredient having a functional activity. Disclosed are passive and active air or surface freshening devices comprising a freshening composition that allow controlled and customized release of the freshening composition or of a component thereof into or onto an environment. The addition of a fragrance release modulator to formulate a freshening composition of the present invention allows for modulation of the release of the freshening composition or of a component thereof.

172 Claims, 6 Drawing Sheets

Related U.S. Application Data which is a continuation-in-part of application No. 16/524,697, filed on Jul. 29, 2019, now Pat. No. 11,806,448.

(60) Provisional application No. 62/712,701, filed on Jul. 31, 2018.

(51) Int. Cl.

| | |
|---|---|
| ***A61L 9/03*** | (2006.01) |
| ***A61L 9/12*** | (2006.01) |
| ***A61L 9/14*** | (2006.01) |
| ***A61L 101/32*** | (2006.01) |
| ***A61L 101/34*** | (2006.01) |
| ***A61L 101/36*** | (2006.01) |
| ***A61L 101/38*** | (2006.01) |
| ***A61L 101/44*** | (2006.01) |

(52) U.S. Cl.

CPC ................ *A61L 9/037* (2013.01); *A61L 9/12* (2013.01); *A61L 9/122* (2013.01); *A61L 9/127* (2013.01); *A61L 9/14* (2013.01); *A61L 2101/32* (2020.08); *A61L 2101/34* (2020.08); *A61L 2101/36* (2020.08); *A61L 2101/38* (2020.08); *A61L 2101/44* (2020.08); *A61L 2209/134* (2013.01)

(58) Field of Classification Search

CPC . A61L 9/122; A61L 9/127; A61L 9/14; A61L 2101/32; A61L 2101/34; A61L 2101/36; A61L 2101/38; A61L 2101/44; A61L 2209/134; A61L 2209/133; A61L 9/014; C11B 9/0061; C11B 9/008; C11B 9/00; C11B 9/0015; C11B 9/0019; C11B 9/003; C11B 9/0076; A01P 17/00; A61K 8/34; A61K 8/345; A61K 8/37; A61K 8/585; A61K 8/891; A61Q 13/00; A01N 25/18

See application file for complete search history.

(56) References Cited

U.S. PATENT DOCUMENTS

| | | | |
|---|---|---|---|
| 6,716,805 | B1 | 4/2004 | Sherry et al. |
| 8,603,963 | B1 | 12/2013 | Steward et al. |
| 2002/0193281 | A1 | 12/2002 | Mansfeld et al. |
| 2003/0199402 | A1 | 10/2003 | Triplett et al. |
| 2007/0187404 | A1 | 8/2007 | Caunt et al. |
| 2008/0023569 | A1 | 1/2008 | O'Leary et al. |
| 2008/0248120 | A1 | 10/2008 | Anderson et al. |
| 2009/0202446 | A1 | 8/2009 | Vlad et al. |
| 2012/0097754 | A1 | 4/2012 | Vlad et al. |
| 2012/0328548 | A1 | 12/2012 | Touitou |
| 2014/0115765 | A1 | 5/2014 | Carpenter et al. |
| 2014/0323388 | A1 | 10/2014 | Diersing et al. |
| 2015/0196677 | A1 | 7/2015 | Vlad et al. |
| 2016/0089465 | A1 | 3/2016 | Frankenbach et al. |
| 2016/0367713 | A1 | 12/2016 | Morgan et al. |
| 2016/0367715 | A1 | 12/2016 | Turner et al. |
| 2018/0008740 | A1 | 1/2018 | Morgan, III et al. |
| 2018/0028708 | A1 | 2/2018 | Lynch et al. |
| 2018/0064838 | A1 | 3/2018 | Blondeau et al. |
| 2018/0296716 | A1 | 10/2018 | Vlad et al. |
| 2020/0038537 | A1 | 2/2020 | Vlad et al. |
| 2024/0016966 | A1 | 1/2024 | Vlad et al. |

FOREIGN PATENT DOCUMENTS

| | | | |
|---|---|---|---|
| GB | 2 358 586 | A | 8/2001 |
| JP | 2001-104462 | A | 4/2001 |
| WO | WO1991/018586 | | 12/1991 |
| WO | WO2016/180893 | A1 | 11/2016 |
| WO | WO2016/205028 | A1 | 12/2016 |
| WO | WO2017/015273 | A1 | 1/2017 |
| WO | WO2017/180453 | A1 | 10/2017 |

OTHER PUBLICATIONS

Disclosed Anonymously; Title: New fragrance compositions and air care devices; IP.com No. IPCOM000240482D, Feb. 3, 2015.

USPTO; Vlad, et al., U.S. Appl. No. 16/524,697 (now U.S. Pat. No. 11,806,448); filed Jul. 29, 2019.

USPTO; Vlad, et al., U.S. Appl. No. 18/471,555, filed Sep. 21, 2023.

FRESHENING COMPOSITIONS COMPRISING CONTROLLED RELEASE MODULATORS

CROSS REFERENCE TO RELATED APPLICATIONS

This application is a continuation-in-part application of application Ser. No. 18/471,555, filed Sep. 21, 2023, now U.S. Pat. No. 12,496,370, issued Dec. 16, 2025, which claims the benefit of application Ser. No. 16/524,697, filed Jul. 29, 2019, now U.S. Pat. No. 11,806,448, issued Nov. 7, 2023, which claims the benefit of, and priority to provisional patent application Ser. No. 62/712,701, filed Jul. 31, 2018, and entitled "FRESHENING COMPOSITIONS COMPRISING CONTROLLED RELEASE MODULATORS," the disclosures of each of which are incorporated herein by reference in their entireties and for all purposes.

FIELD OF THE INVENTION

This invention relates to freshening compositions, preferably liquid freshening compositions, more preferably liquid air freshening compositions. This invention also relates to non-water-based freshening compositions, preferably non-water based liquid freshening compositions, more preferably non-water-based liquid air freshening compositions. Freshening compositions of the present invention may comprise one or more of a perfume raw material and a fragrance release modulator. Optional components of a freshening composition of the present invention comprise a solvent and/or a functional ingredient. The invention also relates to air care products and devices comprising a freshening composition. Further, the invention relates to methods for manufacturing a freshening composition, methods for manufacturing an air care product or device comprising a freshening composition, methods for using a freshening composition to freshen the atmosphere, the air, or a surface, and methods for modulating the release of a freshening composition or of a component thereof.

BACKGROUND OF THE INVENTION

Air care products, such as wicking-based, diffusion-based, spraying-based, or steam-based products have been commonly used to deliver various freshening compositions into the air or onto a surface. Exemplary freshening compositions used with such air care products may include volatile materials such as perfume compositions, perfume compositions in conjunction with malodor counteracting compositions, perfume compositions in conjunction with insect repelling compositions, or perfume compositions in conjunction with antimicrobial compositions.

When an air care product is based on a wicking releasing mechanism it mainly consists of (i) a liquid freshening composition, (ii) a container, (iii) a delivery element, which can be a wick or a plurality of wicks, a reed or a plurality of reeds, a stick or a plurality of sticks, a fiber or a plurality of fibers, a mesh, a porous or semi-porous substrate, and, optionally, (iv) an evaporation assisting device, such as in-wall electrical plug-in device, a heating device, or a fan. Commonly known air care products based on a wicking releasing mechanism include reed diffusers, wall electrical plug-ins and diffusers associated with a fan or heating system.

Diffusion-based air care products mainly consist of (i) a liquid freshening composition, (ii) a container, (iii) a diffusing interface, for example a membrane, and, optionally, (iv) a heating device, and (v) an air circulating device, such as a fan, or a combination thereof.

Spraying-based air care products mainly consist of (i) a container for accepting and storing (ii) an air freshening composition, which may contain a perfume composition or a perfume composition in conjunction with an active composition, such as a malodor counteracting composition, (iii) a propellant as a compressed gas, and (iv) a dispenser.

Steam-based air care products mainly consist of (i) a liquid freshening composition, (ii) a container, and (iii) a steam forming and releasing device.

Wicking, also known as wicking process, refers to a spontaneous transport of a liquid through a porous medium as a result of capillary suction taking place at liquid-gas interfaces at the surface or within the porous medium. Several wick-based systems designed to release perfumes or insect repellent liquids through a combined action of wicking process and evaporation are known. The performance a customer expects for an air care freshener based on a wicking process may include (i) an immediate hedonic experience, i.e., a strong perceived impression with respect to strength and character of the fragrance, also known in the art as "fragrance burst" or "fragrance blooming," and simply referred to as, smell, and (ii) a long-lasting hedonic experience, i.e., a long-lasting fragrance strength and character during the lifespan of the air care freshener product. To meet such customer's expectation, there is an imperative and unresolved need to provide and optimize a liquid freshening composition, to provide a freshening composition which can be released at a controlled and/or customizable rate. The design, geometrical characteristics, and physical parameters of a device delivering such air freshening composition may be taken into consideration. Further, the design of an evaporative assistance device, if such an element is involved, needs to be taken in consideration. In other words, a preferred air care product, such as an air care freshener would comprise a releasing profile of the liquid freshening composition that follows a two stage releasing regime: (i) an initial transitory regime, which is associated with an unusually high amount of liquid freshening composition release, and (ii) a steady-state release regime, which would require a linear release of the air care freshening composition into the external environment until, or very close to its full completion. Such an air care freshener product would operate until its entire liquid freshening composition is released into the external environment with no further human intervention. For example, in a reed diffuser, there should be no need to flip the reeds to achieve the abovementioned hedonic experiences.

Most of the wicking air care fresheners on the current market fail to provide such a release performance. This failure can be attributed mainly due to (i) the lack of an initial transitory regime, which is responsible for the initial fragrance burst, which translates into a fragrance hedonic experience, (ii) the linear release of a freshening composition until its full completion, which is responsible for delivering the need fragrance experience, strength and character, and sometimes (iii) the high amount of residual product left in a reservoir that is not released. Therefore, there is a need in the art to provide an air care freshener satisfying the above-mentioned requirements.

Despite the critical role of the wicking process with respect to the release of the liquid freshening composition, most of the prior art air care products solely address the volatility of the freshening composition with respect to the fragrance delivery performance of an air freshening compositions, which is expressed based on the vapor pressure of the air freshening composition. Hence, it is of no surprise why known air care products are more concerned with (i) the rate of evaporation of a specific freshening composition, e.g., by taking into account the volatility of the fragrance ingredients, and that of solvents and diluents, and (ii) the design of a particular air care freshener device that may enhance the rate of evaporation of an air care freshening composition, such as an electrical external heater or fan.

Wicking air care fresheners known in the art most commonly used as a solvent or diluent glycol ethers and isoparaffins whose vapor pressures are below 0.1 mm Hg. While complying with the requirements imposed by the Environmental Protection Agency (EPA) and The California Air Resources Board (CARB) with respect to atmospheric emission of organic compounds, and more particularly with the restrictions on the emission level of the so-called "volatile organic compounds" (VOC), and displaying good performance to dissolve fragrance ingredients and having acceptable volatility, glycol ethers can impart specific undesired off-notes, which negatively affect the hedonic performance of an air care freshener product. Further, based on the recent ingredient disclosure initiatives (a new norm accepted and embraced by the consumer goods industry to disclose to the customers the names of the ingredients into their products including the fragrance ingredients), glycol ethers are chemicals that become less and less desired, if not undesired, by customers.

Some silicon solvents, which are exempted by the EPA and CARB and not considered being VOC, can also be used in the formulation of a wicking air freshener diffuser. However, due to their fragrance solubility issues and high cost, the use of silicon solvents in air care freshener products is restricted.

The volatility of a freshening composition varies based on the particular compounds of the composition. As the vapor pressure of a freshening composition increases, the rate at which the freshening composition volatilizes, i.e., evaporates, also increases. As a result, the lifespan of an air care product comprising such freshening composition can be dependent upon the particular freshening composition used. In some cases, solvents or diluents are used to slow down the rate of evaporation of a freshening composition. However, adding solvents or diluents to slow down the evaporation rate of a freshening composition may significantly reduce the level of perfume materials in the freshening composition or may even change the character of the freshening composition and its scent characteristics.

Exemplary air freshening devices comprising a water-based fragrance emitter and a means for heating the emitter are described in U.S. Pub. 2018/0064838 A1. The water-based fragrance emitters, e.g., a plurality of water beads, include water, a water-absorbing polymer, and a fragrance composition. The means for heating the emitter, also referred to as warming device, heated water-based fragrance emitter, or fragrance warmer typically include a power supply, a heating element, or a warmer tray (U.S. Pub 2018/0064838 A1). To achieve evaporation of a fragrance composition those devices require structural elements, other than a mere reservoir for the fragrance composition, and elevated temperature.

There is an unfulfilled need for a freshening composition that delivers long-lasting scent. There is an unfulfilled need for a non-water based freshening composition that delivers long-lasting scent. There is an unfulfilled need for a freshening composition that can be evaporated without structural elements, such as a means for heating, to achieve such evaporation. There is an unfulfilled need for a freshening composition that delivers long-lasting scent without heating the freshening composition. There is an unfulfilled need for a freshening composition that delivers long-lasting scent at ambient temperature. There is an unfulfilled need for a freshening composition whose evaporation can be controlled by a chemical compound. There is an unfulfilled need for a freshening composition whose evaporation at ambient temperature can be controlled by a chemical compound. The present invention provides such freshening compositions, air care products and devices comprising same and methods for manufacturing and using same. The present invention also provides methods for modulating the release of a fragrance composition or of a component thereof using a chemical compound, referred to herein as fragrance release modulator.

Further, there is an unfulfilled need for a method to manufacture and to provide an air care freshening wicking product that (i) releases an air freshening composition over a specific period of time without human intervention so that no or very minimal residual amounts of that composition will remain in a reservoir and (ii) provides for a two-stage product releasing regime wherein an initial transitory regime is associated with a high amount of liquid freshening composition release, and wherein a steady-state release regime provides for the linear release of the air care freshening composition into the external environment until, or very close to its full completion. The present invention provides such liquid freshening compositions, air care products and devices comprising same and methods for manufacturing and using same.

Further, there is a long-felt but unmet need in the fragrance industry to control the release of a fragrance or perfume mixture, referred to herein also as freshening composition, or of a component thereof over time. In certain situations, it is desirable to increase, i.e., accelerating or up-regulating the release of a freshening composition or of a component thereof, in others it is more desirable to decrease, i.e., reducing or down-regulating the release of a freshening composition or of a component thereof. The present invention offers an easy and effective solution to that problem and satisfies the long-felt but unmet need.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

BRIEF SUMMARY OF THE INVENTION

The present invention provides a variety of freshening compositions, a variety of air freshener devices comprising (1) a reservoir and (2) a freshening composition as well as a variety of methods for manufacturing a freshening composition and a variety of methods for manufacturing an air freshener device comprising (1) a reservoir and (2) a freshening composition. Disclosed also are methods for modulating the release of a freshening composition or of a component thereof and methods for delivering a smell or a scent of a freshening composition or of a component thereof into or onto an environment.

The present invention provides a variety of freshening compositions. In some embodiments of the present invention, a freshening composition comprises from about 0.1 wt % to about 95 wt % perfume raw material. In some embodiments of the present invention, a freshening composition comprises (i) from about 0.1 wt % to about 95 wt % perfume raw material and (ii) from about 0.01 wt % to about 90 wt % of a fragrance release modulator.

Various perfume raw materials may be used in a freshening composition, in an air freshener device comprising (1) a reservoir and (2) a freshening composition, and in the methods of the present invention. In some embodiments of the present invention, a perfume raw material is selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials.

Fragrance release modulators of the present invention are characterized in several ways. In some embodiments of the present invention, a fragrance release modulator is characterized by having one or more, two or more, or three or more characteristics selected from the group consisting of (a) a flash point of greater than about 100° F., (b) a surface tension of less than about 60 mN/m, (c) a dynamic viscosity from about 0.5 cp to about 100 cp, and (d) a density from about 600 g/l to about 1,300 g/l. Surface tension values can be expressed either as mN/m or as dyne/cm. Dynamic viscosity can be expressed either as cp or as mPa-s. A preferred fragrance release modulator has two or more of the above-listed characteristics.

Various fragrance release modulators may be used in a freshening composition, in an air freshener device comprising (1) a reservoir and (2) a freshening composition, and in a method of the present invention. Fragrance release modulators of the present invention are chemical compounds. Preferred fragrance release modulators are alcohols, aryl compounds, and alkyl compounds. Other chemical compounds may also be used as fragrance release modulators. In some embodiments of the present invention, a fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulators, and a mixture of any of the preceding fragrance release modulators.

In some embodiments of the present invention, the amount of the fragrance release modulator in a freshening composition is sufficient to modulate, i.e., to up-regulate or down-regulate, the release of the freshening composition or of a component thereof, relative to a control not comprising the fragrance release modulator and assigned a value of 100%, by at least 1%.

In some embodiments of the present invention, a freshening composition is adapted to have one or more, two or more, or three or more of a characteristic selected from the group consisting of (a) a flash point higher than about 100° F., (b) a surface tension of about 10 mN/m to about 40 mN/m, (c) a dynamic viscosity from about 1 cp to about 30 cp, and (d) a density from about 650 g/l to about 1,300 g/l. A preferred freshening composition has two or more of the above-listed characteristics. Another preferred freshening composition has three or more of the above-listed characteristics.

In some embodiments of the present invention, a freshening composition comprises (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators. In some embodiments, a freshening composition comprising (i) and (ii) as listed in this paragraph is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. In some embodiments of the present invention, the amount of the fragrance release modulator in the freshening composition is sufficient to modulate the release of the freshening composition or of a component thereof, relative to a control not comprising the fragrance release modulator and being assigned a value of 100%, by at least 1%.

In some embodiments of the present invention, modulation by a fragrance release modulator is up-regulating the release of the freshening composition or of a component thereof. In some embodiments of a freshening composition of the present invention, the freshening composition comprises the fragrance release modulator in an amount sufficient to up-regulate the release of the freshening composition or of a component thereof by at least about 2%, by at least about 3%, by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

In some embodiments of the present invention, modulation by a fragrance release modulator is down-regulating the release of the freshening composition or of a component thereof. In some embodiments of a freshening composition of the present invention, the freshening composition comprises the fragrance release modulator in an amount sufficient to down-regulate the release of the freshening composition or of a component thereof by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

In some embodiments of a freshening composition, of an air freshener device comprising (1) a reservoir and (2) a freshening composition, and of a method of the present invention, a fragrance release modulator is selected from the group consisting of ethanol, n-propanol, iso-propanol, n-butanol, t-butanol, 3-methyl-3-methoxyl butanol, 1-pentanol, 2pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

In some embodiments of a freshening composition, of an air freshener device comprising (1) a reservoir and (2) a freshening composition, and of a method of the present invention, a freshening composition comprises one or more additional ingredients. In some embodiments of a freshening composition of an air freshener device comprising (1) a reservoir and (2) a freshening composition, and of a method of the present invention, a freshening composition further comprises less than about 50 wt % of an ingredient having a functional activity. In some embodiments, the ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a freshening composition, of an air freshener device comprising (1) a reservoir) and (2) a freshening composition and of a method of the present invention, a freshening composition further comprises less than about 50 wt % of an ingredient having a functional activity. In some embodiments of the present invention, the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

It is understood and one of ordinary skill in the art will appreciate that, if not clearly contradicted by the content of this specification, each embodiment of a freshening composition and/or features/elements disclosed as part of that embodiment can be combined with any of the embodiments hereinabove or hereinbelow.

The present invention provides a variety of air freshener devices comprising (1) a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or lid, and (2) a freshening composition. The freshening composition typically houses in the reservoir.

In some embodiments of the present invention, an air freshener device comprises (1) a reservoir and (2) a freshening composition as described herein. An exemplary non-limiting air freshener device of the present invention comprises (1) a reservoir and (2) a freshening composition comprising (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators. In some embodiments of an air freshener device or of a method for manufacturing an air freshener device comprising (1) a reservoir and (2) a freshening composition, the freshening composition comprises (i) and (ii) as listed in this paragraph and is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

In some embodiments of an air fresher device of the present invention, the amount of the fragrance release modulator in the freshening composition is sufficient to modulate the release of the freshening composition or of a component thereof, relative to a control not comprising the fragrance release modulator and being assigned a value of 100%, by at least 1%.

In some embodiments of an air freshener device comprising (1) a reservoir and (2) a freshening composition and in a method for manufacturing an air freshener device comprising (1) a reservoir and (2) a freshening composition, the air freshener comprises a freshening composition comprising an ingredient having a functional activity in an amount of less than about 50 wt %, in an amount of less than about 40 wt %, in an amount of less than about 30 wt %, in an amount of less than about 20%, in an amount of less than about 10 wt %, or in an amount of less than about 5 wt %. In some embodiments, the ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity. In some embodiments of the present invention, the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of an air freshener device comprising (1) a reservoir and (2) a freshening composition, in a method for manufacturing an air freshener device comprising (1) a reservoir and (2) a freshening composition, or in another method of the present invention, a variety of reservoirs may be used. In some embodiments of an air freshener device comprising (1) a reservoir and (2) a freshening composition, in a method for manufacturing an air freshener device comprising (1) a reservoir and (2) a freshening composition, or in another method of the present invention, the air freshener device comprises a reservoir selected from the group consisting of a bottle, a bowl, a tray, a plate, a glass, a shell, a box, a sphere, a globe, a vessel, and a container.

In some embodiments of an air freshener device comprising (1) a reservoir and (2) a freshening composition, in a method for manufacturing an air freshener device comprising (1) a reservoir and (2) a freshening composition, or in another method of the present invention, the air freshener device comprises and one or more additional components. A variety of additional components may be used.

In some embodiments of an air freshener device comprising (1) a reservoir and (2) a freshening composition, in a method for manufacturing an air freshener device comprising (1) a reservoir and (2) a freshening composition, or in another method of the present invention, the air freshener device further comprises a delivery system comprising an element in communication or in contact with the freshening composition. The delivery system may be attached to the reservoir. A variety of delivery systems may be used. In some embodiments of an air freshener device comprising (1) a reservoir and (2) a freshening composition, in a method for manufacturing an air freshener device comprising (1) a reservoir and (2) a freshening composition, or in another method of the present invention, the air freshener device comprises a delivery system selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

In some embodiments of an air freshener device comprising (1) a reservoir and (2) a freshening composition, in a method for manufacturing an air freshener device comprising (1) a reservoir and (2) a freshening composition, or in another method of the present invention, the air freshener device further comprises an evaporative assistance element. The evaporative assistance element may be attached to the reservoir. A variety of evaporative assistance elements may be used. In some embodiments of an air freshener device comprising (1) a reservoir and (2) a freshening composition, in a method for manufacturing an air freshener device comprising (1) a reservoir and (2) a freshening composition, or in another method of the present invention, the air freshener device comprises an evaporative assistance element selected from the group consisting of a heater, a fan, an agitator, and a combination of any preceding evaporative assistance elements.

The present invention provides a variety of air freshener devices and methods for manufacturing an air freshener device and/or methods for using an air freshener device. In some embodiments of the present invention an air freshener device is selected from the group consisting of a reed diffuser air freshener, an energized air freshener device, an air freshener device comprising a wick, a passive diffuser air fresher device, and a spraying air freshener device.

It is understood and one of ordinary skill in the art will appreciate that, if not clearly contradicted by the content of this specification, each embodiment of an air freshener device comprising (1) a reservoir and (2) a freshening composition and/or features/elements disclosed as part of that embodiment can be combined with any of the embodiments hereinabove or hereinbelow.

The present invention provides a variety of methods for manufacturing a freshening composition. In some embodiments of the present invention, a method for manufacturing a freshening composition comprises the step of combining (i) from about 0.1 wt % to about 95 wt % perfume raw material and (ii) from about 0.01 wt % to about 90 wt % fragrance release modulator. In some embodiments of the present invention, a method for manufacturing a freshening composition comprises the step of combining (i) from about 0.1 wt % to about 95 wt % perfume raw material, (ii) from about 0.01 wt % to about 90 wt % fragrance release modulator, and (iii) less than about 50 wt % of an ingredient having a functional activity. Ingredients (i), (ii), and (iii) are different from each other and may be any as described herein.

An exemplary and non-limiting method for manufacturing a freshening composition comprises the step of combining (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators. In some embodiments of method for manufacturing a freshening composition, the method comprises the steps of combining (i) and (ii) as listed in this paragraph and adapting the freshening composition to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. The fragrance release modulator is combined with the perfume raw material in an amount sufficient to modulate the release of the resulting freshening composition or of a component thereof, relative to a control not comprising the fragrance release modulator and being assigned a value of 100%, by at least 1%.

It is understood and one of ordinary skill in the art will appreciate that, if not clearly contradicted by the content of this specification, each embodiment of a method for manufacturing a freshening composition and/or features/elements disclosed as part of that embodiment can be combined with any of the embodiments hereinabove or hereinbelow.

The present invention provides a variety of methods for manufacturing an air freshener device comprising (1) a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid, and (2) a freshening composition.

In some embodiments of a method for manufacturing an air freshener device comprising (1) a reservoir and (2) a freshening composition, the method comprises the step of providing a reservoir having a functionality selected from the group consisting of accepting a freshening composition, receiving a freshening composition, holding a freshening composition, housing a freshening composition, storing a freshening composition, accepting a delivery system, accepting an evaporative assistance element, and receiving a seal or a lid.

In some embodiments of a method for manufacturing an air freshener device comprising (1) a reservoir and (2) a freshening composition, the method comprises the step of contacting the reservoir with a freshening composition. In some embodiments of a method for manufacturing an air freshener device comprising (1) a reservoir and (2) a freshening composition, the method comprises the step of contacting the reservoir with a freshening composition comprising (i) from about 0.1 wt % to about 95 wt % perfume raw material and (ii) from about 0.01 wt % to about 90 wt % fragrance release modulator. Ingredients (i) and (ii) are different from each other and may be any as described herein.

In some embodiments of a method for manufacturing an air freshener device comprising (1) a reservoir and (2) a freshening composition, the method comprises the step of contacting a reservoir with a freshening composition comprising (i) from about 0.1 wt % to about 95 wt % perfume raw material, (ii) from about 0.01 wt % to about 90 wt % fragrance release modulator, and (iii) less than about 50 wt % of an ingredient having a functional activity. Ingredients (i), (ii), and (iii) are different from each other and may be any as described herein.

An exemplary and non-limiting method for manufacturing an air freshener device comprising (1) a reservoir and (2) a freshening composition, comprises the step of contacting a reservoir with a freshening composition comprising (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators.

In some embodiments of a method for manufacturing an air freshener device comprising (1) a reservoir and (2) a freshening composition, the method comprises the step of transferring a freshening composition comprising (i) a perfume raw material and (ii) a fragrance release modulator into the reservoir.

In some embodiments of a method for manufacturing an air freshener device comprising (1) a reservoir and (2) a freshening composition, the method comprises the step of housing a freshening composition comprising (i) a perfume raw material and (ii) a fragrance release modulator in the reservoir.

In some embodiments of a method for manufacturing an air freshener device comprising (1) a reservoir and (2) a freshening composition, the method comprises the step of attaching a reservoir housing a freshening composition to an article having a functionality of receiving a reservoir thereby producing an air freshener device comprising (1) a reservoir and (2) a freshening composition.

In some embodiments of a method for manufacturing an air freshener device comprising (1) a reservoir and (2) a freshening composition, the method comprises the step of attaching a delivery system to the reservoir.

In some embodiments of a method for manufacturing an air freshener device comprising (1) a reservoir and (2) a freshening composition the delivery device comprises an element in communication or in contact with the freshening composition.

In some embodiments of a method for manufacturing an air freshener device comprising (1) a reservoir and (2) a freshening composition, the method comprises the step of attaching an evaporative assistant element to the reservoir.

In some embodiments of a method for manufacturing an air freshener device comprising (1) a reservoir and (2) a freshening composition, the method comprises the step of sealing the reservoir with a seal or a lid.

It is understood and one of ordinary skill in the art will appreciate that, if not clearly contradicted by the content of this specification, each embodiment of a method for manufacturing an air freshener device comprising a freshening composition and/or features/elements disclosed as part of that embodiment can be combined with any of the embodiments hereinabove or hereinbelow.

The present invention provides a variety of methods for modulating the release of a freshening composition or of a component thereof. In some embodiments of the present invention, a method for modulating the release of a freshening composition or of a component thereof comprises the step of combining (i) from about 0.1 wt % to about 95 wt % perfume raw material and (ii) from about 0.01 wt % to about 90 wt % fragrance release modulator. Thereby the release of the freshening composition or of the component thereof is modulated.

An exemplary and non-limiting method for modulating the release of a freshening composition or of a component thereof comprises the step of combining (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators. In some embodiments of a method for modulating the release of a freshening composition or of a component thereof, the method comprises the steps of combining (i) and (ii) as listed in this paragraph. The freshening composition is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. The fragrance release modulator is combined with the perfume raw material in an amount sufficient to modulate the release of the resulting freshening composition or of a component thereof, relative to a control not comprising the fragrance release modulator and being assigned a value of 100%, by at least 1%.

In some embodiments of a method for modulating the release of a freshening composition or of a component thereof, modulation by a fragrance release modulator is upregulating the release of the freshening composition or of a component thereof. In some embodiments of a method for modulating the release of a freshening composition or of a component thereof, the freshening composition comprises the fragrance release modulator in an amount sufficient to up-regulate the release of the freshening composition or of a component thereof by at least about 2%, by at least about 3%, by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

In some embodiments of a method for modulating the release of a freshening composition or of a component thereof, modulation by a fragrance release modulator is downregulating the release of the freshening composition or of a component thereof. In some embodiments of a method for modulating the release of a freshening composition or of a component thereof, the freshening composition comprises the fragrance release modulator in an amount sufficient to down-regulate the release of the freshening composition or of a component thereof by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

It is understood and one of ordinary skill in the art will appreciate that, if not clearly contradicted by the content of this specification, each embodiment of a method for modulating the release of a freshening composition or of a component thereof and/or features/elements disclosed as part of that embodiment can be combined with any of the embodiments hereinabove or hereinbelow.

The present invention provides a variety of methods for delivering a smell or scent of a freshening composition or of a component thereof into or onto an environment. In some embodiments of the present invention, a method for delivering a smell or scent of a freshening composition or of a component thereof into or onto an environment comprises the step of placing an air freshener device into or onto an environment, wherein the air freshener device comprises a freshening composition comprising (i) from about 0.1 wt % to about 95 wt % perfume raw material and (ii) from about 0.01 wt % to about 90 wt % fragrance release modulator.

An exemplary and non-limiting method for delivering a smell or scent of a freshening composition or of a component thereof into or onto an environment comprises the step of placing an air freshener device into or onto an environment, wherein the air freshener device comprises a freshening composition comprising (i) from about 0.1 wt % to about 95 wt % perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l and wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators. In some embodiments of a method for delivering a smell or scent of a freshening composition or of a component thereof into or onto an environment, the freshening composition is adapted to have one or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. The freshening composition comprises the fragrance release modulator in an amount sufficient to modulate the release of the resulting freshening composition or of a component thereof, relative to a control not comprising the fragrance release modulator and being assigned a value of 100%, by at least 1%.

In some embodiments of the present invention, a method for delivering a smell or scent of a freshening composition or of a component thereof into or onto an environment comprises the step of dispersing the freshening composition or the component thereof into the atmosphere, air or onto the surface.

In some embodiments of the method for delivering a smell or scent of a freshening composition or of a component thereof into or onto an environment, the step of dispersing the freshening composition or the component thereof into the atmosphere, air or onto the surface is over a controlled or customized period of time.

In some embodiments of the method for delivering a smell or scent of a freshening composition or of a component thereof into or onto an environment, the step of dispersing the freshening composition or the component thereof into the atmosphere, air or onto the surface comprises wicking the freshening composition or the component thereof.

In some embodiments of the method for delivering a smell or scent of a freshening composition or of a component thereof into or onto an environment, the step of dispersing the freshening composition or the component thereof into the atmosphere, air or onto the surface comprises evaporating the freshening composition or the component thereof.

In some embodiments of the method for delivering a smell or scent of a freshening composition or of a component thereof into or onto an environment, the step of dispersing the freshening composition or the component thereof into the atmosphere, air or onto the surface comprises a wicking-evaporation system adapted to deliver the freshening composition or the component thereof into the atmosphere, air or onto a surface. A variety of wicking-evaporations systems may be used. In some embodiments of a method for delivering a smell or scent of a freshening composition or of a component thereof into or onto an environment, a wicking-evaporation system comprises an element selected from the group consisting of a natural wick, a plurality of natural wicks, a synthetic wick, a plurality of synthetic wicks, a stick, a plurality of sticks, a reed, a plurality of reeds, a stick, a plurality sticks, a fiber, a plurality of fibers, a mesh, a conductive mesh, a membrane, a porous substrate, a semi-porous substrate, and a combination of any of the preceding elements.

In some embodiments of the method for delivering a smell or scent of a freshening composition or of a component thereof into or onto an environment, the step of dispersing the freshening composition or the component thereof into the atmosphere, air or onto the surface comprises an evaporative assistance element. A variety of evaporative assistance elements may be used. In some embodiments of a method for delivering a smell or scent of a freshening composition or of a component thereof into or onto an environment, an evaporative assistance element is selected from the group consisting of a heater, a fan, an agitator, and a combination of any of the preceding evaporative assistance elements.

In some embodiments of the method for delivering a smell or scent of a freshening composition or of a component thereof into or onto an environment, the step of dispersing the freshening composition or the component thereof into the atmosphere, air or onto the surface comprises exposing the freshening composition or component thereof into the atmosphere, the air, or onto the surface.

In some embodiments of the method for delivering a smell or scent of a freshening composition or of a component thereof into or onto an environment, the step of dispersing the freshening composition or the component thereof into the atmosphere, air or onto the surface comprises spraying the freshening composition or the component thereof into the atmosphere, the air, or onto the surface.

It is understood and one of ordinary skill in the art will appreciate that, if not clearly contradicted by the content of this specification, each embodiment of a method for delivering a smell or scent of a freshening composition or of a component thereof into or onto an environment and/or features/elements disclosed as part of that embodiment can be combined with any of the embodiments hereinabove or hereinbelow.

DETAILED DESCRIPTION OF THE INVENTION

I. Definitions

Figure 1:
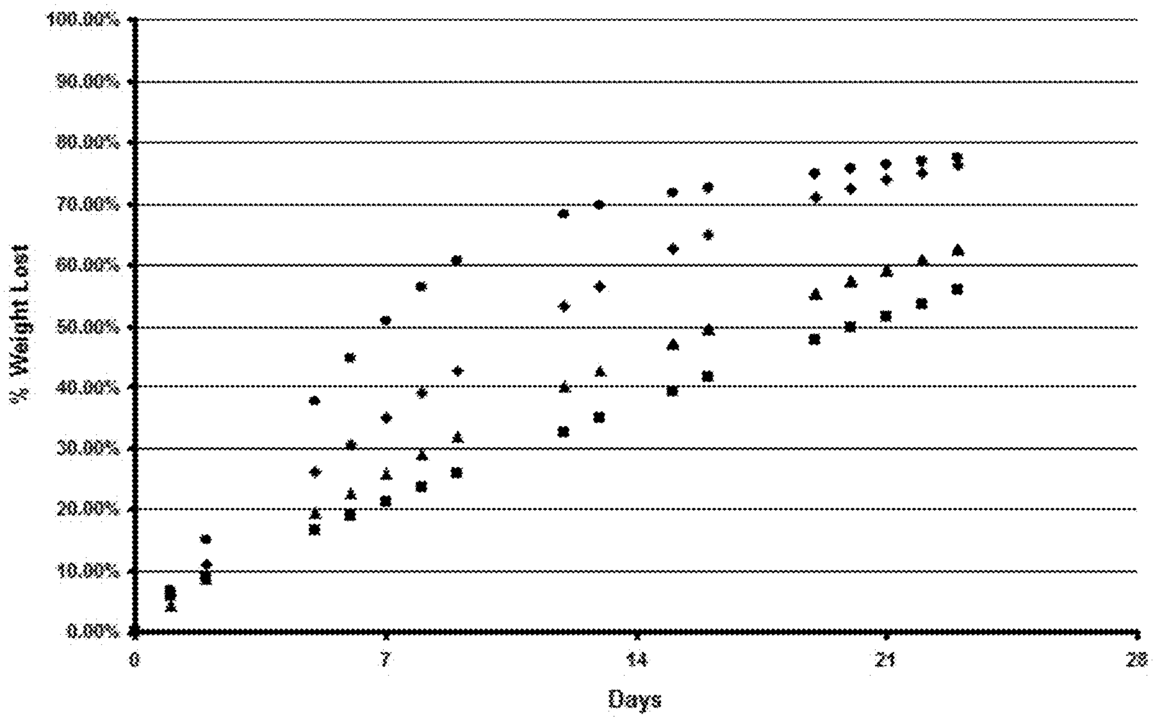
FIG. 1 schematically depicts the influence of different solvents on the release and evaporation of a freshening composition comprising 50 wt % Apple Fragrance (see, Table 9) and 50 wt % solvents as indicated and measured as % weight lost during the time period indicated. The weight percentage refers to the weight percentage of the entire product formulation, i.e., freshening composition. The following solvents were tested: ■, acetone monoglycerol ketal (Augeo Clean Multi® from Solvay); ♦, 3-methyl-1,3-butanediol-acetate (IPD-AC® from Kuraray); ▲ STA-SOL® ESS 165 (dimethyl adipate (DMA) from ST Laboratories Inc.); ●, silicon solvent (VOLASIL® DM-2 from CHEMSIL Silicones, Inc.). Details are described in Example C.

Throughout the present specification and the accompanying claims, the words "comprise," "include," and "have" and variations thereof such as "comprises," "comprising," "includes," "including," "has," and "having" are to be interpreted inclusively. That is, these words are intended to convey the possible inclusion of other elements or integers not specifically recited, where the context allows. The term "consisting essentially of" means that the composition, method, or structure may include additional ingredients, steps and/or parts, but only if the additional ingredients, steps and/or parts do not materially alter the basic and novel characteristics of the claimed composition, method, or structure. As used herein, the term "consisting of" is intended to mean including and limited to whatever follows the phrase "consisting of". Thus, the phrase "consisting of" indicates that the listed elements are required or mandatory and that no other elements may be present. No language in the specification should be construed as indicating any non-claimed element essential to the practice of the invention. It is understood, if not clearly contradicted by the context, that each claim claiming an embodiment of the present invention, may be crafted and presented using either (i) the transitional phrase "comprising of" or a grammatical equivalent thereof, (ii) the transitional phrase "consisting essentially of" or a grammatical equivalent thereof, or (iii) the transitional phrase "consisting of" or a grammatical equivalent thereof.

The terms "a" and "an" and "the" and similar referents used in the context of describing the invention (especially in the context of the following claims) are to be construed to cover both the singular and the plural, unless otherwise indicated herein or clearly contradicted by context.

The term "and/or" where used herein is to be taken as specific disclosure of each of the two specified features or components with or without the other. For example, "A and/or B" is to be taken as specific disclosure of each of (i) A, (ii) B, and (iii) A and B, just as if each is set out individually herein.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, an embodiment includes values from the one particular value to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. With respect to endpoints of ranges, it is understood that when a range is given herein, it discloses alternative ranges, without specifically reciting them, i.e., (a) an "of/from-to" range in which the endpoints are included in the range and (b) an "between-and" range, in which the endpoints are excluded from the range. For example, a disclosure of a freshening composition comprising about 0.1 wt % to about 95 wt % perfume raw material includes (a) a composition comprising the perfume raw material from about 0.1 wt % to about 95 wt %, in which the endpoints 0.1 wt % and 95 wt % are included, and (b) a composition comprising the perfume raw material between about 0.1 wt % and about 95 wt %, in which the endpoints 0.1 wt % and 95 wt % are excluded. Thus, every range defined herein in the format "from/of-to" is to be understood as also disclosing a separate and discrete range defined as "between-and." Likewise, every range defined herein in the format "between-and" is to be understood as also disclosing a separate and discrete range defined as "from/of-to". It is also understood that there are a number of values disclosed herein, and that each value is also herein disclosed as "about" that particular value in addition to the value itself. For example, if the value "10" is disclosed, then "about 10" is also disclosed. Further, the term "about" applies to both cited endpoints of a range, even when it is written only before the lower endpoint. For example, "about X to Y" should be interpreted as "about X to about Y" It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

In the following description it is to be understood that terms such as "forward," "rearward," "front," "back," "right," "left," "upward," "downward," "horizontal," "vertical," "longitudinal," "lateral," "angular," "first," "second" and the like are words of convenience and are not to be construed as limiting terms.

Certain limitations of claim elements are disclosed as Markush groups. It is understood that with the disclosure of a Markush group comprising X members (wherein X is any number), a Markush group missing one or more members, i.e., a Markush group comprising X-1 members, or X-2 members, etc. is disclosed as well. For an illustrative example, where the disclosure provides "a compound is selected from the group consisting of compound A, compound B, compound C, compound D, compound E, compound F, and compound G," the disclosure inherently discloses: "a compound selected from the group consisting of compound B, compound C, compound D, compound E, compound F, and compound G," or "a compound selected from the group consisting of compound C, compound D, compound E, compound F, and compound G," etc.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g., "such as") provided herein is intended merely to better illuminate the invention and does not pose a limitation on the scope of the invention otherwise claimed.

Units, prefixes, and symbols are denoted in their Systeme International de Unites (SI) accepted form. The abbreviations used herein have their conventional meaning within the mechanical, chemical, and biological arts.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: The Cambridge Dictionary of Science and Technology (Walker ed., 1988); *Common fragrance and flavor materials*: Surburg, H. and Panten, *J., Preparation, properties and uses* ($6^{th}$ ed., Wiley-VCH, (2016), ISBN: 978-3-527-33160-4), a standard industry reference on major fragrance and flavor ingredients, including both natural and synthetic materials; Turin, L. and Sanchez, T., Perfumes: The Guide, (Perfumista Publishing, 2028, ISBN: 978-0-99884501-2). Obvious typos of a word or term in this application are to be construed as the word or term as included therein or in a standard dictionary. As used herein, the following terms have the meanings ascribed to them unless specified otherwise.

As used herein, the terms "about" or "approximately" refer to a range of values of plus or minus 20%, preferably, plus or minus 10%, more preferably, plus or minus 5% of a specified value, and more preferably, plus or minus 4% of a specified value, plus or minus 3% of a specified value, plus or minus 2% of a specified value, plus or minus 1% of a specified value, and/or plus or minus 0% of a specified value. For example, the phrase "about 200" includes plus or minus 20% of 200, or from 160 to 240, preferably, plus or minus 10% of 200, or from 180 to 220, more preferably, plus or minus 5% of 200, or from 190 to 210. It includes, also the specified value or concrete number, e.g., "about 200" includes 200.

Unless otherwise indicated herein or otherwise clearly contradicted by context, a step of "adding" or "combining" a first compound to or with second compound is synonymous with "adding" or "combining" the second compound to or with the first compound. Likewise, if three or more compounds are added to each other or are combined, the order of adding or combining is not critical.

The terms "agent," "compound," and "ingredient," unless clearly contradicted by context, are used interchangeably herein. As used herein, an "agent" can be any chemical compound, for example, a macromolecule or a small molecule. An agent can have a formula weight of less than about 100,000 grams per mole, less than 50,000 grams per mole, less than 10,000 grams per mole, less than 5,000 grams per mole, less than 1,000 grams per mole, or less than about 500 grams per mole. An agent can be naturally occurring (e.g., an herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. An agent can be the only substance assayed by a method described herein. Alternatively, a collection of agents can be assayed either consecutively or concurrently by methods described herein.

As used herein, the term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, e.g., groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, e.g., vinyl, 2-propenyl, crotyl, 2-isopentenyl, 2-(butadienyl), 2,4-pentadienyl, 3-(1,4pentadienyl), ethynyl, 1-and 3-propynyl, 3-butynyl, and the higher homologs and isomers.

As used herein, the terms "air care product" or "air freshener device" refer to a product or device suitable for treating or fragrancing an environment, including but not limited to air or a surface. It includes, but is not limited to, a spray, an energized (e.g., electrically powered) air freshening delivery system, (e.g., an electrical wall plug-in or a fan-based diffuser), a liquid electric pluggable air freshener, an electromechanical actuating diffuser, a passive diffuser (e.g., not electrically powered) including, but not limited to a wicking air freshener, such as a reed diffuser, a steam-based freshener, or a membrane-based air freshener, such as a car vent air freshener.

As used herein, the terms "alter," "alteration," "altering," "modulate," modulation," "modulating," and grammatical equivalents thereof are art-recognized and refer to up-regulation (i.e., activation, stimulation, increase), or down-regulation (i.e., inhibition, suppression, reduction, or decrease) of a response, or the two in combination or apart.

As used herein, the term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. The term "aryl" when used in combination with other terms (e.g., aryl-ether, aryl-glycol, aryl-carbonate, aryl-adipate, aryl-benzoate, aryl-citrate, aryl-laureate, aryl-palmitate, aryl-stearate, aryl-myristate, aryl-succinate, aryl-glutarate, aryl-oxy, aryl-thioxy, arylalkyl, and the like) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

As used herein, the terms "connect", "connect to," connected to," "attach", "attach to" or "attached to" or grammatical equivalents thereof mean to fasten on, to fasten together, to affix to, to mount to, mount on, to connect to, to join, to position onto, to position into, to place onto, or to place into. "Attachment" means the act of attaching or the condition of being attached. Attachment can be direct or indirectly. For example, a part A may be attached directly to part B. Alternatively, part A may be attached indirectly to part B through first attaching part A to part C and then attaching part C to part B. More than one intermediary part may be used to attach part A to part B. Attaching can be permanent, temporarily, or for a prolonged time. For example, an air care product or device of the present invention may be attached to a structure, an object, an outlet, etc. temporarily for the time necessary to perform a method of the invention. Alternatively, an air care product or device of the present invention may be attached to a structure, an object, an outlet for a prolonged time, e.g., also when a method of the present invention is not performed.

As used herein, the terms "contacting," "to contact," "contacted to," "contacted with," or grammatical equivalents thereof are used interchangeably with the following: combining with, adding to, mixing with, passing over, incubating with, flowing over, etc. The term "contacting" also includes reference to placement of one substance, e.g., a freshening composition or a component of a freshening composition, as described herein, in direct physical contact or association with another component, such as a reservoir, or with another substance, such as an environment, the atmosphere, air or a surface.

As used herein, the terms "customize," "customization," or grammatical equivalents refer to a process of modifying or adapting something to meet specific, desired, chosen, or predetermined requirements, preferences, or conditions. Typically, a customer or user sets the specific, desired, chosen, or predetermined requirements, preferences, or conditions.

As used herein, the term "different" means not the same, not the same identity.

As used herein, the terms "effective amount," "effective dose," "sufficient amount," "amount effective to," "amount sufficient to" or grammatical equivalents thereof mean a dosage or an amount sufficient to produce a desired result, whether permanent or temporary, lasting or transit that can be associated with the administration of a composition of the present invention. For example, certain freshening compositions of the present invention comprise a fragrance release modulator (FRM) in an amount sufficient to control or to modulate the release of the freshening composition or of a component thereof. In that example, the desired result is the controlled or modulated release of the freshening composition or of a component thereof, a result, which is attributed to the amount of FRM, expressed, e.g., as wt %, added to the freshening composition. An "effective amount," an "effective dose," a "sufficient amount," an "amount effective to" or an "amount sufficient to" in the context of embodiments of the present invention can be determined by one of ordinary skill in the art using the disclosure of the present application, in particular, the Examples.

As used herein, the term "emanating surface" refers to any surface that acts as a point of origin from which something is released or emitted outwardly. It refers to a material interface that, when contacted, e.g., with a freshening composition of the present invention, releases or emits atoms, molecules, ions, energy, or a smell into its surroundings. That can be achieved, e.g., by desorption (molecules leaving the surface), diffusion (atoms, molecules migrating from the bulk of a composition to the surface and out), or by chemical reaction producing gaseous or soluble products at the surface.

As used herein, the term “environment” refers to surroundings or conditions a living organism (a person, an animal, or a plant) or a non-living component finds itself in or occupies. An environment includes a terrestrial environment (e.g., land, soil), an aquatic environment (e.g., marine, ocean, seas, rivers), and atmospheric environment (e.g., air) and any other spatial environment (e.g., a building, a house, a room, etc.). As used herein, an environment includes, but is not limited to, a surface of any material, item, or object, e.g., a surface of a fabric, a surface of a linen, a surface of a wood, a surface of a stone, a surface of a building, a surface of a house, a surface of a room, a surface of a piece of furniture, a surface of any, material, item, or object that may be in a building, house or room.

As used herein, the term “fragrance release modulator,” abbreviated “FRM,” refers to a compound having the capability of modulating the release or evaporation of a freshening composition or a component thereof, when said fragrance release modulator is added to or combined with a perfume raw material as described herein. Release or evaporation of a freshening composition or of a component thereof can be tested as described herein.

As used herein, the term “freshening composition” refers to a composition that comprises one or more perfume raw materials and which may be used to treat, fragrance, and/or fresh an environment, the atmosphere, the air or a surface. A freshening composition may be used with or without an air care product, referred to herein from time to time as an air freshener device. A freshening composition can be in a liquid form.

As used herein, the terms “greater than” or “more than” include the concrete number. For example, greater than 100 or more than 100 mean greater than or equal to 100 or more than or equal to 100. As used herein, the terms “smaller than,” “fewer than.” or “less than” include the concrete number. For example, smaller than 100, fewer than 100, or less than 100 mean smaller than or equal to 100, fewer than or equal to 100, or less than or equal to 100. The term “less than” any specific number also includes “0.” For example, a freshening composition comprising “less than 50 wt %” of an ingredient includes a freshening composition not including that ingredient.

As used herein, the terms “ingredient having antimicrobial activity” or “antimicrobial ingredient” refer to a compound having the capability of eliminating, reducing, or minimizing the presence, occurrence, or growth of microorganisms, such as bacteria, yeasts. or molds.

As used herein, the term “ingredient having malodor counteracting activity” refers to a compound having the capability of eliminating, reducing, or minimizing a malodor.

As used herein, the term “isomer” refers to compounds that have the same molecular formula but differ in the nature or sequence of bonding of their atoms or the arrangement of their atoms in space. Isomers that differ in the arrangement of their atoms in space are termed “stereoisomers.” “Stereoisomer” and “stereoisomers” refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed “diastereomers” and those that are non-superimposable mirror images of each other are termed “enantiomers.” When a compound has an asymmetric center, for example, it is bonded to four different groups, a pair of enantiomers is possible. An enantiomer can be characterized by the absolute configuration of its asymmetric center and is described by the R-and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof Δ mixture containing equal proportions of the enantiomers is called a “racemic mixture”. Unless otherwise indicated, the description of compounds herein is intended to include individual stereoisomers as well as mixtures. The methods for the determination of stereochemistry and the separation of stereoisomers are well known in the art (see, discussion in Chapter 4 of ADVANCED ORGANIC CHEMISTRY, 4th edition J. March, John Wiley and Sons, New York, 1992) differ in the chirality of one or more stereocenters.

The terms “modulate,” “modulation,” or “modulating” are art-recognized and refer to up-regulation (i.e., activation, stimulation, increase, facilitation, enhancement), or down regulation (i.e., inhibition, suppression, reduction, or decrease) of a response, or the two in combination or apart. Thus, as used herein, the term modulate encompasses up-regulation (i.e., activation, stimulation, increase, facilitation, enhancement), or down regulation (i.e., inhibition, suppression, reduction, or decrease) of a response. In some embodiments, of particular interest are compounds, referred to herein as fragrance release modulator, which have the capability to modulate the release or evaporation of a freshening composition. In some embodiments of the present invention, a fragrance release modulator of the present invention up-regulates the release or evaporation of a freshening composition, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more. In some embodiments of the present invention, a fragrance release modulator of the present invention down-regulates the release or evaporation of a freshening composition, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, by at least about 95% or more.

As used herein, the term “natural origin fragrance compound” refers to a compound isolated or purified from a natural origin and wherein said isolated or purified compound retains the smell, scent, or hedonic benefit one of ordinary skill in the art would associate with said natural origin. As a non-limiting example, a compound isolated from a grapefruit will be referred to herein as a natural origin fragrance if that compound retains a smell, scent, or hedonic benefit one of ordinary skill in the art would associate with a grapefruit.

As used herein, the terms "non-water-based freshening composition" and "non-water-based air freshening composition," used interchangeably herein, refer to a freshening composition, wherein none of the ingredients (a perfume raw material, a solvent or diluent, a fragrance release modulator, an ingredient having a functional activity), is water. In some embodiments of the present invention, the terms "non-water-based freshening composition" and "non-water-based air freshening composition," also refer to a freshening composition not comprising water.

As used herein, "optional" or "optionally" means that the subsequently described event, component, element, feature, or circumstance may or may not occur or may or may not be present, and that the description includes instances where said event, component, element, feature or circumstance occurs and/or is present and instances where said event, component, element, feature, or circumstance does not occur and/or is not present. As a non-limiting example, a composition A may optionally comprise compound B. In that example, the invention provides (i) a composition A comprising compound B and (ii) a composition not comprising compound B.

As used herein, the term "porous" means a material having minute spaces, pores or holes through which a liquid or gas may pass. A "non-porous" material means the material does not have minute spaces, pores, or holes, so that liquids or gases may not pass. A "semiporous" material means that the material is partially porous and has smaller spaces, pores, and holes than a porous material, so that only small molecules can pass through.

As used herein, the terms "release profile," "releasing profile," or grammatical equivalents thereof in the context of a chemical composition refer to a pattern or rate at which the chemical composition or a component thereof is released from a material, formulation, or system over time. A releasing profile also is a description of how much of a chemical composition or component thereof (e.g., a freshening composition of the present invention, a drug formulation, a coating, or material) is released from the chemical composition as a function of time, environment, or other condition. When a chemical composition releases a component thereof it typically does not happen all at once. A releasing profile shows how fast and how steadily a release occurs. That can be expressed as a graph (e.g., see, Examples and Figures herein), a function (describing release kinetics (e.g., zero-order, first-order, diffusion-controlled)), or as a percentage or cumulative value showing how much of the total substance has been released over time (e.g., see, Examples and Figures herein).

As used herein, the term "scent" refers to a distinctive smell and is often used to refer to a pleasant or characteristic odor produced by natural or synthetic substances, e.g., freshening compositions of then present invention. "To scent" means to impart a fragrance to something, or to detect a smell. While smell is meant to be neutral (good or bad), a scent usually implies a pleasant or intentional fragrance.

As used herein, the terms "smell" or "olfaction" refer to a sensation or perception resulting from the detection of a volatile chemical substance or molecule by the olfactory system in the nose. "To smell" means to perceive or detect an odor through the nose or for something to emit an odor.

As used herein, the terms "solvent" and "diluent" are art-recognized and are used interchangeably. They refer to any substance, usually a liquid, which is capable of dissolving one or several other substances, thus creating a solution.

As used herein, the term "synthetic" in the context of an agent, a compound, an ingredient, or a substance means that the agent, the compound, the ingredient, or the substance is made by chemical synthesis, i.e., is made artificially by chemical reaction(s). An agent, a compound, an ingredient, or a substance made by chemical synthesis means that after its synthesis the agent, the compound, the ingredient, or the substance imitates a corresponding natural product, e.g., has the same structure.

As used herein, the terms "treating air or a surface" or "fragrancing air or a surface" refer to a process resulting in delivering an air freshening composition or a component thereof into the air or bringing an air freshening composition or a component thereof into contact with a surface and producing a desired result. In some embodiments of the present invention, such desired result is eliminating, reducing, or minimizing a malodor.

Where appropriate and not contradicted by the disclosure herein, embodiments and elements/features within individual embodiments may be freely combined with those of other embodiments. As a non-limiting example, a preferred viscosity disclosed within the context of a composition itself will also be disclosed within the context of an air care product or device comprising that composition, without specifically reciting again such preferred viscosity in the context of such air care product or device. Thus, unless defined otherwise, and where consistent with the teaching herein, any feature within any embodiment of the invention may be combined with any feature within any other embodiment of the invention, and the skilled person understands and appreciates such combination as being encompassed in the original disclosure of the present application. This applies in particular to embodiments relating to freshening compositions per se, in respect to other embodiments relating to air freshener devices comprising a freshening composition, methods for manufacturing freshening compositions, methods for manufacturing air freshener devices comprising a freshening composition, methods of using a freshening composition, and/or methods for using an air freshener device comprising a freshening composition, including any interrelationship of such embodiments. This also applies in particular to embodiments relating to the various ingredients in a freshening composition, for example, the choice of perfume raw material or materials as well as its/their amount/s and physical characteristic/s, the choice of functional ingredient or ingredients as well as its/their amount/s and physical characteristic/s, the choice of fragrance release modulator or modulators and its/their amount/s and physical characteristic/s, and/or the choice of solvent, diluent, and solubilizer or solvents, diluents, and solubilizers and its/their amount/s and physical characteristic/s.

Obvious typos of a word, term, and/or phrase are to be construed as the correct writing of that word, term, and/or phrase as shown in a standard dictionary in the respective art and/or as known in the art.

II. Freshening Compositions

The present invention provides freshening compositions. It is understood and one of ordinary skill in the art will appreciate that, if not clearly contradicted by the content of this specification, each embodiment of a freshening composition and/or features/elements disclosed as part of that embodiment can be combined with any of the embodiments hereinabove or hereinbelow. In some embodiments of the present invention, a freshening composition is an air freshening composition. As described herein, an air freshening composition may be used, e.g., to freshen the atmosphere, the air, or a surface, to fragrance the atmosphere, the air or fragrance a surface, or to deliver a scent of the freshening composition or of a component thereof into or onto an environment.

In some embodiments of the present invention, a freshening composition is a liquid freshening composition. As will be understood by one of skilled in the art, a liquid freshening composition consists primarily of a liquid composition and is substantially devoid of solid components.

In some embodiments of the present invention, a freshening composition is a clear freshening composition. As will be understood by one of skilled in the art, a clear freshening composition is a transparent, see-through, or translucent composition.

In some embodiments of the present invention, a freshening composition is a homogeneous freshening composition. As will be understood by one of skilled in the art, a homogeneous freshening composition is a uniform composition.

In some embodiments of the present invention, a freshening composition is a liquid air freshening composition. In some embodiments of the present invention, a freshening composition is a clear liquid freshening composition. In some embodiments of the present invention, a freshening composition is a clear liquid air freshening composition. In some embodiments of the present invention, a freshening composition is a homogeneous, clear liquid air freshening composition. Each of the above combines the characteristics and attributes of the induvial composition.

In some embodiments of the present invention, a freshening composition is a non-water-based freshening composition. In some embodiments of the present invention, a freshening composition does not comprise water.

For ease, when referring herein to "freshening composition," it is understood that this term includes (i) an air freshening composition, (ii) a liquid freshening composition, (iii) a clear freshening composition, (iv) a homogeneous freshening composition, (v) a liquid air freshening composition, (vi) a clear air freshening composition, (vii) a clear liquid air freshening composition, (viii) a homogeneous, clear liquid air freshening composition, (ix) a non-water-based freshening composition, and (x) a freshening composition not comprising water.

In some embodiments of the present invention, a freshening composition comprises a perfume raw material ("PRM"). The "PRMs" disclosed herein, claimed and/or used in a freshening composition comprise stereoisomers of such materials.

In some embodiments of the present invention, a freshening composition comprises a solvent or diluent. The solvents or diluents disclosed herein, claimed and/or used in a freshening composition comprise stereoisomers of such materials.

In some embodiments of the present invention, a freshening composition comprises a fragrance release modulator (FRM). The fragrance release modulators (FRMs) disclosed herein, claimed and/or used in a freshening composition comprise stereoisomers of such materials.

In some embodiments of the present invention, a freshening composition comprises an ingredient having a functional activity. The ingredients having a functional activity disclosed herein, claimed and/or used in a freshening composition comprise stereoisomers of such materials.

In some embodiments of the present invention, a freshening composition comprises a PRM, a solvent or diluent, and a fragrance release modulator.

In some embodiments of the present invention, a freshening composition comprises a PRM, a solvent or diluent, a fragrance release modulator, and an ingredient having a functional activity.

In some embodiments of the present invention, a freshening composition comprises a PRM and a fragrance release modulator.

In some embodiments of the present invention, a freshening composition comprises a PRM, a fragrance release modulator, and an ingredient having a functional activity.

Freshening compositions and fragrance release modulators (FRMs) of the present invention can be characterized by their flash point, surface tension, dynamic viscosity, density, vapor pressure, and evaporation rates. Values for flash point, surface tension, dynamic viscosity, density, and evaporation rate provided herein are measured under normal temperature and pressure (NTP) conditions. At NTP, pressure is equal to 1 atm (14.696 psi, 101.325 kPa) and temperature is equal to 293.15 K (20° C., 68° F.) (National Institute of Standards and Technology, NIST).

The flash point of an agent, ingredient, compound, substance, or material is the lowest liquid temperature at which, under certain standardized conditions (e.g., NTP), a liquid gives off vapors in a quantity such as to be capable of forming an ignitable vapor or a mixture. The lower the flash point, the easier it is to ignite a material. There are two basic types of flash point measurements: open cup and closed cup. Both can be used to measure the flash point of a freshening composition or of a component thereof. Closed cup methods include e.g., Pensky-Martens Closed Cup (PMCC, Standard ASTM D93/ISO 2719, preferred for oil-based and alcohol-based freshening compositions and compounds), Tag Closed Cup (TCC, Standard ASTM D56, preferred for volatile freshening compositions and compounds), and SetaFlash Closed Cup (Standard ASTM D3828/ISO 3679, preferred for alcohol-based freshening compositions and compounds methods) and are art-recognized methods for measuring flash points of volatile, flammable, especially alcohol-based freshening compositions. Flash points of a freshening composition and of FRMs, as used herein, can be determined using the SetaFlash Closed Cup method.

In some embodiments of the present invention, a freshening composition has a flash point in the range from about 100° C. to about 250° C. In some embodiments of the present invention, a freshening composition has a flash point in the range from about 110° C. to about 250° C. In some embodiments of the present invention, a freshening composition has a flash point in the range from about 120° C. to about 250° C. In some embodiments of the present invention, a freshening composition has a flash point in the range from about 130° C. to about 250° C. In some embodiments of the present invention, a freshening composition has a flash point in the range from about 140° C. to about 250° C. In some embodiments of the present invention, a freshening composition has a flash point in the range from about 150° C. to about 240° C. In some embodiments of the present invention, a freshening composition has a flash point in the range from about 160° C. to about 230° C. In some embodiments of the present invention, a freshening composition has a flash point in the range from about 170° C. to about 200° C.

In some embodiments of the present invention, a freshening composition has a flash point in the range of between about 100° C. and about 250° C. In some embodiments of the present invention, a freshening composition has a flash point in the range of between about 110° C. and about 250° C. In some embodiments of the present invention, a freshening composition has a flash point in the range of between about 120° C. and about 250° C. In some embodiments of the present invention, a freshening composition has a flash point in the range of between about 130° C. and about 250° C. In some embodiments of the present invention, a freshening composition has a flash point in the range of between about 140° C. and about 250° C. In some embodiments of the present invention, a freshening composition has a flash point in the range of between about 150° C. and about 240° C. In some embodiments of the present invention, a freshening composition has a flash point in the range of between about 160° C. and about 230° C. In some embodiments of the present invention, a freshening composition has a flash point in the range of between about 170° C. and about 200° C.

In some embodiments of the present invention, a freshening composition has a flash point of greater than about 100° F. In some embodiments of the present invention, a freshening composition has a flash point of greater than about 110° F. In some embodiments of the present invention, a freshening composition has a flash point of greater than about 120° F. In some embodiments of the present invention, a freshening composition has a flash point of greater than about 130° F. In some embodiments of the present invention, a freshening composition has a flash point of greater than about 140° F. In some embodiments of the present invention, a freshening composition has a flash point of greater than about 150° F. In some embodiments of the present invention, a freshening composition has a flash point of greater than about 160° F. In some embodiments of the present invention, a freshening composition has a flash point of greater than about 170° F. In some embodiments of the present invention, a freshening composition has a flash point of greater than about 180° F. In some embodiments of the present invention, a freshening composition has a flash point of greater than about 190° F. In some embodiments of the present invention, a freshening composition has a flash point of greater than about 200° F. In some embodiments of the present invention, a freshening composition has a flash point of greater than about 210° F. In some embodiments of the present invention, a freshening composition has a flash point of greater than about 220° F. In some embodiments of the present invention, a freshening composition has a flash point of greater than about 230° F. In some embodiments of the present invention, a freshening composition has a flash point of greater than about 240° F. In some embodiments of the present invention, a freshening composition has a flash point of greater than about 250° F. In some embodiments of the present invention, a freshening composition has a flash point of greater than about 260° F.

In some embodiments of the present invention, a freshening composition has a flash point of less than about 100° F. In some embodiments of the present invention, a freshening composition has a flash point of less than about 110° F. In some embodiments of the present invention, a freshening composition has a flash point of less than about 120° F. In some embodiments of the present invention, a freshening composition has a flash point of less than about 130° F. In some embodiments of the present invention, a freshening composition has a flash point of less than about 140° F. In some embodiments of the present invention, a freshening composition has a flash point of less than about 150° F. In some embodiments of the present invention, a freshening composition has a flash point of less than about 160° F. In some embodiments of the present invention, a freshening composition has a flash point of less than about 170° F. In some embodiments of the present invention, a freshening composition has a flash point of less than about 180° F. In some embodiments of the present invention, a freshening composition has a flash point of less than about 190° F. In some embodiments of the present invention, a freshening composition has a flash point of less than about 200° F. In some embodiments of the present invention, a freshening composition has a flash point of less than about 210° F. In some embodiments of the present invention, a freshening composition has a flash point of less than about 220° F. In some embodiments of the present invention, a freshening composition has a flash point of less than about 230° F. In some embodiments of the present invention, a freshening composition has a flash point of less than about 240° F. In some embodiments of the present invention, a freshening composition has a flash point of less than about 250° F. In some embodiments of the present invention, a freshening composition has a flash point of less than about 260° F.

Freshening compositions and FRMs of the present invention also are characterized by their surface tension. Measuring the surface tension of a freshening composition is important to understand how it behaves during spraying, spreading in an environment, wetting on a surface, etc. Surface tension is the tendency of a fluid surface to shrink into the minimum surface area possible. Because of the relatively high attraction of water molecules to each other through hydrogen bonds, water has a higher surface tension (72.8 millinewtons per meter [mN/m] at 20° C.) than most other liquids. There are several methods available in the art to measure surface tension, including but not limited to, e.g., the Du Noüy ring method, Wilhelmy plate method, spinning drop method, pendant drop method, bubble pressure method, drop volume method, capillary rise method, stalagmometric method, sessile drop method, Du Noüy-Padday method, and drop-bounce method. Each of the above art-recognized methods can be used to measure surface tension. A preferred method to measure surface tension of a freshening composition and of FRMs, as used herein, is the Wilhelmy plate method.

In some embodiments of the present invention, a freshening composition has a surface tension in the range from about 5 mN/m to about 100 mN/m. In some embodiments of the present invention, a freshening composition has a surface tension in the range from about 10 mN/m to about 90 mN/m. In some embodiments of the present invention, a freshening composition has a surface tension in the range from about 15 mN/m to about 80 mN/m. In some embodiments of the present invention, a freshening composition has a surface tension in the range from about 20 mN/m to about 70 mN/m. In some embodiments of the present invention, a freshening composition has a surface tension in the range from about 20 mN/m to about 60 mN/m. In some embodiments of the present invention, a freshening composition has a surface tension in the range from about 20 mN/m to about 50 mN/m.

In some embodiments of the present invention, a freshening composition has a surface tension in the range of between about 5 mN/m and about 100 mN/m. In some embodiments of the present invention, a freshening composition has a surface tension in the range of between about 10 mN/m and about 90 mN/m. In some embodiments of the present invention, a freshening composition has a surface tension in the range of between about 15 mN/m and about 80 mN/m. In some embodiments of the present invention, a freshening composition has a surface tension in the range of between about 20 mN/m and about 70 mN/m. In some embodiments of the present invention, a freshening composition has a surface tension in the range of between about 20 mN/m and about 60 mN/m. In some embodiments of the present invention, a freshening composition has a surface tension in the range of between about 20 mN/m and about 50 mN/m.

In some embodiments of the present invention, a freshening composition has a surface tension of greater than about 5 mN/m, alternatively, greater than about 10 mN/m, alternatively, greater than about 15 mN/m, alternatively, greater than about 20 mN/m, alternatively, greater than about 25 mN/m, alternatively, greater than about 30 mN/m, alternatively, greater than about 35 mN/m, alternatively, greater than about 40 mN/m, alternatively, greater than about 45 mN/m, alternatively, greater than about 50 mN/m, alternatively, greater than about 55 mN/m, alternatively, greater than about 60 mN/m, alternatively, greater than about 65 mN/m, alternatively, greater than about 70 mN/m, alternatively, greater than about 75 mN/m, alternatively, greater than about 80 mN/m, alternatively, greater than about 85 mN/m, alternatively, greater than about 90 mN/m, alternatively, greater than about 95 mN/m, alternatively, greater than about 100 mN/m.

In some embodiments of the present invention, a freshening composition has a surface tension of less than about 5 mN/m, alternatively, less than about 10 mN/m, alternatively, less than about 15 N/m, alternatively, less than about 20 mN/m, alternatively, less than about 25 mN/m, alternatively, less than about 30 mN/m, alternatively, less than about 35 mN/m, alternatively, less than about 40 mN/m, alternatively, less than about 45 mN/m, alternatively, less than about 50 mN/m, alternatively, less than about 55 mN/m, alternatively, less than about 60 mN/m, alternatively, less than about 65 mN/m, alternatively, less than about 70 mN/m, alternatively, less than about 75 mN/m, alternatively, less than about 80 mN/m, alternatively, less than about 85 mN/m, alternatively, less than about 90 mN/m, alternatively, less than about 95 mN/m, alternatively, less than about 100 mN/m.

A preferred freshening composition of the present invention has a surface tension in the range from about 10 mN/m to about 40 mN/m. A preferred freshening composition of the present invention has a surface tension in the range from about 20 mN/m to about 35 mN/m.

Freshening compositions and FRMs of the present invention also are characterized by their dynamic viscosity. Dynamic viscosity (also known as absolute viscosity) is the resistance to movement of one layer of a fluid over another. It is a measure of the resistance of a fluid to deform under shear stress. It is measured with various types of viscometers (e.g., capillary or vibrating) and rheometers (e.g., rotational, or microfluidic). The SI (International System of Units) unit of a dynamic viscosity is the pascal-second (Pa-s), or equivalent kilogram per meter per second ($kg*m^{-1}*s^{-1}$). The CGS (Centimetre-gram-second system of units) unit is called the poise (P). It is commonly expressed, particularly in ASTM (American Society for Testing and Materials) standards, as centipoise (cp) since the latter is equal to the SI multiple millipascal seconds (mPA-s). Art-recognized methods for measuring dynamic viscosity of freshening compositions and FRMs, include, but are not limited to, employing (i) Capillary Viscometer (U-Tube or Ostwald Type, measuring then time it takes for a liquid to flow through a capillary under gravity, Standard: ASTM D445, ISO 3104), (ii) Rotational Viscometer (cone-and-plate or cylinder type, measuring torque required to rotate or spindle or cone at a fixed speed in a liquid, Standard: ASTM D2196, ISO 2555), (iii) Vibrational Viscometer (measuring damping of an oscillating probe immersed in a liquid), and (iv) Microfluidic (Chip-based) Viscometer (measuring flow through a tiny microchannel using pressure sensors or flow rate detectors). A preferred method to measure dynamic viscosity of a freshening composition or of FRMs, as used herein, is employing the Capillary Viscometer method.

In some embodiments of the present invention, a freshening composition has a dynamic viscosity range in the range of between about 0.1 cp and about 150 cp. In some embodiments of the present invention, a freshening composition has a dynamic viscosity range in the range of between about 0.2 cp and about 140 cp. In some embodiments of the present invention, a freshening composition has a dynamic viscosity range in the range of between about 0.3 cp and about 130 cp. In some embodiments of the present invention, a freshening composition has a dynamic viscosity range in the range of between about 0.5 cp and about 120 cp. In some embodiments of the present invention, a freshening composition has a dynamic viscosity range in the range of between about 0.7 cp and about 110 cp. In some embodiments of the present invention, a freshening composition has a dynamic viscosity range in the range of between about 0.8 cp and about 100 cp. In some embodiments of the present invention, a freshening composition has a dynamic viscosity range in the range of between about 1 cp and about 100 cp. In some embodiments of the present invention, a freshening composition has a dynamic viscosity range in the range of between about 1 cp and about 90 cp. In some embodiments of the present invention, a freshening composition has a dynamic viscosity range in the range of between about 1 cp and about 80 cp. In some embodiments of the present invention, a freshening composition has a dynamic viscosity range in the range of between about 1 cp and about 70 cp. In some embodiments of the present invention, a freshening composition has a dynamic viscosity range in the range of between about 1 cp and about 60 cp. In some embodiments of the present invention, a freshening composition has a dynamic viscosity range in the range of between about 1 cp and about 50 cp. In some embodiments of the present invention, a freshening composition has a dynamic viscosity range in the range of between about 1 cp and about 40 cp. In some embodiments of the present invention, a freshening composition has a dynamic viscosity range in the range of between about 1 cp and about 30 cp. In some embodiments of the present invention, a freshening composition has a dynamic viscosity range in the range of between about 1 cp and about 20 cp. In some embodiments of the present invention, a freshening composition has a dynamic viscosity range in the range of between about 1 cp and about 10 cp.

In some embodiments of the present invention, a freshening composition has a dynamic viscosity range in the range from about 0.1 cp to about 150 cp. In some embodiments of the present invention, a freshening composition has a dynamic viscosity range in the range from about 0.2 cp to about 140 cp. In some embodiments of the present invention, a freshening composition has a dynamic viscosity range in the range from about 0.3 cp to about 130 cp. In some embodiments of the present invention, a freshening composition has a dynamic viscosity range in the range from about 0.5 cp to about 120 cp. In some embodiments of the present invention, a freshening composition has a dynamic viscosity range in the range from about 0.7 cp to about 110 cp. In some embodiments of the present invention, a freshening composition has a dynamic viscosity range in the range from about 0.8 cp to about 100 cp. In some embodiments of the present invention, a freshening composition has a dynamic viscosity range in the range from about 1 cp to about 100 cp. In some embodiments of the present invention, a freshening composition has a dynamic viscosity range in the range from about 1 cp to about 90 cp. In some embodiments of the present invention, a freshening composition has a dynamic viscosity range in the range from about 1 cp to about 80 cp. In some embodiments of the present invention, a freshening composition has a dynamic viscosity range in the range from about 1 cp to about 70 cp. In some embodiments of the present invention, a freshening composition has a dynamic viscosity range in the range from about 1 cp to about 60 cp. In some embodiments of the present invention, a freshening composition has a dynamic viscosity range in the range from about 1 cp to about 50 cp. In some embodiments of the present invention, a freshening composition has a dynamic viscosity range in the range from about 1 cp to about 40 cp. In some embodiments of the present invention, a freshening composition has a dynamic viscosity range in the range from about 1 cp to about 30 cp. In some embodiments of the present invention, a freshening composition has a dynamic viscosity range in the range from about 1 cp to about 20 cp. In some embodiments of the present invention, a freshening composition has a dynamic viscosity range in the range from about 1 cp to about 10 cp.

In some embodiments of the present invention, a freshening composition has a dynamic viscosity of greater than about 0.1 cp. In some embodiments of the present invention, a freshening composition has a dynamic viscosity of greater than about 0.2 cp. In some embodiments of the present invention, a freshening composition has a dynamic viscosity of greater than about 0.3 cp. In some embodiments of the present invention, a freshening composition has a dynamic viscosity of greater than about 0.4 cp. In some embodiments of the present invention, a freshening composition has a dynamic viscosity of greater than about 0.5 cp. In some embodiments of the present invention, a freshening composition has a dynamic viscosity of greater than about 0.7 cp. In some embodiments of the present invention, a freshening composition has a dynamic viscosity of greater than about 1 cp. In some embodiments of the present invention, a freshening composition has a dynamic viscosity of greater than about 2 cp. In some embodiments of the present invention, a freshening composition has a dynamic viscosity of greater than about 3 cp. In some embodiments of the present invention, a freshening composition has a dynamic viscosity of greater than about 5 cp. In some embodiments of the present invention, a freshening composition has a dynamic viscosity of greater than about 7 cp. In some embodiments of the present invention, a freshening composition has a dynamic viscosity of greater than about 10 cp. In some embodiments of the present invention, a freshening composition has a dynamic viscosity of greater than about 15 cp. In some embodiments of the present invention, a freshening composition has a dynamic viscosity of greater than about 20 cp. In some embodiments of the present invention, a freshening composition has a dynamic viscosity of greater than about 25 cp. In some embodiments of the present invention, a freshening composition has a dynamic viscosity of greater than about 30 cp. In some embodiments of the present invention, a freshening composition has a dynamic viscosity of greater than about 35 cp. In some embodiments of the present invention, a freshening composition has a dynamic viscosity of greater than about 40 cp. In some embodiments of the present invention, a freshening composition has a dynamic viscosity of greater than about 45 cp. In some embodiments of the present invention, a freshening composition has a dynamic viscosity of greater than about 50 cp.

In some embodiments of the present invention, a freshening composition has a dynamic viscosity of less than about 0.1 cp. In some embodiments of the present invention, a freshening composition has a dynamic viscosity of less than about 0.2 cp. In some embodiments of the present invention, a freshening composition has a dynamic viscosity of less than about 0.3 cp. In some embodiments of the present invention, a freshening composition has a dynamic viscosity of less than about 0.4 cp. In some embodiments of the present invention, a freshening composition has a dynamic viscosity of less than about 0.5 cp. In some embodiments of the present invention, a freshening composition has a dynamic viscosity of less than about 0.7 cp. In some embodiments of the present invention, a freshening composition has a dynamic viscosity of less than about 1 cp. In some embodiments of the present invention, a freshening composition has a dynamic viscosity of less than about 2 cp. In some embodiments of the present invention, a freshening composition has a dynamic viscosity of less than about 3 cp. In some embodiments of the present invention, a freshening composition has a dynamic viscosity of less than about 5 cp. In some embodiments of the present invention, a freshening composition has a dynamic viscosity of less than about 7 cp. In some embodiments of the present invention, a freshening composition has a dynamic viscosity of less than about 10 cp. In some embodiments of the present invention, a freshening composition has a dynamic viscosity of less than about 15 cp. In some embodiments of the present invention, a freshening composition has a dynamic viscosity of less than about 20 cp. In some embodiments of the present invention, a freshening composition has a dynamic viscosity of less than about 25 cp. In some embodiments of the present invention, a freshening composition has a dynamic viscosity of less than about 30 cp. In some embodiments of the present invention, a freshening composition has a dynamic viscosity of less than about 35 cp. In some embodiments of the present invention, a freshening composition has a dynamic viscosity of less than about 40 cp. In some embodiments of the present invention, a freshening composition has a dynamic viscosity of less than about 45 cp. In some embodiments of the present invention, a freshening composition has a dynamic viscosity of less than about 50 cp. In some embodiments of the present invention, a freshening composition has a dynamic viscosity of less than about 60 cp. In some embodiments of the present invention, a freshening composition has a dynamic viscosity of less than about 70 cp. In some embodiments of the present invention, a freshening composition has a dynamic viscosity of less than about 80 cp. In some embodiments of the present invention, a freshening composition has a dynamic viscosity of less than about 90 cp. In some embodiments of the present invention, a freshening composition has a dynamic viscosity of less than about 100 cp.

A freshening composition and a fragrance release modulator (FRM) of the present invention can also be characterized by their mass density. Mass density of a composition or object is defined as its mass per unit volume. A preferred freshening composition of the present invention has a mass density in the range from about 650 g/l to about 1,300 g/l. Another preferred freshening composition of the present invention has a mass density in the range from about 700 g/l to about 1,300 g/i. Another preferred freshening composition of the present invention has a mass density in the range of between 650 g/l and about 1,300 g/l. Another preferred freshening composition of the present invention has a mass density in the range of between about 700 g/l and about 1,300 g/l.

Various techniques, including, but not limited to, e.g., the use of a hydrometer (a buoyancy method for liquids, Standard: ASTM D1298, ISO 3675), hydrostatic balance (a buoyancy method for liquids and solids), immersed body method (a buoyancy method for liquids), pycnometer (liquids and solids, Standard: ASTM D941, ISO 2811-1), and digital density meter/oscillating densitometer (liquids, Standard: ASTM D4052, ISO 12185) can be used to measure mass density. A preferred method to measure mass density of a freshening composition or of FRMs, as used herein, is employing the Digital Density Meter method or the pycnometer method.

A preferred freshening composition of the present invention has a flash point higher than about 140° F., a surface tension from about 10 mN/m to about 40 mN/m. a dynamic viscosity from about 1 cp to about 20 cp, and a density in the range from about 700 g/l to about 1,200 g/l. Another preferred freshening composition of the present invention has a flash point higher than about 140° F., a surface tension in the range of between 10 mN/m and about 40 mN/m. a dynamic viscosity in the range of between about 1 cp and about 20 cp, and a density in the range of between about 700 g/l and about 1,200 g/l.

A freshening composition and a fragrance release modulator (FRM) of the present invention can also be characterized by their vapor pressure or equilibrium vapor pressure. Vapor pressure or equilibrium vapor pressure is a measure of the tendency of a material to change into the gaseous or vapor state and describes the pressure exerted by a vapor in equilibrium with its liquid (or solid) phase at a given temperature. It increases with temperature and is an indication of a liquid's thermodynamic tendency to evaporate. A preferred freshening composition of the present invention has a vapor pressure of less than about 0.1 atm.

Various art-recognized techniques, including, but not limited to, e.g., isothermal thermogravimetric analysis, gas saturation method (effusion 7 carrier gas), and headspace analysis (static or dynamic headspace) can be used to measure vapor pressure. A preferred method to measure vapor pressure of a freshening composition or of FRMs, as used herein, is employing the headspace analysis In some embodiments of the present invention, the freshening composition is adapted to have one or more, two or more, or three or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l. Measurement of the respective parameters has been described herein. Preparing a freshening composition, combining varying amounts (wt %) of (i) a perfume raw material, (ii) a solvent or diluent, (iii) a fragrance release modulator, and (iv) an ingredient having a functional activity, a skilled artisan will be able to adapt or to adjust any of the above parameters to fall within a desired range or value, simply by adjusting the wt % of (i), (ii), (iii), and/or (iv). Similarly, preparing a freshening composition, combining varying amounts of (i) a perfume raw material and (ii) a fragrance release modulator, a skilled artisan will be able to adapt or to adjust any of the above parameters to fall within a desired range or value, simply by adjusting the wt % of (i) and/or (ii).

Preferred freshening compositions of the present invention comply with VOC, CARB, and safety-toxicity requirements by having a flash point higher than about 140° F. and being substantially free of volatile organic compounds ("VOCs"), i.e., they contain no more than about 18 wt % VOCs.

The freshening compositions of the present invention may be used with or without an air care product or with or without a device as further described herein.

The freshening compositions of the present invention may be combined with any air care freshening product wherein the freshening composition may be used directly or after dilution with a solvent or a diluent.

In some embodiments of the present invention, a freshening composition comprises a perfume raw material and a fragrance release modulator. In some embodiments of the present invention, an air freshening composition comprises a perfume raw material and a fragrance release modulator. In some embodiments of the present invention, a liquid freshening composition comprises a perfume raw material and a fragrance release modulator. In some embodiments of the present invention, a clear freshening composition comprises a perfume raw material and a fragrance release modulator. In some embodiments of the present invention, a homogenous freshening composition comprises a perfume raw material and a fragrance release modulator. In some embodiments of the present invention, a clear liquid freshening composition comprises a perfume raw material and a fragrance release modulator. In some embodiments of the present invention, a liquid air freshening composition comprises a perfume raw material and a fragrance release modulator. In some embodiments of the present invention, a homogeneous clear liquid air freshening composition comprises a perfume raw material and a fragrance release modulator. In some embodiments of the present invention, a homogeneous clear liquid air freshening composition comprises a perfume raw material and a fragrance release modulator. In some embodiments of the present invention, a non-water-based air freshening composition comprises a perfume raw material and a fragrance release modulator.

In some embodiments of the present invention, a freshening composition comprises a perfume raw material and a solvent or diluent. In some embodiments of the present invention, an air freshening composition comprises a perfume raw material and a solvent or diluent. In some embodiments of the present invention, a liquid freshening composition comprises a perfume raw material and a solvent or diluent. In some embodiments of the present invention, a clear freshening composition comprises a perfume raw material and a solvent or diluent. In some embodiments of the present invention, a homogenous freshening composition comprises a perfume raw material and a solvent or diluent. In some embodiments of the present invention, a clear liquid freshening composition comprises a perfume raw material and a solvent or diluent. In some embodiments of the present invention, a liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a non-water-based air freshening composition comprises a perfume raw material and a solvent or diluent.

In some embodiments of the present invention, a freshening composition comprises a perfume raw material and an ingredient having a functional activity. In some embodiments of the present invention, an air freshening composition comprises a perfume raw material and an ingredient having a functional activity. In some embodiments of the present invention, a liquid freshening composition comprises a perfume raw material and an ingredient having a functional activity. In some embodiments of the present invention, a clear freshening composition comprises a perfume raw material and an ingredient having a functional activity. In some embodiments of the present invention, a homogenous freshening composition comprises a perfume raw material and an ingredient having a functional activity. In some embodiments of the present invention, a clear liquid freshening composition comprises a perfume raw material and an ingredient having a functional activity. In some embodiments of the present invention, a liquid air freshening composition comprises a perfume raw material and an ingredient having a functional activity. In some embodiments of the present invention, a homogeneous clear liquid air freshening composition comprises a perfume raw material and an ingredient having a functional activity. In some embodiments of the present invention, a homogeneous clear liquid air freshening composition comprises a perfume raw material and an ingredient having a functional activity. In some embodiments of the present invention, a non-water-based air freshening composition comprises a perfume raw material and an ingredient having a functional activity.

In some embodiments of the present invention, a freshening composition comprises a perfume raw material, a solvent or diluent, and a fragrance release modulator. In some embodiments of the present invention, an air freshening composition comprises a perfume raw material, a solvent or diluent, and a fragrance release modulator. In some embodiments of the present invention, a liquid freshening composition comprises a perfume raw material, a solvent or diluent, and a fragrance release modulator. In some embodiments of the present invention, a clear freshening composition comprises a perfume raw material, a solvent or diluent, and a fragrance release modulator. In some embodiments of the present invention, a homogenous freshening composition comprises a perfume raw material, a solvent or diluent, and a fragrance release modulator. In some embodiments of the present invention, a clear liquid freshening composition comprises a perfume raw material, a solvent or diluent, and a fragrance release modulator. In some embodiments of the present invention, a liquid air freshening composition comprises a perfume raw material, a solvent or diluent, and a fragrance release modulator. In some embodiments of the present invention, a homogeneous clear liquid air freshening composition comprises a perfume raw material, a solvent or diluent, and a fragrance release modulator. In some embodiments of the present invention, a homogeneous clear liquid air freshening composition comprises a perfume raw material, a solvent or diluent, and a fragrance release modulator. In some embodiments of the present invention, a non-water-based air freshening composition comprises a perfume raw material, a solvent or diluent, and a fragrance release modulator.

In some embodiments of the present invention, a freshening composition comprises a perfume raw material, a fragrance release modulator, and an ingredient having a functional activity. In some embodiments of the present invention, an air freshening composition comprises a perfume raw material, a fragrance release modulator, and an ingredient having a functional activity. In some embodiments of the present invention, a liquid freshening composition comprises a perfume raw material, a fragrance release modulator, and an ingredient having a functional activity. In some embodiments of the present invention, a clear freshening composition comprises a perfume raw material, a fragrance release modulator, and an ingredient having a functional activity. In some embodiments of the present invention, a homogenous freshening composition comprises a perfume raw material, a fragrance release modulator, and an ingredient having a functional activity. In some embodiments of the present invention, a clear liquid freshening composition comprises a perfume raw material, a fragrance release modulator, and an ingredient having a functional activity. In some embodiments of the present invention, a liquid air freshening composition comprises a perfume raw material, a fragrance release modulator, and an ingredient having a functional activity. In some embodiments of the present invention, a homogeneous clear liquid air freshening composition comprises a perfume raw material, a fragrance release modulator, and an ingredient having a functional activity. In some embodiments of the present invention, a homogeneous clear liquid air freshening composition comprises a perfume raw material, a fragrance release modulator, and an ingredient having a functional activity. In some embodiments of the present invention, a non-water-based air freshening composition comprises a perfume raw material, a fragrance release modulator, and an ingredient having a functional activity.

In some embodiments of the present invention, a freshening composition comprises a perfume raw material, a fragrance release modulator, a solvent or diluent, and an ingredient having a functional activity. In some embodiments of the present invention, an air freshening composition comprises a perfume raw material, a fragrance release modulator, a solvent or diluent, and an ingredient having a functional activity. In some embodiments of the present invention, a liquid freshening composition comprises a perfume raw material, a fragrance release modulator, a solvent or diluent, and an ingredient having a functional activity. In some embodiments of the present invention, a clear freshening composition comprises a perfume raw material, a fragrance release modulator, a solvent or diluent, and an ingredient having a functional activity. In some embodiments of the present invention, a homogenous freshening composition comprises a perfume raw material, a fragrance release modulator, a solvent or diluent, and an ingredient having a functional activity. In some embodiments of the present invention, a clear liquid freshening composition comprises a perfume raw material, a fragrance release modulator, a solvent or diluent, and an ingredient having a functional activity. In some embodiments of the present invention, a liquid air freshening composition comprises a perfume raw material, a fragrance release modulator, a solvent or diluent, and an ingredient having a functional activity. In some embodiments of the present invention, a homogeneous clear liquid air freshening composition comprises a perfume raw material, a fragrance release modulator, a solvent or diluent, and an ingredient having a functional activity. In some embodiments of the present invention, a homogeneous clear liquid air freshening composition comprises a perfume raw material, a fragrance release modulator, a solvent or diluent, and an ingredient having a functional activity. In some embodiments of the present invention, a non-water-based air freshening composition comprises a perfume raw material, a fragrance release modulator, a solvent or diluent, and an ingredient having a functional activity.

A. Perfume Raw Materials

In some embodiments of the present invention, a freshening composition comprises a perfume raw material. It is understood and one of ordinary skill in the art will appreciate that, if not clearly contradicted by the content of this specification, each embodiment of a perfume raw material and/or features/elements disclosed as part of that embodiment can be combined with any of the embodiments hereinabove or hereinbelow.

In some embodiments of the present invention, an air freshening composition comprises a perfume raw material. In some embodiments of the present invention, a liquid freshening composition comprises a perfume raw material. In some embodiments of the present invention, a clear freshening composition comprises a perfume raw material. In some embodiments of the present invention, a homogenous freshening composition comprises a perfume raw material. In some embodiments of the present invention, a clear liquid freshening composition comprises a perfume raw material. In some embodiments of the present invention, a liquid air freshening composition comprises a perfume raw material. In some embodiments of the present invention, a homogeneous clear liquid air freshening composition comprises a perfume raw material. In some embodiments of the present invention, a homogeneous clear liquid air freshening composition comprises a perfume raw material. In some embodiments of the present invention, a non-water-based air freshening composition comprises a perfume raw material.

In some embodiments of the present invention, a perfume raw material comprises one or more ingredients. Perfume raw materials comprise a variety of compounds and, e.g., include compounds referred to as a fragrance ingredient, a flavor ingredient, an essential oil, a natural extract, and synthetic substances thereof Δ fragrance ingredient, as used herein, refers to any perfume raw material that is utilized for its fragrance, scent and/or hedonic benefit.

Thus, a freshening composition of this invention may include various, different PRMs. A freshening composition of this invention may include a plurality of PRMs. These PRMs are not particularly limited as far as their use as part of a freshening composition is concerned. Exemplary perfume raw materials are disclosed herein and have been disclosed elsewhere, e.g., in U.S. Pat. Nos. 5,663,134; 5,670,475; 5,783,544; 5,939,060; and 6,146,621, each of which is incorporated herewith by reference. Other known synthetic aroma chemicals and natural origin fragrance compounds that may be used as a PRM are described in "Perfume and Flavor Chemicals", Vols. I and II, Steffen Arctander, Allured Pub. Co. (1994); "Perfumery Material Performance V3.3", Boelens Aroma Chemical Information Service (1996); and "Flower Oils and Floral Compounds In Perfumery", Danute Lajaujis Anonis, Allured Pub. Co. (1993), each of which is incorporated herewith by reference. Herein, a synthetic aroma chemical also is referred to as a synthetic origin fragrance compound.

Perfume raw materials described herein may be characterized by their volatility and fall into three categories: highly volatile (top not), medium volatile (medium not), and low volatile (bottom not).

Any perfume raw material or any blend of a plurality of perfume raw materials that can be smelled is also referred to herein as a perfume or a fragrance. Specific fragrances that are described in great detail herein, include, but are not limited to, e.g., Apple Fragrance and Floral Fresh Fragrance, each of which comprises a blend of a plurality of perfume raw materials. Acetic acid, on the other hand is a non-limiting compound of a single ingredient that has a smell and hence, may also be referred to as a perfume or fragrance. Blending, mixing, combining a plurality of perfume raw materials allows the practitioner to create various and different smells.

In some embodiments of the present invention, a perfume raw material comprises an ingredient selected from the group consisting of an ester, an alcohol, an aldehyde, a ketone, an acetal, a phenol, an ether, a lactone, a furan, a hydrocarbon, an acid, a natural origin fragrance material, a synthetic origin fragrance compound, a stereoisomer of any preceding perfume raw material, and a mixture of any of the preceding perfume raw materials. In some embodiments of the present invention, a perfume raw material comprises an ingredient selected from the aforementioned group missing one or more group members, e.g., from the aforementioned group not including an alcohol.

In some embodiments of the present invention, a perfume raw material comprises an ester. A variety of esters may be used without diverging from the scope of the present invention. In some embodiments of the present invention, a perfume raw material is an ester selected from the group consisting of an acrylic ester (methyl, ethyl, etc.), an acetoacetic ester (methyl, ethyl, etc.), an anisic ester (methyl, ethyl, etc.), a benzoic ester (allyl, isoamyl, ethyl, geranyl, linalyl, phenylethyl, hexyl, cis-3-hexenyl, benzyl, methyl, etc.), an anthranilic ester (cinnamyl, cis-3-hexenyl, methyl, ethyl, linalyl, isobutyl, etc.), an N-methylanthranilic ester (methyl, ethyl etc.), an isovaleric ester (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), an isobutyric ester (isoamyl, geranyl, citronellyl, terpenyl, cinnamyl, octyl, neryl, phenylethyl, phenylpropyl, phenoxyethyl, butyl, propyl, isopropyl, hexyl, benzyl, methyl, ethyl, linalyl, rhodinyl, etc.), an undecylenic ester (allyl, isoamyl, butyl, ethyl, methyl, etc.), an octanoic ester (allyl, isoamyl, ethyl, octyl, hexyl, butyl, methyl, linalyl, etc.), an octenoic ester (methyl, ethyl, etc.), an octyne carboxylic ester (methyl, ethyl, etc.), a caproic ester (allyl, amyl, isoamyl, methyl, ethyl, isobutyl, propyl, hexyl, cis-3-hexenyl, trans-2-hexenyl, linalyl, geranyl, cyclohexyl, etc.), a hexenoic ester (methyl, ethyl, etc.), a valeric ester (amyl, isopropyl, isobutyl, ethyl, cis-3-hexenyl, trans-2-hexenyl, cinnamyl, phenylethyl, methyl, etc.), a formic ester (anisyl, isoamyl, isopropyl, ethyl, octyl, geranyl, citronellyl, cinnamyl, cyclohexyl, terpenyl, phenylethyl, butyl, propyl, hexyl, cis-3-hexenyl, benzyl, linalyl, rhodinyl, etc.), a crotonic ester (isobutyl, ethyl, cyclohexyl, etc.), a cinnamic ester (allyl, ethyl, methyl, isopropyl, propyl, 3-phenylpropyl, benzyl, cyclohexyl, methyl, etc.), a succinic ester (mono-methyl, diethyl, dimethyl, etc.), an acetic ester (anisyl, amyl, alpha-amylcinnamyl, isoamyl, isobutyl, isopropyl, isobornyl, isoeugenyl, eugenyl, 2-ethylbutyl, ethyl, 3-octyl, p-cresyl, o-cresyl, geranyl, α-santalyl, β-santalyl, cyclohexyl, cyclonenyl, dihydrocuminyl, dimethylbenzylcarbinyl, cinnamyl, styrallyl, decyl, dodecyl, terpenyl, guanyl, neryl, nonyl, phenylethyl, phenylpropyl, butyl, furfuryl, propyl, hexyl, cis-3-hexenyl, trans-2-hexenyl, cis-3-nonenyl, cis-6-nonenyl, cis-3, cis-6-nonadienyl, 3-methyl-2-butenyl, heptyl, benzyl, borayl, myrcenyl, dihydromyrcenyl, myrtenyl, methyl, 2-methylbutyl, menthyl, linalyl, rhodinyl, etc.), an salicylic ester (allyl, isoamyl, phenyl, phenylethyl, benzyl, ethyl, methyl, etc.), a cyclohexyl alkanoic ester (ethyl cyclohexyl acetate, allyl cyclohexyl propionate, allyl cyclohexyl butyrate, allyl cyclohexyl hexanoate, allyl cyclohexyl decanoate, allyl cyclohexyl valerate, etc.), a stearic ester (ethyl, propyl, butyl, etc.), a sebacic ester (diethyl, dimethyl, etc.), a decanoic ester (isoamyl, ethyl, butyl, methyl, etc.), a dodecanoic ester (isoamyl, ethyl, butyl, etc.), a lactic ester (isoamyl, ethyl, butyl, etc.), a nonanoic ester (ethyl, phenylethyl, methyl, etc.), a nonenoic ester (allyl, ethyl, methyl, etc.), a hydroxyhexanoic ester (ethyl, methyl, etc.), a phenylacetic ester (isoamyl, isobutyl, ethyl, geranyl, citronellyl, cis-3-hexenyl, methyl, etc.), a phenoxyacetic ester (allyl, ethyl, methyl, etc.), a furancarboxylic ester (ethyl furancarboxylate, methyl furancarboxylate, hexyl furancarboxylate, isobutyl furanpropionate, etc.), a propionic ester (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linalyl, terpenyl, α-methylpropionyl, β-methylpropionyl, etc.), a heptanoic ester (allyl, ethyl, octyl, propyl, methyl, etc.), a heptin carboxylic ester (allyl, ethyl, propyl, methyl, etc.), a myristic ester (isopropyl, ethyl, methyl, etc.), a phenylglycidic ester (ethyl phenyl glycidate, ethyl 3methylphenylglycidate, ethyl p-methyl-P-phenylglycidate, etc.), 2-methylbutyric ester (methyl, ethyl, octyl, phenylethyl, butyl, hexyl, benzyl, etc.), 3-methylbutyric ester (methyl, ethyl, etc.), a butyric ester (anisyl, amyl, allyl, isoamyl, methyl, ethyl, propyl, octyl, guanyl, linalyl, geranyl, cyclohexyl, citronellyl, cinnamyl, neryl, terpenyl, phenylpropyl, P-phenylethyl, butyl, hexyl, cis3-hexenyl, trans-2-hexenyl, benzyl, rhodinyl, etc.), and a hydroxybutyric ester (methyl, ethyl, menthyl, and the like of 3-hydroxybutyrate), a stereoisomer of any preceding ester, and a mixture of any of the preceding esters. In some embodiments of the present invention, an ester is selected from the aforementioned group missing one or more group members, e.g., from the aforementioned group of esters not including an acrylic ester.

In some embodiments of the present invention, a perfume raw material comprises an alcohol. A variety of alcohols may be used without diverging from the scope of the present invention. In some embodiments of the present invention, a perfume raw material is an alcohol selected from the group consisting of a primary alcohol (methanol, ethanol, butanol, propanol, 2-methylpropan-1-ol, etc.), a secondary alcohol (propan-2-ol, cyclohexanol, etc.), a tertiary alcohol (tert-amyl alcohol, etc.), an aliphatic alcohol (isoamyl alcohol, 2-ethylhexanol, 1-octanol, 3-octanol, 1-octen-3-ol, 1-decanol, 1-dodecanol, 2,6-nonadienol, nonanol, 2-nonanol, cis-6-nonenol, trans-2, cis-6-nonadienol, cis-3, cis-6-nonadienol, butanol, hexanol, cis-3-hexenol, trans-2-hexenol, 1-undecanol, heptanol, 2-heptanol, 3-methyl-1-pentanol, etc.), a polyhydric alcohol (ethane-1,2-diol, propane-1,2-diol, propane-1,2,3-triol, butane-1,2,3,4-tetrol, pentane-1,2,3,4,5-pentol, heptane-1,2,3,4,5,6,7-heptol, etc.), an unsaturated aliphatic alcohol (prop-2-ene-1-ol, 3,7-dimethylocta-2,6-dien-1-ol, etc.), an alicyclic alcohol (cyclohexane-1,2,3,4,5,6-hexol, 5-methyl-2-(propan-s-yl)cyclohexan-a-ol, etc.) a terpene alcohol (borneol, isoborneol, carveol, geraniol, α-santalol, β-santalol, citronellol, 4-thujanol, terpineol, 4-terpineol, nerol, myrcenol, myrtenol, dihydromyrcenol, tetrahydromyrcenol, nerolidol, hydroxycitronerol, farnesol, perilla alcohol, rhodinol, linalool, etc.), an aromatic alcohol (anise alcohol, alpha-amylcinnamic alcohol, isopropylbenzylcarbinol, carvacrol, cumin alcohol, dimethylbenzylcarbinol, cinnamic alcohol, α-phenylethyl alcohol, phenylethylcarbinol, β-phenylethyl alcohol, 3-phenylpropyl alcohol, benzyl alcohol, etc.), a stereoisomer of any preceding alcohol, and a mixture of any of the preceding alcohols. In some embodiments of the present invention, an alcohol is selected from the aforementioned group missing one or more group members, e.g., from the aforementioned group of alcohols not including a primary alcohol.

In some embodiments of the present invention, a perfume raw material comprises an aldehyde. A variety of aldehydes may be used without diverging from the scope of the present invention. In some embodiments of the present invention, a perfume raw material is an aldehyde selected from the group consisting of an aliphatic aldehyde (acetoaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.), an aromatic aldehyde (anisaldehyde, α-amylcinnamic aldehyde, α-methylcinnamic aldehyde, cyclamen aldehyde, p-isopropylphenylacetaldehyde, ethylvanillin, cuminaldehyde, salicylaldehyde, cinnamic aldehyde, o-tolylaldehyde, m-tolylaldehyde, p-tolylaldehyde, vanillin, piperonal, phenylacetaldehyde, heliotropin, benzaldehyde, 4-methyl-2-phenyl-2-pentenal, p-methoxycinnamic aldehyde, p-methoxybenzaldehyde, etc.), a terpene aldehyde (geranial, citral, citronellal, α-sinensal, β-sinensal, perillaldehyde, hydroxycitronellal, tetrahydrocitral, myrtenal, cyclocitral, isocyclocitral, citronellyloxyacetaldehyde, neral, methylenecitronellal, myrac aldehyde, vernaldehyde, safranal, etc.), a stereoisomer of any preceding aldehyde, and a mixture of any of the preceding aldehydes. In some embodiments of the present invention, an aldehyde is selected from the aforementioned group missing one or more group members, e.g., from the aforementioned group of aldehydes not including an aliphatic aldehyde.

In some embodiments of the present invention, a perfume raw material comprises a ketone. A variety of ketones may be used without diverging from the scope of the present invention. In some embodiments of the present invention, a perfume raw material is a ketone selected from the group consisting of a cyclic ketone (1-acetyl-3,3-dimethyl-1-cyclohexene, cisjasmone, α-irone, β-irone, γ-irone, ethylmaltol, cyclotene, dihydronootkatone, 3,4-dimethyl-1,2-cyclopentadione, sotolone, α-damascone, β-damascone, γ-damascene, δ-damascone, α-damascenone, β-damascenone, γ-damascenone, nootkatone, 2-sec-butylcyclohexanone, maltol, α-ionone, β-ionone, γ-ionone, α-methylionone, β-methylionone, γ-methylionone, α-isomethylionone, β-isomethylionone, γ-isomethylionone, furaneol, camphor, etc.), an aromatic ketone (acetonaphthone, acetophenone, anisylideneacetone, raspberry ketone, p-methylacetopheneon, anisylacetone, p-methoxyacetophenone, etc.), a linear ketone (diacetyl, 2-nonanone, 2-heptanone, 2,3-heptanedione, 2-pentanone, methyl amyl ketone, methyl nonyl ketone, β-methyl naphthyl ketone, methylheptanone, 3-heptanone, 4-heptanone, 3-octanone, 2,3-hexanedione, 2-undecanone, dimethyloctenone, δ-methyl-5-hepten-2-one, etc.), a stereoisomer of any preceding ketone, and a mixture of any of the preceding ketones. In some embodiments of the present invention, a ketone is selected from the aforementioned group missing one or more group members, e.g., from the aforementioned group of ketones not including a cyclic ketone.

In some embodiments of the present invention, a perfume raw material comprises an acetal. A variety of acetals may be used without diverging from the scope of the present invention. In some embodiments of the present invention, a perfume raw material is an acetal selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, ambersage (from Givaudan Flavors Corporation, East Hanover, NJ, USA), acetoacetate ethyl ethylene glycol acetal, 2-phenylpropanal dimethyl acetal, a stereoisomer of any preceding acetal, and a mixture of any of the preceding acetals. In some embodiments of the present invention, an acetal is selected from the aforementioned group missing one or more group members, e.g., from the aforementioned group of acetals not including acetaldehyde diethyl acetal.

In some embodiments of the present invention, a perfume raw material comprises a phenol. A variety of phenols may be used without diverging from the scope of the present invention. In some embodiments of the present invention, a perfume raw material is a phenol selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols. In some embodiments of the present invention, a phenol is selected from the aforementioned group missing one or more group members, e.g., from the aforementioned group of phenols not including eugenol.

In some embodiments of the present invention, a perfume raw material comprises an ether. A variety of ethers may be used without diverging from the scope of the present invention. In some embodiments of the present invention, a perfume raw material is an ether selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers. In some embodiments of the present invention, an ether is selected from the aforementioned group missing one or more group members, e.g., from the aforementioned group of ethers not including anethole.

In some embodiments of the present invention, a perfume raw material comprises a lactone. A variety of lactones may be used without diverging from the scope of the present invention. In some embodiments of the present invention, a perfume raw material is a lactone selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, δ-methylcoumarin, a stereoisomer of any preceding lactone, and a mixture of any of the preceding lactones. In some embodiments of the present invention, a lactone is selected from the aforementioned group missing one or more group members, e.g., from the aforementioned group of lactones not including γ-decalactone.

In some embodiments of the present invention, a perfume raw material comprises a furan. A variety of furans may be used without diverging from the scope of the present invention. In some embodiments of the present invention, a perfume raw material is a furan selected from the group consisting of furan, 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2(5H)-furanone (sotolone), 2-ethyl-4-hydroxy-5-methyl-3(2H)-furanone (homofuraneol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans. In some embodiments of the present invention, a furan is selected from the aforementioned group missing one or more group members, e.g., from the aforementioned group of furans not including 2-methyl furan.

In some embodiments of the present invention, a perfume raw material comprises a hydrocarbon. A variety of hydrocarbons may be used without diverging from the scope of the present invention. In some embodiments of the present invention, a perfume raw material is a hydrocarbon selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons. In some embodiments of the present invention, a hydrocarbon is selected from the aforementioned group missing one or more group members, e.g., from the aforementioned group of hydrocarbons not including α-bisabolene.

In some embodiments of the present invention, a perfume raw material comprises an acid. A variety of acids may be used without diverging from the scope of the present invention. In some embodiments of the present invention, a perfume raw material is an acid selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids. In some embodiments of the present invention, an acid is selected from the aforementioned group missing one or more group members, e.g., from the aforementioned group of acids not including geranic acid.

In some embodiments of the present invention, a perfume raw material comprises a natural origin fragrance compound. A variety of natural origin fragrance compounds may be used without diverging from the scope of the present invention. In some embodiments of the present invention, a perfume raw material is a natural origin fragrance compound isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, licorice, and a mixture of any of the preceding perfume raw materials. In some embodiments of the present invention, a natural origin fragrance compound is selected from the aforementioned group missing one or more group members, e.g., from the aforementioned group of natural origin fragrance compounds not including basil.

In some embodiments of the present invention, a perfume raw material is a synthetic origin fragrance compound selected from the group consisting of an ester, an alcohol, an aldehyde, a ketone, an acetal, a phenol, an ether, a lactone, a furan, a hydrocarbon, an acid, a stereoisomer of any preceding perfume raw material, and a mixture of any of the preceding perfume raw materials. In some embodiments of the present invention, a perfume raw material comprises an ingredient selected from the aforementioned group missing one or more group members, e.g., from the aforementioned group of synthetic fragrance compounds not including an acid.

In some embodiments of the present invention a synthetic origin fragrance is a compound imitating a natural origin fragrance compound, i.e., a synthetic origin fragrance compound having the same chemical structure as a natural origin fragrance compound.

In some embodiments of the present invention, a perfume raw material comprises one or more compounds selected from the group of compounds listed in Table 1 of published U.S. Pat. Appl. No. 2018/0008740 A1.

In some embodiments of the present invention, a perfume raw material is selected from the group consisting of a compound having CAS number 100-52-7, a compound having CAS number 10094-34-5, a compound having CAS number 101-48-4, a compound having CAS number 101-86-0, a compound having CAS number 103-60-6, a compound having CAS number 103-95-7, a compound having CAS number 104-61-0, a compound having CAS number 104-67-6, a compound having CAS number 105-95-3, a compound having CAS number 110-41-8, a compound having CAS number 112-45-8, a compound having CAS number 115-95-7, a compound having CAS number 1205-17-0, a compound having CAS number 121-32-4, a compound having CAS number 123-68-2, a compound having CAS number 1335-46-2, a compound having CAS number 1335-66-6, a compound having CAS number 142-19-8, a compound having CAS number 142-92-7, a compound having CAS number 151-05-3, a compound having CAS number 18479-58-8, a compound having CAS number 24851-98-7, a compound having CAS number 2705-87-5, a compound having CAS number 32210-23-4, a compound having CAS number 32388-55-9, a compound having CAS number 3681-71-8, a compound having CAS number 3738-00-9, a compound having CAS number 39255-32-8, a compound having CAS number 4940-11-8, a compound having CAS number 5413-60-5, a compound having CAS number 54464-57-2, a compound having CAS number 56973-85-4, a compound having CAS number 6259-76-3, a compound having CAS number 63500-71-0, a compound having CAS number 6413-10-1, a compound having CAS number 6728-26-3, a compound having CAS number 67634-00-8, a compound having CAS number 67634-14-4, a compound having CAS number 67634-15-5, a compound having CAS number 67634-00-8, a compound having CAS number 68039-49-6, a compound having CAS number 7452-79-1, a compound having CAS number 78-70-6, a compound having CAS number 8000-27-9, a compound having CAS number 88-41-5, a compound having CAS number 928-96-1, a compound having CAS number 93-92-5, and a compound having CAS number 97-53-0, a stereoisomer of any preceding perfume raw material, and a mixture of any of the preceding perfume raw materials.

In some embodiments of the present invention, perfume raw materials, perfumes or fragrances, when too concentrated, are being combined with a solvent or diluent (as described herein). As not all perfume raw materials are liquid, combining them with a solvent or diluent will also solve solid raw perfume ingredients.

In some embodiments of the present invention, perfume raw materials, perfumes or fragrances in concentrated or diluted form are being combined with a fragrance release modulator (as described herein), which will allow the modulation of the releasing rate, or the modulation of the dispersing pattern of the respective freshening composition.

The amount of perfume raw material in a freshening composition of the present invention may vary depending on the type of perfume raw material being used. Generally, the amount of perfume raw material in a freshening composition of the present invention ranges from about 0.001 wt % to about 90 wt %. When the amount of the perfume raw material is too low, fragrance intensity may not be sufficient. When the amount of the perfume raw material is too high, the cost of the freshening composition may become unattractive for a consumer. Taking these points into account, one of skill in the art will appreciate that it is desirable that the amount of a perfume raw material is appropriately selected depending on the type of perfume raw material being used. Using guidance provided herein, one of ordinary skill in the art will be able to determine an appropriate amount of a perfume raw material to be used when formulating a freshening composition.

The amount of perfume raw material, such as a fragrance ingredient, added to formulate a freshening composition of the present invention may vary. In some embodiments of the present invention, a freshening composition comprises greater than about 0.001 wt % of a perfume raw material. In other embodiments of the present invention, a freshening composition comprises greater than about 0.005 wt %, greater than about 0.01 wt %, greater than about 0.02 wt %, greater than about 0.03 wt %, greater than about 0.04 wt %, greater than about 0.05 wt 0 greater than about 0.06 wt % greater than about 0.07 wt %, greater than about 0.08 wt %, greater than about 0.09 wt % greater than about 0.1 wt %, greater than about 0.2 wt %, greater than about 0.3 wt %, greater than about 0.4 wt %, greater than about 0.5 wt %, greater than about 1 wt %, greater than about 2 wt %, greater than about 3 wt %, greater than about 4 wt %, greater than about 5 wt %, greater than about 6 wt %, greater than about 7 wt %, greater than about 8 wt %, greater than about 9 wt %, greater than about 10 wt %, greater than about 15 wt %, greater than about 20 wt %, greater than about 25 wt %, greater than about 30 wt %, greater than about 40 wt %, greater than about 50 wt %, greater than about 60 wt %, greater than about 70 wt %, greater than about 80 wt %, or greater than about 85 wt % of a perfume raw material. Wt % is based on the total weight of the freshening composition.

In some embodiments of the present invention, a freshening composition comprises less than about 0.001 wt % of a perfume raw material. In other embodiments of the present invention, a freshening composition comprises less than about 0.005 wt %, less than about 0.01 wt %, less than about 0.02 wt %, less than about 0.03 wt %, less than about 0.04 wt %, less than about 0.05 wt %, less than about 0.06 wt %, less than about 0.07 wt %, less than about 0.08 wt %, less than about 0.09 wt %, less than about 0.1 wt %, less than about 0.2 wt %, less than about 0.3 wt %, less than about 0.4 wt %, less than about 0.5 wt %, less than about 0.6 wt %, less than about 0.7 wt %, less than about 0.8 wt %, less than about 0.9 wt %, less than about 1 wt %, less than about 2 wt %, less than about 3 wt %, less than about 4 wt %, rises less than about 5 wt % less than about 6 wt %, less than about 7 wt %, less than about 8 wt %, less than about 9 wt % less than about 10 wt %, less than about 15 wt %, less than about 20 wt %, less than about 25 wt %, less than about 30 wt %, less than about 40 wt %, less than about 50 wt %, less than about 60 wt %, less than about 70 wt %, less than about 80 wt %, or less than about 85 wt % of a perfume raw material. Wt % is based on the total weight of the freshening composition.

In some embodiments of the present invention, a freshening composition comprises a perfume raw material in the range from about 0.001 wt % to about 90 wt %. In other embodiments of the present invention, a freshening composition comprises a perfume raw material in the range from about 0.01 wt % to about 85 wt %, from about 0.1 wt % to about 85 wt %, from about 0.2 wt % to about 80 wt %, from about 0.5 wt % to about 70 wt %, from about 0.75 wt % to about 65 wt %, from about 1 wt % to about 60 wt %, from about 2 wt % to about 55 wt %, from about 3 wt % to about 50 wt %, from about 5 wt % to about 45 wt %, from about 7.5 wt % to about 40 wt %, from about 10 wt % to about 35 wt %, from about 15 wt % to about 30 wt %, or from about 20 wt % to about 25 wt %. Wt % is based on the total weight of the freshening composition.

1. Preferred Blends of Perfume Raw Materials

One of ordinary skill in the art given the guidance of this disclosure will be able to formulate an unlimited variety of freshening composition comprising one or more of the compounds described herein. Some non-limiting, preferred blends of perfume raw materials for use in freshening compositions of the present invention are described herein, and more specifically in the Examples. A blend of perfume raw materials comprises a plurality of perfume raw materials. It is understood and one of ordinary skill in the art will appreciate that, if not clearly contradicted by the content of this specification, each embodiment of a preferred blend of perfume raw materials and/or features/elements disclosed as part of that embodiment can be combined with any of the embodiments hereinabove or hereinbelow.

In some embodiments of the present invention, a blend of perfume raw materials, referred to herein from time to time as Fragrance "Apple" or Apple Fragrance comprises one or more of the compounds listed in Table 1:

TABLE 1

Compounds in Fragrance Apple as identified by their respective CAS numbers and IUPAC nomenclature. One of ordinary skill in the art will appreciate that in this table and in Tables 2-4, allyl hexanoate refers to hexanoic acid, 2-propenyl ester, allyl heptanoate refers to heptanoic acid, 2-propyl ester, benzaldehyde refers to phenylmethanol aldehyde, and hexyl acetate refers to acetate C-6.

| CAS # | IUPAC NOMENCLATURE |
|---|---|
| 67634-00-8 | Allyl (3-methylbutoxy) acetate |
| 123-68-2 | Allyl hexanoate |

TABLE 1-continued

Compounds in Fragrance Apple as identified by their respective CAS numbers and IUPAC nomenclature. One of ordinary skill in the art will appreciate that in this table and in Tables 2-4, allyl hexanoate refers to hexanoic acid, 2-propenyl ester, allyl heptanoate refers to heptanoic acid, 2-propyl ester, benzaldehyde refers to phenylmethanol aldehyde, and hexyl acetate refers to acetate C-6.

| CAS # | IUPAC NOMENCLATURE |
|---|---|
| 2705-87-5 | Allyl 3-cyclohexylpropanoate |
| 142-19-8 | Allyl heptanoate |
| 100-52-7 | Benzaldehyde |
| 103-95-7 | 3-(4-Isopropylphenyl)-2-methylpropanal |
| 18479-58-8 | 2,6-Dimethyloct-7-en-2-ol |
| 151-05-3 | 1,1-Dimethyl-2-phenylethyl acetate |
| 10094-34-5 | 1,1-Dimethyl-2-phenylethyl butyrate |
| 7452-79-1 | Ethyl 2-methylbutanoate |
| 4940-11-8 | 2-Ethyl-3-hydroxy-4H-pyran-4-one |
| 121-32-4 | 3-Ethoxy-4-hydroxybenzaldehyde |
| 105-95-3 | 1,4-Dioxacycloheptadecane-5,17-dione |
| 97-53-0 | 4-Allyl-2-methoxyphenol |
| 6413-10-1 | Ethyl (2-methyl-1,3-dioxolan-2-yl) acetate |
| 24851-98-7 | Methyl (3-oxo-2-pentylcyclopentyl) acetate |
| 6728-26-3 | Hex-2-enal |
| 142-92-7 | Hexyl acetate |
| 101-86-0 | 2-Benzylideneoctanal |
| 1335-66-6 | 4,5,6-Trimethylcyclohex-3-ene-1-carbaldehyde |
| 54464-57-2 | 1-(2,3,8,8-Tetramethyl-1,2,3,4,5,6,7,8-octahydronaphthalen-2-yl) ethanone |
| 3681-71-8 | Hex-3-en-1-yl acetate |
| 928-96-1 | Hex-3-en-1-ol |
| 39255-32-8 | Ethyl 2-methylpentanoate |
| 104-61-0 | 5-Pentyldihydrofuran-2(3H)-one |
| 103-60-6 | 2-Phenoxyethyl 2-methylpropanoate |
| 93-92-5 | 1-Phenylethyl acetate |
| 68039-49-6 | 2,4-Dimethylcyclohex-3-ene-1-carbaldehyde |
| 104-67-6 | 5-Heptyldihydrofuran-2(3H)-one |
| 88-41-5 | 2-tert-Butylcyclohexyl acetate |

Thus, a preferred freshening composition of the present invention comprises a blend of perfume raw materials, which comprises one or more compounds selected from the group consisting of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-phenylethyl acetate, 2,4-dimethylcyclohex-3-ene-1-carbaldehyde, 5-heptyldihydrofuran-2(3H)-one, and 2-tert-butylcyclohexyl acetate. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple," consists of the compounds listed in Table 1.

Thus, a preferred blend of perfume raw materials of the present invention consists of allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 1-pentyldihydrofuran-2(3H)-one, 2-phenoxyethyl 2-methypropanoate, 1-phenylethyl acetate, 2,4-dimethylcyclohex-3-ene-1-carbaldehyde, 5-heptyldihydrofuran-2(3H)-one, and 2-tert-butylcyclohexyl acetate. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance, comprises one or more compounds listed in Table 2 at the indicated weight percentage range.

TABLE 2

Compounds in Fragrance Apple as identified by their respective CAS numbers, IUPAC nomenclatures and weight percentage ranges. Weight percentage range given for each compound is in reference to the total weight of the blend of perfume raw materials.

| CAS # | IUPAC NOMENCLATURE | WEIGHT PERCENTAGE RANGE |
|---|---|---|
| 67634-00-8 | Allyl (3-methylbutoxy) acetate | About 0.1-20.0 |
| 123-68-2 | Allyl hexanoate | About 0.1-10.0 |
| 2705-87-5 | Allyl 3-cyclohexylpropanoate | About 0.1-10.0 |
| 142-19-8 | Allyl heptanoate | About 0.1-10.0 |
| 100-52-7 | Benzaldehyde | About 0.1-10.0 |
| 103-95-7 | 3-(4-Isopropylphenyl)-2-methylpropanal | About 0.1-10.0 |
| 18479-58-8 | 2,6-Dimethyloct-7-en-2-ol | About 1.0-20.0 |
| 151-05-3 | 1,1-Dimethyl-2-phenylethyl acetate | About 0.1-10.0 |
| 10094-34-5 | 1,1-Dimethyl-2-phenylethyl butyrate | About 1.0-20.0 |
| 7452-79-1 | Ethyl 2-methylbutanoate | About 0.1-10.0 |
| 4940-11-8 | 2-Ethyl-3-hydroxy-4H-pyran-4-one | About 0.1-10.0 |
| 121-32-4 | 3-Ethoxy-4-hydroxybenzaldehyde | About 0.1-10.0 |
| 105-95-3 | 1,4-Dioxacycloheptadecane-5,17-dione | About 1.0-50.0 |
| 97-53-0 | 4-Allyl-2-methoxyphenol | About 1.0-20.0 |
| 6413-10-1 | Ethyl (2-methyl-1,3-dioxolan-2-yl) acetate | About 0.1-20.0 |
| 24851-98-7 | Methyl (3-oxo-2-pentylcyclopentyl) acetate | About 1.0-20.0 |
| 6728-26-3 | Hex-2-enal | About 0.01-10.0 |
| 142-92-7 | Hexyl acetate | About 0.1-10.0 |
| 101-86-0 | 2-Benzylideneoctanal | About 1.0-20.0 |
| 1335-66-6 | 4,5,6-Trimethylcyclohex-3-ene-1-carbaldehyde | About 1.0-20.0 |
| 54464-57-2 | 1-(2,3,8,8-Tetramethyl-1,2,3,4,5,6,7,8-octahydronaphthalen-2-yl) ethanone | About 1.0-20.0 |
| 3681-71-8 | Hex-3-en-1-yl acetate | About 0.1-10.0 |
| 928-96-1 | Hex-3-en-1-ol | About 0.1-10.0 |
| 39255-32-8 | Ethyl 2-methylpentanoate | About 0.1-10.0 |
| 104-61-0 | 5-Pentyldihydrofuran-2(3H)-one | About 0.1-10.0 |
| 103-60-6 | 2-Phenoxyethyl 2-methylpropanoate | About 0.1-20 |
| 93-92-5 | 1-Phenylethyl acetate | About 0.1-10 |
| 68039-49-6 | 2,4-Dimethylcyclohex-3-ene-1-carbaldehyde | About 0.1-20.0 |

TABLE 2-continued

Compounds in Fragrance Apple as identified by their respective CAS numbers, IUPAC nomenclatures and weight percentage ranges. Weight percentage range given for each compound is in reference to the total weight of the blend of perfume raw materials.

| CAS # | IUPAC NOMENCLATURE | WEIGHT PERCENTAGE RANGE |
|---|---|---|
| 104-67-6 | 5-Heptyldihydrofuran-2(3H)-one | About 2.0-80.0 |
| 88-41-5 | 2-tert-Butylcyclohexyl acetate | About 2.0-80.0 |
| | TOTAL | 100.00 |

Thus, a preferred blend of perfume raw materials of the present invention comprises one or more compounds with a weight percentage range selected from the group consisting of from about 0.1-20.0 wt % of allyl (3-methylbutoxy) acetate, from about 0.1-10.0 wt 00 of allyl hexanoate, from about 0.1-10.0 wt 00 of allyl 3-cyclohexylpropanoate, from about 0.1-10.0 wt 0% of allyl heptanoate, from about 0.1-10.0 wt 00 of benzaldehyde, from about 0.1-10.0 wt 0% of 3-(4-isopropylphenyl)-2-methylpropanal, from about 1.0-20.0 wt 00 of 2,6-dimethyloct-7-en-2-ol, from about 0.1-10.0 wt 00 of 1,1-dimethyl-2-phenyl ethyl acetate, from about 1.0-20.0 wt 00 of 1,1-dimethyl-2-phenyl ethyl butyrate, from about 0.1-10.0 wt 00 of ethyl 2-methylbutanoate, from about 0.1-10.0 wt % of 2-ethyl-3-hydroxy-4H-pyran-4-one, from about 0.1-10.0 wt % of 3-ethoxy-4-hydroxybenzaldehyde, from about 1.0-50.0 wt % of 1,4-dioxacycloheptadecane-5,17-dione, from about 1.0-20.0 wt % of 4-allyl-2-methoxyphenol, from about 0.1-20.0 wt % of ethyl (2-methyl-1,3-dioxolan-2-yl) acetate, from about 1.0-20.0 wt % of methyl (3-oxo-2-pentylcyclopentyl) acetate, from about 0.01-10.0 wt % of hex-2-enal, from about 0.1-10.0 wt % of hexyl acetate, from about 1.0-20.0 wt % of 2-benzylideneoctanal, from about 1.0-20.0 wt % of 4,5,6-trimethylcyclohex-3-ene-1-carbaldehyde, from about 1.0-20.0 wt % of 1-(2,3,8,8-tetramethyl-1,2,3,4,5,6,7,8-octahydronaphthalen-2-yl) ethanone, from about 0.1-10.0 wt % of hex-3-en-1-yl acetate, from about 0.1-10.0 wt % of hex-3-en-1-ol, from about 0.1-10.0 wt % of ethyl 2-methylpentanoate, from about 0.1-10.0 wt % of 5-pentyldihydrofuran-2(3H)-one, from about 0.1-20.0 wt % of 2,4-dimethylcyclohex-3-ene-1-carbaldehyde, from about 2.0-80.0 wt % of 5-heptyldihydrofuran-2(3H)-one, and from about 2.0-80.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple" or Apple Fragrance consists of the compounds listed in Table 2 at the indicated weight percentage range.

Thus, a preferred blend of perfume raw materials of the present invention consists of from about 0.1-20.0 wt % of allyl (3-methylbutoxy) acetate, from about 0.1-10.0 wt % of allyl hexanoate, from about 0.1-10.0 wt % of allyl 3-cyclohexylpropanoate, from about 0.1-10.0 wt % of allyl heptanoate, from about 0.1-10.0 wt % of benzaldehyde, from about 0.1-10.0 wt % of 3-(4-isopropylphenyl)-2-methylpropanal, from about 1.0-20.0 wt % of 2,6-dimethyloct-7-en-2-ol, from about 0.1-10.0 wt % of 1,1-dimethyl-2-phenylethyl acetate, from about 1.0-20.0 wt % of 1,1-dimethyl-2-phenylethyl butyrate, from about 0.1-10.0 wt % of ethyl 2-methylbutanoate, from about 0.1-10.0 wt % of 2-ethyl-3-hydroxy-4H-pyran-4-one, from about 0.1-10.0 wt % of 3-ethoxy-4-hydroxybenzaldehyde, from about 1.0-50.0 wt % of 1,4-dioxacycloheptadecane-5,17-dione, from about 1.0-20.0 wt % of 4-allyl-2-methoxyphenol, from about 0.1-20.0 wt % of ethyl (2-methyl-1,3-dioxolan-2-yl) acetate, from about 1.0-20.0 wt % of methyl (3-oxo-2-entylcyclopentyl) acetate, from about 0.01-10.0 wt % of hex-2-enal, from about 0.1-10.0 wt % of hexyl acetate, from about 1.0-20.0 wt % of 2-benzylideneoctanal, from about 1.0-20.0 wt % of 4,5,6-trimethylcyclohex-3-ene-1-carbaldehyde, from about 1.0-20.0 wt % of 1-(2,3,8,8-tetramethyl-1,2,3,4,5,6,7,8-octahydronaphthalen-2-yl) ethanone, from about 0.1-10.0 wt % of hex-3-en-1-yl acetate, from about 0.1-10.0 wt % of hex-3-en-1-ol, from about 0.1-10.0 wt % of ethyl 2-methylpentanoate, from about 0.1-10.0 wt % of 5-pentyldihydrofuran-2(3H)-one, from about 0.1-20.0 wt % of 2,4-dimethylcyclohex-3-ene-1-carbaldehyde, from about 2.0-80.0 wt % of 5-heptyldihydrofuran-2(3H)-one, and from about 2.0-80.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance comprises one or more compounds listed in Table 3 at the indicated weight percentage range.

TABLE 3

Compounds in Fragrance Apple as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 67634-00-8 | Allyl (3-methylbutoxy) acetate | About 0.2-10.0 |
| 123-68-2 | Allyl hexanoate | About 0.1-4.0 |
| 2705-87-5 | Allyl 3-cyclohexylpropanoate | About 0.1-5.0 |
| 142-19-8 | Allyl heptanoate | About 0.1-5.0 |
| 100-52-7 | Benzaldehyde | About 0.1-3.0 |
| 103-95-7 | 3-(4-Isopropylphenyl)-2-methylpropanal | About 0.1-5.0 |
| 18479-58-8 | 2,6-Dimethyloct-7-en-2-ol | About 1.0-10.0 |
| 151-05-3 | 1,1-Dimethyl-2-phenylethyl acetate | About 0.1-5.0 |
| 10094-34-5 | 1,1-Dimethyl-2-phenylethyl butyrate | About 1.0-10.0 |
| 7452-79-1 | Ethyl 2-methylbutanoate | About 0.1-5.0 |
| 4940-11-8 | 2-Ethyl-3-hydroxy-4H-pyran-4-one | About 0.1-2.0 |
| 121-32-4 | 3-Ethoxy-4-hydroxybenzaldehyde | About 0.1-5.0 |
| 105-95-3 | 1,4-Dioxacycloheptadecane-5,17-dione | About 1.0-20.0 |
| 97-53-0 | 4-Allyl-2-methoxyphenol | About 1.0-10.0 |
| 6413-10-1 | Ethyl (2-methyl-1,3-dioxolan-2-yl) acetate | About 0.2-10.0 |
| 24851-98-7 | Methyl (3-oxo-2-pentylcyclopentyl) acetate | About 1.0-10.0 |

TABLE 3-continued

Compounds in Fragrance Apple as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 6728-26-3 | Hex-2-enal | About 0.01-1.0 |
| 142-92-7 | Hexyl acetate | About 0.1-8.0 |
| 101-86-0 | 2-Benzylideneoctanal | About 1.0-10.0 |
| 1335-66-6 | 4,5,6-Trimethylcyclohex-3-ene-1-carbaldehyde | About 1.0-10.0 |
| 54464-57-2 | 1-(2,3,8,8-Tetramethyl-1,2,3,4,5,6,7,8-octahydronaphthalen-2-yl) ethanone | About 1.0-10.0 |
| 3681-71-8 | Hex-3-en-1-yl acetate | About 0.1-5.0 |
| 928-96-1 | Hex-3-en-1-ol | About 0.1-7.0 |
| 39255-32-8 | Ethyl 2-methylpentanoate | About 0.1-5.0 |
| 104-61-0 | 5-Pentyldihydrofuran-2(3H)-one | About 0.1-7.0 |
| 103-60-6 | 2-Phenoxyethyl 2-methylpropanoate | About 0.1-10.0 |
| 93-92-5 | 1-Phenylethyl acetate | About 0.1-3.0 |
| 68039-49-6 | 2,4-Dimethylcyclohex-3-ene-1-carbaldehyde | About 0.2-10.0 |
| 104-67-6 | 5-Heptyldihydrofuran-2(3H)-one | About 2.0-50.0 |
| 88-41-5 | 2-tert-Butylcyclohexyl acetate | About 2.0-50.0 |
| | TOTAL | 100.00 |

Thus, a preferred blend of perfume raw materials of the present invention comprises one or more compounds with a weight percentage range selected from the group consisting of from about 0.2-10.0 wt % of allyl (3-methylbutoxy) acetate, from about 0.1-4.0 wt % of allyl hexanoate, from about 0.1-5.0 wt % of allyl 3-cyclohexylpropanoate, from about 0.1-5.0 wt % of allyl heptanoate, from about 0.1-3.0 wt % of benzaldehyde, from about 0.1-5.0 wt % of 3-(4-isopropylphenyl)-2-methylpropanal, from about 1.0-10.0 wt % of 2,6-dimethyloct-7-en-2-ol, from about 0.1-5.0 wt % of 1,1-dimethyl-2-phenylethyl acetate, from about 1.0-10.0 wt % of 1,1-dimethyl-2-phenylethyl butyrate, from about 0.1-5.0 wt % of ethyl 2-methylbutanoate, from about 0.1-2.0 wt % of 2-ethyl-3-hydroxy-4H-pyran-4-one, from about 0.1-5.0 wt % of 3-ethoxy-4-hydroxybenzaldehyde, from about 1.0-20.0 wt % of 1,4-dioxacycloheptadecane-5,17-dione, from about 1.0-10.0 wt % of 4-allyl-2-methoxyphenol, from about 0.2-10.0 wt % of ethyl (2-methyl-1,3-dioxolan-2-yl) acetate, from about 1.0-10.0 wt % of methyl (3-oxo-2-pentylcyclopentyl) acetate, from about 0.01-1.0 wt % of hex-2-enal, from about 0.1-8.0 wt % of hexyl acetate, from about 1.0-10.0 wt % of 2-benzylideneoctanal, from about 1.0-10.0 wt % of 4,5,6-trimethylcyclohex-3-ene-1-carbaldehyde, from about 1.0-10.0 wt % of 1-(2,3,8,8-tetramethyl-1,2,3,4,5,6,7,8-octahydronaphthalen-2-yl) ethanone, from about 0.1-5.0 wt % of hex-3-en-1-yl acetate, from about 0.1-7.0 wt % of hex-3-en-1-ol, from about 0.1-5.0 wt % of ethyl 2-methylpentanoate, from about 0.1-7.0 wt % of 5-pentyldihydrofuran-2(3H)-one, from about 0.2-10.0 wt % of 2-phenoxyethyl 2-methylpropanoate, from about 0.1-3.0 wt % of 1-phenylethyl acetate, from about 0.2-10.0 wt % of 2,4-dimethylcyclohex-3-ene-1-carbaldehyde, from about 2.0-50.0 wt % of 5-heptyldihydrofuran-2(3H)-one, and from about 2.0-50.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Apple or Apple Fragrance" consists of the compounds listed in Table 3 at the indicated weight percentage range.

Thus, a preferred blend of perfume raw materials of the present invention consists of from about 0.2-10.0 wt % of allyl (3-methylbutoxy) acetate, from about 0.1-4.0 wt % of allyl hexanoate, from about 0.1-5.0 wt % of allyl 3-cyclohexylpropanoate, from about 0.1-5.0 wt % of allyl heptanoate, from about 0.1-3.0 wt % of benzaldehyde, from about 0.1-5.0 wt % of 3-(4-isopropylphenyl)-2-methylpropanal, from about 1.0-10.0 wt % of 2,6-dimethyloct-7-en-2-ol, from about 0.1-5.0 wt % of 1,1-dimethyl-2-phenylethyl acetate, from about 1.0-10.0 wt % of 1,1-dimethyl-2-phenylethyl butyrate, from about 0.1-5.0 wt % of ethyl 2-methylbutanoate, from about 0.1-2.0 wt % of 2-ethyl-3-hydroxy-4H-pyran-4-one, from about 0.1-5.0 wt % of 3-ethoxy-4-hydroxybenzaldehyde, from about 1.0-20.0 wt % of 1,4-dioxacycloheptadecane-5,17-dione, from about 1.0-10.0 wt % of 4-allyl-2-methoxyphenol, from about 0.2-10.0 wt % of ethyl (2-methyl-1,3-dioxolan-2-yl) acetate, from about 1.0-10.0 wt % of methyl (3-oxo-2-pentylcyclopentyl) acetate, from about 0.01-1.0 wt % of hex-2-enal, from about 0.1-8.0 wt % of hexyl acetate, from about 1.0-10.0 wt % of 2-benzylideneoctanal, from about 1.0-10.0 wt % of 4,5,6-trimethylcyclohex-3-ene-1-carbaldehyde, from about 1.0-10.0 wt % of 1-(2,3,8,8-tetramethyl-1,2,3,4,5,6,7,8-octahydronaphthalen-2-yl) ethanone, from about 0.1-5.0 wt % of hex-3-en-1-yl acetate, from about 0.1-7.0 wt % of hex-3-en-1-ol, from about 0.1-5.0 wt % of ethyl 2-methylpentanoate, from about 0.1-7.0 wt % of 5-pentyldihydrofuran-2(3H)-one, from about 0.2-10.0 wt % of 2-phenoxyethyl 2-methylpropanoate, from about 0.1-3.0 wt % of 1-phenylethyl acetate, from about 0.2-10.0 wt % of 2,4-dimethylcyclohex-3-ene-1-carbaldehyde, from about 2.0-50.0 wt % of 5-heptyldihydrofuran-2(3H)-one, and from about 2.0-50.0 wt % of 2-tert-butylcyclohexyl acetate, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Apple" or Apple Fragrance comprises one or more compounds listed in Table 4 at the indicated weight percentage.

TABLE 4

Compounds in Fragrance Apple as identified by their respective CAS numbers, IUPAC nomenclatures and weight percentages. Weight percentage given for each compound is in reference to the total weight of the blend of the perfume raw materials.

| CAS # | IUPAC NOMENCLATURE | WEIGHT PERCENTAGE |
|---|---|---|
| 67634-00-8 | Allyl (3-methylbutoxy) acetate | About 2.0 |
| 123-68-2 | Allyl hexanoate | About 0.4 |
| 2705-87-5 | Allyl 3-cyclohexylpropanoate | About 0.5 |
| 142-19-8 | Allyl heptanoate | About 1.0 |
| 100-52-7 | Benzaldehyde | About 0.3 |
| 103-95-7 | 3-(4-Isopropylphenyl)-2-methylpropanal | About 0.5 |
| 18479-58-8 | 2,6-Dimethyloct-7-en-2-ol | About 5.0 |
| 151-05-3 | 1,1-Dimethyl-2-phenylethyl acetate | About 1.0 |
| 10094-34-5 | 1,1-Dimethyl-2-phenylethyl butyrate | About 5.0 |
| 7452-79-1 | Ethyl 2-methylbutanoate | About 0.5 |
| 4940-11-8 | 2-Ethyl-3-hydroxy-4H-pyran-4-one | About 0.2 |
| 121-32-4 | 3-Ethoxy-4-hydroxybenzaldehyde | About 1.0 |
| 105-95-3 | 1,4-Dioxacycloheptadecane-5,17-dione | About 10.0 |
| 97-53-0 | 4-Allyl-2-methoxyphenol | About 3.0 |
| 6413-10-1 | Ethyl (2-methyl-1,3-dioxolan-2-yl) acetate | About 2.0 |
| 24851-98-7 | Methyl (3-oxo-2-pentylcyclopentyl) acetate | About 5.0 |
| 6728-26-3 | Hex-2-enal | About 0.1 |
| 142-92-7 | Hexyl acetate | About 0.8 |
| 101-86-0 | 2-Benzylideneoctanal | About 5.0 |
| 1335-66-6 | 4,5,6-Trimethylcyclohex-3-ene-1-carbaldehyde | About 5.0 |
| 54464-57-2 | 1-(2,3,8,8-Tetramethyl-1,2,3,4,5,6,7,8-octahydronaphthalen-2-yl) ethanone | About 5.0 |
| 3681-71-8 | Hex-3-en-1-yl acetate | About 0.5 |
| 928-96-1 | Hex-3-en-1-ol | About 0.7 |
| 39255-32-8 | Ethyl 2-methylpentanoate | About 0.5 |
| 104-61-0 | 5-Pentyldihydrofuran-2(3H)-one | About 0.7 |
| 103-60-6 | 2-Phenoxyethyl 2-methylpropanoate | About 2.0 |
| 93-92-5 | 1-Phenylethyl acetate | About 0.3 |
| 68039-49-6 | 2,4-Dimethylcyclohex-3-ene-1-carbaldehyde | About 2.0 |
| 104-67-6 | 5-Heptyldihydrofuran-2(3H)-one | About 15.0 |
| 88-41-5 | 2-tert-Butylcyclohexyl acetate | About 25.0 |
| | TOTAL | 100.00 |

Thus, a preferred blend of perfume raw material of the present invention comprises one or more compounds with a weight percentage selected from the group consisting of about 2.0 wt % of allyl (3-methylbutoxy) acetate, about 0.4 wt % of allyl hexanoate, about 0.5 wt % of allyl 3-cyclohexylpropanoate, about 1.0 wt % of allyl heptanoate, about 0.3 wt % of benzaldehyde, about 0.5 wt % of 3-(4-isopropylphenyl)-2-methylpropanal, about 5.0 wt % of 2,6-dimethyloct-7-en-2-ol, about 1.0 wt % of 1,1-dimethyl-2-phenylethyl acetate, about 5.0 wt % of 1,1-dimethyl-2-phenylethyl butyrate, about 0.5 wt % of ethyl 2-methylbutanoate, about 0.2 wt % of 2-ethyl-3-hydroxy-4H-pyran-4-one, about 1.0 wt % of 3-ethoxy-4-hydroxybenzaldehyde, about 10.0 wt % of 1,4-dioxacycloheptadecane-5,17-dione, about 3.0 wt % of 4-allyl-2-methoxyphenol, about 2.0 wt % of ethyl (2-methyl-1,3-dioxolan-2-yl) acetate, about 5.0 wt % of methyl (3-oxo-2-pentylcyclopentyl) acetate, about 0.1 wt % of hex-2-enal, about 0.8 wt % of hexyl acetate, about 5.0 wt % of 2-benzylideneoctanal, about 5.0 wt % of 4,5,6-trimethylcyclohex-3-ene-1-carbaldehyde, about 5.0 wt % of 1-(2,3,8,8-tetramethyl-1,2,3,4,5,6,7,8-octahydronaphthalen-2-yl) ethanone, about 0.5 wt % of hex-3-en-1-yl acetate, about 0.7 wt % of hex-3-en-1-ol, about 0.5 wt % of ethyl 2-methylpentanoate, about 0.7 wt % of 5-pentyldihydrofuran-2(3H)-one, about 2.0 wt % of 2-phenoxyethyl 2-methylpropanoate, about 0.3 wt % of 1-phenylethyl acetate, about 2.0 wt % of 2,4-dimethylcyclohex-3-ene-1-carbaldehyde, about 15.0 wt % of 5-heptyldihydrofuran-2(3H)-one, and about 25.0 wt % of 2-tert-butylcyclohexyl acetate, wherein the weight percentage of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a preferred blend of perfume raw materials, referred to herein from time to time as Fragrance "Apple or Apple Fragrance" consists of the compounds listed in Table 4 at the indicated weight percentage.

Thus, a preferred blend of perfume raw materials of the present invention consists of about 2.0 wt % of allyl (3-methylbutoxy) acetate, about 0.4 wt % of allyl hexanoate, about 0.5 wt % of allyl 3-cyclohexylpropanoate, about 1.0 wt % of allyl heptanoate, about 0.3 wt % of benzaldehyde, about 0.5 wt % of 3-(4-isopropylphenyl)-2-methylpropanal, about 5.0 wt % of 2,6-dimethyloct-7-en-2-ol, about 1.0 wt % of 1,1-dimethyl-2-phenylethyl acetate, about 5.0 wt % of 1,1-dimethyl-2-phenylethyl butyrate, about 0.5 wt % of ethyl 2-methylbutanoate, about 0.2 wt % of 2-ethyl-3-hydroxy-4H-pyran-4-one, about 1.0 wt % of 3-ethoxy-4-hydroxybenzaldehyde, about 10.0 wt % of 1,4-dioxacycloheptadecane-5,17-dione, about 3.0 wt % of 4-allyl-2-methoxyphenol, about 2.0 wt % of ethyl (2-methyl-1,3-dioxolan-2-yl) acetate, about 5.0 wt % of methyl (3-oxo-2-pentylcyclopentyl) acetate, about 0.1 wt % of hex-2-enal, about 0.8 wt % of hexyl acetate, about 5.0 wt % of 2-benzylideneoctanal, about 5.0 wt % of 4,5,6-trimethylcyclohex-3-ene-1-carbaldehyde, about 5.0 wt % of 1-(2,3,8,8-tetramethyl-1,2,3,4,5,6,7,8-octahydronaphthalen-2-yl) ethanone, about 0.5 wt % of hex-3-en-1-yl acetate, about 0.7 wt % of hex-3-en-1-ol, about 0.5 wt % of ethyl 2-methylpentanoate, about 0.7 wt % of 5-pentyldihydrofuran-2(3H)-one, about 2.0 wt % of 2-phenoxyethyl 2-methylpropanoate, about 0.3 wt % of 1-phenylethyl acetate, about 2.0 wt % of 2,4-dimethylcyclohex-3-ene-1-carbaldehyde, about 15.0 wt % of 5-heptyldihydrofuran-2(3H)-one, and about 25.0 wt % of 2-tert-butylcyclohexyl acetate, wherein the weight percentage of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, comprises one or more of the compounds listed in Table 5.

TABLE 5

Compounds in Fragrance Floral Fresh as identified by their respective CAS numbers and IUPAC nomenclature. One of ordinary skill in the art will appreciate that hexyl salicylate refers to benzoic acid, 2-hydroxy-, hexyl ester.

| CAS # | IUPAC NOMENCLATURE |
|---|---|
| 54464-57-2 | 1-(2,3,8,8-Tetramethyl-1,2,3,4,5,6,7,8-octahydronaphthalen-2-yl) ethanone |

TABLE 5-continued

Compounds in Fragrance Floral Fresh as identified by their respective CAS numbers and IUPAC nomenclature. One of ordinary skill in the art will appreciate that hexyl salicylate refers to benzoic acid, 2-hydroxy-, hexyl ester.

| CAS # | IUPAC NOMENCLATURE |
|---|---|
| 24851-98-7 | Methyl (3-oxo-2-pentylcyclopentyl) acetate |
| 101-86-0 | 2-Benzylideneoctanal |
| 32388-55-9 | 1-Cedr-8-en-9-ylethanone |
| 32210-23-4 | 4-tert-Butylcyclohexyl acetate |
| 115-95-7 | 1,5-Dimethyl-1-vinylhex-4-en-1-yl acetate |
| 78-70-6 | 3,7-Dimethylocta-1,6-dien-3-ol |
| 1335-46-2 | 1-(2,6,6-Trimethylcyclohex-2-en-1-yl) pent-1-en-3-one |
| 63500-71-0 | 2-Isobutyl-4-methyltetrahydro-2H-pyran-4-ol |
| 105-95-3 | 1,4-Dioxacycloheptadecane-5,17-dione |
| 18479-58-8 | 2,6-Dimethyloct-7-en-2-ol |
| 103-95-7 | 3-(4-Isopropylphenyl)-2-methylpropanal |
| 6259-76-3 | Hexyl salicylate |
| 67634-15-5 | 3-(4-Ethylphenyl)-2,2-dimethylpropanal |
| 67634-14-4 | 3-(2-ethylphenyl)-2,2-dimethylpropanal |
| 5413-60-5 | 3a,4,5,6,7,7a-Hexahydro-1H-4,7-methanoinden-6-yl acetate |
| 8000-27-9 | Cedarwood oil, Virginian (*Juniperus virginiana L.*)* |
| 110-41-8 | 2-Methylundecanal |
| 101-48-4 | (2,2-Dimethoxyethyl) benzene |
| 112-45-8 | Undec-10-enal |
| 928-96-1 | Hex-3-en-1-ol |
| 1205-17-0 | 3-(1,3-Benzodioxol-5-yl)-2-methylpropanal |
| 93-92-5 | 1-Phenylethyl acetate |
| 3738-00-9 | 3a,6,6,9a-Tetramethyldodecahydronaphtho[2,1-b] furan |
| 67634-00-8 | Allyl (3-methylbutoxy) acetate |
| 56973-85-4 | 1-(5,5-Dimethylcyclohex-1-en-1-yl) pent-4-en-1-one |

*Cedarwood oil, Virginian (*Juniperus virginiana L.*) is entered in this table and in Tables 6-8 and 10 as the principal RIFM (Research Institute of Fragrance Materials) botanical nomenclature as it could not be found in the IUPAC database. In general, cedarwood oils extracted from *Juniperus virginiana* of the Cypressaceae family, also known as Virginian, red, eastern red or southern red cedar, as well as Bedford cedarwood, may be used. The main chemical components of cedarwood oil are α-cedrene, β-cedrene, thujopsene, other sesquiterpenes, cedrol and widdrol Thus, a preferred blend of perfume raw materials of the present invention comprises one or more compounds selected from the group consisting of 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7a-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9-atetramethyldodecahydronaphtho[2,1-b]furan, allyl (3-methylbutoxy) acetate, and 1-(5,5-dimethylcyclohex-1-en-1-yl) pent-4-en-1-one. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 5.

Thus, a preferred blend of perfume raw materials of the present invention consists of 1-(2,3,8,8-tetramethyl-1,2,3,4, 5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7α-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9α-tetramethyldodecahydronaphtho[2,1-b]furan, allyl (3-methylbutoxy) acetate, and 1-(5,5-dimethylcyclohex-1-en-1-yl) pent-4-en-1-one. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as "Floral Fresh" or Floral Fresh Fragrance, comprises one or more compounds listed in Table 6 at the indicated weight percentage range.

TABLE 6

Compounds in Fragrance Floral Fresh as identified by their respective CAS numbers, IUPAC nomenclatures and weight percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 54464-57-2 | 1-(2,3,8,8-Tetramethyl-1,2,3,4,5,6,7,8-octahydronaphthalen-2-yl) ethanone | About 1.0-50.0 |
| 24851-98-7 | Methyl (3-oxo-2-pentylcyclopentyl) acetate | About 1.0-50.0 |
| 101-86-0 | 2-Benzylideneoctanal | About 1.0-50.0 |
| 32388-55-9 | 1-Cedr-8-en-9-ylethanone | About 0.5-20.0 |
| 32210-23-4 | 4-tert-Butylcyclohexyl acetate | About 0.5-20.0 |
| 115-95-7 | 1,5-Dimethyl-1-vinylhex-4-en-1-yl acetate | About 0.5-20.0 |
| 78-70-6 | 3,7-Dimethylocta-1,6-dien-3-ol | About 0.5-20.0 |
| 1335-46-2 | 1-(2,6,6-Trimethylcyclohex-2-en-1-yl) pent-1-en-3-one | About 0.5-20.0 |
| 63500-71-0 | 2-Isobutyl-4-methyltetrahydro-2H-pyran-4-ol | About 0.5-20.0 |
| 105-95-3 | 1,4-Dioxacycloheptadecane-5,17-dione | About 0.5-20.0 |
| 18479-58-8 | 2,6-Dimethyloct-7-en-2-ol | About 0.5-20.0 |
| 103-95-7 | 3-(4-Isopropylphenyl)-2-methylpropanal | About 0.1-15.0 |
| 6259-76-3 | Hexyl salicylate | About 0.1-15.0 |
| 67634-15-5 | 3-(4-Ethylphenyl)-2,2-dimethylpropanal | About 0.1-15.0 |
| 67634-14-4 | 3-(2-ethylphenyl)-2,2-dimethylpropanal | About 0.1-15.0 |
| 5413-60-5 | 3a,4,5,6,7,7a-Hexahydro-1H-4,7-methanoinden-6-yl acetate | About 0.1-15.0 |
| 8000-27-9 | Cedarwood oil, Virginian (*Juniperus virginiana L.*) | About 0.1-15.0 |
| 110-41-8 | 2-Methylundecanal | About 0.1-15.0 |
| 101-48-4 | (2,2-Dimethoxyethyl) benzene | About 0.1 15.0 |
| 112-45-8 | Undec-10-enal | About 0.1-15.0 |
| 928-96-1 | Hex-3-en-1-ol | About 0.1-15.0 |
| 1205-17-0 | 3-(1,3-Benzodioxol-5-yl)-2-methylpropanal | About 0.1-15.0 |
| 93-92-5 | 1-Phenylethyl acetate | About 0.1-15.0 |
| 3738-00-9 | 3a,6,6,9a-Tetramethyldodecahydronaphtho[2,1-b] furan | About 0.1-15.0 |
| 67634-00-8 | Allyl (3-methylbutoxy) acetate | About 0.1-15.0 |
| 56973-85-4 | 1-(5,5-Dimethylcyclohex-1-en-1-yl) pent-4-en-1-one | About 0.01 15.0 |
| | TOTAL | 100.00 |

Thus, a preferred blend of perfume raw materials of the present invention comprises one or more compounds with a weight percentage selected from the group consisting of from about 1.0-50.0 wt % of 1-(2,3,8,8-tetramethyl-1,2,3,4,5,6,7,8-octahydronaphthalen-2-yl) ethanone, from about 1.0-50.0 wt % of methyl (3-oxo-2-pentylcyclopentyl) acetate, from about 1.0-50.0 wt % of 2-benzylideneoctanal, from about 0.5-20.0 wt % of 1-cedr-8-en-9-ylethanone, from about 0.5-20.0 wt % of 4-tert-butylcyclohexyl acetate, from about 0.5-20.0 wt % of 1,5-dimethyl-1-vinylhex-4-en-1-yl acetate, from about 0.5-20.0 wt % of 3,7-dimethylocta-1,6-dien-3-ol, from about 0.5-20.0 wt % of 1-(2,6,6-trimethylcyclohex-2-en-1-yl) pent-1-en-3-one, from about 0.5-20.0 wt % of 2-isobutyl-4-methyltetrahydro-2H-pyran-4-ol, from about 0.5-20.0 wt % of 1,4-dioxacycloheptadecane-5,17-dione, from about 0.5-20.0 wt % of 2,6-dimethyloct-7-en-2-ol, from about 0.1-15.0 wt % of 3-(4-isopropylphenyl)-2-methylpropanal, hexyl salicylate, from about 0.1-15.0 wt % of 3-(4-ethylphenyl)-2,2-dimethylpropanal, from about 0.1-15.0 wt % of 3-(2-ethylphenyl)-2,2-dimethylpropanal, from about 0.1-15.0 wt % of 3a,4,5,6,7,7α-hexahydro-1H-4,7-methanoinden-6-yl acetate, from about 0.1-15.0 wt % of Cedarwood oil, Virginian (*Juniperus virginiana* L.), from about 0.1-15.0 wt % of 2-methylundecanal, (2,2-dimethoxyethyl) benzene, from about 0.1-15.0 wt % of undec-10-enal, from about 0.1-15.0 wt % of hex-3-en-1-ol, from about 0.1-15.0 wt % of 3-(1,3-benzodioxol-5-yl)-2-methylpropanal, from about 0.1-15.0 wt % of 1-phenylethyl acetate, from about 0.1-15.0 wt % of 3a,6,6,9-atetramethyldodecahydronaphtho[2,1-b]furan, from about 0.1-15.0 wt % of allyl (3-methylbutoxy) acetate, and from about 0.01-15.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 6 at the indicated weight percentage range.

Thus, a preferred blend of perfume raw materials of the present invention consists of from about 1.0-50.0 wt % of 1-(2,3,8,8-tetramethyl-1,2,3,4,5,6,7,8-octahydronaphthalen-2-yl) ethanone, from about 1.0-50.0 wt % of methyl (3-oxo-2-pentylcyclopentyl) acetate, from about 1.0-50.0 wt % of 2-benzylideneoctanal, from about 0.5-20.0 wt % of 1-cedr-8-en-9-ylethanone, from about 0.5-20.0 wt % of 4-tert-butylcyclohexyl acetate, from about 0.5-20.0 wt % of 1,5-dimethyl-1-vinylhex-4-en-1-yl acetate, from about 0.5-20.0 wt % of 3,7-dimethylocta-1,6-dien-3-ol, from ab out 0.5-20.0 wt % of 1-(2,6,6-trimethylcyclohex-2-en-1-yl) pent-1-en-3-one, from about 0.5-20.0 wt % of 2-isobutyl-4-methyltetrahydro-2H-pyran-4-ol, from about 0.5-20.0 wt % of 1,4-dioxacycloheptadecane-5,17-dione, from about 0.5-20.0 dimethylpropanal, from about 0.1-15.0 wt % of 3-(2-ethylphenyl)-2,2-dimethylpropanal, from about 0.1-15.0 wt % of 3a,4,5,6,7,7α-hexahydro-1H-4,7-methanoinden-6-yl acetate, from about 0.1-15.0 wt % of Cedarwood oil, Virginian (*Juniperus virginiana* L.), from about 0.1-15.0 wt % of 2-methylundecanal, (2,2-dimethoxyethyl) benzene, from about 0.1-15.0 wt % of undec-10-enal, from about 0.1-15.0 wt % of hex-3-en-1-ol, from about 0.1-15.0 wt % of 3-(1,3-benzodioxol-5-yl)-2-methylpropanal, from about 0.1-15.0 wt % of 1-phenylethyl acetate, from about 0.1-15.0 wt % of 3a,6,6,9-atetramethyldodecahydronaphtho[2,1-b]furan, from about 0.1-15.0 wt % of allyl (3-methylbutoxy) acetate, and from about 0.01-15.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw material of the present invention, referred to herein from time to time as Fragrance "Floral Fresh" or Floral Fresh Fragrance, comprises one or more compounds listed in Table 7 at the indicated weight percentage range.

TABLE 7

Compounds in Fragrance Floral Fresh as identified by their respective CAS numbers, IUPAC nomenclatures and weigh percentage ranges. Weight percentage range given for each compound is in reference to the total weight of the blend of the perfume raw materials.

| CAS # | IUPAC NOMENCLATURE | WEIGHT PERCENTAGE RANGE |
|---|---|---|
| 54464-57-2 | 1-(2,3,8,8-Tetramethyl-1,2,3,4,5,6,7,8-octahydronaphthalen-2-yl) ethanone | About 1.0-25.0 |
| 24851-98-7 | Methyl (3-oxo-2-pentylcyclopentyl) acetate | About 1.0-25.0 |
| 101-86-0 | 2-Benzylideneoctanal | About 1.0-25.0 |
| 32388-55-9 | 1-Cedr-8-en-9-ylethanone | About 1.0-10.0 |
| 32210-23-4 | 4-tert-Butylcyclohexyl acetate | About 1.0-10.0 |
| 115-95-7 | 1,5-Dimethyl-1-vinylhex-4-en-1-yl acetate | About 1.0-10.0 |
| 78-70-6 | 3,7-Dimethylocta-1,6-dien-3-ol | About 1.0-10.0 |
| 1335-46-2 | 1-(2,6,6-Trimethylcyclohex-2-en-1-yl) pent-1-en-3-one | About 1.0-10.0 |
| 63500-71-0 | 2-Isobutyl-4-methyltetrahydro-2H-pyran-4-ol | About 1.0-10. |
| 105-95-3 | 1,4-Dioxacycloheptadecane-5,17-dione | About 1.0-10.0 |
| 18479-58-8 | 2,6-Dimethyloct-7-en-2-ol | About 1.0-10.0 |
| 103-95-7 | 3-(4-Isopropylphenyl)-2-methylpropanal | About 0.1-10.0 |
| 6259-76-3 | Hexyl salicylate | About 0.1-10.0 |
| 67634-15-5 | 3-(4-Ethylphenyl)-2,2-dimethylpropanal | About 0.1-10.0 |
| 67634-14-4 | 3-(2-ethylphenyl)-2,2-dimethylpropanal | About 0.1-6.0 |
| 5413-60-5 | 3a,4,5,6,7,7a-Hexahydro-1H-4,7-methanoinden-6-yl acetate | About 0.1-10.0 |
| 8000-27-9 | Cedarwood oil, Virginian (*Juniperus virginiana L.*) | About 0.1-10.0 |
| 110-41-8 | 2-Methylundecanal | About 0.1-10.0 |
| 101-48-4 | (2,2-Dimethoxyethyl) benzene | About 0.1-8.0 |
| 112-45-8 | Undec-10-enal | About 0.1-6.0 |
| 928-96-1 | Hex-3-en-1-ol | About 0.1-6.0 |
| 1205-17-0 | 3-(1,3-Benzodioxol-5-yl)-2-methylpropanal | About 0.1-6.0 |
| 93-92-5 | 1-Phenylethyl acetate | About 0.1-5.0 |
| 3738-00-9 | 3a,6,6,9a-Tetramethyldodecahydronaphtho[2,1-b] furan | About 0.1-5.0 |
| 67634-00-8 | Allyl (3-methylbutoxy) acetate | About 0.1-5.0 |
| 56973-85-4 | 1-(5,5-Dimethylcyclohex-1-en-1-yl) pent-4-en-1-one | About 0.01-5.0 |
| | TOTAL | 100.00 |

wt % of 2,6-dimethyloct-7-en-2-ol, from about 0.1-15.0 wt % of 3-(4-isopropylphenyl)-2-methylpropanal, hexyl salicylate, from about 0.1-15.0 wt % of 3-(4-ethylphenyl)-2,2-

Thus, a preferred blend of perfume raw materials of the present invention comprises one or more compounds with a weight percentage selected from the group consisting of from about 1.0-25.0 wt % of 1-(2,3,8,8-tetramethyl-1,2,3,4,5,6,7,8-octahydronaphthalen-2-yl) ethanone, from about 1.0-25.0 wt % of methyl (3-oxo-2-pentylcyclopentyl) acetate, from about 1.0-25.0 wt % of 2-benzylideneoctanal, from about 1.0-10.0 wt % of 1-cedr-8-en-9-ylethanone, 1.0-10.0 wt % of 4-tert-butylcyclohexyl acetate, from about 1.0-10.0 wt % of 1,5-dimethyl-1-vinylhex-4-en-1-yl acetate, from about 1.0-10.0 wt % of 3,7-dimethylocta-1,6-dien-3-ol, from about 1.0-10.0 wt % of 1-(2,6,6-trimethylcyclohex-2-en-1-yl) pent-1-en-3-one, from about 1.0-10.0 wt % of 2-isobutyl-4-methyltetrahydro-2H-pyran-4-ol, from about 1.0-10.0 wt % of 1,4-dioxacycloheptadecane-5,17-dione, from about 1.0-10.0 wt % of 2,6-dimethyloct-7-en-2-ol, from about 0.1-10.0 wt % of 3-(4-isopropylphenyl)-2-methylpropanal, from about 0.1-10.0 wt % of hexyl salicylate, from about 0.1-10.0 wt % of 3-(4-ethylphenyl)-2,2-dimethylpropanal, from about 0.1-6.0 wt % of 3-(2-ethylphenyl)-2,2-dimethylpropanal, from about 0.1-10.0 wt % of 3a,4,5,6,7,7a-hexahydro-1H-4,7-methanoinden-6-yl acetate, from about 0.1-10.0 wt % of Cedarwood oil, Virginian (*Juniperus virginiana* L.), from about 0.1-10.0 wt % of 2-methylundecanal, from about 0.1-8.0 wt % of (2,2-dimethoxyethyl) benzene, from about 0.1-6.0 wt % of undec-10-enal, from about 0.1-6.0 wt % of hex-3-en-1-ol, from about 0.1-6.0 wt % of 3-(1,3-benzodioxol-5-yl)-2-methylpropanal, from about 0.1-5.0 wt % of 1-phenylethyl acetate, from about 0.1-5.0 wt % of 3a,6,6,9a-tetramethyldodecahydronaphtho[2,1-b]furan, from about 0.1-5.0 wt % of allyl (3-methylbutoxy) acetate, and from about 0.01-5.0 wt % of 1-(5,5-dimethylcyclohex-1-en-1-yl) pent-4-en-1-one, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

In some embodiments of the present invention, a blend of perfume raw materials, referred to herein from time to time as Fragrance "Floral Fresh" or Floral Fresh Fragrance, consists of the compounds listed in Table 7 at the indicated weight percentage range.

Thus, a preferred blend of perfume raw materials of the present invention consists of from about 1.0-25.0 wt % of 1-(2,3,8,8-tetramethyl-1,2,3,4,5,6,7,8-octahydronaphthalen-2-yl) ethanone, from about 1.0-25.0 wt % of methyl (3-oxo-2-pentylcyclopentyl) acetate, from about 1.0-25.0 wt % of 2-benzylideneoctanal, from about 1.0-10.0 wt % of 1-cedr-8-en-9-ylethanone, from about 1.0-10.0 wt % of 4-tert-butylcyclohexyl acetate, from about 1.0-10.0 wt % of 1,5-dimethyl-1-vinylhex-4-en-1-yl acetate, from about 1.0-10.0 wt % of 3,7-dimethylocta-1,6-dien-3-ol, from about 1.0-10.0 wt % of 1-(2,6,6-trimethylcyclohex-2-en-1-yl) pent-1-en-3-one, from about 1.0-10.0 wt % of 2-isobutyl-4-methyltetrahydro-2H-pyran-4-ol, from about 1.0-10.0 wt % of 1,4-dioxacycloheptadecane-5,17-dione, from about 1.0-10.0 wt % of 2,6-dimethyloct-7-en-2-ol, from about 0.1-10.0 wt % of 3-(4-isopropylphenyl)-2-methylpropanal, from about 0.1-10 wt % of hexyl salicylate, from about 0.1-10.0 wt % of 3-(4-ethylphenyl)-2,2-dimethylpropanal, from about 0.1-6.0 wt % of 3-(2-ethylphenyl)-2,2-dimethylpropanal, from about 0.1-10.0 wt % of 3a,4,5,6,7,7a-hexahydro-1H-4,7-methanoinden-6-yl acetate, from about 0.1-10.0 wt % of Cedarwood oil, Virginian (*Juniperus virginiana* L.), from about 0.1-10.0 wt % of 2-methylundecanal, from about 0.1-8.0 wt % of (2,2-dimethoxyethyl) benzene, from about 0.1-6.0 wt 0% of undec-10-enal, from about 0.1-6.0 wt 00 of hex-3-en-1-ol, from about 0.1-6.0 wt 00 of 3-(1,3-benzodioxol-5-yl)-2-methylpropanal, 0.1-5.0 wt % of 1-phenylethyl acetate, from about 0.1-5.0 wt % of 3a,6,6,9a-tetramethyldodecahydronaphtho[2,1-b]furan, from about 0.1-5.0 wt % of allyl (3-methylbutoxy) acetate, and from about 0.01-5.0 wt 0 of 1-(5,5-dimethylcyclohex-1-en-1-yl) pent-4-en-D-one, wherein the weight percentage range of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and in particular with any embodiment of a fragrance release modulator and/or features/elements disclosed as part of that embodiment.

A further preferred blend of perfume raw materials of the present invention, referred to herein from time to time as Fragrance "Floral Fresh or Floral Fresh Fragrance" ~comprises one or more compounds listed in Table 8 at the indicated weight percentage.

TABLE 8

Compounds in Fragrance Floral Fresh as identified by their respective CAS numbers, IUPAC nomenclatures and weight percentages. Weight percentage given for each compound is in reference to the total weight of the blend of perfume raw materials.

| CAS # | IUPAC NOMENCLATURE | WEIGHT PERCENTAGE |
|---|---|---|
| 54464-57-2 | 1-(2,3,8,8-Tetramethyl-1,2,3,4,5,6,7,8-octahydronaphthalen-2-yl) ethanone | About 14.0 |
| 24851-98-7 | Methyl (3-oxo-2-pentylcyclopentyl) acetate | About 12.0 |
| 101-86-0 | 2-Benzylideneoctanal | About 11.0 |
| 32388-55-9 | 1-Cedr-8-en-9-ylethanone | About 6.0 |
| 32210-23-4 | 4-tert-Butylcyclohexyl acetate | About 6.0 |
| 115-95-7 | 1,5-Dimethyl-1-vinylhex-4-en-1-yl acetate | About 6.0 |
| 78-70-6 | 3,7-Dimethylocta-1,6-dien-3-ol | About 6.0 |
| 1335-46-2 | 1-(2,6,6-Trimethylcyclohex-2-en-1-yl) pent-1-en-3one | About 6.0 |
| 63500-71-0 | 2-Isobutyl-4-methyltetrahydro-2H-pyran-4-ol | About 6.0 |
| 105-95-3 | 1,4-Dioxacycloheptadecane-5,17-dione | About 6.0 |
| 18479-58-8 | 2,6-Dimethyloct-7-en-2-ol | About 6.0 |
| 103-95-7 | 3-(4-Isopropylphenyl)-2-methylpropanal | About 2.0 |

TABLE 8-continued

Compounds in Fragrance Floral Fresh as identified by their respective CAS numbers, IUPAC nomenclatures and weight percentages. Weight percentage given for each compound is in reference to the total weight of the blend of perfume raw materials.

| CAS # | IUPAC NOMENCLATURE | WEIGHT PERCENTAGE |
|---|---|---|
| 6259-76-3 | Hexyl salicylate | About 2.0 |
| 67634-15-5 | 3-(4-Ethylphenyl)-2,2-dimethylpropanal | About 1.40 |
| 67634-14-4 | 3-(2-ethylphenyl)-2,2-dimethylpropanal | About 0.6 |
| 5413-60-5 | 3a,4,5,6,7,7a-Hexahydro-1H-4,7-methanoinden-6-yl acetate | About 2.0 |
| 8000-27-9 | Cedarwood oil, Virginian (*Juniperus virginiana L.*) | About 2.0 |
| 110-41-8 | 2-Methylundecanal | About 1.0 |
| 101-48-4 | (2,2-Dimethoxyethyl) benzene | About 0.8 |
| 112-45-8 | Undec-10-enal | About 0.6 |
| 928-96-1 | Hex-3-en-1-ol | About 0.6 |
| 1205-17-0 | 3-(1,3-Benzodioxol-5-yl)-2-methylpropanal | About 0.6 |
| 93-92-5 | 1-Phenylethyl acetate | About 0.5 |
| 3738-00-9 | 3a,6,6,9a-Tetramethyldodecahydronaphtho[2,1-b] furan | About 0.4 |
| 67634-00-8 | Allyl (3-methylbutoxy) acetate | About 0.4 |
| 56973-85-4 | 1-(5,5-Dimethylcyclohex-1-en-1-yl) pent-4-en-1-one | About 0.1 |
| | TOTAL | 100.00 |

Thus, a preferred blend of perfume raw materials of the present invention comprises one or more compounds with a weight percentage selected from the group consisting of about 14.0 wt 00 of 1-(2,3,8,8-tetramethyl-1,2,3,4,5,6,7,8-octahydronaphthalen-2-yl) ethanone, about 12.0 wt 00 of methyl (3-oxo-2-pentylcyclopentyl) acetate, about 11.0 wt 00 of 2-benzylideneoctanal, about 6.0 wt 00 of 1-cedr-8-en-9-ylethanone, about 6.0 wt 00 of 4-tert-butylcyclohexyl acetate, about 6.0 wt 0% of 1,5-dimethyl-1-vinylhex-4-en-1-yl acetate, about 6.0 wt % of 3,7-dimethylocta-1,6-dien-3-ol, about 6.0 wt % of 1-(2,6,6-trimethylcyclohex-2-en-1-yl) pent-1-en-3-one, about 6.0 wt % of 2-isobutyl-4-methyltetrahydro-2H-pyran-4-ol, about 6.0 wt % of 1,4-dioxacycloheptadecane-5,17-dione, about 6.0 wt % of 2,6-dimethyloct-7-en-2-ol, about 2.0 wt % of 3-(4-isopropylphenyl)-2-methylpropanal, about 2.0 wt % of hexyl salicylate, about 1.4 wt % of 3-(4-ethylphenyl)-2,2-dimethylpropanal, about 0.6 wt % of 3-(2-ethylphenyl)-2,2-dimethylpropanal, about 2.0 wt % of 3a,4,5,6,7,7α-hexahydro-1H-4,7-methanoinden-6-yl acetate, about 2.0 wt % of Cedarwood oil, Virginian (*Juniperus virginiana* L.), about 1.0 wt % of 2-methylundecanal, about 0.8 wt % of (2,2-dimethoxyethyl) benzene, about 0.6 wt % of undec-10-enal, about 0.6 wt % of hex-3-en-1-ol, about 0.6 wt % of 3-(1,3-benzodioxol-5-yl)-2-methylpropanal, about 0.5 wt % of 1-phenylethyl acetate, about 0.4 wt % of 3a,6,6,9α-tetramethyldodecahydronaphtho[2,1-b]furan, about 0.4 wt % of allyl (3-methylbutoxy) acetate, and about 0.1 wt % of 1-(5,5-dimethylcyclohex-1-en-1-yl) pent-4-en-1-one, wherein the weight percentage of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and, in particular, with any embodiment of a fragrance release modulator and/or features/elements disclosed as part of that embodiment.

In some embodiments of the present invention, a blend of perfume raw material, referred to herein from time to time as Fragrance “Floral Fresh” or Floral Fresh Fragrance, consists of the compounds listed in Table 8 at the indicated weight percentage.

Thus, a preferred blend of perfume raw materials of the present invention consists about 14.0 wt % of 1-(2,3,8,8-tetramethyl-1,2,3,4,5,6,7,8-octahydronaphthalen-2-yl) ethanone, about 12.0 wt % of methyl (3-oxo-2-pentylcyclopentyl) acetate, about 11.0 wt % of 2-benzylideneoctanal, about 6.0 wt % of 1-cedr-8-en-9-ylethanone, about 6.0 wt % of 4-tert-butylcyclohexyl acetate, about 6.0 wt % of 1,5-dimethyl-1-vinylhex-4-en-1-yl acetate, about 6.0 wt % of 3,7-dimethylocta-1,6-dien-3-ol, about 6.0 wt % of 1-(2,6,6-trimethylcyclohex-2-en-1-yl) pent-1-en-3-one, about 6.0 wt % of 2-isobutyl-4-methyltetrahydro-2H-pyran-4-ol, about 6.0 wt % of 1,4-dioxacycloheptadecane-5,17-dione, about 6.0 wt % of 2,6-dimethyloct-7-en-2-ol, about 2.0 wt % of 3-(4-isopropylphenyl)-2-methylpropanal, about 2.0 wt % of hexyl salicylate, about 1.4 wt % of 3-(4-ethylphenyl)-2,2-dimethylpropanal, about 0.6 wt % of 3-(2-ethylphenyl)-2,2-dimethylpropanal, about 2.0 wt % of 3a,4,5,6,7,7a-hexahydro-1H-4,7-methanoinden-6-yl acetate, about 2.0 wt % of Cedarwood oil, Virginian (*Juniperus virginiana* L.), about 1.0 wt % of 2-methylundecanal, about 0.8 wt % of (2,2-dimethoxyethyl) benzene, about 0.6 wt % of undec-10-enal, about 0.6 wt % of hex-3-en-1-ol, about 0.6 wt % of 3-(1,3-benzodioxol-5-yl)-2-ethylpropanal, about 0.5 wt % of 1-phenylethyl acetate, about 0.4 wt % of 3a,6,6,9a-tetramethyldodecahydronaphtho[2,1-b]furan, about 0.4 wt % of allyl (3-methylbutoxy) acetate, and about 0.1 wt % of 1-(5,5-dimethylcyclohex-1-en-1-yl) pent-4-en-1-one, wherein the weight percentage of each compound is with reference to the total weight of the blend of the perfume raw materials. It is understood and one of ordinary skill in the art will appreciate that, if not clearly contradicted by the content of this specification, each of the one or more preceding compounds can be combined with any of the embodiments hereinabove or hereinbelow, and, in particular, with any embodiment of a fragrance release modulator and/or features/elements disclosed as part of that embodiment.

Each of the perfume raw materials and each of the blends of perfume raw materials described herein can be combined with any of the solvents or diluents described herein. Each of the perfume raw materials and each of the blends of perfume raw materials described herein can be combined with any of the fragrance release modulators (FRMs)

described herein. Each of the perfume raw materials and each of the blends of the perfume raw materials described herein can be combined with any of the solvents or diluents and fragrance release modulators described herein.

B. Fragrance Release Modulators (Frms)

In some embodiments of the present invention, a freshening composition comprises a fragrance release modulator. In some embodiments of the present invention, an air freshening composition comprises a fragrance release modulator. In some embodiments of the present invention, a liquid freshening composition a fragrance release modulator. In some embodiments of the present invention, a clear freshening composition comprises a fragrance release modulator. In some embodiments of the present invention, a homogenous freshening composition comprises a fragrance release modulator. In some embodiments of the present invention, a clear liquid freshening composition comprises a fragrance release modulator. In some embodiments of the present invention, a liquid air freshening composition comprises a fragrance release modulator. In some embodiments of the present invention, a homogeneous clear liquid air freshening composition comprises a fragrance release modulator. In some embodiments of the present invention, a homogeneous clear liquid air freshening composition comprises a fragrance release modulator. In some embodiments of the present invention, a non-water-based air freshening composition comprises a fragrance release modulator. Sometimes, herein a fragrance release modulator is referred to as "drop-in-fragrance release modulator" or "drop-in FRM." It is understood and one of ordinary skill in the art will appreciate that, if not clearly contradicted by the content of this specification, each embodiment of a fragrance release modulator and/or features/elements disclosed as part of that embodiment can be combined with any of the embodiments hereinabove or hereinbelow.

When a freshening composition comprises a perfume raw material and a fragrance release modulator, those ingredients are different.

Unexpectedly and surprisingly, the inventors have found that specific combinations of a perfume raw material and a fragrance release modulator (FRM) permit the customization, control, and modulation of (i) the lifespan of a freshening composition and (ii) control the releasing profile of the freshening composition. This customization, control, and modulation can be achieved regardless of a solvent or diluent being present in the freshening composition. Examples E, F, G, H, K, and L describe customization, control, and modulation of a freshening composition in the presence of a solvent or diluent, while Examples N and O describe such customization, control, and modulation in the absence of a solvent or diluent. This customization, control and modulation can also be achieved regardless of which wicking device is used. For example, if the wicking device is a reed or a plurality of reeds, a wick or a plurality of wicks, a stick or a plurality of sticks, a fiber or a plurality of fibers, a mesh, or a combination thereof, there is no need to intervene, no need to touch the delivery device or to reverse the flow of the freshening composition through the delivery device during product usage. Moreover, at the end of product usage the reservoir in the delivery device holding the freshening composition, is substantially completely empty.

Further, and equally surprisingly and unexpectedly, the inventors have found that it will be possible to establish a two-stage functional regime and to customize, control and modulate the release of a freshening composition or of a component thereof by controlling the transport process of the freshening composition inside of, e.g., a wicking system to an emanating surface by using a "drop-in" fragrance release modulator ("FRM"). More specifically, the inventors have found that by using the "drop-in" FRM it will be possible to alter, modulate, control, and customize the surface tension, the dynamic viscosity, and the density of such freshening composition. That discovery allows for the optimization, customization, modulation, and control of the mass transport of a freshening composition through a "delivery engine," such as a reed, a stick, a fiber, a mesh, a wick, a membrane, a porous or a semi-porous material. Thus, in some embodiments of the present invention, a fully saturated emanating surface is provided, whereby the lifespan of the air care product is optimized, customized, and controlled. Further, the strength, character, and diffusivity of the scent irrespective of the perfume raw material used, can be optimized, and controlled without altering the capability of the freshening composition to, e.g., address other functions, such as to counteract malodor ingredients or compositions or to have insect repelling activity.

Surprisingly and unexpectedly, the inventors have found that the mass transfer process of a freshening composition inside a wicking or diffusing element, as well as the mass transfer and the diffusion process of the freshening composition can be altered, customized, modulated, and controlled when specific compounds, herein described as fragrance release modulators (FRM), are dropped into a perfume raw material or blend of perfume raw materials—with or without a solvent or diluent—to formulate a freshening composition. The FRM can significantly influence the wicking process inside the delivery device (further described herein), and the releasing rate of the freshening composition at the surface of the emanating device by altering the surface tension, the dynamic viscosity, the density, the flash point, and the volatility of the freshening composition. In other words, an FRM, as described herein, permits the control, the customization, and the modulation of diffusivity and long-lasting characteristics of a freshening composition or of a component thereof, including, but not limited to, the perceived scent's character, the intensity and lifespan of the product. Due to the presence of an FRM, a freshening composition can be released through a two-stage process: (i) an initial transitory regime, which is associated with unusually high amount of freshening composition release, and (ii) a steady-state release regime, which implies a linear release of the freshening composition into an external environment until, or very close to its full completion (see, Examples).

As described herein, an FRM helps to formulate long-lasting air freshening products with customized releasing time, e.g., when the delivery device is a wicking or a diffusing device. There are no known formulation restrictions regarding the selection of perfume raw material, fragrance ingredients, flavor ingredients, essential oils, or functional ingredients that can be employed in combination with an FRM. Further, the inventors have not found any limitation with respect to the type of ingredient and the concentration of such ingredient when used in combination with an FRM.

By dropping an FRM into a freshening composition, which comprises a perfume raw material, the inventors surprisingly and unexpectedly have found that it is possible to control and customize (i) the surface tension of the freshening composition; (ii) the dynamic viscosity of the freshening composition; (iii) the density of the freshening composition; and (iv) the flash point of the freshening composition, all measured under normal temperature and pressure ("NTP") conditions. This finding permits the control of the two critical steps associated with the releasing process of the freshening compositions: (i) the capillary mass transfer of the freshening composition through the "delivery element", which can be a reed, stick, fiber, mesh, wick, semiporous or porous materials; and (ii) the phase and mass transfer processes of the freshening composition at the emanating surface.

Freshening compositions of the present invention comprise specific amounts and compositions of FRM, depending on the desired application. FRMs generally are odorless or low-odor, non-fragrance materials, but fragrance-miscible compounds. They may be used in combination with any perfume raw material (PRM) described herein, i.e., in combination with one or more of an ester, an alcohol, an aldehyde, a ketone, an acetal, a phenol, an ether, a lactone, a furan, a hydrocarbon, an acid, a natural origin fragrance compound, a synthetic origin fragrance compound, stereoisomers, and mixtures thereof, without any restriction, and without any negative impact on the freshening competition's hedonic character and strength, as well as the freshening composition's targeting purpose.

In some embodiments of the present invention, a fragrance release modulator comprises one or more ingredients having almost no hedonic impact on a person's fragrance experience. Those ingredients permit emanating a surface to quickly saturate and to operate as a steady saturated surface during the delivery process of the freshening composition.

The inventors have found that FRMs described herein when combined with a perfume raw material to form a freshening composition bestow the desired and superior characteristics upon the freshening composition. The inventors have found the following FRMs most useful: $C_{2-8}$ linear and $C_{2-8}$ branched alcohols, alkyl- and aryl compounds, silicon compounds, and organic ester compounds, specifically cyclic carbonate esters.

Thus, in some embodiments of the present invention, an FRM is selected from the group consisting of a $C_{2-8}$ linear alcohol, a $C_{2-8}$ branched alcohol, an alkyl compound, an aryl compound, a silicon compound, an organic ester compound, a cyclic carbonate ester compound, a stereoisomer of any preceding fragrance release modulator, and a mixture of any of the preceding release modulators. A preferred freshening composition of the present invention comprises less than about 90 wt % fragrance release modulator selected from the group consisting of a $C_{2-8}$ linear alcohol, a $C_{2-8}$ branched alcohol, an alkyl compound, an aryl compound, a silicon compound, an organic ester compound, a cyclic carbonate ester compound, a stereoisomer of any preceding fragrance release modulator, and a mixture of any of the preceding release modulators. Weight percentage is made with reference to the total weight of the freshening composition.

In some embodiments of the present invention, an FRM is a $C_{2-8}$ linear alcohol. Preferred $C_{2-8}$ linear alcohols for use as an FRM include, but are not limited to, ethanol, n-propanol, n-butanol, 1-pentanol, 2-pentanol, amyl-alcohol, glycerol, propylene glycol, and dipropylene glycol. Thus, in some embodiments of the present invention, an FRM is selected from the group consisting of ethanol, n-propanol, n-butanol, 1-pentanol, 2-pentanol, amyl-alcohol, glycerol, propylene glycol, dipropylene glycol, a stereoisomer of any preceding fragrance release modulator, and a mixture of any of the preceding release modulators. A preferred $C_{2-8}$ linear alcohol is ethanol. Freshening compositions comprising ethanol as an FRM are described herein, e.g., in Examples E, F, and L. Another preferred $C_{2-8}$ linear alcohol is propylene glycol. Another preferred $C_{2-8}$ linear alcohol is dipropylene glycol. Freshening compositions comprising dipropylene glycol (DPG) as an FRM are described herein, e.g., in Examples E, F, K, L, N, and O.

In some embodiments of the present invention, an FRM is a $C_{2-8}$ branched alcohol. Preferred $C_{2-8}$ branched alcohols for use as an FRM include, but are not limited to, isopropanol (2-propanol), t-butanol (2-methyl-2-propanol), isobutanol (2-methyl-1-propanol). s-butanol (2-butanol), 3-methyl-1-butanol (isoamylalcohol), 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, and 3-methyl-3-methoxyl butanol. Thus, in some embodiments of the present invention, an FRM is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, and 3-methyl-3-methoxyl butanol, a stereoisomer of any preceding fragrance release modulator, and a mixture of any of the preceding release modulators. A preferred $C_{2-8}$ branched alcohol is 3-methyl-3-methoxyl butanol, sometimes referred herein as MMB or as 3-methoxy-3-methyl-1-butanol. 3-methyl-3-methoxyl butanol has CAS Number 56539-66-3. Freshening compositions comprising 3-methyl-3-methoxyl butanol (MMB) as an FRM are described herein, e.g., in Examples E, F, K, L, N, and O.

In some embodiments of the present invention, an FRM is an alkyl compound. Preferred alkyl compounds for use as an FRM include, but are not limited to, an alkyl-ether, an alkyl-glycol, an alkyl-carbonate, an alkyl-diol, an alkyl-adipate, an alky-benzoate, an alkyl-citrate, an alkyl-laurate, an alkyl-palmitate, an alkyl-stearate, an alkyl-myristate, an alkyl-succinate, and an alkyl-glutarate. Thus, in some embodiments of the present invention, an FRM is selected from the group consisting of an alkyl-ether, an alkyl-glycol, an alkyl-carbonate, an alkyl-diol, an alkyl-adipate, an alky-benzoate, an alkyl-citrate, an alkyl-laurate, an alkyl-palmitate, an alkyl-stearate, an alkyl-myristate, an alkyl-succinate, an alkyl-glutarate, a stereoisomer of any preceding fragrance release modulator, and a mixture of any of the preceding release modulators. A preferred freshening composition of the present invention comprises less than about 90 wt % fragrance release modulator selected from the group consisting of an alkyl-ether, an alkyl-glycol, an alkyl-carbonate, an alkyl-diol, an alkyl-adipate, an alky-benzoate, an alkyl-citrate, an alkyl-laurate, an alkyl-palmitate, an alkyl-stearate, an alkyl-myristate, an alkyl-succinate, and an alkyl-glutarate, a stereoisomer of any preceding fragrance release modulator, and a mixture of any of the preceding release modulators. Weight percentage is made with reference to the total weight of the freshening composition.

In some embodiments of the present invention, an FRM is an alkyl-ether. Alkylethers are compounds with the general formula R—O—R', where R and R' are alkyl groups. Preferred alky-ethers for use as an FRM include, but are not limited to, dimethyl ether, diethyl ether, methyl ethyl ether, methyl propyl ether, ethyl propyl ether, di-n-propyl ether, methyl butyl ether, ethyl butyl ether, di-n-butyl ether, and di-isopropyl ether. Thus, in some embodiments of the present invention, an FRM is selected from the group consisting of dimethyl ether, diethyl ether, methyl ethyl ether, methyl propyl ether, ethyl propyl ether, di-n-propyl ether, methyl butyl ether, ethyl butyl ether, di-n-butyl ether, di-isopropyl ether, a stereoisomer of any preceding fragrance release modulator, and a mixture of any of the preceding release modulators. A preferred alkyl ether is dimethyl ether.

In some embodiments of the present invention, an FRM is an alkyl-glycol. Alkyl-glycol compounds are typically alkyl ethers of ethylene glycol. Preferred alky-glycols for use as an FRM include, but are not limited to, propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, and diethylene glycol monoethyl ether. Thus, in some embodiments of the present invention, an FRM is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer of any preceding fragrance release modulator, and a mixture of any of the preceding release modulators. A preferred alkyl-glycol is propylene glycol. Another preferred alkyl-glycol is dipropylene glycol. Another preferred alkyl-glycol is hexylene glycol.

In some embodiments of the present invention, an FRM is an alkyl-carbonate. Preferred alkyl-carbonates for use as an FRM include, but are not limited to, diethyl carbonate, dimethyl carbonate, dipropylene glycol dicarbonate, propylene carbonate, ethylene glycol dicarbonate, butylene glycol dicarbonate, and decylene carbonate. Thus, in some embodiments of the present invention, an FRM is selected from the group consisting of diethyl carbonate, dimethyl carbonate, dipropylene glycol dicarbonate, propylene carbonate, ethylene glycol dicarbonate, butylene glycol dicarbonate, decylene carbonate, a stereoisomer of any preceding fragrance release modulator, and a mixture of any of the preceding release modulators. A preferred alkyl-carbonate is dimethyl carbonate.

In some embodiments of the present invention, an FRM is an alkyl-diol. Alkyl diols are compounds with two hydroxyl groups on an alkyl chain. Preferred alkyl-diols for use as an FRM include, but are not limited to, 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, and 1,3-hexanediol. Thus, in some embodiments of the present invention, an FRM is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer of any preceding fragrance release modulator, and a mixture of any of the preceding release modulators. A preferred alkyl-diol is 1,2-hexanediol. Another preferred alkyl-diol is 1,2-pentanediol. Another preferred alkyl-diol is 1,3-propanediol. Another preferred alkyl-diol is 2-methylpentane-2,4-diol (common name, hexylene glycol). Freshening compositions comprising hexylene glycol as an FRM are described herein, e.g., in Examples N and O.

In some embodiments of the present invention, an FRM is an alkyl-adipate. Alkyl-adipates are diesters of adipic acid and various alcohols. Preferred alkyl-adipates for use as an FRM include, but are not limited to, dimethyl adipate, diethyl adipate, dibutyl adipate, diisopropyl adipate, diisobutyl adipate, dioctyl adipate, diisononyl adipate, dihexyl adipate, dipropylene glycol adipate, and a $C_{12-15}$alkyl adipate. Thus, in some embodiments of the present invention, an FRM is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer of any preceding fragrance release modulator, and a mixture of any of the preceding release modulators. A preferred alkyl-adipate is dimethyl adipate. Another preferred alkyl-adipate is dioctyl adipate.

In some embodiments of the present invention, an FRM is an alkyl-benzoate. Alkyl-benzoates are esters of benzoic acid and various alcohols. Preferred alkyl-benzoates for use as an FRM include, but are not limited to, benzyl benzoate, isopropyl benzoate, decyl benzoate, cetyl benzoate, stearyl benzoate, isobutyl benzoate, myristyl benzoate, lauryl benzoate, octyl benzoate, butyl benzoate, and a $C_{12-15}$alkyl benzoate. Thus, in some embodiments of the present invention, an FRM is selected from the group consisting of isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer of any preceding fragrance release modulator, and a mixture of any of the preceding release modulators. A preferred alkyl-benzoate is benzyl benzoate (BB). Freshening compositions comprising benzyl benzoate (BB) as an FRM are described herein, e.g., in Examples E, F, G, H, K, L, N, and O. Another preferred alkyl-benzoate is isopropyl benzoate. Another preferred alkyl-benzoate is myristyl benzoate.

In some embodiments of the present invention, an FRM is an alkyl-citrate. Alkyl-citrates are esters of citric acid and various alcohols. Preferred alkyl-citrates for use as an FRM include, but are not limited to, triethyl citrate, tributyl citrate, acetyl triethyl citrate, triisopropyl citrate, trihexyl citrate, trioctyl citrate, tricaprylyl citrate, triisodecyl citrate, trimethyl citrate, and a $C_{12-15}$alkyl citrate. Thus, in some embodiments of the present invention, an FRM is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer of any preceding fragrance release modulator, and a mixture of any of the preceding release modulators. A preferred alkyl-citrate is triethyl citrate. Freshening compositions comprising triethyl citrate (TEC) as an FRM are described herein, e.g., in Examples E, F, K, L, N, and O.

In some embodiments of the present invention, an FRM is an alkyl-laurate. Alkyl-laurates are esters of lauric acid and various alcohols. Preferred alkyl-laurates for use as an FRM include, but are not limited to, isoamyl laurate, isopropyl laurate, butyl laurate, cetyl laurate, stearyl laurate, myristyl laurate, lauryl laurate, isocetyl laurate, octyldodecyl laurate, decyl laurate, and a $C_{12-15}$alkyl laurate. Thus, in some embodiments of the present invention, an FRM is selected from the group consisting of isoamyl laurate, isopropyl laurate, butyl laurate, cetyl laurate, stearyl laurate, myristyl laurate, lauryl laurate, isocetyl laurate, octyldodecyl laurate, decyl laurate, a $C_{12-15}$alkyl laurate, a stereoisomer of any preceding fragrance release modulator, and a mixture of any of the preceding release modulators. A preferred alkyl-laurate is isoamyl laurate.

In some embodiments of the present invention, an FRM is an alkyl-palmitate. Alkyl-palmitates are esters of palmitic acid and various alcohols. Preferred alkyl-palmitates for use as an FRM include, but are not limited to, methyl palmitate, isopropyl palmitate, cetyl palmitate, stearyl palmitate, myristyl palmitate, cetearyl palmitate, decyl palmitate, lauryl palmitate, isocetyl palmitate, octyl palmitate, and glyceryl palmitate. Thus, in some embodiments of the present invention, an FRM is selected from the group consisting of methyl palmitate, isopropyl palmitate, cetyl palmitate, stearyl palmitate, myristyl palmitate, cetearyl palmitate, decyl palmitate, lauryl palmitate, isocetyl palmitate, octyl palmitate, glyceryl palmitate, a stereoisomer of any preceding fragrance release modulator, and a mixture of any of the preceding release modulators. A preferred alkyl-palmitate is methyl palmitate.

In some embodiments of the present invention, an FRM is an alkyl-stearate. Alkyl-stearates are esters of stearic acid and various alcohols. Preferred alkyl-stearates for use as an FRM include, but are not limited to, methyl stearate, isopropyl stearate, cetyl stearate, stearyl stearate, butyl stearate, isobutyl stearate, octyl stearate, myristyl stearate, cetearyl stearate, and glyceryl stearate. Thus, in some embodiments of the present invention, an FRM is selected from the group consisting of isopropyl stearate, cetyl stearate, stearyl stearate, butyl stearate, isobutyl stearate, octyl stearate, myristyl stearate, cetearyl stearate, glyceryl stearate, a stereoisomer of any preceding fragrance release modulator, and a mixture of any of the preceding release modulators. A preferred alkyl-stearate is methyl stearate.

In some embodiments of the present invention, an FRM is an alkyl-myristate. Alkyl-myristates are esters of myristic acid and various alcohols. Preferred alkyl-myristates for use as an FRM include, but are not limited to, isopropyl myristate, cetyl myristate, stearyl myristate, myristyl myristate, butyl myristate, isobutyl myristate, octyl myristate, decyl myristate, cetearyl myristate, and lauryl myristate. Thus, in some embodiments of the present invention, an FRM is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer of any preceding fragrance release modulator, and a mixture of any of the preceding release modulators. A preferred alkyl myristate is isopropyl myristate.

In some embodiments of the present invention, an FRM is an alkyl-succinate. Alkyl-succinates are esters of succinic acid and various alcohols. Preferred alkyl-succinates for use as an FRM include, but are not limited to, dimethyl succinate, diethyl succinate, dibutyl succinate, diisopropyl succinate, dioctyl succinate, disodium lauryl succinate, diethylhexyl succinate, cetyl succinate, isocetyl succinate, stearyl succinate, and a $C_{12-15}$alkyl succinate. Thus, in some embodiments of the present invention, an FRM is selected from the group consisting of dimethyl succinate, diethyl succinate, dibutyl succinate, diisopropyl succinate, dioctyl succinate, disodium lauryl succinate, diethylhexyl succinate, cetyl succinate, isocetyl succinate, stearyl succinate, a $C_{12-15}$alkyl succinate, a stereoisomer of any preceding fragrance release modulator, and a mixture of any of the preceding release modulators. A preferred alkyl-succinate is dimethyl succinate.

In some embodiments of the present invention, an FRM is an alkyl-glutarate. Alkyl-glutarates are esters of glutaric acid and various alcohols. Preferred alkyl-glutarates for use as an FRM include, but are not limited to, dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, and a $C_{12-15}$alkyl glutarate. Thus, in some embodiments of the present invention, an FRM is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer of any preceding fragrance release modulator, and a mixture of any of the preceding release modulators. A preferred alkyl-glutarate is dimethyl glutarate.

In some embodiments of the present invention, an FRM is an aryl compound. Preferred aryl compounds for use as an FRM include, but are not limited to, an aryl-ether, an aryl-glycol, an aryl-carbonate, an aryl-diol, an aryl-adipate, an aryl-benzoate, an aryl-citrate, an aryl-laurate, an aryl-palmitate, an aryl-stearate, an aryl-myristate, an aryl-succinate, and an aryl-glutarate. Thus, in some embodiments of the present invention, an FRM is selected from the group consisting of an aryl-ether, an aryl-glycol, an aryl-carbonate, an aryl-diol, an aryl-adipate, an aryl-benzoate, an aryl-citrate, an aryl-laurate, an aryl-palmitate, an aryl-stearate, an aryl-myristate, an aryl-succinate, an aryl-glutarate, a stereoisomer of any preceding fragrance release modulator, and a mixture of any of the preceding release modulators. A preferred freshening composition of the present invention comprises less than about 90 wt % fragrance release modulator selected from the group consisting of an aryl-ether, an aryl-glycol, an aryl-carbonate, an aryl-diol, an aryl-adipate, an aryl-benzoate, an aryl-citrate, an aryl-laurate, an aryl-palmitate, an aryl-stearate, an aryl-myristate, an aryl-succinate, and an aryl-glutarate, a stereoisomer of any preceding fragrance release modulator, and a mixture of any of the preceding release modulators. Weight percentage is made with reference to the total weight of the freshening composition.

In some embodiments of the present invention, an FRM is an aryl-ether. Aryl-ethers are organic compounds where an aryl group is bonded to an alkoxy group. Preferred aryl-ethers for use as an FRM include, but are not limited to, diphenyl ether, phenoxyethanol, benzyl phenyl ether, phenyl ethyl ether, phenyl propyl ether, ethylene glycol phenyl ether, and propylene glycol phenyl ether. Thus, in some embodiments of the present invention, an FRM is selected from the group consisting of diphenyl ether, phenoxyethanol, benzyl phenyl ether, phenyl ethyl ether, phenyl propyl ether, ethylene glycol phenyl ether, propylene glycol phenyl ether, a stereoisomer of any preceding fragrance release modulator, and a mixture of any of the preceding release modulators. A preferred aryl ether is diphenyl ether.

In some embodiments of the present invention, an FRM is an aryl-glycol. Aryl-glycols are compounds that contain both an aryl group and one or more hydroxyl groups. Preferred aryl-glycols for use as an FRM include, but are not limited to, phenoxyethanol, benzyl alcohol, 2-phenylethanol, 2-phenoxyethaol acetate, phenylpropanol, 2-phenyl-1,3 propanediol, 4-phenyl-1-butanol, benzyl glycol, phenyl ethyl glycol, and phenolpropanediol. Thus, in some embodiments of the present invention, an FRM is selected from the group consisting of phenoxyethanol, benzyl alcohol, 2-phenylethanol, 2-phenoxyethaol acetate, phenylpropanol, 2-phenyl-1,3 propanediol, 4-phenyl-1-butanol, benzyl glycol, phenyl ethyl glycol, phenolpropanediol, a stereoisomer of any preceding fragrance release modulator, and a mixture of any of the preceding release modulators. A preferred aryl-glycol is phenoxyethanol.

In some embodiments of the present invention, an FRM is an aryl-carbonate. Aryl-carbonates are compounds are esters of carbonic acid where at least one aryl group is bonded through an oxygen atom. Preferred aryl-carbonates for use as an FRM include, but are not limited to, diphenyl carbonate, phenyl ethyl carbonate, benzyl ethyl carbonate, benzyl methyl carbonate, phenyl propyl carbonate, benzyl propylene carbonate, benzyl isopropyl carbonate, phenoxyethyl carbonate, and benzyl dimethyl carbonate. Thus, in some embodiments of the present invention, an FRM is selected from the group consisting of diphenyl carbonate, phenyl ethyl carbonate, benzyl ethyl carbonate, benzyl methyl carbonate, phenyl propyl carbonate, benzyl propylene carbonate, benzyl isopropyl carbonate, phenoxyethyl carbonate, benzyl dimethyl carbonate, a stereoisomer of any preceding fragrance release modulator, and a mixture of any of the preceding release modulators. A preferred aryl-carbonate is diphenyl carbonate.

In some embodiments of the present invention, an FRM is an aryl-diol. Aryl-diols are compounds are compounds containing an aryl group and two hydroxyl groups. Preferred aryl-diols for use as an FRM include, but are not limited to, benzene-1,2-diol, benzene-1,3-diol, benzene-1,4-diol, 2-phenyl-1,3-propanediol, 1-phenyl-1,2-ethanediol, 2-phenylethane-1,2-diol, 4-hydroxybenzyl alcohol, 2-phenoxypropane-1,2-diol, and 4-hydroxyphenylethanol. Thus, in some embodiments of the present invention, an FRM is selected from the group consisting of benzene-1,2-diol, benzene-1,3-diol, benzene-1,4-diol, 2-phenyl-1,3-propanediol, 1-phenyl-1,2-ethanediol, 2-phenylethane-1,2-diol, 4-hydroxybenzyl alcohol, 2-phenoxypropane-1,2-diol, 4-hydroxyphenylethanol, a stereoisomer of any preceding fragrance release modulator, and a mixture of any of the preceding release modulators. A preferred aryl-diol is benzene-1,2-diol.

In some embodiments of the present invention, an FRM is an aryl-adipate. Aryl-adipates are esters formed from adipic acid and aryl-containing alcohols. Preferred aryl-adipates for use as an FRM include, but are not limited to, benzyl adipate, phenethyl adipate, benzyl isopropyl adipate, benzyl ethylhexyl adipate, phenoxyethyl adipate, benzyl butyl adipate, benzyl coco adipate, benzyl myristyl adipate, benzyl caprylyl adipate, and benzyl decyl adipate. Thus, in some embodiments of the present invention, an FRM is selected from the group consisting of benzyl adipate, phenethyl adipate, benzyl isopropyl adipate, benzyl ethylhexyl adipate, phenoxyethyl adipate, benzyl butyl adipate, benzyl coco adipate, benzyl myristyl adipate, benzyl caprylyl adipate, benzyl decyl adipate, a stereoisomer of any preceding fragrance release modulator, and a mixture of any of the preceding release modulators. A preferred aryl-adipate is benzyl adipate.

In some embodiments of the present invention, an FRM is an aryl-benzoate. Aryl-benzoates are compounds where an aryl group is esterified with benzoic acid to form an aryl benzoate ester. Preferred aryl-benzoates for use as an FRM include, but are not limited to, benzyl benzoate, methylphenyl benzoate, phenyl benzoate, diphenyl benzoate, p-cresyl benzoate, 4-tert-butylphenyl benzoate, 4-methoxyphenyl benzoate, 1-naphtyl benzoate, 2-naphtyl benzoate, hxdroxyphenyl benzoate, and ethylphenyl benzoate. Thus, in some embodiments of the present invention, an FRM is selected from the group consisting of benzyl benzoate, methylphenyl benzoate, phenyl benzoate, diphenyl benzoate, p-cresyl benzoate, 4-tertbutylphenyl benzoate, 4-methoxyphenyl benzoate, 1-naphtyl benzoate, 2-naphtyl benzoate, hxdroxyphenyl benzoate, and ethylphenyl benzoate. A preferred aryl-benzoate is benzyl benzoate. Another preferred aryl-benzoate is 4-methoxyphenyl benzoate.

In some embodiments of the present invention, an FRM is an aryl-citrate. Aryl-citrates are esters formed from citric acid and aryl-containing alcohols. Preferred aryl-citrates for use as an FRM include, but are not limited to, benzyl citrate, phenethyl citrate, benzyl ethyl citrate, benzyl isopropyl citrate, benzyl butyl citrate, benzyl coco citrate, benzyl oleyl citrate, benzyl 2-ethylhexyl citrate, benzyl myristyl citrate, and benzyl stearyl citrate. Thus, in some embodiments of the present invention, an FRM is selected from the group consisting of benzyl citrate, phenethyl citrate, benzyl ethyl citrate, benzyl isopropyl citrate, benzyl butyl citrate, benzyl coco citrate, benzyl oleyl citrate, benzyl 2-ethylhexyl citrate, benzyl myristyl citrate, benzyl stearyl citrate, a stereoisomer of any preceding fragrance release modulator, and a mixture of any of the preceding release modulators. A preferred aryl-citrate is benzyl citrate.

In some embodiments of the present invention, an FRM is an aryl-laurate. Aryl-laurates are esters formed from lauric acid and aryl-containing alcohols. Preferred aryl-laurates for use as an FRM include, but are not limited to, benzyl laurate, phenethyl laurate, benzyl coco laurate, benzyl isopropyl laurate, benzyl myristyl laurate, benzyl 2-ethylhexyl laurate, phenoxyethyl laurate, benzyl olelyl laurate, benzyl stearyl laurate, and benzyl cetyl laurate. Thus, in some embodiments of the present invention, an FRM is selected from the group consisting of benzyl laurate, phenethyl laurate, benzyl coco laurate, benzyl isopropyl laurate, benzyl myristyl laurate, benzyl 2-ethylhexyl laurate, phenoxyethyl laurate, benzyl olelyl laurate, benzyl stearyl laurate, benzyl cetyl laurate, a stereoisomer of any preceding fragrance release modulator, and a mixture of any of the preceding release modulators. A preferred aryl-laurate is benzyl laurate.

In some embodiments of the present invention, an FRM is an aryl-palmitate. Aryl-palmitates are esters formed from palmitic acid and aryl-containing alcohols. Preferred aryl-palmitates for use as an FRM include, but are not limited to, benzyl palmitate, phenyl palmitate, anisyl palmitate, p-cresyl palmitate, benzhydryl palmitate, 1-naphtyl palmitate, 2-aphtyl palmitate, tocopheryl palmitate, 4-tert-butylphenyl palmitate, resorcinol monopalmitate, and hydroxyphenyl palmitate. Thus, in some embodiments of the present invention, an FRM is selected from the group consisting of benzyl palmitate, phenyl palmitate, anisyl palmitate, p-cresyl palmitate, benzhydryl palmitate, 1-naphtyl palmitate, 2-naphtyl palmitate, tocopheryl palmitate, 4-tert-butylphenyl palmitate, resorcinol monopalmitate, and hydroxyphenyl palmitate, a stereoisomer of any preceding fragrance release modulator, and a mixture of any of the preceding release modulators. A preferred aryl-palmitate is benzyl palmitate.

In some embodiments of the present invention, an FRM is an aryl-stearate. Aryl-stearates are esters formed from stearic acid and aryl-containing alcohols. Preferred aryl-stearates for use as an FRM include, but are not limited to, benzyl stearate, phenyl stearate, anisyl stearate, p-cresyl stearate, benzhydryl stearate, 1-naphtyl stearate, 2-naphtyl stearate, 4-tert-butylphenyl stearate, hydroxyphenyl stearate, resorcinol monostearate, and tocopheryl stearate. Thus, in some embodiments of the present invention, an FRM is selected from the group consisting of benzyl stearate, phenyl stearate, anisyl stearate, p-cresyl stearate, benzhydryl stearate, 1-naphtyl stearate, 2-naphtyl stearate, 4-tert-butylphenyl stearate, hydroxyphenyl stearate, resorcinol monostearate, and tocopheryl stearate, a stereoisomer of any preceding fragrance release modulator, and a mixture of any of the preceding release modulators. A preferred aryl-stearate is benzyl stearate.

In some embodiments of the present invention, an FRM is an aryl-myristate. Aryl-myristates are esters formed from myristic acid and aryl-containing alcohols. Preferred aryl-stearates for use as an FRM include, but are not limited to, benzyl myristate, phenyl myristate, anisyl myristate, p-cresyl myristate, benzhydryl myristate, 1-naphtyl myristate, 2-naphtyl myristate, 4-tert-butylphenyl myristate, hydroxyphenyl myristate, resorcinol monomyristate, and tocopheryl myristate. Thus, in some embodiments of the present invention, an FRM is selected from the group consisting of benzyl myristate, phenyl myristate, anisyl myristate, p-cresyl myristate, benzhydryl myristate, 1-naphtyl myristate, 2-naphtyl myristate, 4-tert-butylphenyl myristate, hydroxyphenyl myristate, resorcinol monomyristate, and tocopheryl myristate, a stereoisomer of any preceding fragrance release modulator, and a mixture of any of the preceding release modulators. A preferred aryl-myristate is benzyl myristate.

In some embodiments of the present invention, an FRM is an aryl-succinate. Aryl-succinates are ester compounds where one or both hydroxyl groups of succinic acid are replaced with aryl-containing alcohols. Preferred aryl-succinates for use as an FRM include, but are not limited to, dibenzyl succinate, benzyl phenyl succinate, anisyl succinate, diphenyl succinate, 4-methoxyphenyl succinate, dibenzhydryl succinate, p-cresyl succinate, 2-naphpthyl succinate, hydroxyphenyl succinate, and resorcinol succinate. Thus, in some embodiments of the present invention, an FRM is selected from the group consisting of dibenzyl succinate, benzyl phenyl succinate, anisyl succinate, diphenyl succinate, 4-methoxyphenyl succinate, dibenzhydryl succinate, p-cresyl succinate, 2-naphpthyl succinate, hydroxyphenyl succinate, and resorcinol succinate, a stereoisomer of any preceding fragrance release modulator, and a mixture of any of the preceding release modulators. A preferred aryl-succinate is dibenzyl succinate.

In some embodiments of the present invention, an FRM is an aryl-glutarate. Aryl-glutarates are ester compounds formed of glutaric acid with aryl-containing alcohols. A preferred aryl-glutarate for use as an FRM is dimethyl glutarate. Thus, in some embodiments of the present invention, an FRM is dimethyl glutarate or a stereoisomer thereof.

In some embodiments of the present invention, an FRM is a silicon compound. Preferred silicon compounds for use as an FRM include, but are not limited to, dimethicone, disiloxane, trisiloxane, cyclopentasiloxane, cyclohexasiloxane, dimethicone, dimethiconol, phenyl trimethicone, and amodimethicone. Thus, in some embodiments of the present invention, an FRM is selected from the group consisting of dimethicone, disiloxane, trisiloxane, cyclopentasiloxane, cyclohexasiloxane, dimethicone, dimethiconol, phenyl trimethicone, amodimethicone, a stereoisomer of any preceding fragrance release modulator, and a mixture of any of the preceding release modulators. A preferred silicon compound is dimethicone. Another preferred silicon compound is disiloxane. Another preferred silicon compound is trisiloxane.

In some embodiments of the present invention, an FRM is an organic ester. A preferred organic ester for use as an FRM is n-butyl propionate. Thus, in some embodiments of the present invention, an FRM is n-butyl propionate or a stereoisomer thereof.

A preferred cyclic carbonate ester for use as an FRM is propylene carbonate (4-methyl-1,3-dioxolane-2-one). Thus, in some embodiments of the present invention, an FRM is propylene carbonate or a stereoisomer thereof.

In some embodiments of the present invention, a fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, an organic ester, a cyclic carbonate ester, a stereoisomer of any preceding fragrance release modulator, and a mixture of any of the preceding release modulators. A preferred freshening composition of the present invention comprises less than about 90 wt % fragrance release modulator selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, an organic ester, a cyclic carbonate ester, a stereoisomer of any preceding fragrance release modulator, and a mixture of any of the preceding release modulators. Weight percentage is made with reference to the total weight of the freshening composition.

In some embodiments of the present invention, preferred FRMs are ethanol, triethyl citrate, benzyl benzoate, 3-methoxy-3-methyl-1-butanol, 3-methyl-3-methoxyl butanol, 1,2 hexanediol, 1,2 pentanediol, hexylene glycol, glycerol, propylene glycol, dipropylene glycol, dimethyl adipate, dimethyl ether, isoamyl laurate, methyl palmitate, methyl stearate, dimethicone, disiloxane, trisiloxane, stereoisomers, and mixtures thereof. Thus, in some embodiments of the present invention, a fragrance release modulator is selected from the group consisting of ethanol, triethyl citrate, benzyl benzoate, 3-methoxy-3-methyl-1-butanol, 3-methyl-3-methoxyl butanol, 1,2 hexanediol, 1,2 pentanediol, hexylene glycol, glycerol, propylene glycol, dipropylene glycol, dimethyl adipate, dimethyl ether, isoamyl laurate, methyl palmitate, methyl stearate, dimethicone, disiloxane, trisiloxane, a stereoisomer of any preceding fragrance release modulator, and a mixture of any of the preceding fragrance release modulators. In some embodiments of the present invention, a fragrance release modulator is selected from the aforementioned group missing one or more group members, e.g., from the aforementioned group of FRMs not including ethanol, triethyl citrate, benzyl benzoate, 3-methoxy-3-methyl-1-butanol, 3-methyl-3-methoxyl butanol, 1,2 hexanediol, 1,2 pentanediol, hexylene glycol, glycerol, propylene glycol, dipropylene glycol, dimethyl adipate, dimethyl ether, isoamyl laurate, methyl palmitate, methyl stearate, dimethicone, disiloxane, or trisiloxane. In some embodiments of the present invention, a fragrance release modulator is ethanol. Thus, in some embodiments of the present invention, a freshening composition comprises ethanol. In some embodiments of the present invention, a fragrance release modulator is triethyl citrate. Thus, in some embodiments of the present invention a freshening composition comprises triethyl citrate. In some embodiments of the present invention, a fragrance release modulator is benzyl benzoate. Thus, in some embodiments of the present invention a freshening composition comprises benzyl benzoate. In some embodiments of the present invention, a fragrance release modulator is 3-methoxy-3-methyl-1-butanol (or 3-methyl-3-methoxyl butanol or MMB). Thus, in some embodiments of the present invention a freshening composition comprises 3-methoxy-3-methyl-1-butanol (or 3-methyl-3-methoxyl butanol or MMB). In some embodiments of the present invention, a fragrance release modulator is 1,2 hexanediol. Thus, in some embodiments of the present invention a freshening composition comprises 1,2 hexanediol. In some embodiments of the present invention, a fragrance release modulator is 1,2 pentanediol. Thus, in some embodiments of the present invention a freshening composition comprises 1,2 pentanediol. In some embodiments of the present invention, a fragrance release modulator is hexylene glycol. Thus, in some embodiments of the present invention a freshening composition comprises hexylene glycol. In some embodiments of the present invention, a fragrance release modulator is glycerol. Thus, in some embodiments of the present invention a freshening composition comprises glycerol. In some embodiments of the present invention, a fragrance release modulator is propylene glycol. Thus, in some embodiments of the present invention a freshening composition comprises propylene glycol. In some embodiments of the present invention, a fragrance release modulator is dipropylene glycol. Thus, in some embodiments of the present invention a freshening composition comprises dipropylene glycol. In some embodiments of the present invention, a fragrance release modulator is dimethyl adipate. Thus, in some embodiments of the present invention a freshening composition comprises dimethyl adipate. In some embodiments of the present invention, a fragrance release modulator is dimethyl ether. Thus, in some embodiments of the present invention a freshening composition comprises dimethyl ether. In some embodiments of the present invention, a fragrance release modulator is isoamyl laurate. Thus, in some embodiments of the present invention a freshening composition comprises isoamyl laurate. In some embodiments of the present invention, a fragrance release modulator is methyl palmitate. Thus, in some embodiments of the present invention a freshening composition comprises methyl palmitate. In some embodiments of the present invention, a fragrance release modulator is methyl stearate. Thus, in some embodiments of the present invention a freshening composition comprises methyl stearate. In some embodiments of the present invention, a fragrance release modulator is dimethicone. Thus, in some embodiments of the present invention a freshening composition comprises dimethicone. In some embodiments of the present invention, a fragrance release modulator is disoloxane. Thus, in some embodiments of the present invention a freshening composition comprises disiloxane. In some embodiments of the present invention, a fragrance release modulator is trisiloxane. Thus, in some embodiments of the present invention a freshening composition comprises trisiloxane. However, in some embodiments of the present invention, an FRM is not dipropylene glycol. In some embodiments of the present invention, an FRM is not triethyl acetate. In other embodiments of the present invention an FRM is not dimethyl ether. In yet other embodiments of the present invention, an FRM is not dimethyl adipate.

Other preferred FRMs are ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, stereoisomers or a combination thereof. Thus, in some embodiments of the present invention, a fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, stereoisomers, and a mixture of any of the preceding fragrance release modulators. In some embodiments of the present invention, a fragrance release modulator is selected from the aforementioned group missing one or more group members, e.g., from the aforementioned group of FRMs not including ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, or trisiloxane.

A preferred freshening composition of the present invention comprises less than about 90 wt % fragrance release modulator selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl alcohol, n-pentyl alcohol, 1,3 propanediol, 1,2 hexanediol, 1,2 pentanediol, propylene glycol, dipropylene glycol, hexylene glycol, glycerol, dimethyl ether, benzyl benzoate, triethyl citrate, dimethyl adipate, dioctyl adipate, propylene carbonate, dimethyl carbonate, isoamyl laurate, methyl palmitate, methyl stearate, dimethyl ether, dimethyl succinate, dimethyl glutarate, n-butyl propionate, dimethicone, disiloxane, trisiloxane, and a combination of any of the preceding fragrance release modulators. Weight percentage is made with reference to the total weight of the freshening composition.

As described herein, fragrance release modulators of the present invention can be characterized by their flash point, surface tension, dynamic viscosity, density, and vapor pressure, measured as described herein. For example, triethyl citrate (TEC) has a flash point of greater than about 200° F., a surface tension of about 33.7 dyne/cm at 20° C., a dynamic viscosity of about 6.5 mPa·s at 20° C., a density of about 1,137 g/l at 20° C., and a vapor pressure of about 0.0006 mmHg at 25° C. As another example, benzyl benzoate (BB) has a flash point of greater than about 200° F. (298° F.), a surface tension of about 26.6 dyne/cm at 20° C., a dynamic viscosity of about 8.3 mPa·s at 25° C., a density of about 1,118 g/l at 25° C., and a vapor pressure of about 0.0002 mmHg at 25° C.

In some embodiments of the present invention, an FRM has a flash point higher than about 100° F.; preferably, higher than about 125° F.; more preferably, higher than about 150° F.; and most preferably, higher than about 200° F.

In some embodiments of the present invention, an FRM as a surface tension of less than about 60 mN/m; preferably, less than about 50 mN/m; more preferably, less than about 40 mN/m; and most preferably, less than about 30 mN/m.

In some embodiments of the present invention, an FRM has a dynamic viscosity in the range from about 0.5 cp to about 100 cp. Other preferred FRMs of the present invention have a dynamic viscosity of less than about 100 cp; preferably, less than about 50 cp; more preferably, less than about 30 cp; even more preferably, less than about 20 cp; and most preferably, less than about 10 cp.

In some embodiments of the present invention, an FRM has a mass density in the range from about 600 g/l to about 1,300 g/l. Other preferred FRMs of the present invention have a mass density in the range from about 100 g/l to about 2,000 g/l; preferably, in the range from about 200 g/l to about 1,800 g/l; more preferably, in the range from about 400 g/l to about 1,600 g/l; and most preferably, in the range from about 600 g/l to about 1,300 g/l.

In some embodiments of the present invention, an FRM has one or more, two or more, or three or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l.

A freshening composition of the present invention may comprise any of the herein mentioned FRMs at various amounts (wt %). In some embodiments of the present invention, a freshening composition of the present invention comprises a fragrance release modulator in an amount of less than about 99 wt %, less than about 95 wt %, less than about 90 wt %, less than about 85 wt %, less than about 80 wt %, less than about 75 wt %, less than about 70 wt %, less than about 65 wt %, less than about 60 wt %, less than about 55 wt %, less than about 50 wt %, less than about 45 wt %, less than about 40 wt %, less than about 35 wt %, less than about 30 wt %, less than about 25 wt %, less than about 20 wt %, less than about 15 wt %, less than about 10 wt %, less than about 7.5 wt %, less than about 5 wt %, less than about 2 wt %, less than about 1 wt %, less than about 0.5 wt %, less than about 0.2 wt %, less than about 0.1 wt %, less than about 0.05%, less than about 0.02 wt %, or less than about 0.01 wt %, with the weight percentages being relative to the total weight of the freshening composition.

In some embodiments of the present invention, a freshening composition of the present invention comprises a fragrance release modulator in an amount of greater than about 0.01 wt %, greater than about 0.02 wt %, greater than about 0.05 wt %, greater than about 0.1 wt %, greater than about 0.2 wt %, greater than about 0.5 wt %, greater than about 1 wt %, greater than about 2 wt %, greater than about 5 wt %, greater than about 7.5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, greater than about 95 wt %, greater than about 99 wt %, with the weight percentages being relative to the total weight of the freshening composition.

In some embodiments of the present invention, a freshening composition of the present invention comprises a fragrance release modulator in an amount of about 0.01 wt %, about 0.02 wt %, about 0.05 wt %, about 0.1 wt %, about 0.2 wt %, about 0.5 wt %, about 1 wt %, about 2 wt % about 5 wt %, about 7.5 wt %, about 10 wt %, about 15 wt %, about 20 wt about 25 wt %, about 30 wt %, about 35 wt % about 40 wt %, about 45 wt %, about 50 wt %, about 55 wt %, about 60 wt %, about 65 wt %, about 70 wt %, about 75 wt %, about 80 wt 00 about 85 wt % about 90 wt % about 95 wt % about 99 wt % with the weight percentages being relative to the total weight of the freshening composition.

In some embodiments of the present invention, a freshening composition of the present invention comprises a fragrance release modulator in a range from about 0.01 wt % to about 99 wt %, in a range from about 0.02 wt % to about 95 wt %, in a range from about 0.05 wt % to about 95 wt %, in a range from about 0.1 wt % to about 95 wt %, in a range from about 0.2 wt % to about 95 wt %, in a range from about 0.5 wt % to about 95 wt % in a range from about 1 wt % to about 95 wt % in a range from about 2 wt % to about 90 wt % in a range from about 3 wt % to about 85 wt % in a range from about 5 wt % to about 80 wt % in a range from about 10 wt % to about 75 wt %, in a range from about 15 wt % to about 70 wt %, in a range from about 20 wt % to about 65 wt %, in a range from about 25 wt % to about 60 wt %, in a range from about 30 wt % to about 55 wt %, in a range from about 40 wt % to about 50 wt %, with the weight percentages being relative to the total weight of the freshening composition.

In some embodiments of the present invention, a freshening composition of the present invention comprises a fragrance release modulator in a range between about 0.01 wt % and about 99 wt %, in a range between about 0.02 wt % and about 95 wt %, in a range between about 0.05 wt % and about 95 wt %, in a range between about 0.1 wt % and about 95 wt %, in a range between about 0.2 wt % and about 95 wt %, in a range between about 0.5 wt % and about 95 wt %, in a range between about 1 wt % and about 95 wt %, in a range between about 2 wt % and about 90 wt %, in a range between about 3 wt % and about 85 wt %, in a range between about 5 wt % and about 80 wt %, in a range between about 10 wt % and about 75 wt %, in a range between about 15 wt % and about 70 wt %, in a range between about 20 wt % and about 65 wt %, in a range between about 25 wt % and about 60 wt %, in a range between about 30 wt % and about 55 wt %, in a range between about 40 wt % and about 50 wt %, with the weight percentages being relative to the total weight of the freshening composition.

Preferably, a freshening composition comprises from about 0.01 wt % to about 90 wt % fragrance release modulator (FRM); preferably, less than about 75 wt % FRM; more preferably, less than about 50 wt % FRM; and most preferably less than about 25 wt % FRM, with the weight percentages being relative to the total weight of the freshening composition.

In some embodiments of the present invention, a freshening composition comprises a fragrance release modulator in an amount sufficient (typically provided herein as wt % of the freshening composition) to control (or modulate) the release of the freshening composition or of a component thereof. Adding an FRM to a freshening composition, as described herein, allows the user to control (or modulate) the release of the freshening composition or a component thereof into or onto an environment. Depending on the desirability of a user, the release of a freshening composition or of a component thereof can be up-regulated (faster) or down-regulated (slower), compared to a control not comprising an FRM. When a freshening composition comprises (i) X wt % perfume raw material and (ii) Y wt % fragrance release modulator, a control not comprising an FRM would comprise 100 wt % perfume raw material (e.g., see, Examples N and O). When a freshening composition comprises (i) X wt % perfume raw material, (ii) Y wt % fragrance release modulator, and (iii) W wt % solvent or diluent, a control not comprising an FRM would comprise (i) X wt % perfume raw material and (ii) W+Y wt % solvent or diluent (e.g., see, Examples G, H, and K). Likewise, when a freshening composition comprises (i) X wt % perfume raw material, (ii) Y wt % fragrance release modulator, (iii) W wt % solvent or diluent, and (iv) V wt % of an ingredient having a functional activity, a control not comprising an FRM would comprise (i) X wt % perfume raw material (ii) V wt % of an ingredient having a functional activity, and (iii) W+Y wt % solvent or diluent.

In some embodiments of the present invention, release of a freshening composition or of a component thereof is up-regulated or accelerated, i.e., the release of the freshening composition or of a component thereof is faster than what is observed with a control (i.e., a freshening composition not comprising the FRM, but otherwise similar). As exemplified by Example E (FIG. 3) certain FRMs, such as triethyl citrate (TEC), benzyl benzoate (BB), ethanol, 3-methyl-3-methoxyl butanol (MMB) and dipropylene glycol (DPG) up-regulate release of a freshening composition wherein the freshening composition comprises in addition to the FRM and a perfume raw material the solvent 2,2-dimethyl-1,3-dioxolane-4-methanol (Augeo Clean Multi® brand name from Solvay). When the identity and amount of the PRM and solvent are kept constant, the extent of up-regulation depends on the identity of the FRM (see, Example E, FIG. 3; Example F, FIG. 4). In some embodiments of the present invention, a fragrance release modulator of the present invention up-regulates the release or evaporation of a freshening composition or of a component thereof, relative to a control (not comprising said fragrance release modulator and being assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more. Values for the % up-regulation are statistically significant.

A user is able to verify directly and positively such faster release (compared to a control) by, e.g., measuring the time it takes for the freshening composition or component thereof to be fully released (will be faster than the control) or weighing the freshening composition and noticing a reduced weight (compared to the control) over time. Details are described in the Examples herein. For example, the fragrance release modulator MMB when combined with either the Apple Fragrance (see, Example N, FIG. 11) or the Floral Fresh Fragrance (see, Example O, FIG. 12) lead to a faster release of the freshening composition or component thereof. Also, the fragrance release modulator hexylene glycol when combined with either the Apple Fragrance (see, Example N, FIG. 11) or the Floral Fresh Fragrance (see, Example O, FIG. 12) lead to a faster release of the freshening composition or component thereof.

On the other hand, in some embodiments of the present invention, adding an FRM allows a user to down-regulate or slow-down the release of the freshening composition or of a component thereof.

In some embodiments of the present invention, a fragrance release modulator of the present invention down-regulates the release or evaporation of a freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more. Values for the % down-regulation are statistically significant.

A user is able to verify directly and positively such slower release (compared to a control) by, e.g., measuring the time it takes for the freshening composition or component thereof to be fully released (will be slower than the control) or weighing the freshening composition and noticing a higher weight (compared to the control) over time. Details are described in the Examples herein. For example, the fragrance release modulator triethyl citrate (TEC) when combined with either the Apple Fragrance (see, Example N, FIG. 11) or the Floral Fresh Fragrance (see, Example O, FIG. 12) lead to a slower release of the freshening composition or component thereof.

Some fragrance release modulators, exemplified by dipropylene glycol (DPG), have the capacity of either up-regulating or downregulating the release of a freshening composition or of a component thereof—depending on the perfume raw material. For example, the fragrance release modulator dipropylene glycol (DPG) when combined with the Apple Fragrance slows down the release of the freshening composition or of a component thereof (see, Example N, FIG. 11). However, when combined with the Floral Fresh Fragrance, the fragrance release modulator dipropylene glycol (DPG) leads to a faster release of the freshening composition or of a component thereof (see, Example O, FIG. 12).

Figure 5:
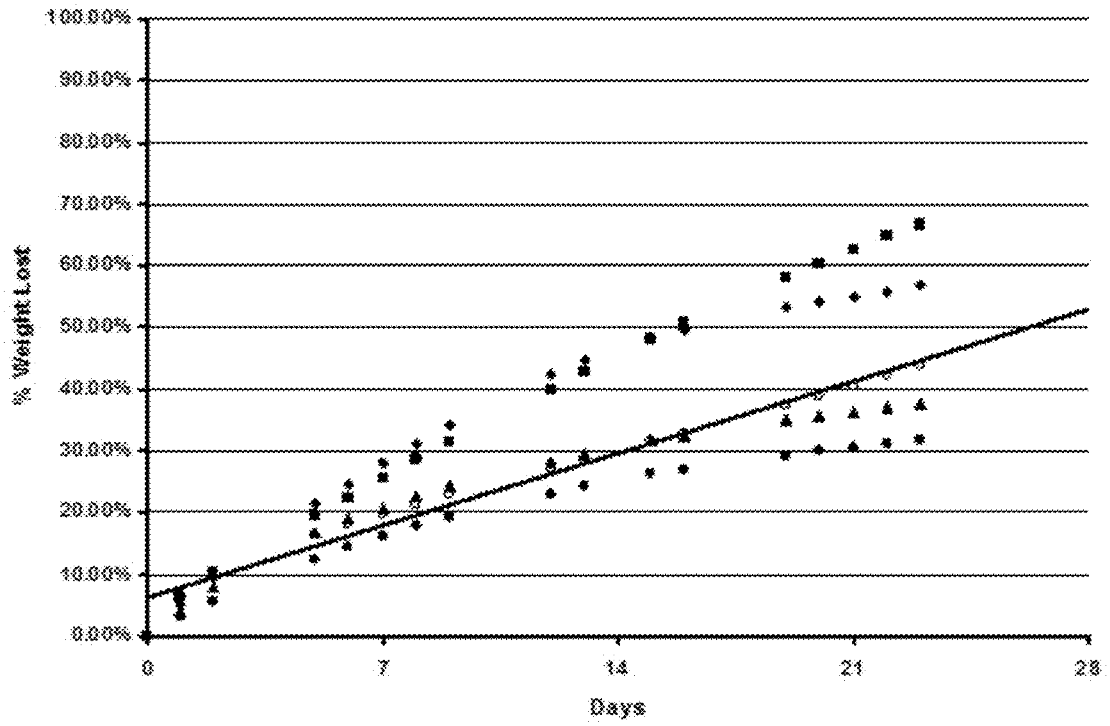
FIG. 5 schematically depicts the influence of various amounts of fragrance release modulator BB (benzyl benzoate) on the release and evaporation of a freshening composition comprising 50 wt % Apple Fragrance (see, Table 9) and various amounts of solvent Augeo Clean Multi® measured as % weight lost during the time period indicated. The weight percentage refers to the weight percentage of the entire product formulation, i.e., freshening composition. The release and evaporation of the following freshening compositions were tested: ○, 50 wt % Apple Fragrance/50 wt % Augeo Clean Multi®; ■, 50 wt % Apple Fragrance/42.5 wt % Augeo Clean Multi®/7.5 wt % BB; ♦, 50 wt % Apple Fragrance/25 wt % Augeo Clean Multi®/25 wt % BB; ▲, 50 wt % Apple Fragrance/7.5 wt % Augeo Clean Multi®/42.5 wt % BB; ●, 50 wt % Apple Fragrance/50 wt % BB. Abbreviations and names are as described for FIGS. 1-4. Details are described in Example G.
Figure 6:
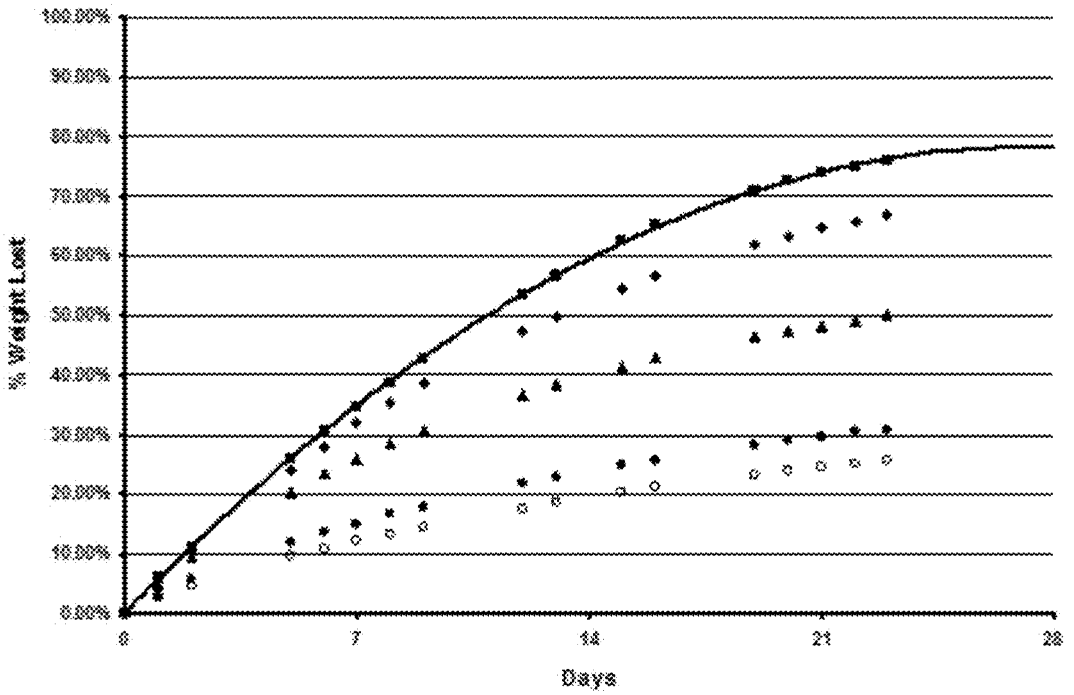
FIG. 6 schematically depicts the influence of fragrance release modulator BB (benzyl benzoate) on the release of a freshening composition comprising 50 wt % Floral Fresh Fragrance (see, Table 10) and various amounts of solvent IPD-AC® and measured as % weight lost during the time period indicated. The weight percentage refers to the weight percentage of the entire product formulation, i.e., freshening composition. The release and evaporation of the following freshening compositions were tested: ♦, 50 wt % Floral Fresh Fragrance/42.5 wt % IPD-AC®/7.5 wt % BB; ▲, 50 wt % Floral Fresh Fragrance/25 wt % IPD-AC®/25 wt % BB; ●, 50 wt % Floral Fresh Fragrance/7.5 wt % IPD-AC®/42.5 wt % BB; ■, 50 wt % Floral Fresh Fragrance/50 wt % IPD-AC®; ○, 50 wt % Floral Fresh Fragrance/50 wt % BB. Abbreviations and names are as described for FIGS. 1-5. Details are described in Example H.
Figure 9:
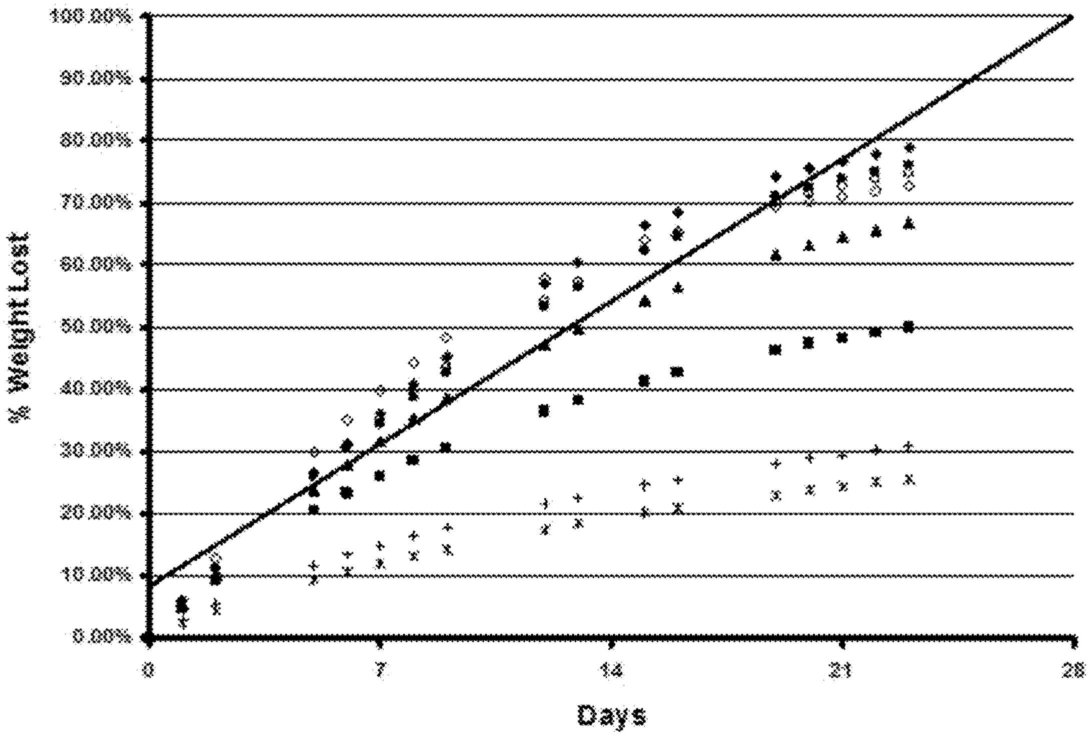
FIG. 9 schematically depicts the influence of different fragrance release modulators (FRM) on the release and evaporation of a freshening composition comprising Floral Fresh Fragrance and as measured as % weight lost during the time period indicated. The weight percentage refers to the weight percentage of the entire product formulation, i.e., freshening composition. The release and evaporation of the following freshening compositions were tested: ○, 50 wt % Floral Fresh Fragrance/42.5 wt % IPD-AC®/7.5 wt % MMB (IPD-AC®, 3-methyl-1,3-butanediol-acetate; MMB, 3-methyl-3-methoxyl butanol); ▲ 50 wt % Floral Fresh Fragrance/42.5 wt % IPD-AC®/7.5 wt % BB (BB, benzyl benzoate); ◇, 50 wt % Floral Fresh Fragrance/42.5 wt % IPD-AC®/7.5 wt % TEC (TEC, triethyl citrate); ♦, 50% Floral Fresh Fragrance/42.5 wt % IPD-AC®/7.5 wt % DPG (DPG, dipropylene glycol); ■, 50% Floral Fresh Fragrance/25 wt % IPD-AC®/25 wt % BB; +, 50 wt % Floral Fresh Fragrance/7.5 wt % IPDAC®/42.5 wt % BB; ●, 50 wt % Floral Fresh Fragrance/50 wt % IPD-AC®; ж, 50 wt % Floral Fresh Fragrance/50 wt % BB. Abbreviations and names are as described for FIGS. 1-8. Details are described in Example K.
Figure 10:
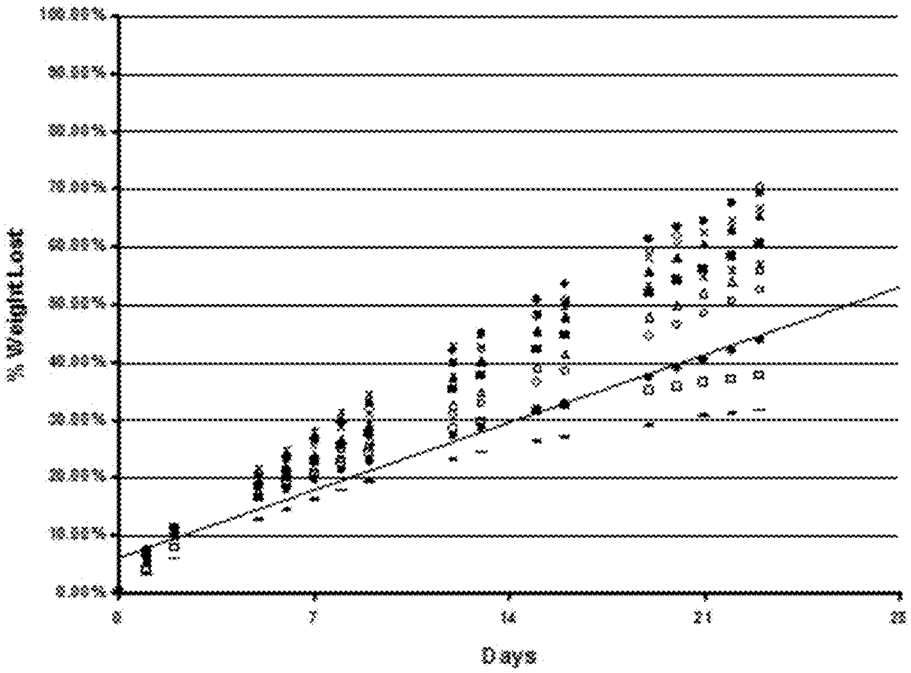
FIG. 10 schematically depicts the influence of different fragrance release modulators (FRM) on the release and evaporation of a freshening composition comprising 50% wt % Apple Fragrance and as measured as % weight lost during the time period indicated. The weight percentage refers to the weight percentage of the entire product formulation, i.e., freshening composition. The release and evaporation of the following fragrance compositions were tested: 0, 50 wt % Apple Fragrance/50 wt % IPD-AC®; ▲, 50 wt % Apple Fragrance/50 wt % STA-SOL® ESS 165; ■, 50 wt % Apple Fragrance/42.5 wt % Augeo Clean Multi®/7.5 wt % MMB; ▲, 50 wt % Apple Fragrance/42.5 wt % Augeo Clean Multi®/7.5 wt % EtOH (EtOH, ethanol); x, 50 wt % Apple Fragrance/42.5 wt % Augeo Clean Multi®/7.5 wt % BB; ●, 50 wt % Apple Fragrance/42.5 wt % Augeo Clean Multi®/7.5 wt % TEC; ○, 50 wt % Apple Fragrance/42.5 wt % Augeo Clean Multi®/7.5 wt % DPG; ж, 50 wt % Apple Fragrance/25 wt % Augeo Clean Multi®/25 wt % BB; □, 50 wt % Apple Fragrance/7.5 wt % Augeo Clean Multi®/42.5 wt % BB; –, 50 wt % Apple Fragrance/50 wt % BB. Abbreviations and names are as described for FIGS. 1-9. Details are described in Example L.

Unexpectedly and surprisingly, the inventors have found that the amount (wt %) of an FRM in a freshening composition determines the % up- or % downregulation of release of a freshening composition or of a component thereof (e.g., see, Example G and FIG. 5, Example H and FIG. 6, Example K and FIG. 9, and Example L and FIG. 10). When the wt % of the perfume raw material is kept constant and the wt % of a solvent or diluent is adjusted to compensate for the various wt % of an FRM present in the freshening composition, varying the wt % of an FRM, as exemplified by the FRM benzyl benzoate (BB), the release of the freshening composition or of the component can be modulated to a customized rate (e.g., see, Example G and FIG. 5, Example H and FIG. 6, Example K and FIG. 9, and Example L and FIG. 10). As can be seen in those Examples, a low wt % of the FRM benzyl benzoate (7.5 wt %) in the freshening composition leads to the fast release. Increasing the wt % of the FRM benzyl benzoate in the freshening composition to e.g., 25 wt %, 42.5 wt % or 50 wt % leads to a slower release of the freshening composition or of a component thereof, compared to the release caused by the FRM at 7.5 wt %. The release of the freshening composition mediated by the FRM benzyl benzoate being present at 50 wt % is slower than the release mediated by 42.5 wt %. The release of the freshening composition mediated by the FRM benzyl benzoate being present at 42.5 wt % is slower than the release mediated by 25 wt %. The release of the freshening composition mediated by the FRM benzyl benzoate being present at 25 wt % is slower than the release mediated by 7.5 wt %. This finding is observed with various freshening compositions comprising different perfume raw materials, e.g., Apple fragrance (see, Example G and FIG. 5; Example L and FIG. 10) or Floral Fresh fragrance (see, Example H and FIG. 6; Example K and FIG. 9). This finding is also observed with various freshening compositions comprising different solvents or diluents, e.g., 2,2-dimethyl-1,3-dioxolane-4-methanol (Augeo Clean Multi® brand name from Solvay; see, Example G and FIG. 5; Example L and FIG. 10) or 3-methyl-1,3-butanediol-1-acetate (IPD-AC® brand name from Kuraray, which is 3-hydroxy-3-methylbutyl acetate, an acetate ester derived from 3-methyl-1.3-butanediol; see, Example H and FIG. 6; Example K and FIG. 9).

Unexpectedly and surprisingly, the inventors have found that some FRMs can be used to up-regulate and to down-regulate release of a freshening composition or of a component thereof. As exemplified by the FRM benzyl benzoate (BB), compared to a control freshening composition not comprising an FRM, lower amounts of BB (e.g., 7.5 wt % and 25 wt %) in a freshening composition lead to an up-regulation of release of the freshening composition or of a component thereof while higher wt % of the BB (42.5 wt % and 50 wt %) in the freshening composition lead to down-regulation of release of the freshening composition or of a component thereof (e.g., see, Example G and FIG. 5; Example L and FIG. 10). Up-regulation of release leads to faster evaporation of the freshening composition or of the component thereof. Thus, in some embodiments of the present invention when a faster evaporation of the freshening composition is desired, a user would add a lower amount of an FRM (e.g., the FRM benzyl benzoate) to the freshening composition. Down-regulation of release leads to slower evaporation of the freshening composition or of the component thereof. Thus, in some embodiments of the present invention when a slower evaporation of the freshening composition is desired, a user would add a larger amount of an FRM (e.g., the FRM benzyl benzoate) to the freshening composition.

C. Solvents and Diluents

The present invention provides solvents or diluents for use in freshening compositions. In some embodiments of the present invention, a freshening composition comprises a perfume raw material and a solvent or diluent. In some embodiments of the present invention, an air freshening composition comprises a perfume raw material and a solvent or diluent. In some embodiments of the present invention, a liquid freshening composition comprises a perfume raw material and a solvent or diluent. In some embodiments of the present invention, a clear freshening composition comprises a perfume raw material and a solvent or diluent. In some embodiments of the present invention, a homogenous freshening composition comprises a perfume raw material and a solvent or diluent. In some embodiments of the present invention, a clear liquid freshening composition comprises a perfume raw material and a solvent or diluent. In some embodiments of the present invention, a liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a homogeneous clear liquid air freshening composition comprises a perfume raw material and a solvent or diluent. In some embodiments of the present invention, a non-water-based air freshening composition comprises a perfume raw material and a solvent or diluent. A solvent or diluent, from time to time, may also be referred to as solubilizer. It is understood and one of ordinary skill in the art will appreciate that, if not clearly contradicted by the content of this specification, each embodiment of a solvent, diluent, or solubilizer and/or features/elements disclosed as part of that embodiment can be combined with any of the embodiments hereinabove or hereinbelow.

When a freshening composition comprises a perfume raw material and a solvent or diluent, those ingredients are different.

In some embodiments of the present invention, a freshening composition comprises a perfume raw material, a solvent or diluent, and a fragrance release modulator (FRM). In some embodiments of the present invention, an air freshening composition comprises a perfume raw material, a solvent or diluent, and an FRM. In some embodiments of the present invention, a liquid freshening composition comprises a perfume raw material, a solvent or diluent, and an FRM. In some embodiments of the present invention, a clear freshening composition comprises a perfume raw material, a solvent or diluent, and an FRM. In some embodiments of the present invention, a homogenous freshening composition comprises a perfume raw material, a solvent or diluent, and an FRM. In some embodiments of the present invention, a clear liquid freshening composition comprises a perfume raw material, a solvent or diluent, and an FRM. In some embodiments of the present invention, a liquid air freshening composition comprises a perfume raw material, a solvent or diluent, and an FRM. In some embodiments of the present invention, a homogeneous clear liquid air freshening composition comprises a perfume raw material, a solvent or diluent, and an FRM. In some embodiments of the present invention, a homogeneous clear liquid air freshening composition comprises a perfume raw material, a solvent or diluent, and an FRM. In some embodiments of the present invention, a non-water-based air freshening composition comprises a perfume raw material, a solvent or diluent, and an FRM.

When a freshening composition comprises a perfume raw material, a solvent or diluent, and an FRM, those ingredients are different.

In some embodiments of the present invention, a solvent is a volatile solvent. With a few exceptions, such as silicon fluids, most high volatile solvents are classified as volatile organic compounds (VOCs). Thus, in some embodiments of the present invention, a solvent is a volatile organic compound. In the United States, acceptable levels of VOC solvents in a final product is restricted by national organizations, such as the Environmental Protection Agency (EPA) or the California Air Resources Board (CARB). The present invention provides freshening compositions that are in compliance with requirements imposed by those agencies.

The inventors have established certain key performance requirements (KPRs) for a solvent to be used for the formulation of a liquid freshening composition as described herein, preferably, for the formulation of a freshening composition for use with a wicking delivery device. According to those KPRs, a preferred solvent is completely miscible with any perfume raw material described herein. A preferred solvent is odorless, or at least of low odor. Also, according to those KPRs, a preferred solvent easily wicks through a delivery device as described herein without clogging it. Another characteristic of a solvent for use in formulating a freshening composition is to easily diffuse from the emanating surface of a delivery device into an external environment, the atmosphere, air, or onto an external surface. Other preferred characteristics of a solvent include compliance with safety requirements, such as being CARB-accepted. Further, they should be cost effective, readily available, and preferably, sustainable.

Thus, one of ordinary skill in the art knows how to characterize solvents based on their polarities, volatilities, functionalities, flash points, densities, viscosities, and surface tensions. Those basic techniques are not set forth herein.

In some embodiments of the present invention, a freshening composition comprises a solvent, a diluent, and/or a solubilizer. A solvent can also function as a diluent. A solvent may also comprise or a blend of solvents with different polarities and volatilities, a functional perfume component, such as a malodor counteracting ingredient, or combinations thereof.

In some embodiments of the present invention, a solvent is a mixture of solvents or a plurality of solvents.

One of ordinary skill in the art will appreciate that a solvent or diluent for use in the present invention(s) is not limited and that various solvents or diluents, not explicitly described herein, can be used to practice the present invention(s). Thus, following the Examples provided herein, a skilled artisan will be able to identify useful solvents or diluents.

In some embodiments of the present invention, a preferred solvent or diluent is an organic solvent or diluent. An organic solvent is a compound having at least one carbon atom in its structure.

In some embodiments of the present invention, a preferred solvent or diluent is an oxygenated solvent or diluent. An oxygenated solvent or diluent contains at least one oxygen in its molecular structure. Examples of oxygenated solvents include, but are not limited to, e.g., alcohols, ethers, esters, glycol ethers, glycol ether esters, ketones. Various glycol ether compounds can be used in embodiments of the present invention. In some embodiments of the present invention a preferred glycol ether is selected from the group consisting of dipropylene glycol (common abbreviation, DPG), tripropylene glycol (common abbreviation, TPG), tripropylene glycol monomethyl ether (common abbreviation, TPM), dipropylene glycol monomethyl ether (common abbreviation, DPM), propylene glycol (common abbreviation, PG), ethylene glycol monoethylether, (common abbreviation, EGEE), ethylene glycol monomethyl ether (common abbreviation, EGME), diethylene glycol monoethyl ether (common abbreviation, DEEGEE), diethylene glycol monomethyl ether (common abbreviation, DGME), butylene glycol (common abbreviation, BG), hexylene glycol (common abbreviation, HG), dipropylene glycol monomethyl ether acetate (common abbreviation, DPMA). A preferred glycol ether is dipropylene glycol (DPG). Another preferred glycol ether is dipropylene glycol monomethyl ether (DPM). Another preferred glycol ether is dipropylene glycol monomethyl ether acetate (DPMA). Another preferred glycol ether is tripropylene glycol monomethyl ether (TPM).

In some embodiments of the present invention, a preferred solvent or diluent is a hydrocarbon solvent or diluent. A hydrocarbon solvent or diluent contains at least one hydrogen and at least one carbon atom in its molecular structure.

In some embodiments of the present invention, a preferred solvent or diluent is a halogenated solvent or diluent. A halogenated solvent or diluent contains at least one halogen atom (F, Cl, Br, I, At) in its molecular structure.

In some embodiments of the present invention, a solvent or diluent is a volatile organic compound (VOC).

Applicants surprisingly have found that in some embodiments of the present invention, certain fragrance release modulator, e.g., dimethyl adipate, also function as solvent or diluent. As such, there is an overlap of ingredients that function as an FRM and as a solvent or diluent. However, when referring to a freshening composition comprising a perfume raw material, an FRM and a solvent or diluent, the PRM, the FRM and the solvent or diluent are different ingredients.

In some embodiments of the present invention, a solvent or diluent for use in a freshening composition of the present invention excludes glycol ethers. Thus, in some embodiments of the present invention, a solvent or diluent is a non-glycol solvent. In some embodiments of the present invention, a solvent or diluent is a non-glycol ether solvent.

A preferred solvent or diluent includes, but is not limited to, 3-methyl-1,3butanediol-1-acetate (IPD-AC® brand name from Kuraray, which is 3-hydroxy-3-methylbutyl acetate, an acetate ester derived from 3-methyl-1.3-butanediol), 2,2-dimethyl-1,3-dioxolane-4-methanol (Augeo Clean Multi® brand name from Solvay), dimethyl adipate (DMA), Isopar M® (trade name from ExxonMobil), dimethicone, disiloxane, trisiloxane, cyclosiloxane, and a combination of any of the preceding solvents or diluents. Thus, in some embodiments of the present invention, a solvent or diluent is selected from the group consisting of 3-methyl-1,3-butanediol-1-acetate, 2,2-dimethyl-1,3-dioxolane-4-methanol, dimethyl adipate, Isopar M®, dimethicone, disiloxane, trisiloxane, cyclosiloxane, and a combination of any of the preceding solvents or diluents. In some embodiments of the present invention, a solvent or diluent is selected from the group consisting of 2,2-dimethyl-1,3-dioxolane-4-methanol, 3-methyl-1,3-butanediol-1-acetate, dimethyl adipate, dimethicone, disiloxane, trisiloxane, a cyclosiloxane, Isopar M®, and a combination of any of the preceding solvents or diluents. In some embodiments of the present invention, a solvent or diluent is selected from the group consisting of 2,2-dimethyl-1,3-dioxolane-4-methanol, 3-methyl-1,3-butanediol-1-acetate, dimethyl adipate, a $C_{15-19}$alkane, a $C_{13-19}$isoparaffine, an alkylcyclosiloxane, an aryl-cyclosiloxane, and a combination of any of the preceding solvents or diluents.

In some embodiments of the present invention, a solvent or diluent is a $C_{15-19}$alkane. Preferred $C_{15-19}$alkanes include, but are not limited to, e.g., Emogreen L-15® (European Community Number: 942-444-6; CAS Number: 68551-20-2; European REACH registration number: 01-2120107955-53) or Emogreen L-19® (European Community Number: 942-446-7; CAS Number: 90622-53-0; European REACH registration number: 01-212010795749), each of which is believed to be a mixture of different fractions.

In some embodiments of the present invention, a solvent or diluent is a $C_{13-19}$isoparaffine. Preferred $C_{13-19}$isoparaffines include, but are not limited to, e.g., Isopar M® (trade name from ExxonMobil, CAS Number: 64742-47-8), Isopar H® (trade name from ExxonMobil, CAS Number: 64742-49-9/90622-57-4), Isopar K® (trade name from ExxonMobil, CAS Number: 64742-48-9), and Isopar L® (trade name from ExxonMobil, CAS Number: 64742-489), each of which is believed to be a mixture of different fractions. Isopar M® Fluid is produced from petroleum-based raw materials, which are treated with hydrogen in the presence of a catalyst to produce a low odor, low aromatic hydrogencarbon solvent. The major components include normal alkanes, isoalkanes, and cycloalkanes. (See, Exxon Mobile Isopar M® Fluid, Product Safety Summary). For EU only: EC No.: 920-901-0 and 927-676-8; Chemical Name: Hydrocarbons, $C_{11}$-$C_{16}$, isoalkanes, <2% aromatics. CAS No. 64742-8; Chemical Name: Distillates (petroleum), Hydrotreated light.

In some embodiments of the present invention, a solvent or diluent is Augeo Clean Multi®. Augeo Clean Multi® is known as acetone monoglycerol ketal (CAS Number 10079-8). It can be obtained from various sources, including Solvay (Vernon, TX, USA). Freshening compositions comprising as a solvent 2,2-dimethyl-1,3-dioxolane-4-methanol (Augeo Clean Multi®) are described herein, e.g., in Examples C, D, F, H, I, J, K, and L.

In some embodiments of the present invention, a solvent or diluent is IPD-AC®. IPD-AC® is known as 3-methyl-1, 3-butanediol-acetate (CAS Number 1609958-13-5). It can be obtained from various sources, including Kuraray America Inc., Kuraray America Chemicals Division (Houston, TX, USA). Freshening compositions comprising as a solvent 3-methyl-1,3-butanediol-1-acetate (IPD-AC®) are described herein, e.g., in Examples C, D, E, G, I, J, and L.

In some embodiments of the present invention, a solvent or diluent is selected from the group consisting of a compound having CAS number 100-79-8, a compound having CAS number 1609958-13-5, a compound having CAS number 64742-47-8, a compound having CAS number 64742-48-9, a compound having CAS number 64742-49-9/90622-57-4, a compound having CAS number 64742-8, a compound having CAS number 68551-20, a compound having CAS number 68551-20-2, a compound having CAS number 90622-53-0, and mixtures of any of the preceding compounds. In some embodiments of the present invention, a solvent or diluent is STA-SOL® ESS 165. STA-SOL® ESS 165 is known as dimethyl adipate (synonyms: hexanedioic acid, 1,6-dimethyl ester, dimethyl ester, adipic acid, dimethyl ester). It can be obtained from various sources, including ST Laboratories, Inc. (Cranston, RI, USA). Freshening compositions comprising as a solvent dimethyl adipate (STASOL® ESS 165) are described herein, e.g., in Examples C, D, and L.

In some embodiments of the present invention, a solvent or diluent is VOLASIL® DM-2. VOLASIL® DM-2 is known as dimethicone. It can be obtained from various sources, including CHEMSIL Silicones, Inc. (Chatsworth, CA, USA). Freshening compositions comprising as a solvent dimethicone (VOLASIL® DM-2) are described herein, e.g., in Examples C, D, and I.

A freshening composition of the present invention may comprise a solvent or diluent at a level of less than about 90 wt %, less than about 80 wt %, less than about 70 wt %, less than about 60 wt %, less than about 50 wt %, less than about 40 wt %, less than about 30 wt % less than about 20 wt %, less than about 10 wt %, less than about 5 wt %, less than about 2 wt % or less than about 1 wt %, with the weight percentages being relative to the total weight of the freshening composition.

A freshening composition of the present invention may comprise a solvent or diluent at a level of greater than about 1 wt %, greater than about 2 wt %, greater than about 5 wt %, greater than about 10 wt %, greater than about 20 wt %, greater than about 30 wt %, greater than about 40 wt %, greater than about 50 wt %, greater than about 60 wt %, greater than about 70 wt %, greater than about 80 wt %, greater than about 90 wt %, with the weight percentages being relative to the total weight of the freshening composition.

A freshening composition of the present invention may comprise a solvent or diluent in a range from about 0.1 wt % to about 99 wt %, in a range from about 0.5 wt % to about 99 wt % in a range from about 1 wt % to about 95 wt % in a range from about 1 wt % to about 90 wt % in a range from about 2 wt % to about 85 wt % in a range from about 5 wt % to about 80 wt % in a range from about 10 wt % to about 70 wt %, in a range from about 15 wt % to about 60 wt %, in a range from about 20 wt % to about 55 wt %, in a range from about 25 wt % to about 50 wt %, in a range from about 30 wt % to about 40 wt %, with the weight percentages being relative to the total weight of freshening composition.

A freshening composition of the present invention may comprise a solvent or diluent in a range between about 0.1 wt % and about 99 wt %, in a range between about 0.5 wt % and about 99 wt %, in a range between about 1 wt % and about 95 wt %, in a range between about 1 wt % and about 90 wt %, in a range between about 2 wt % and about 85 wt %, in a range between about 5 wt % and about 80 wt %, in a range between about 10 wt % and about 70 wt 0 in a range between about 15 wt % and about 60 wt %, in a range between about 20 wt % and about 55 wt %, in a range between about 25 wt % and about 50 wt %, in a range between about 30 wt % and about 40 wt %, with the weight percentages being relative to the total weight of freshening composition.

In a freshening composition comprising a perfume raw material, a solvent or diluent, and a fragrance release modulator (FRM), those ingredients make up at least about 50 wt % of the freshening composition. In some embodiments of the present invention, the three ingredients add up to at least about 60 wt %, at least about 70 wt %, at least about 75 wt %, at least about 80 wt %, at least about 85 wt % at least about 90 wt %, at least about 95 wt %, at least about 99 wt % of the freshening composition. In some embodiments of the present invention, the three ingredients add up to 100 wt % of the freshening composition.

D. Functional Ingredients

In some embodiments of the present invention, a freshening composition comprises a compound having a functional activity, i.e., a functional ingredient. It is understood and one of ordinary skill in the art will appreciate that, if not clearly contradicted by the content of this specification, each embodiment of a compound having a functional activity or a functional ingredient and/or features/elements disclosed as part of that embodiment can be combined with any of the embodiments hereinabove or hereinbelow.

In some embodiments of the present invention, a freshening composition comprises a perfume raw material and a functional ingredient. In some embodiments of the present invention, an air freshening composition comprises a perfume raw material and a functional ingredient. In some embodiments of the present invention, a liquid freshening composition comprises a perfume raw material and a functional ingredient. In some embodiments of the present invention, a clear freshening composition comprises a perfume raw material and a functional ingredient. In some embodiments of the present invention, a homogenous freshening composition comprises a perfume raw material and a functional ingredient. In some embodiments of the present invention, a clear liquid freshening composition comprises a perfume raw material and a functional ingredient. In some embodiments of the present invention, a liquid air freshening composition comprises a perfume raw material and a functional ingredient. In some embodiments of the present invention, a homogeneous clear liquid air freshening composition comprises a perfume raw material and functional ingredient. In some embodiments of the present invention, a homogeneous clear liquid air freshening composition comprises a perfume raw material and a functional ingredient. In some embodiments of the present invention, a non-water-based air freshening composition comprises a perfume raw material and a functional ingredient. When a freshening composition comprises a perfume raw material and a functional ingredient, those ingredients are different.

In some embodiments of the present invention, a freshening composition comprises a perfume raw material, a solvent or diluent, and a functional ingredient. When a freshening composition comprises a perfume raw material, a solvent or diluent, and a functional ingredient, those ingredients are different.

In some embodiments of the present invention, a freshening composition comprises a perfume raw material, a fragrance release modulator (FRM), and a functional ingredient. When a freshening composition comprises a perfume raw material, an FRM, and a functional ingredient, those ingredients are different.

In some embodiments of the present invention, a freshening composition comprises a perfume raw material, a solvent or diluent, a fragrance release modulator (FRM), and a functional ingredient. When a freshening composition comprises a perfume raw material, a solvent or diluent, an FRM, and a functional ingredient, those ingredients are different.

Functional ingredients provide various beneficial activities, such as cleaning, surface care protection, fabric conditioning or softening, fabric refreshing, de-wrinkling, air freshening, air deodorizing, malodor removal, skin moisturizing, body deodorizing, and the like. A functional ingredient may include water or deionized water.

A variety of functional ingredients may be used without diverging from the scope of the present invention. In some embodiments of the present invention, an ingredient having a functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of the present invention, a functional ingredient is an ingredient having a malodor counteracting activity. Thus, in some embodiments of the present invention, a freshening composition comprises an ingredient having malodor counteracting activity. A variety of ingredients having malodor counteracting activity may be used without diverging from the scope of the present invention.

In a freshening composition of the present invention, certain functional ingredients deliver a malodor removal benefit. A malodor removal benefit is defined as both a sensory and analytically measurable (such as by gas chromatography) malodor reduction or malodor decrease. Thus, in some embodiments of the present invention, a freshening composition delivers a malodor removal benefit. A freshening composition will not function merely by using perfume to cover up or mask odors. Rather, in some embodiments of the present invention wherein a freshening composition is provided with a malodor controlling agent, the freshening composition utilizes one or more of several types of odor control mechanisms. A preferred functional ingredient having malodor controlling agent is cyclodextrin. Cyclodextrin" includes α-cyclodextrin, β-cyclodextrin, γ-cyclodextrin. Included within "cyclodextrin" are derivatives of cyclodextrin, e.g., ether, ester, and amide derivatives. In some embodiments of the present invention, β-cyclodextrin is an unmodified β-cyclodextrin. Particularly included within the term "cyclodextrin" are modified cyclodextrins as described in U.S. Pat. Nos. 5,134,127 and 6,407,079. Thus, in some embodiments of the present invention, a freshening composition comprises a cyclodextrin.

In some embodiments of the present invention, a functional ingredient is an ingredient having antimicrobial activity. Thus, in some embodiments of the present invention, a freshening composition comprises an ingredient having antimicrobial activity. An antimicrobial ingredient may also exhibit some bactericidal properties, depending on the dose. The main role of an antimicrobial ingredient is to inhibit the growth of any such microorganism in a freshening composition and on any area which is exposed to such freshening composition.

A variety of ingredients having antimicrobial activity may be used without diverging from the scope of the present invention. Suitable antimicrobial ingredients include, but are not limited to e.g., parabens, i.e., methyl, ethyl, propyl or butyl paraben and mixtures thereof, benzyl alcohol; phenol; cresol; cetrimide and thiomersal. A preferred antimicrobial ingredient is a paraben. Other preferred ingredients having microbial activity are hexylene glycol, 1,2 hexanediol, and phenoxy ethanol.

In some embodiments of the present invention, a functional ingredient is an insect repellant. Thus, in some embodiments of the present invention, a freshening composition comprises an insect repellant. A variety of insect repellants may be used without diverging from the scope of the present invention. Preferred insect repellents include, but are not limited to, e.g., N,N-diethyl-meta-toluamide and methyl nonyl ketone.

In some embodiments of the present invention, a functional ingredient is preservative. Thus, in some embodiments of the present invention, a freshening composition comprises a preservative. A variety of preservatives may be used without diverging from the scope of the present invention. Preferred preservatives include, but are not limited to, e.g., imidazolidinyl urea, diazolidinyl urea, allantoin, and sodium hydroxymethylglycinate.

In some embodiments of the present invention, a functional ingredient is an antioxidant. Thus, in some embodiments of the present invention, a freshening composition comprises an antioxidant. A variety of antioxidants may be used without diverging from the scope of the present invention. Preferred antioxidants include, but are not limited to, e.g., butylate hydroxytoluene, ascorbic acid, and tocopherol.

In some embodiments of the present invention, a functional ingredient is a humectant. Thus, in some embodiments of the present invention, a freshening composition comprises a humectant. A variety of humectants may be used without diverging from the scope of the present invention. Preferred humectants include, but are not limited to, e.g., glycerol, hexylene glycol, and ethyl-hexylglycerin.

In some embodiments of the present invention, a functional ingredient is a UV-blocking agent. Thus, in some embodiments of the present invention, a freshening composition comprises a UV-blocking agent. A variety of UV-blocking agents may be used without diverging from the scope of the present invention. Preferred UV-blocking agents include, but are not limited to, e.g., avobenzone, oxybenzone, dioxybenzone, and octocrylene.

In some embodiments of the present invention, a functional ingredient is a pigment. Thus, in some embodiments of the present invention, a freshening composition comprises a pigment. A variety of pigments may be used without diverging from the scope of the present invention. Preferred pigments include, but are not limited to, e.g., chrome oxide, iron oxide, and ferric ferrocyanate.

In some embodiments of the present invention, a functional ingredient is a dye. Thus, in some embodiments of the present invention, a freshening composition comprises a dye. A variety of dyes may be used without diverging from the scope of the present invention. Such dyes include both water and oil soluble dyes. Preferred dyes include, but are not limited to, e.g., C71100 D&C Yellow #8, C73005 D&C Red #6, and C76002 D&C Green #6.

In some embodiments of the present invention, a functional ingredient is a surfactant. Thus, in some embodiments of the present invention, a freshening composition comprises a surfactant. A variety of surfactants may be used without diverging from the scope of the present invention. Surfactants include nonionic surfactants, anionic surfactants, and cationic surfactants. A preferred nonionic surfactant includes, but is not limited to, polyalkoxylate, glucose, sucrose, and amine oxide. A preferred anionic surfactant includes, but is not limited to, sulfate, sulfonate, carboxylate, and phosphate. Preferred cationic surfactant include, but are not limited to, e.g., alkylammonium salts.

In some embodiments of the present invention, a functional ingredient is an emulsifier. Thus, in some embodiments of the present invention, a freshening composition comprises an emulsifier. A variety of emulsifiers may be used without diverging from the scope of the present invention. Preferred emulsifiers include, but are not limited to, e.g., ethoxylated sorbitols, such as Tween20® or Tween85®. Tween20® is known in the art as polyethylene glycol sorbitan monolaureate (polyoxyethylenesorbitan monolaureate, CAS Number. 9005-64-5; MDL number MFCD00165986). Tween85® is known in the art as polyoxyethylensorbitan trioleate (CAS Number 9005-70-3; MDL number MFCD01779641).

In some embodiments of the present invention, a functional ingredient is a solubilizer. Thus, in some embodiments of the present invention, a freshening composition comprises a solubilizer. A variety of solubilizers may be used without diverging from the scope of the present invention. Preferred solubilizers include, but are not limited to, e.g., propylene glycol, dipropylene glycol, and hexylene glycol.

In some embodiments of the present invention, a functional ingredient is a polymer. Thus, in some embodiments of the present invention, a freshening composition comprises a polymer. A variety of polymers may be used without diverging from the scope of the present invention. Preferred polymers include, but are not limited to, e.g., cellulose derivatives, such as ethyl cellulose, and polyvinyl alcohol.

In some embodiments of the present invention, a functional ingredient is a buffer. Thus, in some embodiments of the present invention, a freshening composition comprises a buffer. A variety of buffers may be used without diverging from the scope of the present invention. Preferred buffers include, but are not limited to, e.g., phosphate buffers.

In some embodiments of the present invention, a perfume raw material comprises a mixture comprising one or more of an ingredient having a functional activity, as described herein. In some embodiments of the present invention the ingredient having a functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

A freshening composition of the present invention may comprise a functional ingredient at a level of less than about 90 wt %, less than about 85 wt %, less than about 80 wt %, less than about 75 wt %, less than about 70 wt %, less than about 65 wt %, less than about 60 wt %, less than about 55 wt %, less than about 50 wt %, less than about 45 wt %, less than about 40 wt %, less than about 35 wt %, less than about 30 wt %, less than about 25 wt %, less than about 20 wt %, less than about 15 wt %, less than about 10 wt %, less than about 5 wt %, less than about 2 wt %, less than about 1 wt %, less than about 0.5 wt %, less than about 0.2 wt %, or less than about 0.1 wt %, with the weight percentages being relative to the total weight of the freshening composition. A preferred amount for a functional ingredient in a freshening composition is less than about 50 wt %.

A freshening composition of the present invention may comprise a functional ingredient at a level of greater than about 0.01 wt %, greater than about 0.1 wt %, greater than about 0.2 wt %, greater than about 0.5 wt %, greater than about 1 wt %, greater than about 2 wt %, greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, with the weight percentages being relative to the total weight of the freshening composition. A preferred amount for a functional ingredient in a freshening composition is greater than about 5 wt %.

In some embodiments of the present invention, a freshening composition of the present invention comprises a functional ingredient in an amount of about 0.01 wt %, about 0.02 wt % about 0.05 wt %, about 0.1 wt %, about 0.2 wt %, about 0.5 wt %, about 1 wt %, about 2 wt %, about 5 wt %, about 7.5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt % about 70 wt %, about 75 wt %, about 80 wt %, about 85 wt %, about 90 wt % with the weight percentages being relative to the total weight of the freshening composition. A preferred amount for a functional ingredient in a freshening composition is about 5 wt %.

In some embodiments of the present invention, a freshening composition of the present invention comprises a functional ingredient in a range from about 0.01 wt % to about 99 wt %, in a range from about 0.02 wt % to about 95 wt %, in a range from about 0.05 wt % to about 95 wt %, in a range from about 0.1 wt % to about 95 wt %, in a range from about 0.2 wt % to about 95 wt %, in a range from about 0.5 wt % to about 95 wt %, in a range from about 1 wt % to about 95 wt % in a range from about 2 wt % to about 90 wt % in a range from about 3 wt % to about 85 wt % in a range from about 5 wt % to about 80 wt % in a range from about 10 wt % to about 75 wt % in a range from about 15 wt % to about 70 wt %, in a range from about 20 wt % to about 65 wt %, in a range from about 25 wt % to about 60 wt %, in a range from about 30 wt % to about 55 wt %, in a range from about 40 wt % to about 50 wt %, with the weight percentages being relative to the total weight of the freshening composition. A preferred range of a functional ingredient in a freshening composition is from about 5 wt % to about 80 wt %.

In some embodiments of the present invention, a freshening composition of the present invention comprises a functional ingredient in a range between about 0.01 wt % and about 99 wt %, in a range between about 0.02 wt % and about 95 wt %, in a range between about 0.05 wt % and about 95 wt %, in a range between about 0.1 wt % and about 95 wt %, in a range between about 0.2 wt % and about 95 wt %, in a range between about 0.5 wt % and about 95 wt %, in a range between about 1 wt % and about 95 wt %, in a range between about 2 wt % and about 90 wt %, in a range between about 3 wt % and about 85 wt %, in a range between about 5 wt % and about 80 wt %, in a range between about 10 wt % and about 75 wt %, in a range between about 15 wt % and about 70 wt %, in a range between about 20 wt % and about 65 wt %, in a range between about 25 wt % and about 60 wt %, in a range between about 30 wt % and about 55 wt %, in a range between about 40 wt % and about 50 wt %, with the weight percentages being relative to the total weight of the freshening composition. A preferred range of a functional ingredient in a freshening composition is between about 5 wt % and about 80 wt 0.

In a freshening composition comprising a perfume raw material, a solvent or diluent, a fragrance release modulator (FRM), and a functional ingredient, those ingredients make up at least about 50 wt % of the freshening composition. In some embodiments of the present invention, the four ingredients add up to at least about 60 wt %, at least about 70 wt %, at least about 75 wt %, at least about 80 wt %, at least about 85 wt %, at least about 90 wt %, at least about 95 wt %, at least about 99 wt % of the freshening composition. In some embodiments of the present invention, the four ingredients add up to 100 wt % of the freshening composition.

III. Articles, Air Care Products, Devices, and Air Fresheners

The present invention also provides articles, air care products, devices, and air fresheners. It is understood and one of ordinary skill in the art will appreciate that, if not clearly contradicted by the content of this specification, each embodiment of an article, air care product, device, or air freshener and/or features/elements disclosed as part of that embodiment can be combined with any of the embodiments hereinabove or hereinbelow.

A freshening composition of the present invention may be used with an article, air care product, device, or air freshener to deliver volatile materials of a freshening composition, such as the scent of a freshening composition or that of a component thereof, into the atmosphere, into the air, or onto a surface. Thus, the present invention also provides articles, air care products, devices, and air fresheners for use with freshening compositions described herein. It is contemplated that the article, air care product, device, or air freshener is configured for use in a variety of applications to deliver volatile materials of a freshening composition, such as the scent of a freshening composition or of a component thereof, into the atmosphere, into the air, onto a surface, or into or onto an environment. In the context of inventions described herein, unless clearly distinguished by context, the terms article, air care product, device, air freshener, and air freshener device are used interchangeably herein.

In some embodiments of the present invention, an air care product or a device comprises (1) a reservoir as described herein and (2) a freshening composition as described herein. In some embodiments of the present invention, an air care product or a device comprises (1) a reservoir and (2) a liquid freshening composition. In some embodiments of the present invention, an air care product or a device comprises (1) a reservoir and (2) a clear freshening composition. In some embodiments of the present invention, an air care product or a device comprises (1) a reservoir and (2) a homogeneous freshening composition. In some embodiments of the present invention, an air care product or a device comprises (1) a reservoir and (2) a clear liquid freshening composition. In some embodiments of the present invention, an air care product or a device comprises (1) a reservoir and (2) an air freshening composition. In some embodiments, an air care product or a device comprises (1) a reservoir and (2) a liquid air freshening composition. In some embodiments of the present invention, an air care product or a device comprises (1) a reservoir and (2) a clear liquid air freshening composition. In some embodiments of the present invention, an air care product or a device comprises (1) a reservoir and (2) a homogeneous liquid air freshening composition. In some embodiments of the present invention, an air care product or a device comprises (1) a reservoir and (2) a homogeneous clear liquid air freshening composition. In some embodiments of the present invention, an air care product or a device comprises (1) a reservoir and (2) a non-water-based air freshening composition.

A freshening composition of the present invention may be combined with any air care product or device wherein the freshening composition may be used directly or after dilution with solvents or diluents.

A freshening composition of the present invention may be combined with any air care product or device adapted for use in a method of the present invention as further described herein.

As will be appreciated by one of skill in the art, the design of an air care product or device comprising a freshening composition of the present invention and for use in a method of the present invention is not limited. In some embodiments of the present invention, an air care product is selected from the group consisting of a spray, an energized air freshening delivery system and a passive delivery device.

In some embodiments of the present invention, an air care product or device comprises a delivery system, which is in communication or in contact with a freshening composition that is also present in such air care product or device. The delivery system then directly or indirectly permits the freshening composition or of a component thereof to be released into the atmosphere, into the air, or onto a surface. A variety of suitable delivery systems are described herein.

In some embodiments of the present invention, an air care product or device comprises an evaporative assistance element which facilitates the evaporation, delivery, and dispersion of a freshening composition. A variety of suitable evaporative assistance elements, including, but not limited to, a heater, a fan, an agitator, and combinations thereof, are described herein. As described herein, release of a freshening composition or of a component thereof can be controlled, customized and/or modulated at room temperature (e.g., see, Examples) by addition of a fragrance release modulator to a freshening composition, i.e., without the addition of an external evaporative assistance element, e.g., a heat source, such as a heater. A heater, nevertheless, may be included in an air care product or device, to further control or facilitate release of the freshening composition or of a component thereof.

In some embodiments of the present invention, an air care product or device comprises a reservoir having a functionality selected from the group consisting of accepting a freshening composition, receiving a freshening composition, holding a freshening composition, housing a freshening composition, storing a freshening composition, accepting a delivery system, accepting an evaporative element, and accepting a seal or lid.

In some embodiments of the present invention, an article, an air care product, a device or an air freshener device consists of a reservoir having a functionality selected from the group consisting of accepting a freshening composition, receiving a freshening composition, holding a freshening composition, housing a freshening composition, storing a freshening composition, accepting a delivery system, accepting an evaporative element, and accepting a seal or lid.

In some embodiments of the present invention, an article, an air care product, a device or an air freshener device comprises a compartment for a battery. In some embodiments of the present invention, an article, an air care product, a device or an air freshener device comprises a compartment for a plurality of batteries. Such energized device may be a battery-operated air freshener.

In some embodiments of the present invention, an air care product or device comprises a plug for an electrical outlet. Such energized device may be an electrical wall plugin air freshener.

Aside from the air care products and devices described herein, one of ordinary skill in the art will appreciate that other commercially available and/or described air care products and devices may be used in combination with a freshening composition of the present invention.

In some embodiments of the present invention, a freshening composition of the present invention resides within an air care product or device as described in published U.S. Pat. Appl. No. US2014/01157665 A1, which hereby is incorporated by this reference in its entirety for all purposes.

In some embodiments of the present invention, a freshening composition of the present invention resides within an air care product or device as described in published U.S. Pat. Appl. No. US2016/0089465 A1, which hereby is incorporated by this reference in its entirety for all purposes.

In some embodiments of the present invention, a freshening composition of the present invention resides within an air care product or device as described in published U.S. Pat. Appl. No. US2016/0367715 A1, which hereby is incorporated by this reference in its entirety for all purposes.

In some embodiments of the present invention, a freshening composition of the present invention resides within an air care product or device as described in published U.S. Pat. Appl. No. US2018/0008740 A1, which hereby is incorporated by this reference in its entirety for all purposes.

A. Air Care Products Comprising a Means for Delivering a Freshening Composition

The present invention also provides air care products comprising a means for delivering a freshening composition. It is understood and one of ordinary skill in the art will appreciate that, if not clearly contradicted by the content of this specification, each embodiment of an air care product comprising a means for delivering a freshening composition and/or features/elements disclosed as part of that embodiment can be combined with any of the embodiments hereinabove or hereinbelow.

In some embodiments of the present invention, an air care product or device comprising a freshening composition is adapted or configured to deliver the freshening composition or a component thereof, preferably into the atmosphere, air, and/or onto a surface. Such air care product or device may be configured in various ways. For example, the air care product may comprise a means for delivering a freshening composition or a component thereof. Means for delivering a freshening composition or a component thereof include, but are not limited to, e.g., an actuator attached to a spraying device, a releasing element in the form of a wick, a reed, a stick, a fiber, a mesh, a membrane, or a porous or semi-porous substrate, including a felt pad.

B. Reed Diffuser Air Freshener

In some embodiments, an air care product or device is a reed diffuser air freshener. It is understood and one of ordinary skill in the art will appreciate that, if not clearly contradicted by the content of this specification, each embodiment of a reed diffuser air freshener and/or features/elements disclosed as part of that embodiment can be combined with any of the embodiments hereinabove or hereinbelow.

A reed diffuser air freshener may be configured in various ways. In some embodiments, a reed diffuser air freshener comprises (i) an air freshening composition, (ii) a reservoir, container, or vessel, (iii) one or more reeds, and (iv) an opening for the one or more reeds. The reservoir (or container, vessel) has a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid. They may be made of different materials, such as glass, ceramic, wood, plastic, or metal, or of a combination of any of the preceding materials. Further, size and shape of the reservoir, (e.g., a bottle, a bowl, a tray, a plate, a glass, a shell, a box, a sphere, a globe, a vessel, or a container) are not limited. Thus, they may be of different sizes and shapes. The one or more reeds can be of natural or synthetic materials.

C. Air Care Products and Devices Configured as Energized Devices

In some embodiments of the present invention, an air care product or device is configured as an energized device. It is understood and one of ordinary skill in the art will appreciate that, if not clearly contradicted by the content of this specification, each embodiment of an air care product or device configured as an energized device and/or features/elements disclosed as part of that embodiment can be combined with any of the embodiments hereinabove or hereinbelow.

Exemplary, non-limiting energized devices include an electrical device. The energized device may be an electrical wall plug-in, or a battery-operated air freshener. They may have a delivery engine such as a wick, which is in direct contact with a freshening composition, and which is used to transport the freshening composition or a component thereof to an emanating surface or into the air, where the freshening composition is released to an external environment.

In some embodiments of the present invention, an energized air freshening delivery system is electrically powered. In some embodiments of the present invention, an energized air freshening delivery system is selected from the group consisting of a fan-based diffuser, a liquid electric pluggable air freshener, and an electromechanical actuating diffuser.

In some embodiments, an energized device is a heating device, e.g., a device powered by a chemical reaction, such as a catalyst fuel system, a solar powered device, etc.

In some embodiments of the present invention, an energized device comprises a micro-fluidic die having either a heater(s) or piezo crystal(s) that are used to dispense droplets of the freshening composition into the air.

An exemplary and preferred energized device is an electrical wall plug-in air freshener. In some embodiments of the present invention, a wall plug-in air freshener comprises a housing. Such housing is connected to an electrical outlet by a plug that is directly or indirectly attached to the housing. The wall plug-in air freshener further comprises at least one reservoir for accepting, receiving, holding and/or storing a freshening composition until it is used up. The housing may serve as a holder for the reservoir(s) and any of the other components of the air freshener. In some embodiments of the present invention, a wall plug-in air freshener further comprises a delivery engine, e.g., in the form of a wick. In some embodiments of the present invention, a wall plug-in air freshener further comprises an evaporative assistance element, e.g., in the form of a heater for dispensing the volatile material.

While some air care products or devices having a single reservoir, a single evaporative assistance element, and a single delivery engine, one of ordinary skill in the art will appreciate that air care products or devices may comprise more than reservoir, more than one evaporative assistance element, and/or more than one delivery engine. In embodiments where an air care product or device comprises more than one reservoir, each reservoir may contain a different freshening composition or may contain the same freshening composition.

D. Air Care Products and Devices Comprising a Wick

In some embodiments, an air care product or device comprises a means for delivering a freshening composition in the form of a wick. It is understood and one of ordinary skill in the art will appreciate that, if not clearly contradicted by the content of this specification, each embodiment of an air care product or device comprising a wick and/or features/elements disclosed as part of that embodiment can be combined with any of the embodiments hereinabove or hereinbelow.

A wick may be configured and be manufactured from different materials. Those materials can be natural or synthetic. They may have different porosities, various different shapes, and sizes. Exemplary, non-limiting wicks include, a wick having a cylindrical form or a wick having an elongate cube shape. Further, a wick may be characterized by its porosity, length, diameter, or width depending on its shape. As will be appreciated by one of ordinary skill in the art, wick porosity and the material of which it is made are critical parameters that influence the capillary diffusion process of a freshening composition or of a component thereof. The length of a wick is not limiting. In some embodiments of the present invention, the length of a preferred wick ranges from about 1 millimeter ("mm") to about 100 mm, from about 5 mm to about 75 mm, or from about 10 mm to about 50 mm. In some embodiments of the present invention, the length of a preferred wick is between about 1 millimeter ("mm") and about 100 mm, between about 5 mm and about 75 mm, or between about 10 mm and about 50 mm. Similarly, the diameter or width of a wick is not limiting. In some embodiments, a preferred wick has a diameter of at least about 1 mm, of at least about 2 mm, of at least about 3 mm, or of at least about 4 mm. In some embodiments, a preferred wick has a width of at least about 1 mm, of at least about 2 mm, of at least about 3 mm, or of at least about 4 mm.

A wick exhibits a density and porosity. Density and porosity of a wick are not critical. In some embodiments of the present invention, the density of a preferred wick ranges from about 0.100 grams/$cm^3$ ("g/cc") to about 1.0 g/cc. In some embodiments of the present invention, the porosity of a preferred wick may be in the range from about 0.35 g/cc to about 0.85 g/cc. In some embodiments of the present invention, the density of a preferred wick is between about 0.100 grams/$cm^3$ ("g/cc") and about 1.0 g/cc. In some embodiments of the present invention, the porosity of a preferred wick is between about 0.35 g/cc and about 0.85 g/cc.

In some embodiments of the present invention, a wick comprises a porous or semi-porous substrate. A wick may comprise various materials and may be manufactured by various methods of construction, including, but not limited to, bundled fibers that may be compressed and/or formed into various shapes via overwrap (such as a non-woven sheet overwrap) or be made of sintered plastics such as polyethylene (PE), high-density polyethylene (HDPE) or other polyolefins. For example, a wick may be made from a plastic material, such as polyethylene or a polyethylene blend.

In some embodiments of the present invention, an air care product or device is a passive diffuser that is not electrically powered. In some embodiments of the present invention, a passive diffuser is a passive air diffuser apparatus. A passive air diffuser apparatus can comprise a breathable membrane for diffusing and evaporating a freshening composition.

In some embodiments of the present invention, a passive diffuser is a wicking air freshener. In some embodiments of the present invention, a wicking air freshener is selected from the group consisting of a reed diffuser, a steam-based freshener, and a membrane-based air freshener. A preferred membrane-based air freshener is a car vent air freshener.

E. Air Care Product and Devices Comprising an Evaporative Surface

Air care products and devices of the present invention typically comprise an evaporative surface with which a freshening composition comes into contact. It is understood and one of ordinary skill in the art will appreciate that, if not clearly contradicted by the content of this specification, each embodiment of an air care product or device comprising an evaporative surface and/or features/elements disclosed as part of that embodiment can be combined with any of the embodiments hereinabove or hereinbelow.

In some embodiments of the present invention, an evaporative surface may be integral or separate from an evaporative assistance element and/or the delivery engine. The evaporative surface may be configured as a porous or semi-porous substrate, a bowl or a plate. That substrate, bowl or plate can be made of wood, of plastic, of glass, of metal or of a combination of any of the preceding materials.

In some embodiments of the present invention, an air care product or device comprises an evaporative assistance element. An evaporative assistance element may be used to achieve or facilitate the evaporation of a freshening composition or of a component thereof from the air care product. Such an evaporative assistance element may be configured in various ways. In some embodiments of the present invention, an evaporative assistance element is selected from the group consisting of a heater, a fan, an agitation member, a powered agitator, a manual agitator, and a combination thereof.

In some embodiments of the present invention, an evaporative assistance element is a heater comprising one or more heating elements. Such one or more heating elements may be used to heat a liquid volatile freshening composition within an air care product. A heater may be configured to heat the delivery system to a desired temperature. A preferred temperature is in the range from about 45° C. to about 75° C.

In some embodiments of the present invention, an evaporative assistance element comprises a chemical constituent. Such chemical constituent may be used to speed up evaporation or release rates of the freshening composition. In some embodiments of the present invention, an evaporative assistance element comprises a chemically heated membrane. Such chemically heated membrane may be used to provide increased evaporation of a freshening composition via exothermic reaction. As one of skill in the art will appreciate, synergistic combinations of a heating element, chemical constituent or chemically heated membrane may be used as well.

An energized device having an evaporative assistance element in the form of a heater may be configured to heat the delivery engine to various temperatures. For example, the energized device may be configured such that the heater heats an evaporative surface, such as a wick, membrane, gel, porous or semi-porous substrate, such as a felt pad, to a temperature from about 30° C. to about 150° C. A preferred energized device comprises a control system such that the heater temperature is adjustable. In some embodiments of the present invention, a control system also cycles the heater temperature to provide greater control over the evaporation process of the freshening composition.

F. Spraying Devices

A preferred air care product is spraying device comprising a freshening composition of the present invention. It is well within the art to convert a freshening composition of the present invention into an aerosol and then use it as a spray. Essentially, a system comprising a freshening composition of the present invention, a container, a propellant, a valve, an actuator/a nozzle allowing the freshening composition of the present invention to be atomized into fine droplets or particles and sprayed into or onto an environment, is designed. It then can be released under pressure.

It is understood that before a freshening composition of the present invention can be sprayed it must be dispersible in a solvent/propellant system. Further, it is noted that the freshening composition of the present invention is chemically compatible with the chosen propellant and container materials so that no reaction, corrosion, or phase separation takes place.

Another requirement is that the freshening composition of the present invention has a viscosity low enough to flow and atomize through the nozzle of the spraying device, typically less than 100 cP.

Choosing a propellant that provides the pressure that expels and atomizes a product such as a freshening composition of the present invention, also is well known in the art. Essentially, there are two broad categories for use as propellants: compressed gases and liquefied gases. In some embodiments of the present invention a spraying device comprises a compressed gas as a propellant. Compressed gases include, but are not limited, to, e.g., nitrogen, carbon dioxide, air, and the like. In some embodiments of the present invention a spraying device comprises a liquefied gas as a propellant. Liquefied gases include, but are not limited to, e.g., propane, butane, isobutane, dimethyl ether, hydrofluorocarbons, and the like. In some embodiments of the present invention, a propellant is a volatile organic solvent (e.g., ethanol), an isoparaffinic hydrocarbon (e.g., Isopar grades), or a volatile silicone (e.g., cyclomethicone) to carry the freshening composition, combined with a liquefied hydrocarbon propellant (e.g., propane, n-butane, isobutane, blends or mixtures thereof) or dimethyl ether (DME).

Various formulations comprising various ratios of (i) a freshening composition of the present invention, (ii) a co-solvent and (iii) a propellant can be made and used. In some embodiments of the present invention, a spraying device comprises an aerosol spray comprising (i) from about 0.01 wt % to about 50 wt % of a freshening composition of the present invention, (ii) from about 1 wt % to about 80 wt % of a co-solvent, and (iii) from about 1 wt % to about 50 wt % of a propellant. In some embodiments of the present invention, a spraying device comprises an aerosol spray comprising (i) from about 1 wt % to about 20 wt % of a freshening composition of the present invention, (ii) from about 30 wt % to about 80 wt % of a co-solvent, and (iii) from about 5 wt % to about 30 wt % of a propellant. Useful co-solvents include, but are not limited to, e.g., ethanol, an isoparaffin, a volatile silicone, and blends and mixtures thereof. Useful propellants include, but are not limited to, e.g., propane, butane, isobutane, DME, blends and mixtures thereof.

As an alternative to using propellants, one can use pump (non-pressurized) sprays with ethanol instead. Various ratios of freshening composition to ethanol in a pump spray can be employed. A preferred pump spray comprises from about 5 wt % to about 30 wt %, of a freshening composition of the present invention and from about 70 wt % to about 95 wt % ethanol.

In some embodiments of the present invention, a co-solvent may be added to a freshening composition of the present invention and a propellant to, e.g., adjust viscosity, control droplet size and to ensure a uniform spray pattern. Suitable co-solvents include, but are not limited to, e.g., ethanol, acetone, mineral spirits and isoparaffins. Care will be taken that a cosolvent does not negatively impact any of the desired characteristics of a freshening composition of the present invention, including its smell and scent.

Further, it is within the knowledge of a skilled artisan to select a suitable container for the spraying device, e.g., a can or a bottle. The container typically is made of metal (tinplate or aluminum) or plastic. It is rated for pressure (typically from about 3 to 10 atm). Attached to the container is a valve assembly controlling the flow rate and product release. Further attached to the container is an actuator or a nozzle designed to atomize a freshening composition of the present invention into the desired spray pattern, e.g., a fine mist. Each of the components of the delivery system (container, valve assembly, actuator/nozzle) are pressure rated and chemically resistant to the freshening composition. The components are properly sealed to prevent leakage or premature, undesired evaporation of the freshening composition.

The aerosol must deliver not only a desired droplet size, typically from about 1 to 50 micrometers for fine mist but also a desired spray rate and angle, stable pressure throughout its shelf life and no phase separation or clogging. To achieve that, a skilled artisan will resort to techniques known in the art and properly adjust the ratio of freshening composition to propellant, solvent volatility, nozzle design and may add viscosity modifiers.

The filling of the container (transferring a freshening composition of the present invention into the container) typically is done in a pressurized environment. The valve, and actuator/nozzle are crimped onto the container. A desired propellant is injected either through the valve (under pressure) or by cold-filling (liquid propellant added at low temperature. After filling, the container is leak-tested and weighed to ensure correct fill.

When the aerosol is sprayed, a pressurized liquid composition (freshening composition, co-solvent when present, propellant) inside the container is released through a nozzle turning the liquid composition into a fine mist or spray of tiny droplets or particles suspended in air, i.e., into or onto an environment. After the spraying, the propellant quickly diffuses into the air. The freshening composition and co-solvent, may evaporate in the air (e.g., freshening the air) or deposit on a surface (e.g., coating a fabric, as further described herein).

Testing and validation of a spraying device of the present invention includes, but is not limited to, e.g., spray pattern analysis, pressure retention and leakage tests, evaporation rate and droplet size measurements, and chemical stability testing—using techniques known in the art.

III. Methods

In some embodiments, the present invention provides methods for formulating a freshening composition, methods for manufacturing an article, an air care product, a device or an air freshener device comprising (1) a reservoir and (2) a freshening composition, methods for using a freshening composition, methods for using an article, an air care product, a device or an air freshener device comprising (1) a reservoir and (2) a freshening composition to deliver a freshening composition or a component thereof, methods for delivering a smell or scent of a freshening composition or of a component thereof, and methods for modulating the release and evaporation of a freshening composition or of a component thereof. In each of the methods of the present invention, described in greater detail below, various elements described herein, can be employed. Those elements include, without limitations, e.g., a freshening composition comprising (i) a perfume raw material and (ii) a fragrance release modulator, a freshening composition comprising (i) a perfume raw material, (ii) a solvent, and (iii) a fragrance release modulator, a freshening composition comprising (i) a perfume raw material, (ii) a solvent, (iii) a fragrance release modulator, and (iv) a functional ingredient, a freshening composition comprising (i) a perfume raw material, (ii) a fragrance release modulator, and (iii) a functional ingredient, an article, an air care product, or an air freshener device comprising (1) a reservoir and (2) a freshening composition, a delivery system, an evaporative assistant element, etc. Following are some general considerations for methods of the present invention.

In some embodiments of a method of the present invention, a freshening composition comprises (i) a perfume raw material as described herein and (ii) a fragrance release modulator as described herein. In some embodiments of a method of the present invention, a freshening composition comprises (i) a perfume raw material as described herein, (ii) a fragrance release modulator as described herein, and (iii) a functional ingredient t as described herein. In some embodiments of a method of the present invention, a freshening composition comprises (i) a perfume raw material as described herein, (ii) a solvent as described herein, and (iii) a fragrance release modulator as described herein. In some embodiments of a method of the present invention, a freshening composition comprises (i) a perfume raw material as described herein, (ii) a solvent as described herein, (iii) a fragrance release modulator as described herein, and (iv) a functional ingredient as described herein.

In some embodiments of a method of the present invention, a freshening composition comprises (i) from about 0.1 wt % to about 95 wt % of a perfume raw material as described herein and (ii) from about 0.01 wt % to about 90 wt % of a fragrance release modulator as described herein. In some embodiments of a method of the present invention, a freshening composition comprises (i) from about 0.1 wt % to about 95 wt % of a perfume raw material as described herein, (ii) from about 0.01 wt % to about 90 wt % of a fragrance release modulator as described herein, and (iii) less than 50 wt % of a functional ingredient as described herein. In some embodiments of a method of the present invention, a freshening composition comprises (i) from about 0.1 wt % to about 95 wt % of a perfume raw material as described herein, (ii) from about 1.0 wt % to about 95 wt % of a solvent as described herein, and (iii) from about 0.01 wt % to about 90 wt % of a fragrance release modulator as described herein. In some embodiments of a method of the present invention, a freshening composition comprises (i) from about 0.1 wt % to about 95 wt % of a perfume raw material as described herein, (ii) from about 1.0 wt % to about 95 wt % of a solvent as described herein, (iii) from about 0.01 wt % to about 90 wt % of a fragrance release modulator as described herein, and (iv) less than 50 wt % of a functional ingredient as described herein.

In some embodiments of a method of a present invention a freshening composition comprises (i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials and (ii) from about 0.01 wt % to about 90 wt % fragrance release modulator having one or more, two or more, or three or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l; wherein the fragrance release modulator is selected from the group consisting of a $C_{2-8}$ linear alcohol, a $C_{2-8}$ branched alcohol, an alkylether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkylbenzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkylsuccinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators.

In some embodiments of a method of a present invention a freshening composition comprises (i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials, (ii) from about 1.0 wt % to about 95 wt % of a solvent or diluent; and (iii) from about 0.01 wt % to about 90 wt % fragrance release modulator having one or more, two or more, or three or more characteristics selected from the group consisting of (a) a flash point higher than about 100° F., (b) a surface tension of less than about 60 mN/m, (c) a dynamic viscosity from about 0.5 cp to about 100 cp, and (d) a density from about 600 g/l to about 1,300 g/l; wherein the fragrance release modulator is selected from the group consisting of a $C_{2-8}$ linear alcohol, a $C_{2-8}$ branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators.

In some embodiments of a method of the present invention, a freshening composition is adapted to have one or more, two or more, or three or more of a characteristic selected from the group consisting of (a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l.

In some embodiments of a method a method of the present invention, a perfume raw material comprises a plurality of perfume raw materials. Suitable perfume raw materials are described herein.

In some embodiments of a method of the present invention, a solvent or diluent is selected from the group consisting of an alkyl-adipate, an aryl-adipate, an alkyl-glycerol, an aryl-glycerol, an alkyl-diol, an aryl-diol, an isoparaffin, a silicon, and a mixture of any of the preceding solvents or diluents.

In some embodiments of a method of the present invention, a solvent or diluent is selected from the group consisting of 2,2-dimethyl-1,3-dioxolane-4-methanol, 3-methyl-1, 3butanediol-1-acetate, dimethyl adipate, dimethicone, disiloxane, trisiloxane, a $C_{15-19}$alkane, a $C_{13-19}$isoparaffine, a cyclosiloxane, Isopar M®, an alkyl-cyclosiloxane, an aryl-cyclosiloxane, and a mixture of any of the preceding solvents or diluents.

In some embodiments of a method of a method of the present invention, a solvent or diluent is selected from the group consisting of a compound having CAS number 100-79-8, a compound having CAS number 1609958-13-5, a compound having CAS number 64742-47-8, a compound having CAS number 64742-48-9, a compound having CAS number 64742-49-9/90622-57-4, a compound having CAS number 64742-8, a compound having CAS number 68551-20, a compound having CAS number 68551-20-2, a compound having CAS number 90622-53-0, and a mixture of any of the preceding compounds.

In some embodiments of a method of a method of the present invention, a fragrance release modulator is selected from the group consisting of ethanol, n-propanol, isopropanol, n-butanol, t-butanol, 3-methoxy-3-methyl-1-butanol, 3-methyl-3-methoxyl butanol, 1pentanol, 2-pentanol, amyl-alcohol, n-pentyl alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, propylene carbonate, dimethyl carbonate, isoamyl laurate, methyl palmitate, methyl stearate, dimethyl ether, dimethyl adipate, dimethyl succinate, dimethyl glutarate, n-butyl propionate, dimethicone, disiloxane, trisiloxane, and a mixture of any of the preceding fragrance release modulators.

In some embodiments of a method of a method of the present invention, a freshening composition comprises less than about 50 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method of the present invention, a freshening composition comprises less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method of the present invention, a freshening composition comprises less than 20 wt % of an ingredient having a functional activity and wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method of the present invention, a freshening composition comprises less than 20 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method of the present invention, an article, air care product, device, or air freshener device comprises a delivery system. In some embodiments of a method of the present invention, an article, air care product, device, or air freshener device comprises a delivery system, wherein the delivery system comprises an element in communication or in contact with a freshening composition. In some embodiments of a method of the present invention, a delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

In some embodiments of a method of the present invention, an article, air care product, device, or air freshener device comprises a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid. In some embodiments of a method of the present invention, a reservoir is selected from the group consisting of a bottle, a bowl, a tray, a plate, a glass, a shell, a box, a sphere, a globe, a vessel, and a container.

In some embodiments of a method of the present invention, an article, air care product, device, or air freshener device comprises an evaporative assistance element. In some embodiments of a method of the present invention, an evaporative assistance element is selected from the group consisting of a heater, a fan, an agitator, and a combination of any of the preceding evaporative assistance elements.

In some embodiments of a method of the present invention, an article, air care product, device, or air freshener device comprises an evaporative assistance element and a delivery system. In some embodiments of a method the present invention, the evaporative assistance element is a heater and wherein the heater is configured to heat the delivery system to a temperature in the range from about 45° C. to about 75° C.

A. Methods for Manufacturing a Freshening Composition

The present invention also provides methods for manufacturing a freshening composition. It is understood and one of ordinary skill in the art will appreciate that, if not clearly contradicted by the content of this specification, each embodiment of a method for manufacturing a freshening composition and/or features/elements disclosed as part of that embodiment can be combined with any of the embodiments hereinabove or hereinbelow.

Freshening compositions of the present invention can be manufactured without any further guidance, other than this disclosure, by one of ordinary skill in the art. As such, the present invention provides a method for manufacturing a freshening composition. The steps for manufacturing a freshening composition, described in detail below, can be performed in any order, consecutively, or contemporaneously.

In some embodiments of a method for manufacturing a freshening composition, the method comprises the step of adding a perfume raw material to a fragrance release modulator or the step of adding a fragrance release modulator to a perfume raw material. As one of ordinary skill in the art will appreciate, the step of adding one ingredient or component to another is synonymous with the step of combining one ingredient or component with the other.

In some embodiments of a method for manufacturing a freshening composition, the method comprises the step of adding a perfume raw material to a solvent or diluent. As one of ordinary skill in the art will appreciate, the step of adding one ingredient or component to another is synonymous with the step of combining one ingredient or component with another.

In some embodiments of a method for manufacturing a freshening composition, the method comprises the step of adding a solvent or diluent to a perfume raw material.

In some embodiments of a method for manufacturing a freshening composition, the method comprises the step of adding a fragrance release modulator to a solvent or diluent.

In some embodiments of a method for manufacturing a freshening composition, the method comprises the step of adding a solvent or diluent to a fragrance release modulator.

In some embodiments of a method for manufacturing a freshening composition, the method comprises the step of adding a perfume raw material to a fragrance release modulator to formulate a first mixture. In some embodiments of a method for manufacturing a freshening composition, the method further comprises the step of adding a solvent or diluent to the first mixture to formulate a second mixture.

Alternatively, in some embodiments of a method for manufacturing a freshening composition, the method comprises the step of adding a perfume raw material to a solvent or diluent to formulate a first mixture. The method then further comprises the step of adding a fragrance release modulator to the first mixture to formulate a second mixture.

In some embodiments of a method for manufacturing a freshening composition, the method comprises the step of combining one or more perfume raw materials. Thus, in some embodiments of a method for manufacturing a freshening composition, the method comprises the step of adding a first perfume raw material to a second perfume raw material. In some embodiments of a method for manufacturing a freshening composition, the method comprises the step of adding a perfume raw material to a plurality of different perfume raw materials.

In some embodiments of a method for manufacturing a freshening composition, the method comprises the step of combining one or more fragrance release modulators. Thus, in some embodiments of a method for manufacturing a freshening composition, the method comprises the step of adding a first fragrance release modulator to a second fragrance release modulator. In some embodiments of a method for manufacturing a freshening composition, the method comprises the step of adding a fragrance release modulator to a plurality of different fragrance release modulators.

In some embodiments of a method for manufacturing a freshening composition, the method comprises the step of combining one or more solvents or one or more diluents. Thus, in some embodiments of a method for manufacturing a freshening composition, the method comprises the step of adding a first solvent or diluent to a second solvent or diluent. In some embodiments of a method for manufacturing a freshening composition, the method comprises the step of adding a solvent or diluent to a plurality of different solvents or diluents.

In some embodiments of the present invention, wherein a perfume raw material is a solid material, it may be first combined with a solvent or diluent that has the capability of solubilizing said solid perfume raw material. In those circumstances, a solvent or diluent may also be described as solubilizer.

In some embodiments of the present invention, a method for manufacturing a freshening composition comprises the step of combining (i) a perfume raw material as described herein and (ii) a fragrance release modulator as described herein, thereby producing a mixture comprising (i) and (ii). In some embodiments, the method comprises combining (i), (ii), and (iii) a functional ingredient as described herein, thereby producing a mixture comprising (i), (ii), and (iii).

In some embodiments of the present invention, a method for manufacturing a freshening composition comprises the step of combining (i) a perfume raw material as described herein, (ii) a solvent as described herein, and (iii) a fragrance release modulator as described herein, thereby producing a mixture comprising (i), (ii), and (iii). In some embodiments, the method comprises combining (i), (ii), (iii), and (iv) a functional ingredient as described herein, thereby producing a mixture comprising (i), (ii), (iii), and (iv).

In some embodiments of a method for manufacturing a freshening composition, the method comprises the step of adding a fragrance release modulator in an amount sufficient to control or modulate the release of the freshening composition or of a component thereof. In some embodiments of a method for manufacturing a freshening composition, the method comprises the step of adding a fragrance release modulator in an amount sufficient to provide a customized or desired rate of release of the freshening composition or of a component thereof. In some embodiments of a method for manufacturing a freshening composition, the method comprises the step of adding a fragrance release modulator in an amount sufficient to provide a customized or desired release profile of the freshening composition or of a component thereof over time.

In some embodiments of a method for manufacturing a freshening composition, the method comprises the step of adding a fragrance release modulator in an amount sufficient to up-regulate the release of the freshening composition or of a component thereof, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

In some embodiments of a method for manufacturing a freshening composition, the method comprises the step of adding a fragrance release modulator in an amount sufficient to down-regulate the release of the freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

In some embodiments of a method for manufacturing a freshening composition, the method comprises the step of combining (i) a perfume raw material and (ii) a fragrance release modulator to make up at least about 50 wt % of the freshening composition. In some embodiments of the present invention, the two ingredients add up to at least about 60 wt %, to at least about 70 wt %, to at least about 75 wt %, to at least about 80 wt %, to at least about 85 wt %, to at least about 90 wt %, to at least about 95 wt %, to at least about 99 wt % of the freshening composition. In some embodiments of the present invention, the two ingredients add up to 100 wt % of the freshening composition.

In some embodiments of a method for manufacturing a freshening composition, the method comprises the step of combining (i) a perfume raw material, (ii) a solvent or diluent, and (iii) a fragrance release modulator to make up at least about 50 wt % of the freshening composition. In some embodiments of the present invention, the three ingredients add up to at least about 60 wt %, to at least about 70 wt %, to at least about 75 wt %, to at least about 80 wt %, to at least about 85 wt %, to at least about 90 wt %, to at least about 95 wt %, to at least about 99 wt % of the freshening composition. In some embodiments of the present invention, the three ingredients add up to 100 wt % of the freshening composition.

In some embodiments of a method for manufacturing a freshening composition, the method further comprises the step of adding to a mixture comprising (i) a perfume raw material and (ii) a fragrance release modulator less than about 50 wt % of an ingredient having a functional activity, wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing a freshening composition, the method further comprises the step of adding to a mixture comprising (i) a perfume raw material, (ii) a solvent or diluent, and (iii) a fragrance release modulator less than about 50 wt % of an ingredient having a functional activity, wherein the ingredient having the functional activity is selected from the group consisting of an ingredient having malodor counteracting activity, an ingredient having antimicrobial activity, an ingredient having an insect repellant activity, an ingredient having a preservative activity, an ingredient having an antioxidant activity, an ingredient having a humectant activity, an ingredient having a UV-blocking activity, an ingredient having a pigment activity, an ingredient having a dye activity, an ingredient having a surfactant activity, an ingredient having an emulsifier activity, an ingredient having a solubilizer activity, an ingredient having a polymer activity, and an ingredient having a buffer activity.

In some embodiments of a method for manufacturing a freshening composition, the method further comprises the step of adding to the mixture comprising (i) a perfume raw material and (ii) a fragrance release modulator less than about 50 wt % of an ingredient having a functional activity, wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method for manufacturing a freshening composition, the method further comprises the step of adding to the mixture comprising (i) a perfume raw material, (ii) a solvent or diluent, and (iii) a fragrance release modulator less than about 50 wt % of an ingredient having a functional activity, wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

In some embodiments of a method for manufacturing a freshening composition, the method comprises the step of combining (i) a perfume raw material, (ii) a fragrance release modulator, and (iii) a functional ingredient to make up at least about 50 wt % of the freshening composition. In some embodiments of the present invention, the three ingredients add up to at least about 60 wt %, to at least about 70 wt %, to at least about 75 wt %, to at least about 80 wt %, to at least about 85 wt %, to at least about 90 wt %, to at least about 95 wt %, to at least about 99 wt % of the freshening composition. In some embodiments of the present invention, the three ingredients add up to 100 wt % of the freshening composition.

In some embodiments of a method for manufacturing a freshening composition, the method comprises the step of combining (i) a perfume raw material, (ii) a solvent or diluent, (iii) a fragrance release modulator, and (iv) a functional ingredient to make up at least about 50 wt % of the freshening composition. In some embodiments of the present invention, the four ingredients add up to at least about 60 wt %, to at least about 70 wt %, to at least about 75 wt 0 to at least about 80 wt %, to at least about 85 wt %, to at least about 90 wt %, to at least about 95 wt %, to at least about 99 wt % of the freshening composition. In some embodiments of the present invention, the four ingredients add up to 100 wt % of the freshening composition.

B. Methods for Manufacturing an Article, an Air Care Product, a Device, or an Air Freshener Device Comprising (1) a Reservoir and (2) a Freshening Composition The present invention also provides methods for manufacturing an article, an air care product, a device, or an air freshener device comprising (1) a reservoir and (2) a freshening composition. It is understood and one of ordinary skill in the art will appreciate that, if not clearly contradicted by the content of this specification, each embodiment of a method for manufacturing an article, an air care product, a device, or an air freshener device comprising (1) a reservoir and (2) a freshening composition and/or features/elements disclosed as part of that embodiment can be combined with any of the embodiments hereinabove or hereinbelow.

Thus, one of ordinary skill in the art using this specification will be able to manufacture an article, an air care product, a device, or an air freshener device comprising (1) a reservoir and (2) a freshening composition of the present invention. As such, the present invention provides methods for manufacturing an article, an air care product, a device, or an air freshener device comprising (1) a reservoir and (2) a freshening composition.

Any freshening composition of the present invention may be used in a variety of forms to manufacture an article, an air care product, a device, or an air freshener device comprising (1) a reservoir and (2) a freshening composition. For example, freshening compositions of the present invention may be used to manufacture sprayable, capillary wicking, membrane diffusing and/or steam-diffusing articles, air care products, devices, or air freshener devices.

Any freshening composition of the present invention may be introduced into an article, an air care product, a device, or an air freshener device without any further guidance, other than this disclosure. An article, air care product, device, or air freshener device is not limiting. An article, air care product, device, or air freshener device can be any article, air care product, device, or freshener device, such as a commercially available article, air care product, device, or air freshener device comprising a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid.

Even an article, air care product, device, or air freshener device not comprising a reservoir can be used in a method for manufacturing an article, an air care product, a device, or an air freshener device comprising (1) a reservoir and (2) a freshening composition. Articles, air care products, devices, or air freshener devices not comprising a reservoir but having a functionality of receiving a reservoir can be used in a method for manufacturing an article, an air care product, a device, or an air freshener device comprising (1) a reservoir and (2) a freshening composition. As detailed herein, in embodiments of methods using an article, air care product, device, or air freshener device not comprising a reservoir but having a functionality of receiving a reservoir, the method comprises the steps of (a) providing an article, air care product, device, or air freshener device having a functionality of accepting a reservoir and (b) attaching a reservoir described herein to the article, air care product, device, or air freshener device. Thus, in some embodiments of an article, air care product, device, or air freshener device, the article, air care product, device, or air freshener device is an article, air care product, device, or air freshener device having a functionality of receiving a reservoir. Such reservoir can be any reservoir as described herein. A preferred reservoir is a reservoir having a functionality selected from the group consisting of accepting a freshening composition, receiving a freshening composition, holding a freshening composition, housing a freshening composition, storing a freshening composition, accepting a delivery system, accepting an evaporative element, and accepting a seal or lid.

The following lists various steps in a method for manufacturing an article, an air care product, a device, or an air freshener device comprising (1) a reservoir and (2) a freshening composition. The order of those steps is not important. They may be performed in any order, consecutively or simultaneously. They may be performed by the same person or by more than one person. Further, as a skilled artisan will appreciate not all steps listed below are necessarily required to manufacture an article, an air care product, a device, or an air freshener device comprising (1) a reservoir and (2) a freshening composition.

1. Providing a Reservoir

In some embodiments of a method for manufacturing an article, an air care product, a device, or an air freshener device comprising (1) a reservoir and (2) a freshening composition, the method comprises the step of providing a reservoir having a functionality selected from the group consisting of accepting a freshening composition, receiving a freshening composition, holding a freshening composition, housing a freshening composition, storing a freshening composition, accepting a delivery system, accepting an evaporative element, and accepting a seal or lid. In some embodiments, the reservoir has the additional functionality of being capable of attaching to or being connected to an article, an air care product, a device, or an air freshener device.

In some embodiments of a method for manufacturing an article, an air care product, a device, or an air freshener device comprising (1) a reservoir and (2) a freshening composition, the method comprises the step of providing an article, an air care product, a device, or an air freshener device comprising a reservoir having a functionality selected from the group consisting of accepting a freshening composition, receiving a freshening composition, holding a freshening composition, housing a freshening composition, storing a freshening composition, accepting a delivery system, accepting an evaporative element, and accepting a seal or lid.

In some embodiments of a method for manufacturing an article, an air care product, a device, or an air freshener device comprising (1) a reservoir and (2) a freshening composition, the method comprises the step of providing an article, air care product, device, or air freshener device having a functionality of accepting a reservoir.

2. Contacting a Reservoir with a Freshening Composition

In some embodiments of a method for manufacturing an article, an air care product, a device, or an air freshener device comprising (1) a reservoir and (2) a freshening composition, the method comprises the step of contacting a reservoir or a reservoir in an article, in an air care product, in a device, or in an air freshener device with a freshening composition comprising (i) a perfume raw material as described herein and (ii) a fragrance release modulator as described herein. In some embodiments, the freshening composition comprises (i) a perfume raw material as described herein, (ii) a fragrance release modulator as described herein, and (iii) a solvent or diluent as described herein. In some embodiments, the freshening composition comprises (i), (ii), and (iii) and (iv) a functional ingredient as described herein. Any freshening composition described herein, e.g., a non-water based freshening composition, can be used. The step of contacting the reservoir with a freshening composition comprising (i) a PRM and (ii) an FRM or (i) a PRM, (ii) an FRM, and (iii) a solvent or diluent, or (i) a PRM, (ii) an FRM, and (iii) a functional ingredient, or (i) a PRM, (ii) an FRM, (iii) a solvent or diluent, and (iv) a functional ingredient can be performed by contacting the reservoir with a preformulated freshening composition already comprising the aforementioned ingredients. Alternatively, the reservoir may be contacted with each ingredient separately, consecutively, in any order, or simultaneously. The order of contacting (i) a PRM, (ii) an FRM, (iii) a solvent or diluent (when present), and (iv) a functional ingredient (when present) to a reservoir is not important as long as a homogeneous solution is obtained.

In some embodiments of the present invention, a method for manufacturing an article, an air care product, a device, or an air freshener device comprising (1) a reservoir and (2) a freshening composition, the method comprises the step of contacting a reservoir residing in an energized device with a freshening composition. Suitable energized devices, such as an electric device (wall plug-in or battery-operated), are described herein.

In some embodiments of the present invention, a method for manufacturing an article, an air care product, a device, or an air freshener device comprising (1) a reservoir and (2) a freshening composition, the method comprises the step of contacting a reservoir residing in a heating device with a freshening composition. Suitable heating devices are described herein.

In some embodiments of the present invention, a method for manufacturing an article, an air care product, a device, or an air freshener device comprising (1) a reservoir and (2) a freshening composition, the method comprises the step of contacting a reservoir residing in a device powered by a chemical reaction with a freshening composition. Suitable devices powered by chemical reactions are described herein.

In some embodiments of the present invention, a method for manufacturing an article, an air care product, a device, or an air freshener device comprising (1) a reservoir and (2) a freshening composition, the method comprises the step of contacting a reservoir residing in a passive air diffuser apparatus with a freshening composition. Suitable passive air diffuser apparatuses are described herein.

In some embodiments of a method for manufacturing an article, an air care product, a device, or an air freshener device comprising (1) a reservoir and (2) a freshening composition, the method comprises the step of contacting a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid, wherein the reservoir is not attached to an article, air care product, device, or air freshener device, with a freshening composition of the present invention.

Upon contacting the reservoir with the freshening composition, the reservoir houses the freshening composition.

3. Combining a Freshening Composition in a Reservoir

In some embodiments of a method for manufacturing an article, an air care product, a device, or an air freshener device comprising (1) a reservoir and (2) a freshening composition, the method comprises the step of combining in a reservoir (i) a perfume raw material as described herein and (ii) a fragrance release modulator as described herein. In some embodiments of a method for manufacturing an article, an air care product, a device, or an air freshener device comprising (1) a reservoir and (2) a freshening composition, the method comprises the step of combining in a reservoir (i) a perfume raw material as described herein, (ii) a fragrance release modulator as described herein, and (iii) an ingredient having a functional activity as described herein. In some embodiments of a method for manufacturing an article, an air care product, a device, or an air freshener device comprising (1) a reservoir and (2) a freshening composition, the method comprises the step of combining in a reservoir (i) a perfume raw material as described herein, (ii) a solvent as described herein, and (iii) a fragrance release modulator as described herein. In some embodiments of a method for manufacturing an article, an air care product, a device, or an air freshener device comprising (1) a reservoir and (2) a freshening composition, the method comprises the step of combining in a reservoir (i) a perfume raw material as described herein, (ii) a solvent as described herein, (iii) a fragrance release modulator as described herein, and (iv) an ingredient having a functional activity as described herein. The step of combining the ingredients typically involves transferring the ingredients into a reservoir. The order of combining the ingredients in the reservoir is not important as long as a homogeneous solution is obtained. The step of combining can be separately, consecutively, in any order, or simultaneously.

A freshening composition may be combined in any reservoir described herein and known in the art, e.g., a standalone reservoir, a reservoir residing in an energized device, a reservoir residing in a heating device, a reservoir residing in a device powered by a chemical reaction, or a reservoir residing in a passive air diffuser apparatus. Any reservoir having a functionality of receiving a freshening composition can be used.

Upon combining a freshening composition in a reservoir, the reservoir houses the freshening composition.

4. Transferring a Freshening Composition into a Reservoir

In some embodiments of a method for manufacturing an article, an air care product, a device, or an air freshener device comprising (1) a reservoir and (2) a freshening composition, the method comprises the step of transferring a freshening composition comprising (i) a perfume raw material as described herein and (ii) a fragrance release modulator as described herein, into a reservoir. In some embodiments of a method for manufacturing an article, an air care product, a device, or an air freshener device comprising (1) a reservoir and (2) a freshening composition, the method comprises the step of transferring a freshening composition comprising (i) a perfume raw material as described herein, (ii) a fragrance release modulator as described herein, and (iii) an ingredient having a functional activity as described herein, into a reservoir. In some embodiments of a method for manufacturing an article, an air care product, a device, or an air freshener device comprising (1) a reservoir and (2) a freshening composition, the method comprises the step of transferring a freshening composition comprising (i) a perfume raw material as described herein, (ii) a solvent as described herein, and (iii) a fragrance release modulator as described herein into a reservoir. In some embodiments of a method for manufacturing an article, an air care product, a device, or an air freshener device comprising (1) a reservoir and (2) a freshening composition, the method comprises the step of transferring a freshening composition comprising (i) a perfume raw material as described herein, (ii) a solvent as described herein, (iii) a fragrance release modulator as described herein, and (iv) an ingredient having a functional activity as described herein, into a reservoir. The step of transferring a freshening composition comprising either of the aforementioned ingredients into a reservoir can be performed by transferring a preformulated freshening composition already comprising one or more of the aforementioned ingredients into a reservoir. Alternatively, each of the aforementioned ingredients may be transferred into a reservoir separately, consecutively, in any order, or simultaneously. The order of transferring the ingredients into a reservoir is not important as long as a homogeneous solution is obtained.

A freshening composition may be transferred into any reservoir described herein and known in the art, e.g., a stand-alone reservoir, a reservoir residing in an energized device, a reservoir residing in a heating device, a reservoir residing in a device powered by a chemical reaction, or a reservoir residing in a passive air diffuser apparatus. Any reservoir having a functionality of receiving a freshening composition can be used.

Upon transferring a freshening composition into a reservoir, the reservoir houses the freshening composition.

5. Housing a Freshening Composition in a Reservoir

In some embodiments of a method for manufacturing an article, an air care product, a device, or an air freshener device comprising (1) a reservoir and (2) a freshening composition, the method comprises the step of housing a freshening composition comprising (i) a perfume raw material as described herein and (ii) a fragrance release modulator as described herein, in a reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a fragrance release modulator as described herein, and (iii) an ingredient having a functional activity as described herein, in a reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a solvent as described herein, and (iii) a fragrance release modulator as described herein, in a reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a solvent as described herein, (iii) a fragrance release modulator as described herein, and (iv) an ingredient having a functional activity as described herein, in a reservoir.

In some embodiments of a method for manufacturing an article, an air care product, a device, or an air freshener device comprising (1) a reservoir and (2) a freshening composition, the method comprises the step of housing a freshening composition comprising (i) a perfume raw material as described herein and (ii) a fragrance release modulator as described herein, in a reservoir within an article, an air care product, a device, or an air freshener device comprising the reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a fragrance release modulator as described herein, and (iii) an ingredient having a functional activity in a reservoir within an article, an air care product, a device, or an air freshener device comprising the reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a solvent as described herein, and (iii) a fragrance release modulator as described herein, in a reservoir within an article, an air care product, a device, or an air freshener device comprising the reservoir. In some embodiments of a method for manufacturing an article, an air care product, a device, or an air freshener device comprising (1) a reservoir and (2) a freshening composition, the method comprises the step of housing a freshening composition comprising (i) a perfume raw material as described herein, (ii) a solvent as described herein, (iii) a fragrance release modulator as described herein, and (iv) an ingredient having a functional activity as described herein, in a reservoir within an article, an air care product, a device, or an air freshener device comprising the reservoir.

A freshening composition may be housed in any reservoir described herein and known in the art, e.g., a stand-alone reservoir, a reservoir residing in an energized device, a reservoir residing in a heating device, a reservoir residing in a device powered by a chemical reaction, or a reservoir residing in a passive air diffuser apparatus. Any reservoir having a functionality of housing a freshening composition can be used.

6. Storing a Freshening Composition in a Reservoir

In some embodiments of a method for manufacturing an article, an air care product, a device, or an air freshener device comprising (1) a reservoir and (2) a freshening composition, the method comprises the step of storing a freshening composition comprising (i) a perfume raw material as described herein and (ii) a fragrance release modulator as described herein, in a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a fragrance release modulator as described herein, and (iii) an ingredient having a functional activity as described herein, in a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a solvent as described herein, and (iii) a fragrance release modulator as described herein, in a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a solvent as described herein, (iii) a fragrance release modulator as described herein, and (iv) an ingredient having a functional activity as described herein, in a reservoir.

In some embodiments of a method for manufacturing an article, an air care product, a device, or an air freshener device comprising (1) a reservoir and (2) a freshening composition, the method comprises the step of storing a freshening composition comprising (i) a perfume raw material as described herein and (ii)) a fragrance release modulator as described herein, in a reservoir within an article, an air care product, a device, or an air freshener device comprising a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a fragrance release modulator as described herein, and (iii) an ingredient having a functional activity as described herein, in a reservoir within an article, an air care product, a device, or an air freshener device comprising a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a solvent as described herein, and (iii) a fragrance release modulator as described herein, in a reservoir within an article, an air care product, a device, or an air freshener device comprising a reservoir. In some embodiments of a method for manufacturing an article, an air care product, a device, or an air freshener device comprising (1) a reservoir and (2) a freshening composition, the method comprises the step of storing a freshening composition comprising (i) a perfume raw material as described herein, (ii) a solvent as described herein, (iii) a fragrance release modulator as described herein, and (iv) an ingredient having a functional activity as described herein, in a reservoir within an article, an air care product, a device, or an air freshener device comprising a reservoir.

Storing a freshening composition in a reservoir can be temporarily or for a longer period of time. Preferably, the freshening composition is stored in the reservoir until the article, air care product, device, or air freshener device is used by a person. Use by a person includes, but is not limited to, releasing the freshening composition or of a component thereof, releasing the freshening composition or of a component thereof to refreshen an environment, delivering a smell or a scent of the freshening composition or of a component thereof into or onto an environment, etc.

A freshening composition may be stored in any reservoir described herein and known in the art, e.g., a stand-alone reservoir, a reservoir residing in an energized device, a reservoir residing in a heating device, a reservoir residing in a device powered by a chemical reaction, or a reservoir residing in a passive air diffuser apparatus. Any reservoir having a functionality of storing a freshening composition can be used.

7. Sealing a Reservoir Housing a Freshening Composition

In some embodiments of a method for manufacturing an article, an air care product, a device, or an air freshener device comprising (1) a reservoir and (2) a freshening composition, the method comprises the step of sealing a reservoir housing a freshening composition. Sealing a reservoir can be done by attaching one or more of a seal, a lid, or a locking mechanism. Any suitable seal, lid, or locking mechanism known in the art to prevent an unwanted or premature release of the freshening composition or of a component thereof, can be used. Thereby, the freshening composition is housed in the reservoir temporarily or for a period of time until the seal, lid, or locking mechanism is removed. Removing the seal, lid or locking mechanism may result in releasing the freshening composition or a component thereof, releasing the freshening composition or a component thereof to refreshen an environment, delivering a scent of the freshening composition or of a component thereof into or onto an environment, etc. Any reservoir having a functionality of accepting a seal, a lid or a locking mechanism can be used.

The seal, lid, or locking mechanism can be made of any material. Suitable materials include, but are not limited to, e.g., plastic, cork, wood, or glass. On top of a first seal, a second seal may be attached. A second seal, e.g., can be a screw cap. A second seal may be employed for various reasons, e.g., to better hold the first seal in position, to provide a tighter protection of evaporation, or for ornamental purposes.

In some embodiments of the present invention, the seal provides an airtight barrier and prevents release of the freshening composition or of a component thereof as long as the seal is attached to the reservoir. This is ensured by providing a secure mechanical or chemical bond between the seal and the reservoir. The seal can be a heat seal (applied by thermal bonding) using a plastic film (e.g., polyethylene (PE), polypropylene (PP), or polyethylene terephthalate (PET)) as it is used most commonly in the food, chemical, and cosmetic industries for jars and bottles.

In some embodiments of the present invention, the seal is a removable seal. Upon removal of the seal, release of the freshening composition or of a component thereof, begins.

8. Attaching a Reservoir to an Article, an Air Care Product, a Device, or an Air Freshener Device In some embodiments of a method for manufacturing an article, an air care product, a device, or an air freshener device comprising (1) a reservoir and (2) a freshening composition, the method comprises the step of attaching a reservoir to an article, an air care product, a device, or an air freshener device. Thereby an article, an air care product, a device, or an air freshener device comprising a reservoir is produced. Upon attaching the reservoir to an article, an air care product, a device, or an air freshener device, (a) the reservoir may be contacted with a freshening composition as described therein, (b) a freshening composition may be combined in the reservoir as describe herein, (c) a freshening composition may be transferred into the reservoir as described herein, (d) a freshening composition may be housed in the reservoir as described herein, or (e) a freshening composition may be stored in the reservoir as described herein. Thereby an article, an air care product, a device, or an air freshener device comprising (1) a reservoir and (2) a freshening composition is produced. Any article, air care product, device, or air freshener device having a functionality of accepting a reservoir can be used.

In some embodiments of a method for manufacturing an article, an air care product, a device, or an air freshener device comprising (1) a reservoir and (2) a freshening composition, the method comprises the step of attaching a reservoir housing a freshening composition to an article, an air care product, a device, or an air freshener device.

Thereby an article, an air care product, a device, or an air freshener device comprising (1) a reservoir and (2) a freshening composition is produced.

9. Attaching a Delivery System

In some embodiments a method for manufacturing an article, an air care product, a device, or an air freshener device comprising (1) a reservoir and (2) a freshening composition, the method comprises the step of attaching a delivery system to a reservoir or to a reservoir in an article, air care product, device, or air freshener device comprising a reservoir. Any reservoir having a functionality of accepting a delivery system can be used. Suitable delivery systems are described herein and are known in the art.

In some embodiments of a method for manufacturing an article, an air care product, a device, or an air freshener device comprising (1) a reservoir and (2) a freshening composition, the method comprises the step of contacting a delivery system to a freshening composition residing in a reservoir. Any delivery system described herein and known in the art can be used.

In some embodiments of a method for manufacturing an article, an air care product, a device, or an air freshener device comprising (1) a reservoir and (2) a freshening composition, the method comprises the step of contacting a delivery system to a freshening composition residing in a reservoir, wherein the reservoir resides in an article, an air care product, a device, or an air freshener device. Any delivery system described herein can be used.

In some embodiments of the present invention, a delivery system is selected from the group consisting of a wick, a plurality of wicks, a stick, a plurality of sticks, a reed, a plurality of reeds, a fiber, a plurality of fibers, a mesh, a conductive mesh, a membrane, a porous substrate, a semi-porous substrate, and a combination of any of the preceding delivery systems.

10. Attaching an Evaporative Assistance Element

In some embodiments a method for manufacturing an article, an air care product, a device, or an air freshener device comprising (1) a reservoir and (2) a freshening composition, the method comprises the step of attaching an evaporative assistance element to a reservoir or to a reservoir in an article, air care product, device, or air freshener device comprising a reservoir. Any reservoir having a functionality of accepting an evaporative assistance element can be used. Suitable evaporative assistance elements are described herein and are known in the art.

11. Attaching a Battery Compartment

In some embodiments a method for manufacturing an article, an air care product, a device, or an air freshener device comprising (1) a reservoir and (2) a freshening composition, the method comprises the step of attaching a battery compartment to a reservoir or to an article, air care product, device, or air freshener device comprising a reservoir. Any reservoir having a functionality of accepting a battery compartment can be used.

12. Attaching a Plug for an Electrical Outlet

In some embodiments a method for manufacturing an article, an air care product, a device, or an air freshener device comprising (1) a reservoir and (2) a freshening composition, the method comprises the step of attaching a plug for an electrical outlet to a reservoir or to an article, air care product, device, or air freshener device comprising a reservoir. Any reservoir having a functionality of accepting a plug for an electrical outlet can be used.

C. Methods for Delivering a Smell or a Scent of a Freshening Composition or Ofa Component Thereof into the Atmosphere, Air, onto a Surface, or into/onto an Environment The present invention also provides methods for delivering a smell or a scent of a freshening composition or of a component thereof into the atmosphere, air, onto a surface, or into/onto an environment. It is understood and one of ordinary skill in the art will appreciate that, if not clearly contradicted by the content of this specification, each embodiment of a method for delivering a smell or scent of a freshening composition or of a component thereof and/or features/elements disclosed as part of that embodiment can be combined with any of the embodiments hereinabove or hereinbelow.

Any freshening composition of the present invention, preferably, the smell or scent of a freshening composition of the present invention, or of a component thereof, may be delivered into the atmosphere, air, onto a surface, or into/onto an environment, without any further guidance, other than this disclosure, by one of ordinary skill in the art. As such, the present invention provides a method for delivering a freshening composition or a component thereof, preferably, the smell or scent of a freshening composition or of a component thereof, into the atmosphere, air, onto a surface, or into/onto an environment. By delivering a freshening composition or a component thereof, preferably, the smell or scent of a freshening composition or of a component thereof, into the atmosphere, air, onto a surface, or into/onto an environment, the atmosphere, air surface or environment is refreshed. By delivering a freshening composition or a component thereof, preferably, the smell or scent of a freshening composition or of a component thereof, into the atmosphere, air, onto a surface or into/onto an environment, any malodor in the atmosphere, air on the surface, or into/onto the environment is reduced.

In some embodiments of a method for delivering a freshening composition or a component thereof, preferably, the smell or scent of a freshening composition or of a component thereof, into the atmosphere, air, onto a surface, or into/onto an environment, the method comprises the step of placing an article comprising a freshening composition, an air care product comprising a freshening composition, a device comprising a freshening composition, or an air freshener device comprising a freshening composition, as described herein, into or onto an environment. In some embodiments of the present invention, the freshening composition comprises (i) a perfume raw material as described herein and (ii) a fragrance release modulator as described herein. In some embodiments of the present invention, the freshening composition comprises (i) a perfume raw material as described herein, (ii) a fragrance release modulator as described herein, and (iii) a functional ingredient as described herein. In some embodiments of the present invention, the freshening composition comprises (i) a perfume raw material as described herein, (ii) a solvent as described herein, and (iii) a fragrance release modulator as described herein. In some embodiments, the freshening composition comprises (i) a perfume raw material, (ii) a fragrance release modulator as described herein, (iii) a solvent as described herein, and (iv) a functional ingredient as described herein. Any freshening composition described herein, e.g., a non-water based freshening composition, can be used.

As described herein, in some embodiments of the present invention, a freshening composition houses in a reservoir within an air care product or device, which is sealed to prevent premature release of the freshening composition or of a component thereof. Thus, in some embodiments of a method for delivering a freshening composition or a component thereof, preferably, the smell or scent of a freshening composition or of a component thereof, into the atmosphere, air, onto a surface, or into/onto an environment, the method comprises the step of removing a seal or lid from a reservoir housing a freshening composition.

In some embodiments of a method for delivering a freshening composition or a component thereof, preferably, the smell or scent of a freshening composition or of a component thereof, in which the reservoir within an article, air care product, device, or air freshener device comprises a seal, lid, or locking mechanism to prevent premature release of the freshening composition or of a component thereof, the method comprises the step of removing the seal, lid or locking mechanism.

In some embodiments of a method for delivering a freshening composition or a component thereof, preferably, the smell or scent of a freshening composition or of a component thereof, into the atmosphere, air, onto a surface, or into/onto an environment, the method comprises the step of delivering the freshening composition or a component thereof, preferably, a liquid freshening composition or a component thereof to a delivery system within an article, air care product, device, or air freshener device. Suitable delivery systems are described herein. Any freshening composition described herein, e.g., a non-water based freshening composition, can be used.

In some embodiments of a method for delivering a freshening composition or a component thereof, preferably, the smell or scent of a freshening composition or a component thereof, into the atmosphere, air, onto a surface or into/onto an environment, the delivery system is a heating device, as described herein. It may be heated to a temperature in the range from about 45° C. to about 75° C.

In some embodiments of a method for delivering a freshening composition or a component thereof, preferably, the smell or scent of a freshening composition or a component thereof, into the atmosphere, air, onto a surface or into/onto an environment, the method comprises the step of dispersing the freshening composition or a component thereof, preferably, a liquid freshening composition or a component thereof into the atmosphere, air, onto a surface, or into/onto an environment. Any freshening composition described herein, e.g., a non-water based freshening composition, can be used.

In some embodiments of a method for delivering a freshening composition or a component thereof, preferably, the smell or scent of a freshening composition or of a component thereof, into the atmosphere, air, onto a surface, or into/onto an environment, the method comprises the step of dispersing the freshening composition or a component thereof, preferably, a liquid freshening composition or a component thereof into the atmosphere, air, onto a surface, or into/onto an environment over a controlled or customized period of time. Any freshening composition described herein, e.g., a non-water based freshening composition, can be used. As described herein (e.g., see, Examples E, F, G, H, K, L, N, and O, the choice of fragrance release modulator and its wt % in a freshening composition can be used as a means for customizing the time it takes for a freshening composition of a component thereof to be released from a freshening composition, i.e., to customize the time it takes to deliver a smell or scent of a freshening composition or of a component thereof, into the atmosphere, air, onto a surface, or into/onto an environment.

In some embodiments of a method for delivering a freshening composition or a component thereof, preferably, the smell or scent of a freshening composition or of a component thereof, the step of dispersing a freshening composition or a component thereof, preferably, a liquid freshening composition or a component thereof into the atmosphere, air, onto a surface, or into/onto an environment comprises wickening and evaporating the liquid freshening composition or a component thereof into the atmosphere, the air, onto the surface, or into/onto the environment. Any freshening composition described herein, e.g., a non-water based freshening composition, can be used.

In some embodiments of a method for delivering a freshening composition or a component thereof, preferably, the smell or scent of a freshening composition or of a component thereof, the step of dispersing a freshening composition or a component thereof, preferably, a liquid freshening composition or a component thereof into the atmosphere, air, onto a surface, or into/onto an environment, comprises a wicking-evaporation system adapted to deliver the liquid freshening composition or a component thereof into the atmosphere, the air, onto the surface, or into/onto the environment. Any freshening composition described herein, e.g., a non-water based freshening composition, can be used.

In some embodiments of a method for delivering a freshening composition or a component thereof, preferably, the smell or scent of a freshening composition or of a component thereof, the step of dispersing a freshening composition or a component thereof, preferably, a liquid freshening composition or a component thereof into the atmosphere, air, onto a surface, or into/onto an environment, comprises a wicking-evaporation system adapted to deliver the liquid freshening composition or a component thereof into the atmosphere, the air, onto the surface, or into/onto the environment over a controlled or customized period of time. Any freshening composition described herein, e.g., a non-water based freshening composition, can be used.

A variety of wicking-evaporation systems may be used. In some embodiments of the present invention, a wicking-evaporation system comprises an element selected from the group consisting of a natural wick, a plurality of natural wicks, a synthetic wick, a plurality of synthetic wicks, a stick, a plurality of sticks, a reed, a plurality of reeds, a stick, a plurality sticks, a fiber, a plurality of fibers, a mesh, a conductive mesh, a membrane, a porous substrate, a semi-porous substrate, and a combination of any of the preceding elements. Any freshening composition described herein, e.g., a non-water based freshening composition, can be used.

In some embodiments of a method for delivering a freshening composition or a component thereof, preferably, the smell or scent of a freshening composition or of a component thereof, the step of dispersing a freshening composition or a component thereof, preferably, a liquid freshening composition or a component thereof into the atmosphere, air, onto a surface, or into/onto an environment comprises exposing and evaporating the liquid freshening composition or a component thereof into the atmosphere, the air, onto the surface, or into/onto the environment. Any freshening composition described herein, e.g., a non-water based freshening composition, can be used.

In some embodiments of a method for delivering a freshening composition or a component thereof, preferably, the smell or scent of a freshening composition or of a component thereof, the step of dispersing a freshening composition or a component thereof, preferably, a liquid freshening composition or a component thereof into the atmosphere, air, onto a surface, or into/onto an environment, comprises spraying the liquid freshening composition or a component thereof into the atmosphere, the air, onto the surface, or into/onto the environment. Any freshening composition described herein, e.g., a non-water based freshening composition, can be used.

In some embodiments of a method for delivering a freshening composition or a component thereof, preferably, the scent of a freshening composition or a component thereof, into the atmosphere, air, onto a surface, or into/onto an environment, wherein the freshening composition or a component thereof resides in an article, an air care product, a device, or an air freshener device, the article, air care product, device, or air freshener device may comprise an evaporative assistance element as described herein. In some embodiments of the present invention, an evaporative assistance element is selected from the group consisting of a heater, a fan, an agitator, and a combination of any of the preceding evaporative assistance elements.

Delivery of a freshening composition or a component thereof, preferably, the smell or scent of a freshening composition or a component thereof, into the atmosphere, air, onto a surface, or into/onto an environment, can be noticed by one of ordinary skill in the art and a customer by sniffing. Upon contacting a surface with a freshening composition of the present invention, the surface may be coated temporarily with the freshening composition.

D. Methods for Customizing, Controlling, and/or Modulating the Release of a Freshening Composition or of a Component Thereof The present invention also provides methods for customizing, controlling, and/or modulating the release of a freshening composition or of a component thereof. It is understood and one of ordinary skill in the art will appreciate that, if not clearly contradicted by the content of this specification, each embodiment of a method for customizing, controlling, and/or modulating the release of a freshening composition or of a component thereof and/or features/elements disclosed as part of that embodiment can be combined with any of the embodiments hereinabove or hereinbelow.

As described in great detail herein, the inventors have found that the release of a freshening composition or of a component thereof can be customized, controlled, or modulated by employing fragrance release modulators. Employing such fragrance release modulators allows for a customizable control of the release of a freshening composition or of a component thereof. By "customized" is meant that by adding a fragrance release modulator in a specific amount (wt %) to a freshening composition, the release profile of a freshening composition or of a component thereof, can be changed in a desired way. For example, by adding the fragrance release modulator benzyl benzoate (BB) in increasing amounts to a freshening composition the release of the freshening composition or of a component thereof can be decreased, slowed down, or down-regulated over a desired period of time (e.g., see, FIGS. 9 and 10). Thus, in view of the teaching herein (see also, Examples and Figures), one of ordinary skill in the art will be able to add a specific wt % of a fragrance release modulator to a freshening composition to achieve a desired percentage release of a freshening composition or of a component thereof by a specific day. By way of example (see, Example N, FIG. 11), a skilled artisan would add 50 wt % of the FRM hexylene glycol to an Apple Fragrance to obtain a desired about 60.00% release of that freshening composition or of a component thereof by day 14. Likewise, a skilled artisan would add 50 wt % of the FRM triethyl citrate (TEC) to the same freshening composition if by day 14 only an about 22% release of the freshening composition would be desired. Using the teaching of the instant application, a skilled artisan will be able to customize the release profile of any perfume material, of any freshening composition or any component thereof, irrespective of what perfume material is used to formulate such freshening composition. As such, a skilled artisan will be able to increase (by slowing down the release of the freshening composition or component thereof) or decrease (by increasing the release of the freshening composition or component thereof) the life span of a freshening composition, simply by adding to the freshening composition a fragrance release modulator which brings about such effect. The Examples provided herein provide guidance to adjust the amount (wt %) of an FRM in a freshening composition to achieve any such desired result over a chosen time period.

As exemplified by Example E (FIG. 3) certain FRMs, such as triethyl citrate (TEC), benzyl benzoate (BB), ethanol, 3-methyl-3-methoxyl butanol (MMB) and dipropylene glycol (DPG) up-regulate release of a freshening composition wherein the freshening composition comprises in addition to the FRM and a perfume raw material the solvent 2,2-dimethyl-1,3-dioxolane-4-methanol (Augeo Clean Multi® brand name from Solvay). When the identity and amount of the PRM and solvent are kept constant, the extent of up-regulation depends on the identity of the FRM (see, Example E, FIG. 3; Example F, FIG. 4). In freshening compositions not comprising a solvent, for example, the fragrance release modulator MMB when combined with either the Apple Fragrance (see, Example N, FIG. 11) or the Floral Fresh Fragrance (see, Example O, FIG. 12) lead to a faster release of the freshening composition or component thereof. Also, the fragrance release modulator hexylene glycol when combined with either the Apple Fragrance (see, Example N, FIG. 11) or the Floral Fresh Fragrance (see, Example O, FIG. 12) lead to a faster release of the freshening composition or component thereof. Thus, in some embodiments of the present invention, a fragrance release modulator is used to up-regulate, to increase the release of a freshening composition or of a component thereof.

In some embodiments of the present invention, a method for customizing, controlling, and/or modulating the release of a freshening composition or of a component thereof comprises the step of combining an amount (wt %) of a fragrance release modulator as described herein with a perfume raw material as described herein to form a freshening composition so that an up-regulation of the release of the freshening composition or of a component thereof, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more is obtained. In some embodiments, up-regulation is by at least about 5%. In some embodiments, up-regulation is by at least about 10%. Upregulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein and a functional ingredient as described herein to form a freshening composition so that an up-regulation of the release of the freshening composition or of a component thereof, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more is obtained. In some embodiments, up-regulation is by at least about 5%. In some embodiments, up-regulation is by at least about 10%. Up-regulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein and a solvent or diluent as described herein to form a freshening composition so that an up-regulation of the release of the freshening composition or of a component thereof, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more is obtained. In some embodiments, up-regulation is by at least about 5%. In some embodiments, up-regulation is by at least about 10%. Up-regulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein, a solvent or diluent as described herein, and a functional ingredient as described herein, to form a freshening composition so that an upregulation of the release of the freshening composition or of a component thereof, relative to a control (not comprising said fragrance release modulator and assigned a value of 100%) by at least about 0.5%, by at least about 1%, by at least about 2%, by at least about 3% by at least about 5%, by at least about 10%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more is obtained. In some embodiments, up-regulation is by at least about 5%. In some embodiments, up-regulation is by at least about 10%. Upregulation can be determined as described herein.

While the FRM triethyl citrate (TEC) in lower concentrations (e.g., 7.5 wt %, Example E, FIG. 3 and Example L, FIG. 10), leads to a faster increase of release of a freshening composition or of a component thereof, at higher concentrations (e.g., at 50 wt %, Example N, FIG. 11, and Example O, FIG. 12), it leads to a slower release of a freshening composition or of a component thereof. Similarly, increasing the concentration of the FRM benzyl benzoate (BB) in a freshening composition, i.e., the wt % of BB in a freshening composition, a decrease, i.e., a down-regulation of release of the freshening composition or of the component thereof is observed (e.g., see, Example K, FIG. 9, and Example L, FIG. 10). Thus, in some embodiments of the present invention, a fragrance release modulator is used to down-regulate, to reduce the release of a freshening composition or of a component thereof.

In some embodiments of the present invention, a method for customizing, controlling, and/or modulating the release of a freshening composition or of a component thereof comprises the step of combining an amount (wt %) of a fragrance release modulator as described herein with a perfume raw material as described herein to form a freshening composition so that a down-regulation of the release of the freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more is obtained. In some embodiments, down-regulation is by at least about 5%. In some embodiments, down-regulation is by at least about 10%. Down-regulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein and a functional ingredient as described herein to form a freshening composition so that a down-regulation of the release of the freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more is obtained. In some embodiments, down-regulation is by at least about 10%. Down-regulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein and a solvent or diluent as described herein to form a freshening composition so that a down-regulation of the release of the freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more is obtained. In some embodiments, down-regulation is by at least about 10%. Down-regulation can be determined as described herein.

In some embodiments of the present invention, a method for customizing, controlling, and/or modulating the release of a freshening composition or of a component thereof comprises the step of combining an amount (wt %) of a fragrance release modulator as described herein with a perfume raw material as described herein, a solvent or diluent as described herein, and a functional ingredient as described herein to form a freshening composition so that a downregulation of the release of the freshening composition or of a component thereof, relative to a control (not comprising said fragrance release modulator and assigned a value of 100%) by at least about 0.5%, by at least about 1%, by at least about 2%, by at least about 3%, by at least about 5%, by at least about 10%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more is obtained. In some embodiments, downregulation is by at least about 10%. Down-regulation can be determined as described herein.

Thus, the present invention provides a method for customizing, controlling, and/or modulating the release of a freshening composition or a component thereof. Examples E-O provide exemplary guidance for performing such method. They demonstrate how an amount (wt %) of a fragrance release modulator is combined with a perfume material, in the absence or presence of a solvent, to achieve a desired up-regulation or down-regulation of release of a freshening composition or of a component thereof by a chosen day. While Examples E-L and N—O have employed two preferred blends of perfume raw materials and Example M employed two individual PRMs, each combined with various preferred fragrance release modulators (including triethyl citrate (TEC), benzyl benzoate (BB), ethanol, 3-methyl 3-methoxl butanol (MMB), dipropylene glycol (DPG), hexylene glycol (HG)) with or without various solvents, the inventors have combined the same and other fragrance release modulators with other blends of perfume raw materials and have obtained similar results. As such, the fragrance release modulators described herein, may be used to customize, control and/or to modulate the release of any freshening composition or of a component thereof, comprising any perfume raw material or any blend of perfume raw materials., i.e., regardless of composition of said freshening composition and concentration of each perfume raw material in such freshening composition.

In some embodiments of a method for customizing, controlling, and/or modulating the release of a freshening composition or a component thereof, the method comprises the step of adding an amount (wt %) of a fragrance release modulator to a perfume raw material. In some embodiments of a method for customizing, controlling, and/or modulating the release of a freshening composition or a component thereof, the method comprises the step of combining an amount (wt %) of a fragrance release modulator and a perfume raw material.

In some embodiments of a method for customizing, controlling, and/or modulating the release of a freshening composition or a component thereof, the method comprises the step of adding an amount (wt %) of a fragrance release modulator to a plurality of perfume raw materials. In some embodiments of a method for customizing, controlling, and/or modulating the release of a freshening composition or a component thereof, the method comprises the step of combining an amount (wt %) of a fragrance release modulator and a plurality of perfume raw materials.

To achieve a customized, controlled, and/or modulated release of a freshening composition or of a component thereof, a fragrance modulator may be added to a perfume raw material or to a plurality of perfume raw materials in various concentrations and amounts. To achieve a customized, controlled, and/or modulated release of a freshening composition or of a component thereof, a fragrance modulator may be combined with a perfume raw material or with a plurality of perfume raw materials in various concentrations and amounts (see, Examples E-L and N—O, and as described herein).

In some embodiments of a method for customizing, controlling, and/or modulating the release of a freshening composition or a component thereof, the method comprises the step of adding an amount (wt %) of a fragrance release modulator to a perfume raw material and to a functional ingredient. In some embodiments of a method for customizing, controlling, and/or modulating the release of a freshening composition or a component thereof, the method comprises the step of combining an amount (wt %) of a fragrance release modulator with a perfume raw material and with a functional ingredient.

In some embodiments of a method for customizing, controlling, and/or modulating the release of a freshening composition or a component thereof, the method comprises the step of adding an amount (wt %) of a fragrance release modulator to a plurality of perfume raw materials and to a functional ingredient. In some embodiments of a method for customizing, controlling, and/or modulating the release of a freshening composition or a component thereof, the method comprises the step of combining an amount (wt %) of a fragrance release modulator with a plurality of perfume raw materials and with a functional ingredient.

To achieve a customized, controlled and/or modulated release of a freshening composition or of a component thereof, an amount (wt %) of a fragrance release modulator may be added to a perfume raw material or to a plurality of perfume raw materials and to a functional ingredient in various concentrations and amounts. To achieve a customized, controlled, and/or modulated release of a freshening composition or of a component an amount (wt %) of a fragrance release modulator may be combined with a perfume raw material or with a plurality of perfume raw materials and with a functional ingredient in various concentrations and amounts.

In some embodiments of a method for customizing, controlling, and/or modulating the release of a freshening composition or a component thereof, the method comprises the step of adding an amount (wt %) of a fragrance release modulator to a solvent or diluent and to a perfume raw material. In some embodiments of a method for customizing, controlling, and/or modulating the release of a freshening composition or a component thereof, the method comprises the step of combining an amount (wt %) of a fragrance release modulator with a solvent or diluent and with a perfume raw material.

In some embodiments of a method for customizing, controlling, and/or modulating the release of a freshening composition or a component thereof, the method comprises the step of adding an amount (wt %) of a fragrance release modulator to a solvent or diluent and to a plurality of perfume raw materials. In some embodiments of a method for customizing, controlling, and/or modulating the release of a freshening composition or a component thereof, the method comprises the step of combining an amount (wt %) of a fragrance release modulator with a solvent or diluent and with a plurality of perfume raw materials.

To achieve a customized, controlled and/or modulated release of a freshening composition or of a component thereof, a fragrance release modulator may be added to a solvent or diluent and to a perfume raw material or to a plurality of perfume raw materials in various concentrations and amounts. To achieve a customized, controlled, and/or modulated release of a freshening composition or of a component a fragrance release modulator may be combined with a solvent or diluent and with a perfume raw material or with a plurality of perfume raw materials in various concentrations and amounts (see, Examples C-L and as described herein).

In some embodiments of a method for customizing, controlling, and/or modulating the release of a freshening composition or a component thereof, the method comprises the step of adding an amount (wt %) of a fragrance release modulator to a perfume raw material, to a solvent or diluent, and to a functional ingredient. In some embodiments of a method for customizing, controlling, and/or modulating the release of a freshening composition or a component thereof, the method comprises the step of combining an amount (wt %) of a fragrance release modulator with a perfume raw material, with a solvent or diluent, and with a functional ingredient.

In some embodiments of a method for customizing, controlling, and/or modulating the release of a freshening composition or a component thereof, the method comprises the step of adding an amount (wt %) of a fragrance release modulator to a plurality of perfume raw materials, to a solvent or diluent, and to a functional ingredient. In some embodiments of a method for customizing, controlling, and/or modulating the release of a freshening composition or a component thereof, the method comprises the step of combining an amount (wt %) of a fragrance release modulator with a plurality of perfume raw materials, with a solvent or diluent, and with a functional ingredient.

To achieve a customized, controlled and/or modulated release of a freshening composition or of a component thereof, a fragrance release modulator may be added to a perfume raw material or to a plurality of perfume raw materials, to a solvent or diluent, and to a functional ingredient in various concentrations and amounts. To achieve a customized, controlled, and/or modulated release of a freshening composition or of a component a fragrance release modulator may be combined with a perfume raw material or with a plurality of perfume raw materials, with a solvent or diluent, and with a functional ingredient in various concentrations and amounts.

The percent (extent) of a desired up-regulation or percent (extent) of a desired down-regulation of release of a freshening composition or of a component thereof can be observed at any day, simply by comparing on a chosen day the weight loss of a control freshening composition not comprising an FRM to that of a freshening composition comprising an FRM (e.g., see, FIGS. 3, 4, 5, 6, 9, 10, 11, and 12). In some embodiments of the present invention, a desired percent up-regulation or a desired percent down-regulation of release of a freshening composition or of a component thereof is measured (observed) after 1 day. In some embodiments of the present invention, a desired percent up-regulation or a desired percent down-regulation of release of a freshening composition or of a component thereof is measured (observed) after 2 days. In some embodiments of the present invention, a desired percent up-regulation or a desired percent down-regulation of release of a freshening composition or of a component thereof is measured (observed) after 3 days. In some embodiments of the present invention, a desired percent up-regulation or a desired percent down-regulation of release of a freshening composition or of a component thereof is measured (observed) after 4 days. In some embodiments of the present invention, a desired percent up-regulation or a desired percent down-regulation of release of a freshening composition or of a component thereof is measured (observed) after 5 days. In some embodiments of the present invention, a desired percent upregulation or a desired percent down-regulation of release of a freshening composition or of a component thereof is measured (observed) after 6 days. In some embodiments of the present invention, a desired percent up-regulation or a desired percent down-regulation of release of a freshening composition or of a component thereof is measured (observed) after 7 days. In some embodiments of the present invention, a desired percent up-regulation or a desired percent down-regulation of release of a freshening composition or of a component thereof is measured (observed) after 8 days. In some embodiments of the present invention, a desired percent up-regulation or a desired percent down-regulation of release of a freshening composition or of a component thereof is measured (observed) after 9 days. In some embodiments of the present invention, a desired percent up-regulation or a desired percent down-regulation of release of a freshening composition or of a component thereof is measured (observed) after 10 days. In some embodiments of the present invention, a desired percent up-regulation or a desired percent down-regulation of release of a freshening composition or of a component thereof is measured (observed) after 11 days. In some embodiments of the present invention, a desired percent up-regulation or a desired percent down-regulation of release of a freshening composition or of a component thereof is measured (observed) after 12 days. In some embodiments of the present invention, a desired percent up-regulation or a desired percent down-regulation of release of a freshening composition or of a component thereof is measured (observed) after 13 days. In some embodiments of the present invention, a desired percent up-regulation or a desired percent down-regulation of release of a freshening composition or of a component thereof is measured (observed) after 14 days. In some embodiments of the present invention, a desired percent up-regulation or a desired percent down-regulation of release of a freshening composition or of a component thereof is measured (observed) after 21 days. In some embodiments of the present invention, a desired percent up-regulation or a desired percent down-regulation of release of a freshening composition or of a component thereof is measured (observed) after 28 days.

Preferred embodiments of this invention are described herein, including the best mode known to the inventors for carrying out the invention. Of course, variations, changes, modifications, and substitution of equivalents of preferred embodiments will become apparent to those of ordinary skill in the art upon reading the foregoing description. The inventors expect skilled artisans to employ such variations, changes, modifications, and substitution of equivalents as appropriate, and the inventors intend for the invention to be practiced otherwise than specifically described herein. Those of skill in the art will readily recognize a variety of non-critical parameters that could be changed, altered, or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent, or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. Citation of a patent, patent publication, and of any other publication herein shall not be construed in any way as an admission that such patent, patent application and other publication is prior art to an invention claimed herein.

As can be appreciated from the disclosure above, the present invention has a wide variety of applications. The invention is further illustrated by the following examples, which are only illustrative and are not intended to limit the definition and scope of the invention in any way.

III. EXAMPLES

The below examples are meant to illustrate specific embodiments of the methods and compositions described herein and should not be construed as limiting the scope of the invention in any way.

Compounds described and used herein can be obtained from various sources, e.g., from Firmenich (Anaheim, CA, USA), Givaudan (Vernier, Switzerland), IFF (International Flavors & Fragrances; New York, NY, USA), Mane, Inc. (Lebanon, OH, USA), Berje, Inc. (Carteret, NJ, USA), Symrise (Elyria, OH, USA), Takasago (Crystal Lake, IL, USA), and Robertet (Piscataway, NJ, USA).

Example A. Preparation of Apple Fragrance, a Blend of Perfume Raw Materials

Allyl (3-methylbutoxy) acetate, allyl hexanoate, allyl 3-cyclohexylpropanoate, allyl heptanoate, benzaldehyde, 3-(4-isopropylphenyl)-2-methylpropanal, 2,6-dimethyloct-7-en-2-ol, 1,1-dimethyl-2-phenylethyl acetate, 1,1-dimethyl-2-phenylethyl butyrate, ethyl 2-methylbutanoate, 2-ethyl-3-hydroxy-4H-pyran-4-one, 3-ethoxy-4-hydroxybenzaldehyde, 1,4-dioxacycloheptadecane-5,17-dione, 4-allyl-2-methoxyphenol, ethyl (2-methyl-1,3-dioxolan-2-yl) acetate, methyl (3-oxo-2-pentylcyclopentyl) acetate, hex-2-enal, hexyl acetate, 2-benzylideneoctanal, 4,5,6-trimethylcyclohex-3-ene-1-carbaldehyde, 1-(2,3,8,8-tetramethyl-1,2,3,4,5,6,7,8-octahydronaphthalen-2-yl) ethanone, hex-3-en-1-yl acetate, hex-3-en-1-ol, ethyl 2-methylpentanoate, 5-pentyldihydrofuran-2(3H)-one, 2-phenoxyethyl 2-methylpropanoate, 1-henylethyl acetate, 2,4-dimethylcyclohex-3-ene-1-carbaldehyde, 5-heptyldihydrofuran-2(3H)-one, and 2-tert-butylcyclohexyl acetate were combined to formulate a blend of perfume raw materials, referred to as Fragrance "Apple" or Apple Fragrance. There is no specific order of addition when combining the individual perfume raw materials to formulate the blend of perfume raw materials.

The freshening composition obtained by the method described in this example is referred to herein, as Fragrance "Apple" or Apple Fragrance. The wt % of each compound in this freshening composition is provided in Table 9:

TABLE 9

Weight percentage of compounds in Fragrance Apple, a blend of perfume raw materials. Weight percentage given for each compound is with reference to the total weight of the blend of perfume raw materials.

| CAS # | IUPAC NOMENCLATURE | WEIGHT PERCENTAGE |
|---|---|---|
| 67634-00-8 | Allyl (3-methylbutoxy) acetate | 2.0 |
| 123-68-2 | Allyl hexanoate | 0.4 |
| 2705-87-5 | Allyl 3-cyclohexylpropanoate | 0.5 |
| 142-19-8 | Allyl heptanoate | 1.0 |
| 100-52-7 | Benzaldehyde | 0.3 |
| 103-95-7 | 3-(4-Isopropylphenyl)-2-methylpropanal | 0.5 |
| 18479-58-8 | 2,6-Dimethyloct-7-en-2-ol | 5.0 |
| 151-05-3 | 1,1-Dimethyl-2-phenylethyl acetate | 1.0 |
| 10094-34-5 | 1,1-Dimethyl-2-phenylethyl butyrate | 5.0 |
| 7452-79-1 | Ethyl 2-methylbutanoate | 0.5 |
| 4940-11-8 | 2-Ethyl-3-hydroxy-4H-pyran-4-one | 0.2 |
| 121-32-4 | 3-Ethoxy-4-hydroxybenzaldehyde | 1.0 |
| 105-95-3 | 1,4-Dioxacycloheptadecane-5,17-dione | 10.0 |
| 97-53-0 | 4-Allyl-2-methoxyphenol | 3.0 |
| 6413-10-1 | Ethyl (2-methyl-1,3-dioxolan-2-yl) acetate | 2.0 |
| 24851-98-7 | Methyl (3-oxo-2-pentylcyclopentyl) acetate | 5.0 |
| 6728-26-3 | Hex-2-enal | 0.1 |
| 142-92-7 | Hexyl acetate | 0.8 |
| 101-86-0 | 2-Benzylideneoctanal | 5.0 |
| 1335-66-6 | 4,5,6-Trimethylcyclohex-3-ene-1-carbaldehyde | 5.0 |
| 54464-57-2 | 1-(2,3,8,8-Tetramethyl-1,2,3,4,5,6,7,8-octahydronaphthalen-2-yl) ethanone | 5.0 |
| 3681-71-8 | Hex-3-en-1-yl acetate | 0.5 |

TABLE 9-continued

Weight percentage of compounds in Fragrance Apple, a blend of perfume raw materials. Weight percentage given for each compound is with reference to the total weight of the blend of perfume raw materials.

| CAS # | IUPAC NOMENCLATURE | WEIGHT PERCENTAGE |
|---|---|---|
| 928-96-1 | Hex-3-en-1-ol | 0.7 |
| 39255-32-8 | Ethyl 2-methylpentanoate | 0.5 |
| 104-61-0 | 5-Pentyldihydrofuran-2(3H)-one | 0.7 |
| 103-60-6 | 2-Phenoxyethyl 2-methylpropanoate | 2.0 |
| 93-92-5 | 1-Phenylethyl acetate | 0.3 |
| 68039-49-6 | 2,4-Dimethylcyclohex-3-ene-1-carbaldehyde | 2.0 |
| 104-67-6 | 5-Heptyldihydrofuran-2(3H)-one | 15.0 |
| 88-41-5 | 2-tert-Butylcyclohexyl acetate | 25.0 |
| | TOTAL | 100.00 |

It is understood and one of ordinary skill in the art will appreciate that, if not clearly contradicted by the content of this specification, each embodiment of an Apple Fragrance and/or features/elements disclosed as part of that embodiment can be combined with any of the embodiments hereinabove or hereinbelow. It is further understood and one of ordinary skill in the art will appreciate that, if not clearly contradicted by the content of this specification, each embodiment of a method for preparing an Apple Fragrance and/or features/elements disclosed as part of that embodiment can be combined with any of the embodiments hereinabove or hereinbelow.

Example B. Preparation of Floral Fresh Fragrance, a Blend of Perfume Raw Materials 1-(2,3,8,8-tetramethyl-1,2,3,4,5,6,7,8-octahydronaphthalen-2-yl) ethanone, methyl (3-oxo-2-pentylcyclopentyl) acetate, 2-benzylideneoctanal, 1-cedr-8-en-9-ylethanone, 4-tert-butylcyclohexyl acetate, 1,5-dimethyl-1-vinylhex-4-en-1-yl acetate, 3,7-dimethylocta-1,6-dien-3-ol, 1-(2,6,6-trimethylcyclohex-2-en-1-yl) pent-1-en-3-one, 2-isobutyl-4-methyltetrahydro-2H-pyran-4-ol, 1,4-dioxacycloheptadecane-5,17-dione, 2,6-dimethyloct-7-en-2-ol, 3-(4-isopropylphenyl)-2-methylpropanal, hexyl salicylate, 3-(4-ethylphenyl)-2,2-dimethylpropanal, 3-(2-ethylphenyl)-2,2-dimethylpropanal, 3a,4,5,6,7,7α-hexahydro-1H-4,7-methanoinden-6-yl acetate, Cedarwood oil, Virginian (*Juniperus virginiana* L.), 2-methylundecanal, (2,2-dimethoxyethyl) benzene, undec-10-enal, hex-3-en-1-ol, 3-(1,3-benzodioxol-5-yl)-2-methylpropanal, 1-phenylethyl acetate, 3a,6,6,9α-tetramethyldodecahydronaphtho[2,1-b]furan, allyl (3-methylbutoxy) acetate, and δ-(5,5-dimethylcyclohex-1-en-1-yl) pent-4-en-1-one were combined to formulate a blend of perfume raw materials, referred to as Fragrance "Floral Fresh" or Floral Fresh Fragrance. There is no specific order for combining the individual perfume raw materials to formulate the blend of perfume raw materials.

The freshening composition obtained by the method described in this example is referred to herein, as Floral Fresh Fragrance. The wt % of each compound in this Table 10 at the indicated weight percentage.

TABLE 10

Weight percentage of compounds in Floral Fresh Fragrance, a blend of perfume raw materials. Weight percentage given for each compound is with reference to the total weight of the blend of perfume raw materials.

| CAS # | IUPAC NOMENCLATURE | WEIGHT PERCENTAGE |
|---|---|---|
| 54464-57-2 | 1-(2,3,8,8-Tetramethyl-1,2,3,4,5,6,7,8-octahydronaphthalen-2-yl) ethanone | 14.0 |
| 24851-98-7 | Methyl (3-oxo-2-pentylcyclopentyl) acetate | 12.0 |
| 101-86-0 | 2-Benzylideneoctanal | 11.0 |
| 32388-55-9 | 1-Cedr-8-en-9-ylethanone | 6.0 |
| 32210-23-4 | 4-tert-Butylcyclohexyl acetate | 6.0 |
| 115-95-7 | 1,5-Dimethyl-1-vinylhex-4-en-1-yl acetate | 6.0 |
| 78-70-6 | 3,7-Dimethylocta-1,6-dien-3-ol | 6.0 |
| 1335-46-2 | 1-(2,6,6-Trimethylcyclohex-2-en-1-yl) pent-1-en-3-one | 6.0 |
| 63500-71-0 | 2-Isobutyl-4-methyltetrahydro-2H-pyran-4-ol | 6.0 |
| 105-95-3 | 1,4-Dioxacycloheptadecane-5,17-dione | 6.0 |
| 18479-58-8 | 2,6-Dimethyloct-7-en-2-ol | 6.0 |
| 103-95-7 | 3-(4-Isopropylphenyl)-2-methylpropanal | 2.0 |
| 6259-76-3 | Hexyl salicylate | 2.0 |
| 67634-15-5 | 3-(4-Ethylphenyl)-2,2-dimethylpropanal | 1.40 |
| 67634-14-4 | 3-(2-ethylphenyl)-2,2-dimethylpropanal | 0.6 |
| 5413-60-5 | 3a,4,5,6,7,7a-Hexahydro-1H-4,7-methanoinden-6-yl acetate | 2.0 |
| 8000-27-9 | Cedarwood oil, Virginian (*Juniperus virginiana L.*)* | 2.0 |
| 110-41-8 | 2-Methylundecanal | 1.0 |
| 101-48-4 | (2,2-Dimethoxyethyl) benzene | 0.8 |
| 112-45-8 | Undec-10-enal | 0.6 |
| 928-96-1 | Hex-3-en-1-ol | 0.6 |
| 1205-17-0 | 3-(1,3-Benzodioxol-5-yl)-2-methylpropanal | 0.6 |
| 93-92-5 | 1-Phenylethyl acetate | 0.5 |
| 3738-00-9 | 3a,6,6,9a-Tetramethyldodecahydronaphtho[2,1-b]furan | 0.4 |
| 67634-00-8 | Allyl (3-methylbutoxy) acetate | 0.4 |
| 56973-85-4 | 1-(5,5-Dimethylcyclohex-1-en-1-yl) pent-4-en-1-one | 0.1 |
| | TOTAL | 100.00 |

It is understood and one of ordinary skill in the art will appreciate that, if not clearly contradicted by the content of this specification, each embodiment of a Floral Fresh Fragrance and/or features/elements disclosed as part of that embodiment can be combined with any of the embodiments hereinabove or hereinbelow. It is further understood and one of ordinary skill in the art will appreciate that, if not clearly contradicted by the content of this specification, each embodiment of a method for preparing a Floral Fresh Fragrance and/or features/elements disclosed as part of that embodiment can be combined with any of the embodiments hereinabove or hereinbelow.

Example C. General Consideration and the Influence of Different Solvents on the Release and Evaporation of a Freshening Composition Comprising 50 Wt % Apple Fragrance Any freshening composition comprising ingredients disclosed herein may be formulated by a skilled artisan. For example, a skilled person will be able to formulate a freshening composition comprising (i) from about 0.1 wt % to about 95 wt % perfume raw material and (ii) from about 0.01 wt % to about 90 wt % fragrance release modulator by combining (i) from about 0.1 wt % to about 95 wt % of any perfume raw material disclosed herein and (ii) from about 0.01 wt % to about 90 wt % of any fragrance release modulator disclosed herein. Further, a skilled person will be able to formulate a freshening composition comprising (i) from about 0.1 wt % to about 95 wt % perfume raw material, (ii) from about 1.0 wt % to about 95 wt % of a solvent, and (iii) from about 0.01 wt % to about 90 wt % fragrance release modulator by combining (i) from about 0.1 wt % to about 95 wt % of any perfume raw material disclosed herein, (ii) from about 1.0 wt % to about 95 wt % of any solvent disclosed herein, and (iii) from about 0.01 wt % to about 90 wt % of any fragrance release modulator disclosed herein. Further, a skilled person will be able to formulate a freshening composition comprising (i) from about 0.1 wt % to about 95 wt % perfume raw material, (ii) from about 0.01 wt % to about 90 wt % fragrance release modulator, and (iii) less than about 50 wt % of an ingredient having a functional activity by combining (i) from about 0.1 wt % to about 95 wt % of any perfume raw material disclosed herein, (ii) from about 0.01 wt % to about 90 wt % of any fragrance release modulator disclosed herein, and (iii) less than about 50 wt % of any ingredient having a functional activity disclosed herein. Further, a skilled person will be able to formulate a freshening composition comprising (i) from about 0.1 wt % to about 95 wt % perfume raw material, (ii) from about 1.0 wt % to about 95 wt % of a solvent, (iii) from about 0.01 wt % to about 90 wt % fragrance release modulator, and (iv) less than about 50 wt % of an ingredient having a functional activity by combining (i) from about 0.1 wt % to about 95 wt % of any perfume raw material disclosed herein, (ii) from about 1.0 wt % to about 95 wt % of any solvent disclosed herein, (iii) from about 0.01 wt % to about 90 wt % of any fragrance release modulator disclosed herein, and (iv) less than about 50 wt % of any ingredient having a functional activity disclosed herein. There is no preferred order of adding the individual ingredients to each other when formulating a freshening composition of the present invention, e.g., a liquid freshening composition or a non-water-based freshening composition. The freshening composition forms by gentle mixing the perfume raw material(s) with the fragrance release modulator(s), solvent(s) or diluent(s), and where desired with the ingredient(s) having a functional activity. A clear, temperature stable freshening composition forms.

The resulting freshening compositions were tested for temperature stability, which means clarity, no precipitate, and no phase separation, at 4° C., at room temperature (RT), at 20° C. to 25° C., and at 40° C. to 42° C. Further, the air freshening compositions were tested for 3 cycles freeze-thaw stability. All experimental data described herein (Examples C-O; FIGS. 1-12) were obtained as described herein and using the same type of electrical plug-in device comprising: (i) a 25 ml glass reservoir, into which the freshening composition is loaded, (ii) a delivery system, which comprises a 70 mm long and 0.8 mm diameter wick (one end of the wick being in direct contact with the freshening composition, while the other end of the wick is exposed to the external environment), and (iii) an electrical plug-in device, into which the reservoir with the attached wick is fitted. It is noted that the use of the electrical plug-in device as described herein, is not limiting. Other devices may be used in combination with the freshening composition of the present invention. 20 g of freshening composition were used, which contained the indicated wt % for each individual ingredient of a freshening composition. For example, a freshening composition comprising (i) a perfume raw material and (ii) a fragrance release modulator would comprise X wt % perfume raw material and Y wt % of an FRM, wherein, when no other component in the freshening composition is present, X+Y=100. Likewise, a freshening composition comprising (i) a perfume raw material, (ii) a solvent, and (iii) a fragrance release modulator would comprise X wt % of perfume raw material, Y wt % of an FRM, and Z wt % of solvent or diluent, wherein, when no other component in the freshening composition is present, X+Y+Z=100. Likewise, a freshening composition comprising (i) a perfume raw material, (ii) a fragrance release modulator, and (iii) a functional ingredient would comprise X wt % of perfume raw material, Y wt % of an FRM, and W wt % of a functional ingredient, wherein, when no other component in the freshening composition is present, X+Y+W=100. Likewise, a freshening composition comprising (i) a perfume raw material, (ii) a fragrance release modulator, (iii) a solvent, and (iv) a functional ingredient would comprise X wt % of perfume raw material, Y wt % of an FRM, Z wt % of a solvent, and W wt % of a functional ingredient, wherein, when no other component in the freshening composition is present, X+Y+Z+W=100)

All measurements (Examples C-O) were taken at room temperature. Percentage weight loss of the freshening composition (starting weight: 20 g) was determined on the days indicated in the figures (typically weekdays). The data presented herein consists of daily cumulative percentage released weight-loss, which is calculated as follows: [(initial weight of the entire freshening composition (which consists of the initial weight of the freshening composition+the weight of the reservoir+the weight of the wick+the weight of the electrical plug-in))−(daily weight of the entire freshening composition (which consists of the weight of the freshening composition+the weight of the reservoir+the weight of the wick+the weight of the electrical plug-in))]/initial weight of the air freshening composition. Typically, the release profiles were analyzed for more than 3 weeks. Typically, by 7 days (sometimes earlier) it was clearly apparent if a tested FRM would up-regulate or down-regulate the release of the freshening composition or of a component thereof.

In this Example, the influence of different solvents on the release and evaporation of a freshening composition comprising 50 wt % of the Apple Fragrance was examined. Various freshening compositions were formulated and tested. Each freshening composition analyzed in this Example consisted of 50 wt % Apple Fragrance (see, Table 9, Example A) and 50 wt % solvents. The following solvents were tested: Augeo Clean Multi® (acetone monoglycerol ketal; from Solvay), IPD-AC® (3-methyl-1,3-butanediol-acetate; from Kuraray), STA-SOL® ESS 165 (dimethyl adipate; from ST Laboratories, Inc.), and VOLASIL® DM-2 (dimethiocone; from CHEMSIL Silicones, Inc.). Upon adding the freshening composition into a reservoir in an electrical plug-in device having a single wick, release and evaporation of the freshening composition was analyzed. Exemplary results are schematically depicted in FIG. 1.

As schematically depicted in FIG. 1, the various solvents cause different release profiles of the Apple Fragrance. While the silicon solvent VOLASIL® DM-2 (dimethiocone) leads to fast release of the freshening composition, the solvent Augeo Clean Multi® (acetone monoglycerol ketal) results in a slower release profile. The solvents IPD-AC® (3-methyl-1,3butanediol-acetate) and STA-SOL® ESS 165 (dimethyl adipate) lead to intermediary release profiles.

Example D. The Influence of Different Solvents on the Release and Evaporation of a Freshening Composition Comprising 50 Wt % Floral Fresh Fragrance In this Example, the influence of different solvents on the release and evaporation of a freshening composition comprising 50 wt % of the Floral Fresh Fragrance was examined. Various freshening compositions were formulated and tested. Each freshening composition analyzed in this Example consisted of 50 wt % Floral Fresh Fragrance (see, Table 10, Example B) and 50 wt % solvents. The following solvents were tested: Augeo Clean Multi® (acetone monoglycerol ketal; from Solvay), IPD-AC® (3-methyl-1,3-butanediol-acetate; from Kuraray), STA-SOL® ESS 165 (dimethyl adipate; from ST Laboratories, Inc.), and VOLASIL® DM-2 (dimethiocone; from CHEMSIL Silicones, Inc.). Release and evaporation of the freshening composition was tested as described in Example C. Exemplary results are schematically depicted in FIG. 2.

Figure 2:
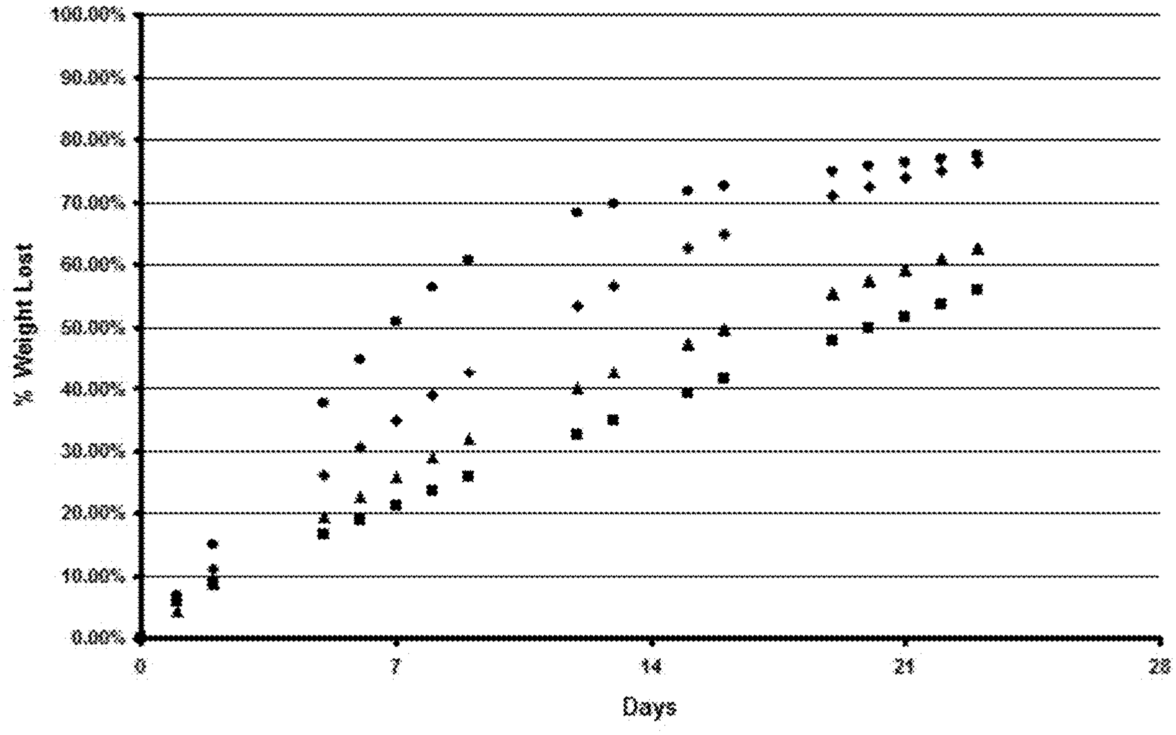
FIG. 2 schematically depicts the influence of different solvents on the release and evaporation of a freshening composition comprising 50 wt % Floral Fresh Fragrance (see, Table 10) and 50 wt % solvents as indicated and measured as % weight lost during the time period indicated. The weight percentage refers to the weight percentage of the entire product formulation, i.e., freshening composition. The following solvents were tested: ●, acetone monoglycerol ketal (Augeo Clean Multi® from Solvay); ♦, 3-methyl-1,3-butanediol-acetate (IPD-AC® from Kuraray); ▲ STA- SOL® ESS 165 (dimethyl adipate (DMA) from ST Laboratories Inc.); ■, silicon solvent (VOLASIL® DM-2 from CHEMSIL Silicones, Inc.). Details are described in Example D.

As schematically depicted in FIG. 2, the various solvents cause different release profiles of the Floral Fresh Fragrance. While the silicon solvent VOLASIL® DM-2 (dimethiocone) leads to fast release of the freshening composition, the solvent Augeo Clean Multi® (acetone monoglycerol ketal) results in a slower release profile. The solvents IPD-AC® (3-methyl-1,3-butanediol-acetate) and STA-SOL® ESS 165 (dimethyl adipate) lead to intermediary release profiles.

Example E. The Influence of Different Fragrance Release Modulators (FRMs) on the Release and Evaporation of a Freshening Composition Comprising 50 Wt % Apple Fragrance and 42.5 Wt % of Solvent Augeo Clean Multi®

In this Example, the influence of various fragrance release modulators (FRMs) on the release and evaporation of a freshening composition comprising (i) 50 wt % of the Apple Fragrance (ii) 42.5 wt % of the solvent Augeo Clean Multi® (acetone monoglycerol ketal) and (iii) 7.5 wt % of various FRMs was examined. Various freshening compositions were formulated and tested. Each freshening composition analyzed in this Example consisted of 50 wt % Apple Fragrance (see, Table 9, Example A) 42.5 wt % solvent Augeo Clean Multi® (acetone monoglycerol ketal), and 7.5 wt %, of the following Fragrance Release Modulators (FRMs): EtOH (ethanol), TEC (triethyl citrate), MMB (3-methyl-3-methoxyl butanol), BB (benzyl benzoate), and DPG (dipropylene glycol). The release and evaporation of the FRM-containing freshening compositions were compared to a control freshening composition not comprising an FRM, i.e., a freshening composition comprising 50 wt % of Apple Fragrance and 50 wt % of the solvent Augeo Clean Multi® (acetone monoglycerol ketal). Release and evaporation of the freshening composition was tested as described in Example C. Exemplary results are schematically depicted in FIG. 3.

Figure 3:
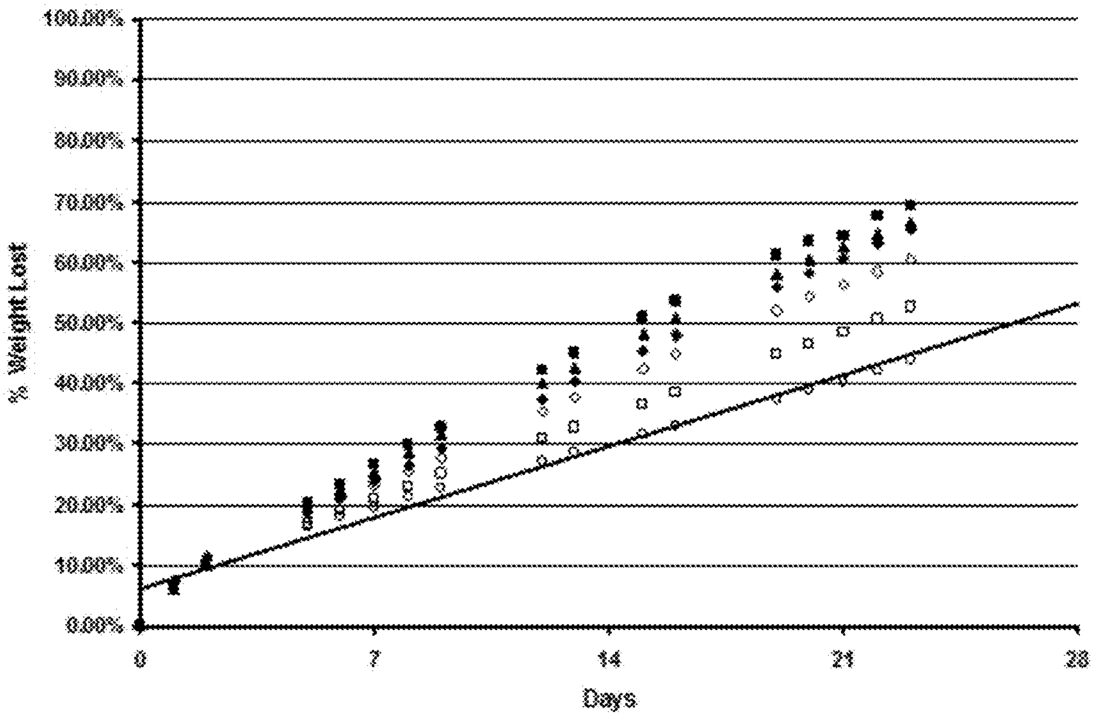
FIG. 3 schematically depicts the influence of different fragrance release modulators (FRM) on the release and evaporation of a freshening composition comprising 50 wt % of an Apple Fragrance (see, Table 9), 42.5 wt % of solvent Augeo Clean Multi® and 7.5 wt % of the indicated FRM and measured as % weight lost during the time period indicated. The weight percentage refers to the weight percentage of the entire product formulation, i.e., freshening composition. The following combinations of Apple Fragrance/Augeo Clean Multi® and FRMs were tested: ○, 50 wt % Apple Fragrance/50 wt % Augeo Clean Multi®; ♦, 50 wt % Apple Fragrance/42.5 wt % Augeo Clean Multi®/7.5 wt % EtOH; ■, 50 wt % Apple Fragrance/42.5 wt % Augeo Clean Multi®/7.5 wt % TEC (TEC, triethyl citrate); ◇, 50 wt % Apple Fragrance/42.5 wt % Augeo Clean Multi®/7.5 wt % MMB (MMB, 3-methyl-3-methoxyl butanol; CAS Number 56539-66-3); ▲ 50 wt % Apple 42.5 wt % Augeo Clean Multi®/7.5 wt % BB (BB, benzyl benzoate); □, 50 wt % Apple Fragrance/42.5 wt % Augeo Clean Multi®/7.5 wt % DPG (DPG, dipropylene glycol). Details are described in Example E.

As schematically depicted in FIG. 3, compared to the control freshening composition, each of the tested FRMs (TEC, BB, EtOH, MMB, and DPG) at 7.5 wt % in the freshening composition and in combination with the solvent Augeo Clean Multi® (acetone monoglycerol ketal) leads to an up-regulation of release of the freshening composition or of a component thereof Δt the tested concentration, TEC is the strongest up-regulator FRM, followed by BB and EtOH. MMB and DPG, while still upregulating significantly, upregulate less than TEC, BB, and EtOH.

Example F. The Influence of Different Fragrance Release Modulators (FRMs) on the Release and Evaporation of a Freshening Composition Comprising 50 Wt % Floral Fresh Fragrance and 42.5 Wt % of Solvent IPD-AC®

In this Example, the influence of various fragrance release modulators (FRMs) on the release and evaporation of a freshening composition comprising (i) 50 wt % of the Floral Fresh Fragrance (ii) 42.5 wt % of the solvent IPD-AC® (3-methyl-1,3-butanediol-acetate) and (iii) 7.5 wt % of various FRMs was examined. Various freshening compositions were formulated and tested. Each freshening composition analyzed in this Example consisted of 50 wt % Floral Fresh Fragrance (see, Table 10, Example B) 42.5 wt % solvent IPD-AC® (3-methyl-1,3-butanediol-acetate) and 7.5 wt % of the following fragrance release modulators (FRMs): EtOH (ethanol), TEC (triethyl citrate), MMB (3-methyl-3-methoxyl butanol), BB (benzyl benzoate), and DPG (dipropylene glycol). The release and evaporation of the FRM-containing freshening compositions were compared to a control freshening composition not comprising an FRM, i.e., a freshening composition comprising 50 wt % of Floral Fresh Fragrance and 50 wt % of the solvent IPD-AC® (3-methyl-1,3-butanediol-acetate). Release and evaporation of the freshening composition was tested as described in Example C. Exemplary results are schematically depicted in FIG. 4.

Figure 4:
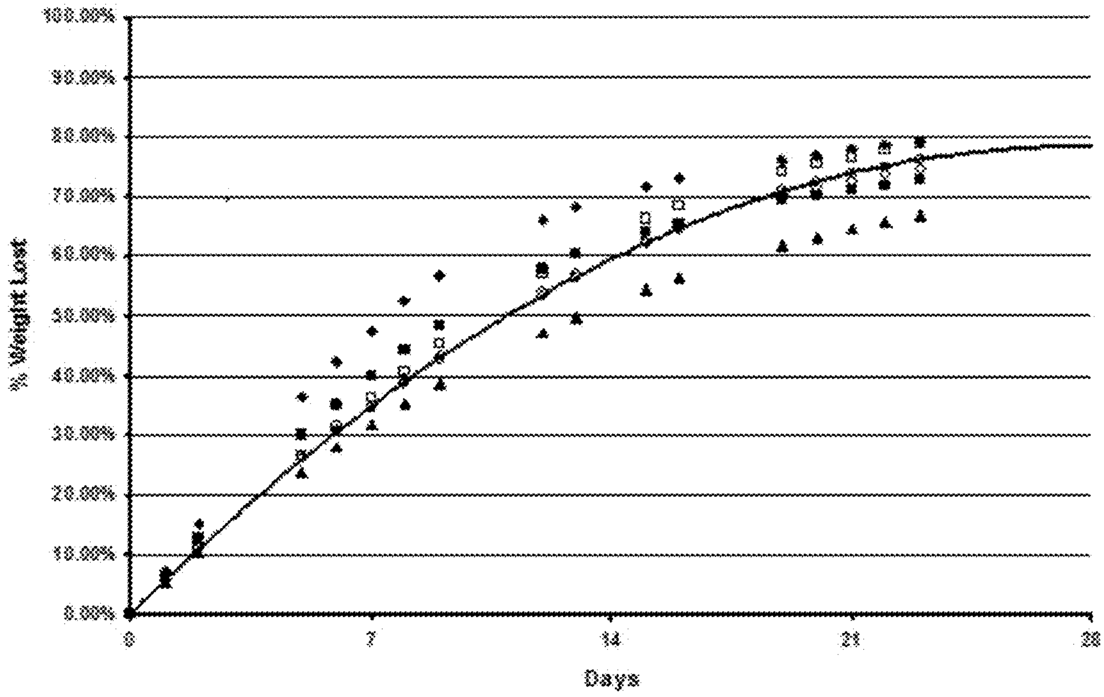
FIG. 4 schematically depicts the influence of different fragrance release modulators (FRM) on the release of a freshening composition comprising 50 wt % of a Floral Fresh Fragrance (see, Table 10), 42.5 wt % of solvent IPD-AC® and 7.5 wt % of the indicated FRM and measured as % weight lost during the time period indicated. The weight percentage refers to the weight percentage of the entire product formulation, i.e., freshening composition. The following combinations of Floral Fresh Fragrance/IPD-AC® and FRMs were tested: ○, 50 wt % Floral Fresh Fragrance/50 wt % IPD-AC®; ♦, 50 wt % Floral Fresh Fragrance/42.5 wt % IPD-AC®/7.5 wt % EtOH; ■, 50 wt % Floral Fresh Fragrance/42.5 wt % IPD-AC®/7.5 wt % TEC (TEC, triethyl citrate); ◇, 50 wt % Floral Fresh Fragrance/42.5 wt % IPD-AC®/7.5 wt % MMB (MMB, 3-methyl-3-methoxyl butanol); ▲ 50 wt % Floral Fresh Fragrance/42.5 wt % IPD-AC®/7.5 wt % BB (BB, benzyl benzoate); □, 50 wt % Floral Fresh Fragrance/42.5 wt % IPD-AC®/7.5 wt % DPG (DPG, dipropylene glycol). Details are described in Example F.

As schematically depicted in FIG. 4, compared to the control freshening composition, the tested FRMs TEC and EtOH at 7.5 wt % in the freshening composition and in combination with the solvent IPD-AC® (3-methyl-1,3-butanediol-acetate) lead to an up-regulation of release of the freshening composition or of a component thereof Δt the tested concentration and conditions, MBB, TEC and BB lead to a down-regulation of release of the freshening composition or component thereof.

Example G. The Influence of Various Concentrations of Fragrance Release Modulator Benzyl Benzoate on the Release and Evaporation of a Freshening Composition Comprising 50 Wt % Apple Fragrance and Solvent Augeo Clean Multi®

In this Example, the influence of various concentrations of the fragrance release modulators benzyl benzoate (BB) on the release and evaporation of a freshening composition comprising (i) 50 wt % of the Apple Fragrance (ii) various wt % of the solvent Augeo Clean Multi® (acetone monoglycerol ketal) and (iii) increasing wt % of BB was examined. Various freshening compositions were formulated and tested. Each freshening composition analyzed in this Example consisted of 50 wt % Apple Fragrance (see, Table 9, Example A), various wt % solvent Augeo Clean Multi® and various wt % of fragrance release modulator BB (benzyl benzoate). The following freshening compositions were formulated and tested: 50 wt % Apple Fragrance/50 wt % Augeo Clean Multi® (control freshening composition not comprising an FRM); 50 wt % Apple Fragrance/42.5 wt % Augeo Clean Multi®/7.5 wt % BB; 50 wt % Apple Fragrance/25 wt % Augeo Clean Multi®/25 wt % BB; 50 wt % Apple Fragrance/7.5 wt % Augeo Clean Multi®/42.5 wt % BB; and 50 wt % Apple Fragrance/50 wt % BB (freshening composition not comprising a solvent). Release and evaporation of the freshening compositions was tested as described in Example C. Exemplary results are schematically depicted in FIG. 5.

As schematically depicted in FIG. 5, compared to a control freshening composition not comprising an FRM, depending on the concentration of the fragrance release modulator BB in the freshening composition, it either up-regulates or down-regulates the release of the freshening composition or of a component thereof. More specifically, when present at concentrations of 7.5 wt % and 25 wt % in the freshening composition, BB up-regulates the release of the freshening composition or of a component thereof. When present at concentrations of 42.5 wt % and 50 wt % in the freshening composition, BB down-regulates the release of the freshening composition or of a component thereof. BB is an FRM, which at low concentrations up-regulates the release of a freshening composition or component thereof and which, at higher concentrations, down-regulates such release. Thus, BB is a preferred FRM to customize, control and/or to modulate the release of a freshening composition or of a component thereof.

Example H. The Influence of Various Concentrations of the Fragrance Release Modulator Benzyl Benzoate on the Release and Evaporation of a Freshening Composition Comprising 50 Wt % Floral Fresh Fragrance and Solvent IPD-AC®

In this Example, the influence of various concentrations of the fragrance release modulators benzyl benzoate (BB) on the release and evaporation of a freshening composition comprising (i) 50 wt % of the Floral Fresh Fragrance (ii) various wt % of the solvent IPD-AC® (3-methyl-1,3-butanediol-acetate) and (iii) increasing wt % of BB was examined. Various freshening compositions were formulated and tested. Each freshening composition analyzed in this Example consisted of 50 wt % Floral Fresh Fragrance (see, Table 10; Example B), various wt % solvent IPD-AC® (3-methyl-1,3-butanediol-acetate) and various wt % of fragrance release modulator BB (benzyl benzoate). The following freshening compositions were formulated and tested: 50 wt % Floral Fresh Fragrance/50 wt % IPD-AC® (control freshening composition not comprising an FRM); 50 wt % Floral Fresh Fragrance/42.5 wt % IPD-AC®/7.5 wt % BB; 50 wt % Floral Fresh Fragrance/25 wt % IPD-AC®/25 wt % BB; 50 wt % Floral Fresh Fragrance/7.5 wt % IPD-AC®/42.5 wt % BB; and 50 wt % Floral Fresh Fragrance/50 wt % BB. Release and evaporation of the freshening compositions was tested as described in Example C. Exemplary results are schematically depicted in FIG. 6.

As schematically depicted in FIG. 6, compared to a control freshening composition not comprising an FRM, the fragrance release modulator BB in the freshening composition, at the concentrations (wt %) tested, down-regulates the release of the freshening composition or of a component thereof. When present at concentrations of 7.5 wt %, 25 wt %, 42.5 wt %, and 50 wt % in the freshening composition, BB down-regulates the release of the freshening composition or of a component thereof. See also, Example G and FIG. 5. Thus, BB is a preferred FRM to customize, control and/or to modulate the release of a freshening composition or of a component thereof, specifically for use as a down-regulator and in combination with the solvent IPD-AC® (3-methyl-1,3-butanediol-acetate).

Example L the Influence of Various Solvents on the Release and Evaporation of a Freshening Composition Comprising Either 50 Wt % Apple Fragrance or 50 Wt % Floral Fresh Fragrance In this Example, the influence of various solvents on the release and evaporation of a freshening composition comprising either (i) 50 wt % of the Apple Fragrance or (ii) 50 wt % of the Floral Fresh Fragrance was examined. Various freshening compositions were formulated and tested. Each freshening composition analyzed in this Example consisted of either 50 wt % Apple Fragrance (see, Table 9, Example A) or 50 wt % Floral Fresh Fragrance (see, Table 10, Example B) and 50 wt % of a solvent as indicated. The following freshening compositions were formulated and tested: 50 wt % Apple Fragrance/50 wt % Augeo Clean Multi®; 50 wt % Apple Fragrance/50 wt % DMA; 50 wt % Apple Fragrance/50 wt % VOLASIL® DM-2; 50 wt % Apple Fragrance/50 wt % IPD-AC®; 50 wt % Floral Fresh Fragrance/50 wt % Augeo Clean Multi®; 50 wt % Floral Fresh Fragrance/50 wt % DMA; 50 wt % Floral Fresh Fragrance/50 wt % VOLASIL DM-2; and 50 wt % Floral Fresh Fragrance/50 wt % IPD-AC®. Release and evaporation of the freshening compositions was tested as described in Example C. Exemplary results are schematically depicted in FIG. 7.

Figure 7:
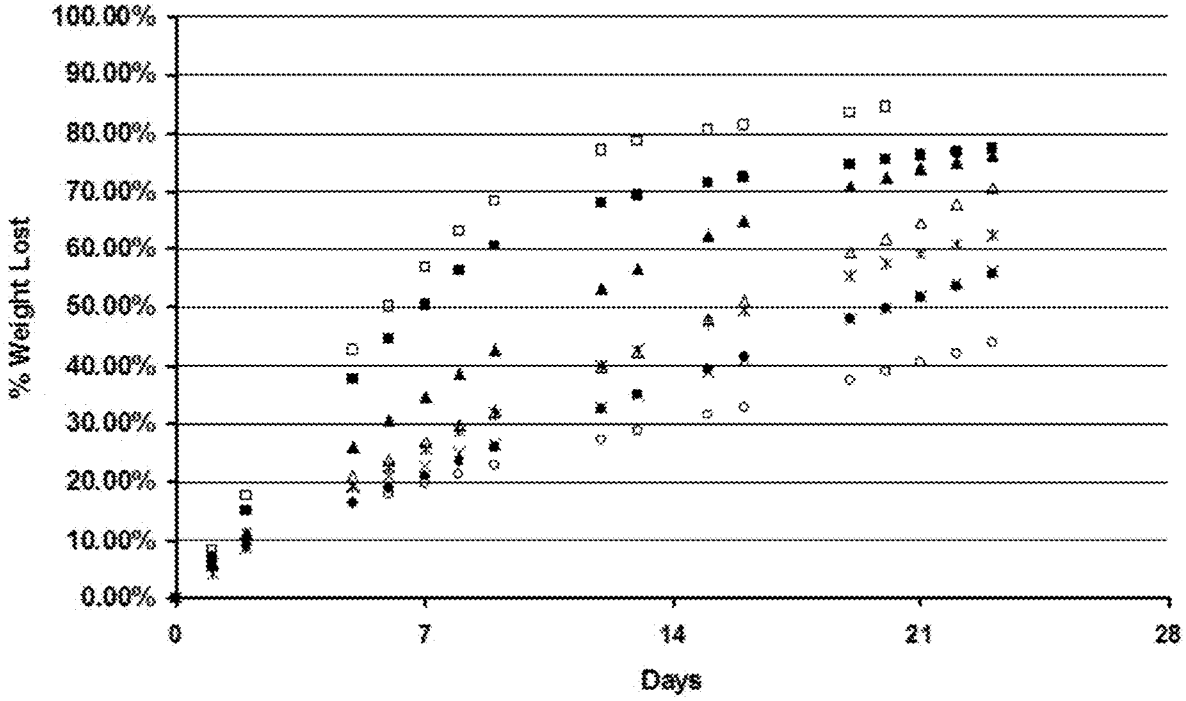
FIG. 7 schematically depicts the influence of different solvents on the release and evaporation of a freshening composition either comprising 50 wt % Apple Fragrance or 50 wt % Floral Fresh Fragrance (see, Tables 9 and 10) and 50 wt % solvents as indicated and measured as % weight lost during the time period indicated. The weight percentage refers to the weight percentage of the entire product formulation, i.e., freshening composition. The release and evaporation of the following freshening compositions were tested: ○, 50 wt % Apple Fragrance/50 wt % Augeo Clean Multi®; ●, 50 wt % Floral Fresh Fragrance/50 wt % Augeo Clean Multi®; x, 50 wt % Apple Fragrance/50 wt % DMA (dimethyl adipate); ж, 50 wt % Floral Fresh Fragrance/50 wt % DMA; Δ, 50 wt % Apple Fragrance/50 wt % IPD-AC®; ▲, 50 wt % Floral Fresh Fragrance/50 wt % IPD-AC®; □, 50 wt % Apple Fragrance/50 wt % VOLASIL® DM-2; ■, 50 wt % Floral Fresh Fragrance/50 wt % VOLASIL® DM-2. Abbreviations are as in FIGS. 1-6. Details are described in Example I.

As schematically depicted in FIG. 7, each of the solvents depicted impacted the release profile of the freshening composition or of a component thereof. Of the four solvents tested, Augeo Clean Multi® led to the slowest release profile and VOLASIL® DM-2 to the fastest. IPD-AC® and DMA lead to an intermediary release.

The result depicted in FIG. 7 is somewhat similar to the results shown in FIGS. 1 and 2, respectively, however, emphasizes a different aspect. FIG. 7 schematically depicts the difference in release performance of the same product compositions (i.e., either Apple Fragrance or Floral Fresh Fragrance) due to the different type of solvent used. As schematically depicted in FIG. 7, air freshener products, regardless of the fragrance used, comprising the VOLASIL® DM-2 solvent are the fastest ones to release the freshening composition, while the Augeo Clean Multi® are the slowest ones to release the freshening compositions.

Example J. The Influence of Solvents Augeo Clean Multi® and IPD-AC® on the Release and Evaporation of a Freshening Composition Comprising Either 50% Apple Fragrance or 50% Floral Fresh Fragrance In this Example, the influence of 50 wt % of solvents IPD-AC®- and Augeo Clean Multi® on the release and evaporation of a freshening composition comprising either (i) 50 wt % of the Apple Fragrance or (ii) 50 wt % of the Floral Fresh Fragrance was examined. Various freshening compositions were formulated and tested. Each freshening composition analyzed in this Example consisted of either 50 wt % Apple Fragrance (see, Table 9, Example A) or 50 wt % Floral Fresh Fragrance (see, Table 10, Example B) and 50 wt % of a solvent as indicated. The following freshening compositions were formulated and tested: 50 wt % Apple Fragrance/50 wt % Augeo Clean Multi®; 50 wt % Apple Fragrance/50 wt % IPD-AC®; 50 wt % Floral Fresh Fragrance/50 wt % Augeo Clean Multi®; and 50 wt % Floral Fresh Fragrance/50 wt % IPD-AC®-Release and evaporation of the freshening compositions was tested as described in Example C. Exemplary results are schematically depicted in FIG. 8.

Figure 8:
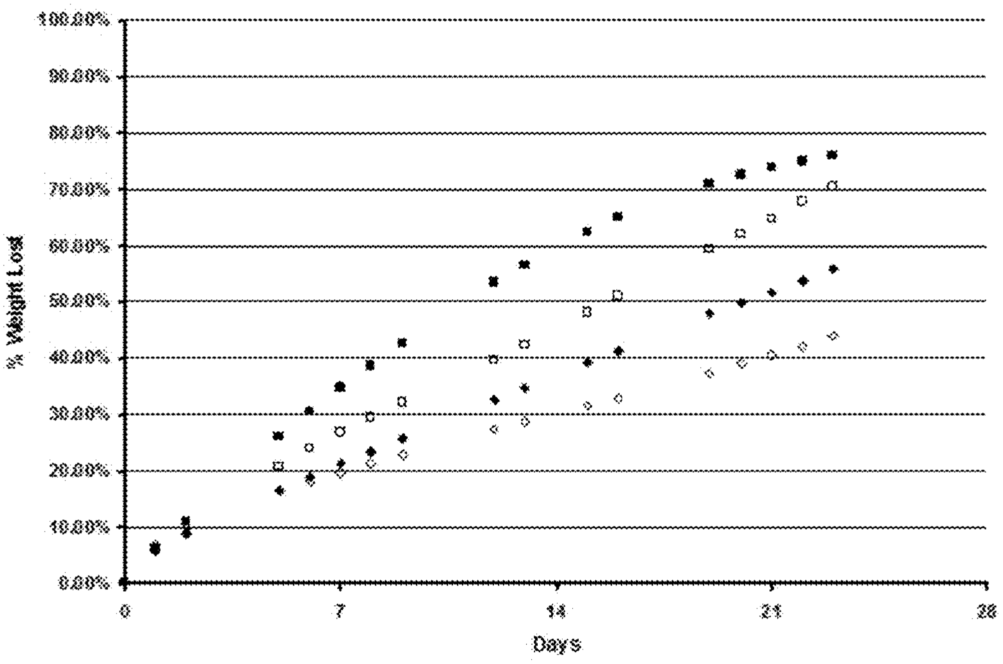
FIG. 8 schematically depicts the influence of different solvents on the release and evaporation of a freshening composition either comprising 50 wt % Apple Fragrance or 50 wt % Floral Fresh Fragrance (see, Tables 9 and 10) and measured as % weight lost during the time period indicated. The weight percentage refers to the weight percentage of the entire product formulation, i.e., freshening composition. Release and evaporation of the following freshening compositions were tested: ◇, 50 wt % Apple Fragrance/50 wt % Augeo Clean Multi®; ♦, 50 wt % Floral Fresh Fragrance/50 wt % Augeo Clean Multi®; □, 50 wt % Apple Fragrance/50 wt % IPD-AC®; ■, 50 wt % Floral Fresh Fragrance/50 wt % IPD-AC®. Abbreviations are as in FIGS. 1-7. Details are described in Example J.

The result schematically depicted in FIG. 8 emphasizes that different PRMs have a different release profile when combined with the solvents IPD-AC®- or Augeo Clean Multi®. The release profile of Floral Fresh Fragrance with either solvent IPD-AC®- or Augeo Clean Multi® is faster than that of Apple Fragrance with either solvent IPD-AC®- or Augeo Clean Multi®.

Example K. The Influence of Different Fragrance Release Modulators (FRMs) on the Release and Evaporation of a Freshening Composition Comprising 50 Wt % Floral Fresh Fragrance and Solvent IPD-AC®

In this Example, the influence of increasing concentrations of the fragrance release modulators benzyl benzoate (BB) on the release and evaporation of a freshening composition comprising (i) 50 wt % of the Floral Fresh Fragrance (ii) various wt % of the solvent IPD-AC® (3-methyl-1,3-butanediol-acetate) and (iii) increasing wt % of BB was examined. Further, the influence of three different FRMs at constant concentration was tested. Various freshening compositions were formulated and tested. Each freshening composition analyzed in this Example consisted of 50 wt % Floral Fresh Fragrance (see, Table 10, Example B), various wt % of solvent IPD-AC® and various wt % of a fragrance release modulator as indicated. The following freshening compositions were formulated and tested: 50 wt % Floral Fresh Fragrance/42.5 wt % IPD-AC®/7.5 wt % MMB; 50 wt % Floral Fresh Fragrance/42.5 wt % IPD-AC®/7.5 wt % BB; 50 wt % Floral Fresh Fragrance/42.5 wt % IPD-AC®/7.5 wt % TEC; 50 wt % Floral Fresh Fragrance/42.5 wt % IPD-AC®/7.5 wt % DPG; 50 wt % Floral Fresh Fragrance/25 wt % IPD-AC®/25 wt % BB; 50 wt % Floral Fresh Fragrance/7.5 wt % IPD-AC®/42.5 wt % BB; 50% Floral Fresh Fragrance/50 wt % IPD-AC® (control freshening composition not comprising an FRM); 50% Floral Fresh Fragrance/50 wt % BB (freshening composition not comprising a solvent). Release and evaporation of the freshening compositions was tested as described in Example C. Exemplary results are schematically depicted in FIG. 9.

As schematically depicted in FIG. 9, the different FRMs tested (DPG, MMB, TEC, and BB) lead to a different release profile. Of the FRMs tested, DPG lead to the fastest release—at the tested concentration and in combination with the solvent IPD-AC® and the Floral Fresh Fragrance. BB was led to the slowest release. As already tested in Example H, increasing the concentration of BB (from 7.5 wt % to 50 wt %) leads to a further down-regulation of release of the freshening composition or of a component thereof.

Example L. The Influence of Different Fragrance Release Modulators (FRMs) on the Release and Evaporation of a Freshening Composition Comprising 50 Wt % Apple Fragrance, Solvent Augeo Clean Multi® and Various Fragrance Release Modulators In this Example, the influence of increasing concentrations of the fragrance release modulators benzyl benzoate (BB) on the release and evaporation of a freshening composition comprising (i) 50 wt % of the Apple Fragrance (ii) various wt % of the solvent IPD-AC® (3-methyl-1,3-butanediol-acetate) and (iii) increasing wt % of BB was examined. Further, the influence of three different FRMs at constant concentration was tested. Various freshening compositions were formulated and tested. Each freshening composition analyzed in this Example consisted of 50 wt % Apple Fragrance (see, Table 9, Example A), various wt % of solvent Augeo Clean Multi® and various wt % of a fragrance release modulator as indicated. The following freshening compositions were formulated and tested: 50 wt % Apple Fragrance/50 wt % IPD-AC® (control freshening composition not comprising an FRM); 50 wt % Apple Fragrance/50 wt % STA-SOL® ESS 165 (control freshening composition not comprising an FRM); 50 wt % Apple Fragrance/42.5 wt % Augeo Clean Multi®/7.5 wt % MMB; 50 wt % Apple Fragrance/42.5 wt % Augeo Clean Multi®/7.5 wt % EtOH; 50 wt % Apple Fragrance/42.5 wt % Augeo Clean Multi®/7.5 wt % BB; 50 wt % Apple Fragrance/42.5 wt % Augeo Clean Multi®/7.5 wt % TEC; 50 wt % Apple Fragrance/42.5 wt % Augeo Clean Multi®/7.5 wt % DPG; 50 wt % Apple Fragrance/25 wt % Augeo Clean Multi®/25 wt % BB; 50 wt % Apple Fragrance/7.5 wt % Augeo Clean Multi®/42.5 wt % BB; 50 wt % Apple Fragrance/50 wt % BB (freshening composition not comprising a solvent). Release and evaporation of the freshening compositions was tested as described in Example C. Exemplary results are schematically depicted in FIG. 10.

As schematically depicted in FIG. 10, the different FRMs tested (DPG, TEC, BB, EtOH, and MMB) lead to a different release profile. Of the FRMs tested, DPG lead to the fastest release—at the tested concentration and in combination with the solvent Augeo Clean Multi® and the Apple Fragrance. As already tested in Example G, increasing the concentration of BB (from 7.5 wt % to 50 wt %) leads to a down-regulation of release of the freshening composition or of a component thereof.

Example M. No Statistically Significant Modulation of Release of a Freshening Composition or of a Component Thereof without a Fragrance Release Modulator Various freshening compositions were formulated. As described herein, in some embodiments, a fragrance release modulator is an aryl-ether. However, not every aryl-ether functions as a fragrance release modulator. Eucalyptol, for example, is an aryl-ether. To test whether eucalyptol functions as an FRM, the following freshening compositions, comprising two different perfume raw materials were formulated and tested: Freshening composition #1: 50 wt % linalool (a perfume raw material), 45 wt % Augeo Clean Multi® (a solvent) and 5 wt % eucalyptol (an aryl ether); Freshening composition #2: 50 wt % linalool (a perfume raw material), 50 wt % Augeo Clean Multi® (a solvent) and 0 wt % eucalyptol (an aryl ether). Freshening composition #3: 50 wt % benzyl acetate (a perfume raw material), 45 wt % Augeo Clean Multi® (a solvent) and 5 wt % eucalyptol (an aryl ether); Freshening composition #4: 50 wt % benzyl acetate (a perfume raw material), 50 wt % Augeo Clean Multi® (a solvent) and 0 wt % eucalyptol (an aryl ether). As described in Example C, 20 g of each freshening composition were added into a device, and the total weight of freshening composition and device was taken at Day 0. Release of the freshening composition was determined (as described in Example C) by measuring on subsequent days the weight of the device including the remaining freshening composition in the device.

Percentage release of the freshening compositions or of a component thereof was calculated as follows: First, total weight loss was determined by subtracting the total weight at any tested subsequent days from the total starting weight on Day 0. Percentage weight loss was then determined by dividing the evaporated amount (weight loss in g) by 20 g (the starting material of the freshening composition). The following results were obtained:

TABLE 11

Release of a freshening composition.
Data as measured for freshening composition #1 (Example M).
Freshening Composition #1

| Day | Weight (g) | Weight Loss (g) | Weight Loss (%) |
|---|---|---|---|
| 0 | 129.8 | 0.0 | 0.0 |
| 1 | 127.2 | 2.6 | 13.0 |
| 2 | 124.7 | 5.1 | 25.5 |
| 3 | 122.1 | 7.7 | 38.5 |
| 4 | 119.6 | 10.2 | 51.0 |
| 7 | 112.9 | 16.9 | 84.5 |

TABLE 12

Release of a freshening composition.
Data as measured for freshening composition #2 (Example M).
Freshening Composition #2

| Day | Weight (g) | Weight Loss (g) | Weight Loss (%) |
|---|---|---|---|
| 0 | 129.9 | 0.0 | 0.0 |
| 1 | 127.4 | 2.5 | 12.0 |
| 2 | 124.9 | 5.0 | 25.0 |
| 3 | 122.5 | 7.4 | 37.0 |
| 4 | 119.9 | 10.0 | 50.0 |
| 7 | 112.7 | 17.2 | 86.0 |

One of ordinary skill in the art will appreciate that there is no statistically significant difference between the data obtained with Freshening Composition #1 (including eucalyptol) and Freshening Composition #2 (not including eucalyptol) with respect to the release of the freshening composition or of a component thereof Δs such, in combination with the perfume raw material linalool and the solvent Augeo Clean Multi®, the ingredient eucalyptol does not function as a fragrance release modulator.

The data obtained with Freshening Composition #3 and Freshening Composition

TABLE 13

Release of a freshening composition.
Data as measured for freshening composition #3 (Example M).
Freshening Composition #3

| Day | Weight (g) | Weight Loss (g) | Weight Loss (%) |
|---|---|---|---|
| 0 | 130.9 | 0.0 | 0.0 |
| 1 | 127.9 | 3.0 | 15.0 |
| 2 | 125.0 | 5.9 | 29.5 |
| 3 | 122.0 | 8.9 | 44.5 |
| 4 | 119.3 | 11.6 | 58.0 |
| 7 | 111.6 | 19.3 | 96.5 |

TABLE 14

Release of a freshening composition.
Data as measured for freshening composition #4 (Example M).
Freshening Composition #4

| Day | Weight (g) | Weight Loss (g) | Weight Loss (%) |
|---|---|---|---|
| 0 | 130.6 | 0.0 | 0.0 |
| 1 | 127.8 | 2.8 | 13.8 |
| 2 | 125.0 | 5.6 | 27.9 |
| 3 | 122.2 | 8.4 | 42.0 |
| 4 | 119.3 | 11.3 | 56.4 |
| 7 | 111.4 | 19.2 | 96.1 |

One of ordinary skill in the art will appreciate that there is no statistically significant difference between the data obtained with Freshening Composition #3 (including eucalyptol) and Freshening Composition #4 (not including eucalyptol) with respect to the release of the freshening composition or of a component thereof Δs such, also in combination with another perfume raw material (benzyl acetate) and the solvent Augeo Clean Multi®, the ingredient eucalyptol does not function as fragrance release modulator.

To test a higher concentration of eucalyptol in the freshening compositions of above, the concentration of eucalyptol in Freshening Compositions #1 and #3 was increased to 12.5 wt % (in the presence of 37.5 wt % Augeo Clean Multi® and 50 wt % of the same perfume raw materials). Even with a higher wt % of the ingredient eucalyptol, it did not function as a fragrance release modulator (data not shown).

Example N. Influence of Various Fragrance Release Modulators on the Release of a Freshening Composition Comprising the Apple Fragrance and Fragrance Release Modulator Only In this Example the influence of various fragrance release modulators on the release of a freshening composition comprising only an FRM and a blend of perfume raw materials but no solvent was tested. The following freshening compositions were formulated and tested. Freshening composition #1: 50 wt % Apple Fragrance (a perfume raw material; see, Table 9, Example A) and 50 wt % dipropylene glycol (DPG, an FRM); Freshening composition #2: 50 wt % Apple Fragrance, and 50 wt % triethyl citrate (TEC, an FRM); Freshening composition #3: 50 wt % Apple Fragrance, and 50 wt % 3-methyl-3-methoxyl butanol (MMB, an FRM); Freshening composition #4: 50 wt % Apple Fragrance, and 50 wt % hexylene glycol (HG, an FRM); and Freshening composition #5: 100 wt % Apple Fragrance, (control freshening composition not comprising an FRM). As described in Example C, 20 g of each freshening composition were added into an electrical wall plug-in device, and the total weight of freshening composition and device was taken at Day 0. Release of the freshening composition was determined (as described in Example C) by measuring on subsequent days the weight of the device including the remaining freshening composition in the device.

Percentage release of the freshening compositions or of a component thereof was calculated as follows: First, total weight loss was determined by subtracting the total weight at any tested subsequent days from the total starting weight on Day 0. Percentage weight loss was then determined by dividing the evaporated amount (weight loss in g) by 20 g (the starting material of the freshening composition). The following results were obtained:

TABLE 15

Release of a freshening composition.
Data as measured for freshening composition #1 (Example N).
Freshening Composition #1

| Day | Weight (g) | Weight Loss (%) |
|---|---|---|
| 0 | 140.48 | 0.00 |
| 1 | 139.52 | 4.80 |
| 2 | 138.83 | 8.25 |
| 3 | 138.28 | 11.00 |
| 4 | 137.78 | 13.50 |
| 7 | 136.52 | 19.80 |
| 8 | 136.18 | 21.50 |
| 9 | 135.81 | 23.35 |
| 10 | 135.44 | 25.20 |
| 11 | 135.06 | 27.10 |
| 14 | 134.06 | 32.10 |
| 15 | 133.68 | 34.00 |
| 16 | 133.37 | 35.55 |
| 17 | 133.01 | 37.35 |
| 18 | 132.71 | 38.85 |
| 21 | 131.72 | 43.80 |
| 22 | 131.45 | 45.15 |
| 23 | 131.12 | 46.80 |
| 24 | 130.75 | 48.65 |
| 25 | 130.39 | 50.45 |
| 28 | 128.89 | 57.95 |

TABLE 16

Release of a freshening composition.
Data as measured for freshening composition #2 (Example N).
Freshening Composition #2

| Day | Weight (g) | Weight Loss (%) |
|---|---|---|
| 0 | 140.18 | 0.00 |
| 1 | 139.67 | 2.55 |
| 2 | 139.16 | 5.10 |
| 3 | 138.76 | 7.10 |
| 4 | 138.37 | 9.05 |
| 7 | 137.39 | 13.95 |
| 8 | 137.11 | 15.35 |
| 9 | 136.85 | 16.65 |
| 10 | 136.63 | 17.75 |
| 11 | 136.38 | 19.00 |
| 14 | 135.79 | 21.95 |
| 15 | 135.60 | 22.90 |
| 16 | 135.45 | 23.65 |
| 17 | 135.28 | 24.50 |
| 18 | 135.11 | 25.35 |
| 21 | 134.65 | 27.65 |
| 22 | 134.50 | 28.40 |
| 23 | 134.38 | 29.00 |
| 24 | 134.23 | 29.75 |

TABLE 16-continued

Release of a freshening composition.
Data as measured for freshening composition #2 (Example N).
Freshening Composition #2

| Day | Weight (g) | Weight Loss (%) |
|---|---|---|
| 25 | 134.09 | 30.45 |
| 28 | 133.60 | 32.90 |

TABLE 17

Release of a freshening composition.
Data as measured for freshening composition #3 (Example N).
Freshening Composition #3

| Day | Weight (g) | Weight Loss (%) |
|---|---|---|
| 0 | 127.85 | 0.00 |
| 1 | 125.14 | 13.55 |
| 2 | 123.04 | 24.05 |
| 3 | 121.52 | 31.65 |
| 4 | 119.63 | 41.10 |
| 7 | 115.23 | 63.10 |
| 8 | 114.53 | 66.60 |
| 9 | 114.01 | 69.02 |
| 10 | 113.50 | 71.75 |
| 11 | 113.04 | 74.05 |
| 14 | 112.15 | 78.50 |
| 15 | 111.99 | 79.30 |
| 16 | 111.78 | 80.35 |
| 17 | 111.60 | 81.25 |
| 18 | 111.48 | 81.85 |
| 21 | 111.14 | 83.55 |
| 22 | 111.04 | 84.05 |
| 23 | 110.88 | 84.85 |
| 24 | 110.76 | 85.45 |
| 25 | 110.69 | 85.80 |
| 28 | 110.24 | 88.08 |

TABLE 18

Release of a freshening composition.
Data as measured for freshening composition #4 (Example N).
Freshening Composition #4

| Day | Weight (g) | Weight Loss (%) |
|---|---|---|
| 0 | 133.28 | 0.00 |
| 1 | 131.85 | 7.15 |
| 2 | 130.67 | 13.05 |
| 3 | 129.57 | 18.55 |
| 4 | 128.60 | 23.40 |
| 7 | 125.73 | 37.75 |
| 8 | 124.89 | 41.95 |
| 9 | 124.15 | 45.65 |
| 10 | 123.56 | 48.60 |
| 11 | 122.90 | 51.90 |
| 14 | 121.15 | 60.65 |
| 15 | 120.63 | 63.25 |
| 16 | 120.24 | 65.20 |
| 17 | 119.82 | 67.30 |
| 18 | 119.39 | 69.45 |
| 21 | 117.99 | 76.45 |
| 22 | 117.64 | 78.20 |
| 23 | 117.35 | 79.65 |
| 24 | 117.03 | 81.25 |
| 25 | 116.75 | 82.65 |
| 28 | 116.14 | 85.70 |

TABLE 19

Release of a freshening composition.
Data as measured for freshening composition #5 (Example N).
Freshening Composition #5

| Day | Weight (g) | Weight Loss (%) |
|---|---|---|
| 0 | 140.16 | 0.00 |
| 1 | 139.38 | 3.90 |
| 2 | 138.70 | 7.30 |
| 3 | 138.11 | 10.25 |
| 6 | 136.27 | 19.45 |
| 7 | 135.84 | 21.60 |
| 8 | 135.37 | 23.95 |
| 9 | 134.94 | 26.10 |
| 10 | 134.49 | 28.35 |
| 14 | 132.87 | 36.45 |
| 15 | 132.56 | 38.00 |
| 16 | 132.32 | 39.20 |
| 17 | 131.98 | 40.90 |
| 20 | 131.33 | 44.15 |
| 21 | 130.92 | 46.20 |
| 22 | 130.68 | 47.40 |
| 23 | 130.45 | 48.55 |
| 24 | 130.18 | 49.90 |
| 27 | 129.52 | 53.20 |
| 28 | 129.24 | 54.60 |

Figure 11:
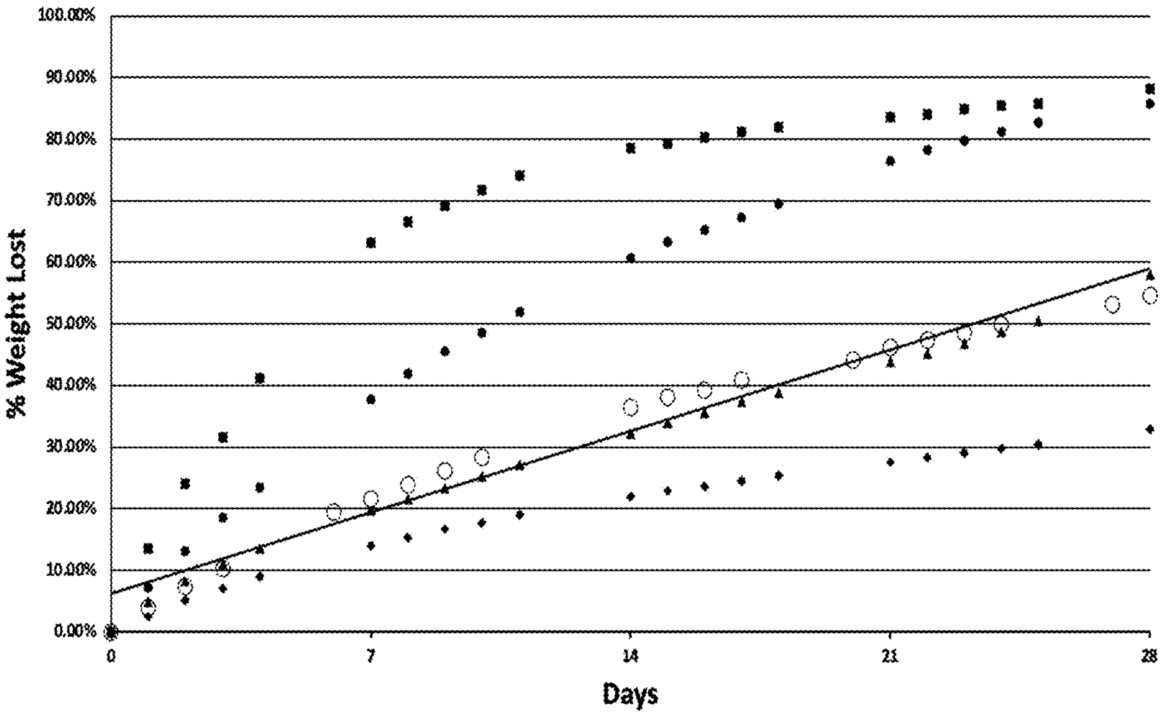
FIG. 11 schematically depicts the influence of different fragrance release modulators (FRM) on the release and evaporation of a freshening composition comprising 50% wt % Apple Fragrance and 50 wt % of the indicated FRMs or of a control freshening composition (100 wt % Apple Fragrance). Release is measured as % weight lost during the time period indicated. The weight percentage refers to the weight percentage of the entire product formulation, i.e., freshening composition. The release and evaporation of the following fragrance compositions were tested: ○, 1000 wt % Apple Fragrance; ♦, 50% Apple Fragrance/50 wt % triethyl citrate (TEC); ▲, 50 wt % Apple Fragrance/50 wt % dipropylene glycol (DPG)); ●, 50 wt % Apple Fragrance/50 wt % hexylene glycol (HG); and ■, 50 wt % Apple Fragrance/50 wt % 3-methyl-3-methoxyl butanol (MMB). Abbreviations and names are as described for FIGS. 1-10. Details are described in Example N.

The data gathered from Tables 15-19 are schematically depicted in FIG. 11. The data demonstrate that, in the absence of a solvent or diluent, different fragrance release modulators lead to different release profiles of the freshening composition comprising the same blend of perfume raw materials (Apple Fragrance, Example A) and the respective fragrance release modulators. More specifically, among the tested fragrance release modulators, 3-methyl-3-methoxyl butanol (MMB) leads to the fastest up-regulation of release of the freshening composition or of a component thereof. Hexylene glycol (HG) can be considered a medium-strong up-regulator of release of the freshening composition or of a component thereof. Dipropylene glycol (DPG) can be considered a slow up-regulator of release of the freshening composition or of a component thereof. Triethyl citrate (TEC) can be considered a down-regulator of release of the freshening composition or of a component thereof.

Example O. Influence of Various Fragrance Release Modulators on the Release of a Freshening Composition Comprising the Floral Fresh Fragrance and Fragrance Release Modulator Only In this Example the influence of various fragrance release modulators on the release of a freshening composition comprising only an FRM and a blend of perfume raw materials but no solvent was tested. The following freshening compositions were formulated and tested. Freshening composition #1: 50 wt % Floral Fresh Fragrance (a perfume raw material; see, Table 10, Example B) and 50 wt % dipropylene glycol (DPG, an FRM); Freshening composition #2: 50 wt % Floral Fresh Fragrance and 50 wt % triethyl citrate (TEC, an FRM); Freshening composition #3: 50 wt % Floral Fresh Fragrance and 50 wt % 3-methyl-3-methoxyl butanol (MMB, an FRM); Freshening composition #4: 50 wt % Floral Fresh Fragrance and 50 wt % hexylene glycol (HG, an FRM); and Freshening composition #5: 100 wt % Floral Fresh Fragrance (control freshening composition not comprising an FRM). As described in Example C, 20 g of each freshening composition were added into an electrical wall plug-in device, and the total weight of freshening composition and device was taken at Day 0. Release of the freshening composition was determined (as described in Example C) by measuring on subsequent days the weight of the device including the remaining freshening composition in the device.

Percentage release of the freshening compositions or of a component thereof was calculated as follows: First, total weight loss was determined by subtracting the total weight at any tested subsequent days from the total starting weight on Day 0. Percentage weight loss was then determined by dividing the evaporated amount (weight loss in g) by 20 g (the starting material of the freshening composition). The following results were obtained:

TABLE 20

Release of a freshening composition.
Data as measured for freshening composition #1 (Example O).
Freshening Composition #1

| Day | Weight (g) | Weight Loss (%) |
|---|---|---|
| 0 | 125.47 | 0.00 |
| 1 | 124.66 | 4.05 |
| 2 | 123.97 | 7.50 |
| 3 | 123.50 | 9.85 |
| 4 | 123.07 | 12.00 |
| 7 | 121.89 | 17.90 |
| 8 | 121.49 | 19.90 |
| 9 | 121.05 | 22.10 |
| 10 | 120.70 | 23.85 |
| 11 | 120.26 | 26.05 |
| 14 | 119.03 | 32.20 |
| 15 | 118.60 | 34.35 |
| 16 | 118.25 | 36.10 |
| 17 | 117.86 | 38.05 |
| 18 | 117.47 | 40.00 |
| 21 | 116.38 | 45.45 |
| 22 | 115.97 | 47.50 |
| 23 | 115.59 | 49.40 |
| 24 | 115.20 | 51.35 |
| 25 | 114.83 | 53.20 |
| 28 | 113.33 | 60.70 |

TABLE 21

Release of a freshening composition.
Data as measured for freshening composition #2 (Example O).
Freshening Composition #2

| Day | Weight (g) | Weight Loss (%) |
|---|---|---|
| 0 | 140.80 | 0.00 |
| 1 | 140.39 | 2.05 |
| 2 | 140.07 | 3.65 |
| 3 | 139.80 | 5.00 |
| 4 | 139.52 | 6.40 |
| 7 | 138.78 | 10.10 |
| 8 | 138.59 | 11.05 |
| 9 | 138.37 | 12.15 |
| 10 | 138.19 | 13.05 |
| 11 | 138.00 | 14.00 |
| 14 | 137.39 | 17.05 |
| 15 | 137.22 | 17.90 |
| 16 | 137.06 | 18.70 |
| 17 | 136.90 | 19.50 |
| 18 | 136.72 | 20.40 |
| 21 | 136.26 | 22.70 |
| 22 | 136.11 | 23.45 |
| 23 | 135.98 | 24.10 |
| 24 | 135.82 | 24.90 |
| 25 | 135.69 | 25.55 |
| 28 | 135.19 | 28.05 |

TABLE 22

Release of a freshening composition.
Data as measured for freshening composition #3 (Example O).
Freshening Composition #3

| Day | Weight (g) | Weight Loss (%) |
|---|---|---|
| 0 | 132.04 | 0.00 |
| 1 | 130.02 | 10.10 |
| 2 | 128.12 | 19.06 |
| 3 | 126.44 | 28.00 |
| 4 | 125.21 | 34.15 |
| 7 | 121.92 | 50.60 |
| 8 | 121.34 | 53.50 |
| 9 | 120.66 | 58.90 |
| 10 | 120.08 | 59.80 |
| 11 | 119.57 | 62.35 |
| 14 | 118.03 | 68.70 |
| 15 | 118.03 | 70.05 |
| 16 | 117.91 | 70.65 |
| 17 | 117.71 | 71.65 |
| 18 | 117.52 | 72.60 |
| 21 | 117.10 | 74.70 |
| 22 | 116.93 | 75.55 |
| 23 | 116.86 | 75.90 |
| 24 | 116.70 | 76.70 |
| 25 | 116.55 | 77.45 |
| 28 | 116.25 | 78.95 |

TABLE 23

Release of a freshening composition.
Data as measured for freshening composition #4 (Example O).
Freshening Composition #4

| Day | Weight (g) | Weight Loss (%) |
|---|---|---|
| 0 | 134.02 | 0.00 |
| 1 | 132.52 | 7.50 |
| 2 | 131.29 | 13.65 |
| 3 | 130.18 | 19.20 |
| 4 | 129.17 | 24.25 |
| 7 | 126.53 | 37.45 |
| 8 | 125.83 | 40.95 |
| 9 | 125.18 | 44.20 |
| 10 | 124.63 | 46.95 |
| 11 | 124.04 | 49.90 |
| 14 | 122.55 | 57.35 |
| 15 | 122.08 | 59.70 |
| 16 | 121.75 | 61.35 |
| 17 | 121.41 | 63.05 |
| 18 | 121.08 | 64.70 |
| 21 | 120.10 | 69.60 |
| 22 | 119.90 | 70.60 |
| 23 | 119.73 | 71.45 |
| 24 | 119.46 | 72.80 |
| 25 | 119.23 | 73.95 |
| 28 | 118.63 | 76.95 |

TABLE 24

Release of a freshening composition.
Data as measured for freshening composition #5 (Example O).
Freshening Composition #5

| Day | Weight (g) | Weight Loss (%) |
|---|---|---|
| 0 | 139.88 | 0.00 |
| 1 | 139.41 | 2.35 |
| 2 | 138.95 | 4.65 |
| 3 | 138.52 | 6.60 |
| 6 | 137.15 | 13.65 |
| 7 | 136.78 | 15.50 |
| 8 | 136.46 | 17.10 |
| 9 | 136.19 | 18.45 |
| 10 | 135.86 | 20.10 |

TABLE 24-continued

Release of a freshening composition.
Data as measured for freshening composition #5 (Example O).
Freshening Composition #5

| Day | Weight (g) | Weight Loss (%) |
|---|---|---|
| 14 | 134.70 | 25.90 |
| 15 | 134.43 | 27.25 |
| 16 | 134.21 | 28.35 |
| 17 | 133.95 | 29.65 |
| 20 | 133.34 | 32.70 |
| 21 | 133.16 | 33.60 |
| 22 | 132.95 | 34.65 |
| 23 | 132.77 | 35.55 |
| 24 | 132.57 | 36.55 |
| 27 | 132.09 | 38.95 |
| 28 | 131.87 | 40.05 |

Figure 12:
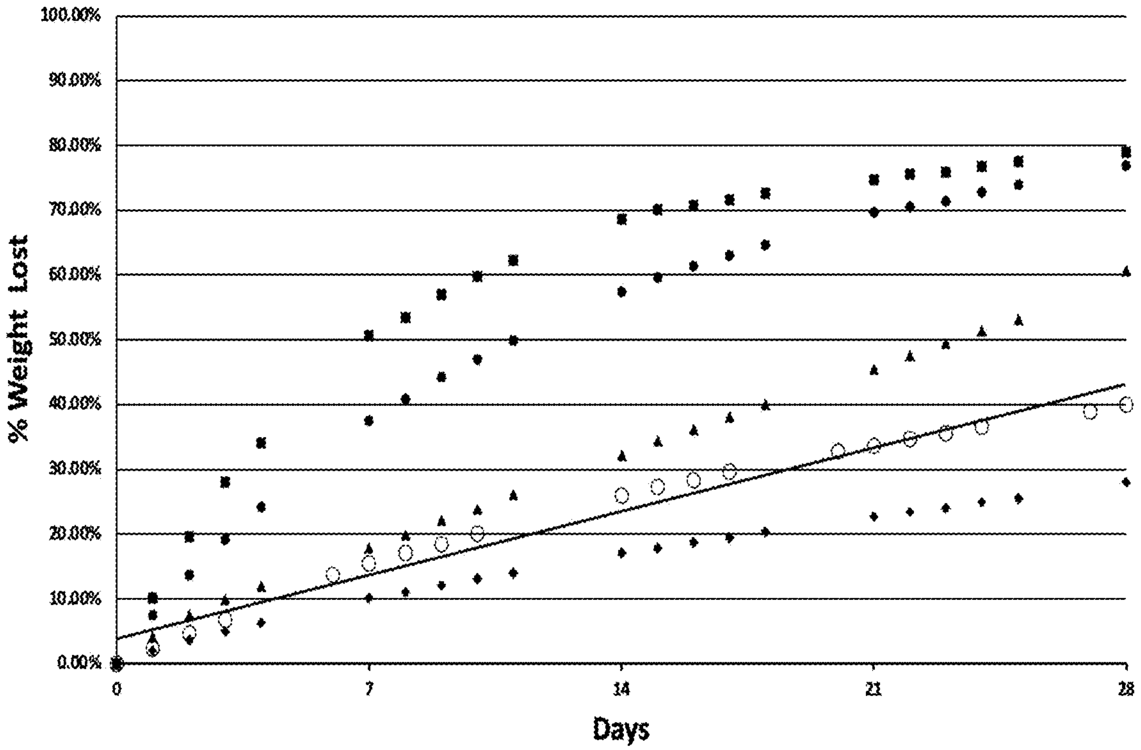
FIG. 12 schematically depicts the influence of different fragrance release modulators (FRM) on the release and evaporation of a freshening composition comprising 50% wt % Floral Fresh Fragrance and 50 wt % of the indicated FRMs or of a control (100 wt % Floral Fresh Fragrance). Release is measured as % weight lost during the time period indicated. The weight percentage refers to the weight percentage of the entire product formulation, i.e., freshening composition. The release and evaporation of the following fragrance compositions were tested: ○, 100 wt % Floral Fresh Fragrance; ♦, 50% Floral Fresh Fragrance/50 wt % triethyl citrate (TEC); ▲, 50 wt % Floral Fresh Fragrance/50 wt % dipropylene glycol (DPG)); ●, 50 wt % Floral Fresh Fragrance/50 wt % hexylene glycol (HG); and ■, 50 wt % Floral Fresh Fragrance/50 wt % 3-methyl-3-methoxyl butanol (MMB). Abbreviations and names are as described for FIGS. 1-11. Details are described in Example O.

The data gathered from Tables 20-24 are schematically depicted in FIG. 12. The data demonstrate that, in the absence of a solvent or diluent, different fragrance release modulators lead to different release profiles of the freshening composition comprising the same blend of perfume raw materials (Floral Fresh Fragrance, Example B) and the respective fragrance release modulators. More specifically, among the tested fragrance release modulators, 3-methyl-3-methoxyl butanol (MMB) leads to the fastest up-regulation of release of the freshening composition or of a component thereof. Hexylene glycol (HG) can be considered a medium-strong up-regulator of release of the freshening composition or of a component thereof. Dipropylene glycol (DPG) can be considered a slow up-regulator of release of the freshening composition or of a component thereof. Triethyl citrate (TEC) can be considered a downregulator of release of the freshening composition or of a component thereof. The data obtained in Example N, using the Apple Fragrance, is very similar to the data obtained in Example O using the Floral Fresh Fragrance.

What is claimed is:

1. A freshening composition comprising:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator is sufficient to modulate release of the freshening composition or of a component thereof, relative to a control not comprising the fragrance release modulator and being assigned a value of 100%, by at least 10%.

2. The freshening composition according to claim 1, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

3. The freshening composition according to claim 1, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

4. The freshening composition according to claim 1, wherein the fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

5. The freshening composition according to claim 1, further comprising less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

6. The freshening composition according to claim 1, wherein the $C_{2-8}$ branched alcohol is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, a stereoisomer thereof, and a mixture thereof.

7. The freshening composition according to claim 6, wherein the $C_{2-8}$ branched alcohol is 3-methoxy-3-methyl-1-butanol.

8. The freshening composition according to claim 1, wherein the alkyl-glycol is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer thereof, and a mixture thereof.

9. The freshening composition according to claim 8, wherein the alkyl-glycol is propylene glycol or dipropylene glycol.

10. The freshening composition according to claim 1, wherein the alkyl-diol is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer thereof, and a mixture thereof.

11. The freshening composition according to claim 10, wherein the alkyl-diol is 2-methylpentane-2,4-diol.

12. The freshening composition according to claim 1, wherein the alkyl-adipate is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer thereof, and a mixture thereof.

13. The freshening composition according to claim 12, wherein the alkyl-adipate is dimethyl adipate.

14. The freshening composition according to claim 1, wherein the alkyl-benzoate is selected from the group consisting of benzyl benzoate, isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer thereof, and a mixture thereof.

15. The freshening composition according to claim 14, wherein the alkyl-benzoate is benzyl benzoate.

16. The freshening composition according to claim 1, wherein the alkyl-citrate is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer thereof, and a mixture thereof.

17. The freshening composition according to claim 16, wherein the alkyl-citrate is triethyl citrate.

18. The freshening composition according to claim 1, wherein the alkyl-myristate is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer thereof, and a mixture thereof.

19. The freshening composition according to claim 18, wherein the alkyl-myristate is isopropyl myristate.

20. The freshening composition according to claim 1, wherein the alkyl-glutarate is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer thereof, and a mixture thereof.

21. The freshening composition according to claim 20, wherein the alkyl-glutarate is dimethyl glutarate.

22. The freshening composition according to claim 1, wherein the fragrance release modulator is 3-methyl-3-methoxyl butanol.

23. The freshening composition according to claim 1, further comprising a compound selected from the group consisting of 2,2-dimethyl-1,3-dioxolane-4-methanol, 3-methyl-1,3-butanediol-1-acetate, ethylene glycol monoethyl ether, ethylene glycol monomethyl ether, diethylene glycol monoethyl ether, diethylene glycol monomethyl ether, dipropylene glycol monomethyl ether, dipropylene glycol monomethyl ether acetate, and tripropylene glycol monomethyl ether.

24. The freshening composition according to claim 1, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters;

wherein the alcohol is selected from the group consisting of an aliphatic alcohol, a terpene alcohol, an aromatic alcohol, a stereoisomer of any preceding alcohol, and a mixture of any of the preceding alcohols;

wherein the aldehyde is selected from the group consisting of an aliphatic aldehyde, an aromatic aldehyde, a terpene aldehyde, a stereoisomer of any preceding aldehyde, and a mixture of any of the preceding aldehydes;

wherein the ketone is selected from the group consisting of a cyclic ketone, an aromatic ketone, a linear ketone, a stereoisomer of any preceding ketone, and a mixture of any of the preceding ketones;

wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals;

wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols;

wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers;

wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones;

wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2 (5H)-furanone (sotolone), 2-ethyl-4-hydroxy-5-methyl-3 (2H)-furanone (homofuraneol), 5-ethyl-3-hydroxy-4-methyl-2 (5H) furanone (homosotolone), 3-methyl-1,2-cyclopentanedione (cyclotene), 2 (5H)-furanone, 4-methyl-2 (5H)-furanone, 5-methyl-2 (5H)-furanone, 2-methyl-3 (2H)-furanone, 5-methyl-3 (2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans;

wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons;

wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids; or wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

25. An air freshener device comprising:

(1) a reservoir; and (2) a freshening composition comprising:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition houses in the reservoir;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator is sufficient to modulate release of the freshening composition or of a component thereof, relative to a control not comprising the fragrance release modulator and being assigned a value of 100%, by at least 10%.

26. The air freshener device according to claim 25, wherein the fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

27. The air freshener device according to claim 25, wherein the freshening composition further comprises (iii) less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

28. The air freshener device according to claim 25, wherein the reservoir is selected from the group consisting of a bottle, a bowl, a tray, a plate, a glass, a shell, a box, a sphere, a globe, a vessel, and a container.

29. The air freshener device according to claim 25, further comprising a delivery system comprising an element in communication or in contact with the freshening composition.

30. The air freshener device according to claim 29, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

31. The air freshener device according to claim 25, further comprising an evaporative assistance element attached to the reservoir.

32. The air freshener device according to claim 31, wherein the evaporative assistance element is selected from the group consisting of a heater, a fan, an agitator, and a combination of any of the preceding evaporative assistance elements.

33. The air freshener device according to claim 25, wherein the air freshener device is selected from the group consisting of a spraying device, a capillary wicking device, a membrane diffusing device, a steam-diffusing device, an energized device, a heating device, a device comprising a delivery system, a device powered by a chemical reaction, an air freshener device comprising a wick, a passive air diffuser device, a device comprising an evaporative assistance element, and a reed diffuser air freshener.

34. The freshening composition according to claim 5, wherein the ingredient having malodor counteracting activity is cyclodextrin;

wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol;

wherein the insect repellent is N,N-diethyl-meta-toluamide or methyl nonyl ketone;

wherein the preservative is selected from the group consisting of imidazolidinyl urea, diazolidinyl urea, allantoin, and sodium hydroxymethylglycinate;

wherein the antioxidant is selected from the group consisting of butylate hydroxytoluene, ascorbic acid, and tocopherol;

wherein the humectant is selected from the group consisting of glycerol, hexylene glycol, and ethyl-hexylglycerin;

wherein the UV blocking agent is selected from the group consisting of avobenzone, oxybenzone, dioxybenzone, and octocrylene;

wherein the pigment is selected from the group consisting of chrome oxide, iron oxide, and ferric ferrocyanate;

wherein the surfactant is selected from the group consisting of a nonionic surfactant, an anionic surfactant, and a cationic surfactant;

wherein the emulsifier is an ethoxylated sorbitol;

wherein the solubilizer is selected from the group consisting of propylene glycol, dipropylene glycol, and hexylene glycol;

wherein the polymer is a cellulose derivative; or wherein the buffer is a phosphate buffer.

35. The air freshener device according to claim 25, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

36. The air freshener device according to claim 25, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

37. The air freshener device according to claim 25, wherein the $C_{2-27}$ branched alcohol is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, a stereoisomer thereof, and a mixture thereof.

38. The air freshener device according to claim 37, wherein the $C_{2-27}$ branched alcohol is 3-methoxy-3-methyl-1-butanol.

39. The air freshener device according to claim 25, wherein the alkyl-glycol is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer thereof, and a mixture thereof.

40. The air freshener device according to claim 39, wherein the alkyl-glycol is propylene glycol or dipropylene glycol.

41. The air freshener device according to claim 25, wherein the alkyl-diol is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer thereof, and a mixture thereof.

42. The air freshener device according to claim 41, wherein the alkyl-diol is 2-methylpentane-2,4-diol.

43. The air freshener device according to claim 25, wherein the alkyl-adipate is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer thereof, and a mixture thereof.

44. The air freshener device according to claim 43, wherein the alkyl-adipate is dimethyl adipate.

45. The air freshener device according to claim 25, wherein the alkyl-benzoate is selected from the group consisting of benzyl benzoate, isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer thereof, and a mixture thereof.

46. The air freshener device according to claim 45, wherein the alkyl-benzoate is benzyl benzoate.

47. The air freshener device according to claim 25, wherein the alkyl-citrate is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer thereof, and a mixture thereof.

48. The air freshener device according to claim 47, wherein the alkyl-citrate is triethyl citrate.

49. The air freshener device according to claim 25, wherein the alkyl-myristate is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer thereof, and a mixture thereof.

50. The air freshener device according to claim 49, wherein the alkyl-myristate is isopropyl myristate.

51. The air freshener device according to claim 25, wherein the alkyl-glutarate is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer thereof, and a mixture thereof.

52. The air freshener device according to claim 51, wherein the alkyl-glutarate is dimethyl glutarate.

53. The air freshener device according to claim 25, wherein the fragrance release modulator is 3-methyl-3-methoxyl butanol.

54. The air freshener device according to claim 25, further comprising a compound selected from the group consisting of 2,2-dimethyl-1,3-dioxolane-4-methanol, 3-methyl-1,3-butanediol-1-acetate, ethylene glycol monoethyl ether, ethylene glycol monomethyl ether, diethylene glycol monoethyl ether, diethylene glycol monomethyl ether, dipropylene glycol monomethyl ether, dipropylene glycol monomethyl ether acetate, and tripropylene glycol monomethyl ether.

55. The air freshener device according to claim 25, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters;

wherein the alcohol is selected from the group consisting of an aliphatic alcohol, a terpene alcohol, an aromatic alcohol, a stereoisomer of any preceding alcohol, and a mixture of any of the preceding alcohols;

wherein the aldehyde is selected from the group consisting of an aliphatic aldehyde, an aromatic aldehyde, a terpene aldehyde, a stereoisomer of any preceding aldehyde, and a mixture of any of the preceding aldehydes;

wherein the ketone is selected from the group consisting of a cyclic ketone, an aromatic ketone, a linear ketone, a stereoisomer of any preceding ketone, and a mixture of any of the preceding ketones;

wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals;

wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols;

wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers;

wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones;

wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2 (5H)-furanone (sotolone), 2-ethyl-4-hydroxy-5-methyl-3 (2H)-furanone (homofuraneol), 5-ethyl-3-hydroxy-4-methyl-2 (5H) furanone (homosotolone), 3-methyl-1,2-cyclopentanedione (cyclotene), 2 (5H)-furanone, 4-methyl-2 (5H)-furanone, 5-methyl-2 (5H)-furanone, 2-methyl-3 (2H)-furanone, 5-methyl-3 (2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans;

wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons;

wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids; or wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

56. The air freshener device according to claim 27, wherein the ingredient having malodor counteracting activity is cyclodextrin;

wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol;

wherein the insect repellent is N,N-diethyl-meta-toluamide or methyl nonyl ketone;

wherein the preservative is selected from the group consisting of imidazolidinyl urea, diazolidinyl urea, allantoin, and sodium hydroxymethylglycinate;

wherein the antioxidant is selected from the group consisting of butylate hydroxytoluene, ascorbic acid, and tocopherol;

wherein the humectant is selected from the group consisting of glycerol, hexylene glycol, and ethyl-hexylglycerin;

wherein the UV blocking agent is selected from the group consisting of avobenzone, oxybenzone, dioxybenzone, and octocrylene;

wherein the pigment is selected from the group consisting of chrome oxide, iron oxide, and ferric ferrocyanate;

wherein the surfactant is selected from the group consisting of a nonionic surfactant, an anionic surfactant, and a cationic surfactant;

wherein the emulsifier is an ethoxylated sorbitol;

wherein the solubilizer is selected from the group consisting of propylene glycol, dipropylene glycol, and hexylene glycol;

wherein the polymer is a cellulose derivative; or wherein the buffer is a phosphate buffer.

57. The air freshener device according to claim 33, wherein the air freshener device is the spraying device, and wherein the spraying device comprises from about 0.01 wt % to about 50 wt % of the freshening composition, from about 1 wt % to about 80 wt % of a co-solvent, and from about 1 wt % to about 50 wt % of a propellant.

58. The air freshener device according to claim 33, wherein the air freshener device is the spraying device, and wherein the spraying device comprises the freshening composition and ethanol.

59. The air freshener device according to claim 33, wherein the air freshener device is the energized device.

60. The air freshener device according to claim 59, wherein the energized device is selected from the group consisting of an electrically powered air freshener device, an electrical wall plug-in, a fan-based diffuser, a liquid electric pluggable air freshener device, an electromechanical actuating diffuser, a heating device, a device powered by a chemical reaction, a battery-operated air freshener device, and an energized device comprising a micro-fluidic die having a heater or a piezo crystal.

61. The air freshener device according to claim 60, which is the electrical wall plug-in.

62. A method for manufacturing a freshening composition, the method comprising the step of combining:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator is sufficient to modulate release of the freshening composition or of a component thereof, relative to a control not comprising the fragrance release modulator and being assigned a value of 100%, by at least 10%;

thereby producing a freshening composition comprising (i) and (ii).

63. The method according to claim 62, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

64. The method according to claim 62, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

65. The method according to claim 62, wherein the fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

66. The method according to claim 62, wherein the freshening composition further comprises less than about 50 wt % of an ingredient having a functional activity and wherein the ingredient having the functional activity is selected from the group consisting of an ingredient having malodor counteracting activity, an ingredient having antimicrobial activity, an insect repellent, a preservative, an antioxidant, a humectant, a UV-blocking agent, a pigment, a dye, a surfactant, an emulsifier, a solubilizer, a polymer, and a buffer.

67. The method according to claim 62, wherein the $C_{2-27}$ branched alcohol is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, a stereoisomer thereof, and a mixture thereof.

68. The method according to claim 67, wherein the $C_{2-27}$ branched alcohol is 3-methoxy-3-methyl-1-butanol.

69. The method according to claim 62, wherein the alkyl-glycol is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer thereof, and a mixture thereof.

70. The method according to claim 69, wherein the alkyl-glycol is propylene glycol or dipropylene glycol.

71. The method according to claim 62, wherein the alkyl-diol is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer thereof, and a mixture thereof.

72. The method according to claim 71, wherein the alkyl-diol is 2-methylpentane-2,4-diol.

73. The method according to claim 62, wherein the alkyl-adipate is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer thereof, and a mixture thereof.

74. The method according to claim 73, wherein the alkyl-adipate is dimethyl adipate.

75. The method according to claim 62, wherein the alkyl-benzoate is selected from the group consisting of benzyl benzoate, isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer thereof, and a mixture thereof.

76. The method according to claim 75, wherein the alkyl-benzoate is benzyl benzoate.

77. The method according to claim 62, wherein the alkyl-citrate is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer thereof, and a mixture thereof.

78. The method according to claim 77, wherein the alkyl-citrate is triethyl citrate.

79. The method according to claim 62, wherein the alkyl-myristate is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer thereof, and a mixture thereof.

80. The method according to claim 79, wherein the alkyl-myristate is isopropyl myristate.

81. The method according to claim 62, wherein the alkyl-glutarate is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer thereof, and a mixture thereof.

82. The method according to claim 81, wherein the alkyl-glutarate is dimethyl glutarate.

83. The method according to claim 62, wherein the fragrance release modulator is 3-methyl-3-methoxyl butanol.

84. The method according to claim 62, further comprising a compound selected from the group consisting of 2,2-dimethyl-1,3-dioxolane-4-methanol, 3-methyl-1,3-butanediol-1-acetate, ethylene glycol monoethyl ether, ethylene glycol monomethyl ether, diethylene glycol monoethyl ether, diethylene glycol monomethyl ether, dipropylene glycol monomethyl ether, dipropylene glycol monomethyl ether acetate, and tripropylene glycol monomethyl ether.

85. The method according to claim 62, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters;

wherein the alcohol is selected from the group consisting of an aliphatic alcohol, a terpene alcohol, an aromatic alcohol, a stereoisomer of any preceding alcohol, and a mixture of any of the preceding alcohols;

wherein the aldehyde is selected from the group consisting of an aliphatic aldehyde, an aromatic aldehyde, a terpene aldehyde, a stereoisomer of any preceding aldehyde, and a mixture of any of the preceding aldehydes;

wherein the ketone is selected from the group consisting of a cyclic ketone, an aromatic ketone, a linear ketone, a stereoisomer of any preceding ketone, and a mixture of any of the preceding ketones;

wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals;

wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols;

wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers;

wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones;

wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2 (5H)-furanone (sotolone), 2-ethyl-4-hydroxy-5-methyl-3 (2H)-furanone (homofuraneol), 5-ethyl-3-hydroxy-4-methyl-2 (5H) furanone (homosotolone), 3-methyl-1,2-cyclopentanedione (cyclotene), 2 (5H)-furanone, 4-methyl-2 (5H)-furanone, 5-methyl-2 (5H)-furanone, 2-methyl-3 (2H)-furanone, 5-methyl-3 (2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans;

wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons;

wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids; or wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

86. The method according to claim 66, wherein the ingredient having malodor counteracting activity is cyclodextrin;

wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol;

wherein the insect repellent is N,N-diethyl-meta-toluamide or methyl nonyl ketone;

wherein the preservative is selected from the group consisting of imidazolidinyl urea, diazolidinyl urea, allantoin, and sodium hydroxymethylglycinate;

wherein the antioxidant is selected from the group consisting of butylate hydroxytoluene, ascorbic acid, and tocopherol;

wherein the humectant is selected from the group consisting of glycerol, hexylene glycol, and ethyl-hexylglycerin;

wherein the UV blocking agent is selected from the group consisting of avobenzone, oxybenzone, dioxybenzone, and octocrylene;

wherein the pigment is selected from the group consisting of chrome oxide, iron oxide, and ferric ferrocyanate;

wherein the surfactant is selected from the group consisting of a nonionic surfactant, an anionic surfactant, and a cationic surfactant;

wherein the emulsifier is an ethoxylated sorbitol;

wherein the solubilizer is selected from the group consisting of propylene glycol, dipropylene glycol, and hexylene glycol;

wherein the polymer is a cellulose derivative; or wherein the buffer is a phosphate buffer.

87. A method for manufacturing an air freshener device comprising a freshening composition, the method comprising the step of contacting a reservoir in an air freshener device with a freshening composition;

wherein the freshening composition comprises:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator is sufficient to modulate release of the freshening composition or of a component thereof, relative to a control not comprising the fragrance release modulator and being assigned a value of 100%, by at least 10%;

thereby producing the air freshener device comprising the freshening composition.

88. The method according to claim 87, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

89. The method according to claim 87, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

90. The method according to claim 87, wherein the fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

91. The method according to claim 87, wherein the freshening composition further comprises less than about 50 wt % of an ingredient having a functional activity and wherein the ingredient having the functional activity is selected from the group consisting of an ingredient having malodor counteracting activity, an ingredient having anti-microbial activity, an insect repellant, a preservative, an antioxidant, a humectant, a UV-blocking agent, a pigment, a dye, a surfactant, an emulsifier, a solubilizer, a polymer, and a buffer.

92. The method according to claim 87, wherein the $C_{2-27}$ branched alcohol is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, a stereoisomer thereof, and a mixture thereof.

93. The method according to claim 92, wherein the $C_{2-27}$ branched alcohol is 3-methoxy-3-methyl-1-butanol.

94. The method according to claim 87, wherein the alkyl-glycol is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer thereof, and a mixture thereof.

95. The method according to claim 94, wherein the alkyl-glycol is propylene glycol or dipropylene glycol.

96. The method according to claim 87, wherein the alkyl-diol is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer thereof, and a mixture thereof.

97. The method according to claim 96, wherein the alkyl-diol is 2-methylpentane-2,4-diol.

98. The method according to claim 87, wherein the alkyl-adipate is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer thereof, and a mixture thereof.

99. The method according to claim 98, wherein the alkyl-adipate is dimethyl adipate.

100. The method according to claim 87, wherein the alkyl-benzoate is selected from the group consisting of benzyl benzoate, isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer thereof, and a mixture thereof.

101. The method according to claim 100, wherein the alkyl-benzoate is benzyl benzoate.

102. The method according to claim 87, wherein the alkyl-citrate is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer thereof, and a mixture thereof.

103. The method according to claim 102, wherein the alkyl-citrate is triethyl citrate.

104. The method according to claim 87, wherein the alkyl-myristate is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer thereof, and a mixture thereof.

105. The method according to claim 104, wherein the alkyl-myristate is isopropyl myristate.

106. The method according to claim 87, wherein the alkyl-glutarate is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer thereof, and a mixture thereof.

107. The method according to claim 106, wherein the alkyl-glutarate is dimethyl glutarate.

108. The method according to claim 87, wherein the fragrance release modulator is 3-methyl-3-methoxyl butanol.

109. The method according to claim 87, further comprising a compound selected from the group consisting of 2,2-dimethyl-1,3-dioxolane-4-methanol, 3-methyl-1,3-butanediol-1-acetate, ethylene glycol monoethyl ether, ethylene glycol monomethyl ether, diethylene glycol monoethyl ether, diethylene glycol monomethyl ether, dipropylene glycol monomethyl ether, dipropylene glycol monomethyl ether acetate, and tripropylene glycol monomethyl ether.

110. The method according to claim 87, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters;

wherein the alcohol is selected from the group consisting of an aliphatic alcohol, a terpene alcohol, an aromatic alcohol, a stereoisomer of any preceding alcohol, and a mixture of any of the preceding alcohols;

wherein the aldehyde is selected from the group consisting of an aliphatic aldehyde, an aromatic aldehyde, a terpene aldehyde, a stereoisomer of any preceding aldehyde, and a mixture of any of the preceding aldehydes;

wherein the ketone is selected from the group consisting of a cyclic ketone, an aromatic ketone, a linear ketone, a stereoisomer of any preceding ketone, and a mixture of any of the preceding ketones;

wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals;

wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols;

wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers;

wherein the lactone is selected from the group consisting of γ-decalactone, δ-decalactone, γ-heptalactone, γ-nonalactone, γ-hexalactone, δ-hexalactone, γ-octalactone, δ-octalactone, γ-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones;

wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2

(5H)-furanone (sotolone), 2-ethyl-4-hydroxy-5-methyl-3 (2H)-furanone (homofuraneol), 5-ethyl-3-hydroxy-4-methyl-2 (5H) furanone (homosotolone), 3-methyl-1,2-cyclopentanedione (cyclotene), 2 (5H)-furanone, 4-methyl-2 (5H)-furanone, 5-methyl-2 (5H)-furanone, 2-methyl-3 (2H)-furanone, 5-methyl-3 (2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans;

wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons;

wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids; or wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

111. The method according to claim 91, wherein the ingredient having malodor counteracting activity is cyclodextrin;

wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol;

wherein the insect repellent is N,N-diethyl-meta-toluamide or methyl nonyl ketone;

wherein the preservative is selected from the group consisting of imidazolidinyl urea, diazolidinyl urea, allantoin, and sodium hydroxymethylglycinate;

wherein the antioxidant is selected from the group consisting of butylate hydroxytoluene, ascorbic acid, and tocopherol;

wherein the humectant is selected from the group consisting of glycerol, hexylene glycol, and ethyl-hexylglycerin;

wherein the UV blocking agent is selected from the group consisting of avobenzone, oxybenzone, dioxybenzone, and octocrylene;

wherein the pigment is selected from the group consisting of chrome oxide, iron oxide, and ferric ferrocyanate;

wherein the surfactant is selected from the group consisting of a nonionic surfactant, an anionic surfactant, and a cationic surfactant;

wherein the emulsifier is an ethoxylated sorbitol;

wherein the solubilizer is selected from the group consisting of propylene glycol, dipropylene glycol, and hexylene glycol;

wherein the polymer is a cellulose derivative; or wherein the buffer is a phosphate buffer.

112. The method according to claim 87, wherein the reservoir is a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid.

113. The method according to claim 87, wherein the reservoir is selected from the group consisting of a bottle, a bowl, a tray, a plate, a glass, a shell, a box, a sphere, a globe, a vessel, and a container.

114. The method according to claim 87, wherein the air freshener device comprises a delivery system comprising an element in communication or in contact with the freshening composition.

115. The method according to claim 114, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

116. The method according to claim 87, wherein the air freshener device comprises an evaporative assistance element attached to the reservoir.

117. The method according to claim 116, wherein the evaporative assistance element is selected from the group consisting of a heater, a fan, an agitator, and a combination of any of the preceding evaporative assistance elements.

118. The method according to claim 87, wherein the air freshener device is selected from the group consisting of a spraying device, a capillary wicking device, a membrane diffusing device, a steam-diffusing device, an energized device, a heating device, a device comprising a delivery system, a device powered by a chemical reaction, an air freshener device comprising a wick, a passive air diffuser device, a device comprising an evaporative assistance element, and a reed diffuser air freshener.

119. The method according to claim 118, wherein the air freshener device is the spraying device, and wherein the spraying device comprises from about 0.01 wt % to about 50 wt % of the freshening composition, from about 1 wt % to about 80 wt % of a co-solvent, and from about 1 wt % to about 50 wt % of a propellant.

120. The method according to claim 118, wherein the air freshener device is the spraying device, and wherein the spraying device comprises the freshening composition and ethanol.

121. The method according to claim 118, wherein the air freshener device is the energized device.

122. The method according to claim 121, wherein the energized device is selected from the group consisting of an electrically powered air freshener device, an electrical wall plug-in, a fan-based diffuser, a liquid electric pluggable air freshener device, an electromechanical actuating diffuser, a device powered by a chemical reaction, and a battery-operated air freshener device.

123. The method according to claim 122, wherein the air freshener device is the electrical wall plug-in.

124. A method for modulating release of a freshening composition or of a component thereof, the method comprising the step of combining:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator in the freshening composition is sufficient to modulate release of the freshening composition or of a component thereof, relative to a control not comprising the fragrance release modulator and being assigned a value of 100%, by at least 10%;

thereby the release of the freshening composition or of the component thereof is modulated.

125. The method according to claim 124, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

126. The method according to claim 124, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

127. A method for delivering a smell or scent of a freshening composition or of a component thereof into an atmosphere, air, or onto a surface, the method comprising the step of delivering a freshening composition or a component thereof to a delivery system within an air freshener device;

wherein the freshening composition comprises:

(i) from about 0.1 wt % to about 95 wt % perfume raw material, the perfume raw material comprising one or more ingredients selected from the group consisting of an ester, an alcohol, an aldehyde, a ketone, an acetal, a phenol, an ether, a lactone, a furan, a hydrocarbon, an acid, a natural origin fragrance compound, a synthetic origin fragrance compound, a stereoisomer of any preceding perfume raw material, and a mixture of any of the preceding perfume raw materials; and (ii) from about 0.01 wt % to about 90 wt % fragrance release modulator having two (ii) or more characteristics selected from the group consisting of:

(a) a flash point higher than about 100° F., (b) a surface tension of less than about 60 mN/m, (c) a dynamic viscosity from about 0.5 cp to about 100 cp, and (d) a density from about 600 g/l to about 1,300 g/l;

wherein the fragrance release modulator is selected from the group consisting of a C2-8 linear alcohol, a C2-8 branched alcohol, an alkyl-ether, an aryl-ether, an alkyl-glycol, an aryl-glycol, an alkyl-carbonate, an aryl-carbonate, propylene carbonate, an alkyl-diol, an aryl-diol, an alkyl-adipate, an aryl-adipate, an alkyl-benzoate, an aryl-benzoate, an alkyl-citrate, an aryl-citrate, an alkyl-laurate, an aryl-laurate, an alkyl-palmitate, an aryl-palmitate, an alkyl-stearate, an aryl-stearate, an alkyl-myristate, an aryl-myristate, an alkyl-succinate, an aryl-succinate, an alkyl-glutarate, an aryl-glutarate, a silicon solvent, n-butyl propionate, a stereoisomer of any preceding fragrance release modulator, and a mixture of any of the preceding fragrance release modulators;

wherein the freshening composition is adapted to have two or more of a characteristic selected from the group consisting of:

(a) a flash point higher than about 100° F., (b) a surface tension from about 10 mN/m to about 40 mN/m, (c) a dynamic viscosity from about 1 cp to about 30 cp, and (d) a density from about 650 g/l to about 1,300 g/l; and wherein the amount of the fragrance release modulator in the freshening composition is sufficient to modulate the release of the freshening composition or of a component thereof, relative to a control not comprising the fragrance release modulator and being assigned a value of 100%, by at least 10%;

thereby the smell or the scent of the freshening composition or of the component thereof is delivered into the atmosphere, the air, or onto the surface.

128. The method according to claim 127, wherein the amount of the fragrance release modulator is sufficient to up-regulate the release of the freshening composition or of the component thereof, relative to the control not comprising the fragrance release modulator and assigned a value of 100%, by at least about 20%, by at least about 30%, by at least about 40%, by at least about 50%, by at least about 60%, by at least about 70%, by at least about 80%, by at least about 90%, by at least about 100%, by at least about 110%, by at least about 120%, by at least about 130%, by at least about 140%, by at least about 150%, by at least about 160%, by at least about 170%, by at least about 180%, by at least about 190%, by at least about 200%, by at least about 250%, by at least about 300%, by at least about 400%, by at least about 500%, or by at least about 1,000-3,000% or more.

129. The method according to claim 127, wherein the amount of the fragrance release modulator is sufficient to down-regulate the release of the freshening composition or of the component thereof, relative to the control not comprising the fragrance release modulator and assigned a value of 100%, by at least about 15%, by at least about 20%, by at least about 25%, by at least about 30%, by at least about 35%, by at least about 40%, by at least about 45%, by at least about 50%, by at least about 55%, by at least about 60%, by at least about 65%, by at least about 70%, by at least about 75%, by at least about 80%, by at least about 85%, by at least about 90%, or by at least about 95% or more.

130. The method according to claim 127, wherein the fragrance release modulator is selected from the group consisting of ethanol, n-propanol, iso-propanol, n-butanol, t-butanol, 3-methoxy-3-methyl-1-butanol, 3-methyl-3-methoxyl butanol, 1-pentanol, 2-pentanol, amyl-alcohol, 1,3 propanediol, 1,2 hexanediol, 1,2 pentanediol, dimethyl ether, propylene glycol, dipropylene glycol, hexylene glycol, glycerol, benzyl benzoate, triethyl citrate, dioctyl adipate, dimethyl carbonate, isoamyl laurate, methyl palmitate, methyl stearate, dimethyl adipate, dimethyl succinate, dimethyl glutarate, dimethicone, disiloxane, trisiloxane, and a mixture of any of the preceding fragrance release modulators.

131. The method according to claim 127, wherein the $C_{2-27}$ branched alcohol is selected from the group consisting of isopropanol, t-butanol, isobutanol, s-butanol, 3-methyl-1-butanol, 2-methyl-2-butanol, 2-ethyl-1-butanol, 3-methyl-3-pentanol, 2-methyl-3-hexanol, 2,4-dimethyl-3-pentanol, 3-methoxy-3-methyl-1-butanol, a stereoisomer thereof, and a mixture thereof.

132. The method according to claim 131, wherein the $C_{2-27}$ branched alcohol is 3-methoxy-3-methyl-1-butanol.

133. The method according to claim 127, wherein the alkyl-glycol is selected from the group consisting of propylene glycol, dipropylene glycol, tripropylene glycol, butylene glycol, ethylene glycol monoethyl ether, diethylene glycol monoethyl ether, propylene glycol methyl ether, dipropylene glycol methyl ether, hexylene glycol, diethylene glycol monoethyl ether, a stereoisomer thereof, and a mixture thereof.

134. The method according to claim 133, wherein the alkyl-glycol is propylene glycol or dipropylene glycol.

135. The method according to claim 127, wherein the alkyl-diol is selected from the group consisting of 2-methylpentane-2,4-diol, 1,2-hexanediol, 1,2-octanediol, 1,2-pentanediol, 1,2-decanediol, 1,2-butanediol, 1,3-propanediol, 2-methyl-1,3-propanediol, 1,2-propylene glycol, 1,3-hexanediol, a stereoisomer thereof, and a mixture thereof.

136. The method according to claim 135, wherein the alkyl-diol is 2-methylpentane-2,4-diol.

137. The method according to claim 127, wherein the alkyl-adipate is selected from the group consisting of dimethyl adipate, diethyl adipate, dibutyl adipate, diisopropyl adipate, diisobutyl adipate, dioctyl adipate, diisononyl adipate, dihexyl adipate, dipropylene glycol adipate, a $C_{12-15}$alkyl adipate, a stereoisomer thereof, and a mixture thereof.

138. The method according to claim 137, wherein the alkyl-adipate is dimethyl adipate.

139. The method according to claim 127, wherein the alkyl-benzoate is selected from the group consisting of benzyl benzoate, isopropyl benzoate, decyl benzoate, cetyl benzoate, stearyl benzoate, isobutyl benzoate, myristyl benzoate, lauryl benzoate, octyl benzoate, butyl benzoate, a $C_{12-15}$alkyl benzoate, a stereoisomer thereof, and a mixture thereof.

140. The method according to claim 139, wherein the alkyl-benzoate is benzyl benzoate.

141. The method according to claim 127, wherein the alkyl-citrate is selected from the group consisting of triethyl citrate, tributyl citrate, acetyl triethyl citrate, triisopropyl citrate, trihexyl citrate, trioctyl citrate, tricaprylyl citrate, triisodecyl citrate, trimethyl citrate, a $C_{12-15}$alkyl citrate, a stereoisomer thereof, and a mixture thereof.

142. The method according to claim 141, wherein the alkyl-citrate is triethyl citrate.

143. The method according to claim 127, wherein the alkyl-myristate is selected from the group consisting of isopropyl myristate, cetyl myristate, stearyl myristate, myristyl myristate, butyl myristate, isobutyl myristate, octyl myristate, decyl myristate, cetearyl myristate, lauryl myristate, a stereoisomer thereof, and a mixture thereof.

144. The method according to claim 143, wherein the alkyl-myristate is isopropyl myristate.

145. The method according to claim 127, wherein the alkyl-glutarate is selected from the group consisting of dimethyl glutarate, diethyl glutarate, dibutyl glutarate, diisopropyl glutarate, dioctyl glutarate, diethylhexyl glutarate, isopropyl glutarate, butyl glutarate, hexyl glutarate, lauryl glutarate, a $C_{12-15}$alkyl glutarate, a stereoisomer thereof, and a mixture thereof.

146. The method according to claim 145, wherein the alkyl-glutarate is dimethyl glutarate.

147. The method according to claim 127, wherein the fragrance release modulator is 3-methyl-3-methoxyl butanol.

148. The method according to claim 127, further comprising a compound selected from the group consisting of 2,2-dimethyl-1,3-dioxolane-4-methanol, 3-methyl-1,3-butanediol-1-acetate, ethylene glycol monoethyl ether, ethylene glycol monomethyl ether, diethylene glycol monoethyl ether, diethylene glycol monomethyl ether, dipropylene glycol monomethyl ether, dipropylene glycol monomethyl ether acetate, and tripropylene glycol monomethyl ether.

149. The method according to claim 127, wherein the ester is selected from the group consisting of an acrylic ester, an acetoacetic ester, an anisic ester, a benzoic ester, an anthranilic ester, an N-methylanthranilic ester, an isovaleric ester, an isobutyric ester, an undecylenic ester, an octanoic ester, an octenoic ester, an octyne carboxylic ester, a caproic ester, a hexenoic ester, a valeric ester, a formic ester, a crotonic ester, a cinnamic ester, a succinic ester, an acetic ester, an salicylic ester, a cyclohexyl alkanoic ester, a stearic ester, a sebacic ester, a decanoic ester, a dodecanoic ester, a lactic ester, a nonanoic ester, a nonenoic ester, a hydroxyhexanoic ester, a phenylacetic ester, a phenoxyacetic ester, a furancarboxylic ester, a propionic ester, a heptanoic ester, a heptin carboxylic ester, a myristic ester, a phenylglycidic ester, a 2-methylbutyric ester, a 3-methylbutyric ester, a butyric ester, a hydroxybutyric ester, a stereoisomer of any preceding ester, and a mixture of any of the preceding esters;

wherein the alcohol is selected from the group consisting of an aliphatic alcohol, a terpene alcohol, an aromatic alcohol, a stereoisomer of any preceding alcohol, and a mixture of any of the preceding alcohols;

wherein the aldehyde is selected from the group consisting of an aliphatic aldehyde, an aromatic aldehyde, a terpene aldehyde, a stereoisomer of any preceding aldehyde, and a mixture of any of the preceding aldehydes;

wherein the ketone is selected from the group consisting of a cyclic ketone, an aromatic ketone, a linear ketone, a stereoisomer of any preceding ketone, and a mixture of any of the preceding ketones;

wherein the acetal is selected from the group consisting of acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenyl acetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dimethyl acetal, nonanal dimethyl acetal, decanal dimethyl acetal, decanal diethyl acetal, 2-methylundecanal dimethyl acetal, citronellal dimethyl acetal, acetoacetate ethyl ethylene glycol acetal, 2-phenylpropanal dimethyl acetal, a stereoisomer of any preceding acetal, and a mixture of any of the preceding acetals;

wherein the phenol is selected from the group consisting of eugenol, isoeugenol, 2-methoxy-4-vinylphenol, thymol, carvacrol, guaiacol, chavicol, a stereoisomer of any preceding phenol, and a mixture of any of the preceding phenols;

wherein the ether is selected from the group consisting of anethole, 1,4-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, alpha-terpinyl methyl ether, citronellyl ethyl ether, geranyl ethyl ether, rose furan, decyl methyl ether, methyl phenylmethyl ether, a stereoisomer of any preceding ether, and a mixture of any of the preceding ethers;

wherein the lactone is selected from the group consisting of γ-decalactone, δ-decalactone, γ-heptalactone, γ-nonalactone, γ-hexalactone, δ-hexalactone, γ-octalactone, δ-octalactone, Y-undecalactone, δ-undecalactone, δ-dodecalactone, δ-2-decenolactone, methyllactone, 5-hydroxy-8-undecenoic acid δ-lactone, jasmine lactone, menthalactone, dihydrocoumarin, octahydrocoumarin, 6-methylcoumarin, a stereoisomer of any preceding lactone, and a mixture of any of the preceding lactones;

wherein the furan is selected from the group consisting of 2-methyl furan, 2-ethylfuran, 2,5-diethyltetrahydrofuran, 3-hydroxy-2-methyltetrahydrofuran, 2-(methoxymethyl) furan, 2,3-dihydrofuran, furfural, 5-methylfurfural, 3-(2-furyl)-2-methyl-2-propenal, 5-(hydroxymethyl) furfural, 2,5-dimethyl-4-hydroxy-3 (2H)-furanone (furaneol), 4,5-dimethyl-3-hydroxy-2 (5H)-furanone (sotolone), 2-ethyl-4-hydroxy-5-methyl-3 (2H)-furanone (homofuraneol), 5-ethyl-3-hydroxy-4-methyl-2 (5H) furanone (homosotolone), 3-methyl-1,2-cyclopentanedione (cyclotene), 2 (5H)-furanone, 4-methyl-2 (5H)-furanone, 5-methyl-2 (5H)-furanone, 2-methyl-3 (2H)-furanone, 5-methyl-3 (2H)-furanone, 2-acetylfuranone, 2-acetyl-5-methylfuran, furfuryl alcohol, methyl 2-furancarboxylate, ethyl 2-furancarboxylate, furfuryl acetate, a stereoisomer of any preceding furan, and a mixture of any of the preceding furans;

wherein the hydrocarbon is selected from the group consisting of α-bisabolene, β-bisabolene, β-caryophyllene, p-cymene, terpinene, terpinolene, cadinene, farnesene, limonene, ocimene, myrcene, α-pinene, β-pinene, 1,3,5-undecatriene, valencene, a stereoisomer of any preceding hydrocarbon, and a mixture of any of the preceding hydrocarbons;

wherein the acid is selected from the group consisting of geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, a stereoisomer of any preceding acid, and a mixture of any of the preceding acids; or wherein the natural origin fragrance compound is isolated or purified from a natural origin selected from the group consisting of anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamon, cassia, cinnamon, pepper, perilla, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birch, capsicum, celery, tolu balsam, djenne, inmortel, benzoin, jasmine, cassia, tuberose, mignonette, marigold, mimosa, opopanax, orris, vanilla, and licorice.

150. The method according to claim 127, wherein the freshening composition further comprises less than about 50 wt % of an ingredient having a functional activity and wherein the ingredient having the functional activity is selected from the group consisting of an ingredient having malodor counteracting activity, an ingredient having antimicrobial activity, an insect repellant, a preservative, an antioxidant, a humectant, a UV-blocking agent, a pigment, a dye, a surfactant, an emulsifier, a solubilizer, a polymer, and a buffer.

151. The method according to claim 150, wherein the ingredient having malodor counteracting activity is cyclodextrin;

wherein the ingredient having antimicrobial activity is selected from the group consisting of a paraben, benzyl alcohol, phenol, cresol, cetrimide, thiomersal, hexylene glycol, 1,2 hexanediol, and phenoxy ethanol;

wherein the insect repellent is N,N-diethyl-meta-toluamide or methyl nonyl ketone;

wherein the preservative is selected from the group consisting of imidazolidinyl urea, diazolidinyl urea, allantoin, and sodium hydroxymethylglycinate;

wherein the antioxidant is selected from the group consisting of butylate hydroxytoluene, ascorbic acid, and tocopherol;

wherein the humectant is selected from the group consisting of glycerol, hexylene glycol, and ethyl-hexylglycerin;

wherein the UV blocking agent is selected from the group consisting of avobenzone, oxybenzone, dioxybenzone, and octocrylene;

wherein the pigment is selected from the group consisting of chrome oxide, iron oxide, and ferric ferrocyanate;

wherein the surfactant is selected from the group consisting of a nonionic surfactant, an anionic surfactant, and a cationic surfactant;

wherein the emulsifier is an ethoxylated sorbitol;

wherein the solubilizer is selected from the group consisting of propylene glycol, dipropylene glycol, and hexylene glycol;

wherein the polymer is a cellulose derivative; or wherein the buffer is a phosphate buffer.

152. The method according to claim 127, wherein the air freshener device comprises a reservoir having a functionality selected from the group consisting of accepting a freshening composition, receiving a freshening composition, holding a freshening composition, housing a freshening composition, storing a freshening composition, accepting a delivery system, accepting an evaporative assistance element, and accepting a seal or a lid.

153. The method according to claim 152, wherein the reservoir is selected from the group consisting of a bottle, a bowl, a tray, a plate, a glass, a shell, a box, a sphere, a globe, a vessel, and a container.

154. The method according to claim 127, wherein the delivery system is selected from the group consisting of a reed, a plurality of reeds, a stick, a plurality of sticks, a fiber, a plurality of fibers, a wick, a plurality of wicks, a mesh material, a conductive mesh material, a porous substrate, a semi-porous substrate, and a combination of any of the preceding delivery systems.

155. The method according to claim 127, wherein the air freshener device comprises an evaporative assistance element.

156. The method according to claim 155, wherein the evaporative assistance element is selected from the group consisting of a heater, a fan, an agitator, and a combination of any of the preceding evaporative assistance elements.

157. The method according to claim 127, wherein the air freshener device is selected from the group consisting of a spraying device, a capillary wicking device, a membrane diffusing device, a steam-diffusing device, an energized device, a heating device, a device comprising a delivery system, a device powered by a chemical reaction, an air freshener device comprising a wick, a passive air diffuser device, a device comprising an evaporative assistance element, and a reed diffuser air freshener.

158. The method according to claim 157, wherein the air freshener device is the spraying device, and wherein the spraying device comprises from about 0.01 wt % to about 50 wt % of the freshening composition, from about 1 wt % to about 80 wt % of a co-solvent, and from about 1 wt % to about 50 wt % of a propellant.

159. The method according to claim 157, wherein the air freshener device is the spraying device, and wherein the spraying device comprises the freshening composition and ethanol.

160. The method according to claim 157, wherein the air freshener device is the energized device.

161. The method according to claim 160, wherein the energized device is selected from the group consisting of an electrically powered air freshener device, an electrical wall plug-in, a fan-based diffuser, a liquid electric pluggable air freshener device, an electromechanical actuating diffuser, a heating device, a device powered by a chemical reaction, a battery-operated air freshener device, and an energized device comprising a micro-fluidic die having a heater or a piezo crystal.

162. The method according to claim 161, wherein the air freshener device is the electrical wall plug-in.

163. The method according to claim 127, further comprising the step of dispersing the freshening composition or the component thereof into the atmosphere, the air, or onto the surface.

164. The method according to claim 163, wherein step of dispersing the freshening composition or the component thereof into the atmosphere, the air, or onto the surface is over a controlled or customized period of time.

165. The method according to claim 163, wherein the step of dispersing the freshening composition or the component thereof into the atmosphere, the air, or onto the surface comprises wicking the freshening composition or the component thereof.

166. The method according to claim 163, wherein the step of dispersing the freshening composition or the component thereof into the atmosphere, the air, or onto the surface comprises evaporating the freshening composition or the component thereof.

167. The method according to claim 163, wherein the step of dispersing the freshening composition or the component thereof into the atmosphere, the air, or onto the surface comprises a wicking-evaporation system adapted to deliver the freshening composition or the component thereof into the atmosphere, the air, or onto the surface.

168. The method according to claim 167, wherein the wicking-evaporation system comprises an element selected from the group consisting of a natural wick, a plurality of natural wicks, a synthetic wick, a plurality of synthetic wicks, a stick, a plurality of sticks, a reed, a plurality of reeds, a stick, a plurality sticks, a fiber, a plurality of fibers, a mesh, a conductive mesh, a membrane, a porous substrate, a semi-porous substrate, and a combination thereof.

169. The method according to claim 163, wherein the step of dispersing the freshening composition or the component thereof into the atmosphere, the air, or onto the surface comprises an evaporative assistance element.

170. The method according to claim 169, wherein the evaporative assistance element is selected from the group consisting of a heater, a fan, an agitator, and a combination thereof.

171. The method according to claim 163, wherein the step of dispersing the freshening composition or the component thereof into the atmosphere, the air, or onto the surface comprises exposing the freshening composition or the component thereof into the atmosphere, the air, or onto the surface.

172. The method according to claim 163, wherein the step of dispersing the freshening composition or the component thereof into the atmosphere, the air, or onto the surface comprises spraying the freshening composition or the component thereof into the atmosphere, the air, or onto the surface.

* * * * *